(12) United States Patent
Varma et al.

(10) Patent No.: US 12,576,024 B2
(45) Date of Patent: *Mar. 17, 2026

(54) COMPOSITIONS COMPRISING PROPIONIBACTERIUM ACNES BACTERIOPHAGES FOR TREATING ACNE

(71) Applicant: PHI THERAPEUTICS, INC., San Francisco, CA (US)

(72) Inventors: Yug Varma, San Francisco, CA (US); Nancy Van Prooyen, San Francisco, CA (US)

(73) Assignee: PHI THERAPEUTICS, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/413,988

(22) Filed: Jan. 16, 2024

(65) Prior Publication Data

US 2024/0189220 A1    Jun. 13, 2024

Related U.S. Application Data

(60) Division of application No. 17/819,050, filed on Aug. 11, 2022, now Pat. No. 11,903,984, which is a
(Continued)

(51) Int. Cl.
*A61K 35/76* (2015.01)
*A61K 8/06* (2006.01)
(Continued)

(52) U.S. Cl.
CPC ............... *A61K 8/99* (2013.01); *A61K 8/062* (2013.01); *A61K 8/064* (2013.01); *A61K 8/22* (2013.01); *A61K 8/23* (2013.01); *A61K 8/347*

(2013.01); *A61K 8/368* (2013.01); *A61K 8/66* (2013.01); *A61K 8/671* (2013.01); *A61K 9/0014* (2013.01); *A61K 31/05* (2013.01); *A61K 31/327* (2013.01); *A61K 31/60* (2013.01); *A61K 33/04* (2013.01); *A61K 35/741* (2013.01); *A61K 35/76* (2013.01); *A61K 38/47* (2013.01); *A61K 45/06* (2013.01);
(Continued)

(58) Field of Classification Search
CPC ................................ A61K 35/76; A61K 35/74
See application file for complete search history.

(56) References Cited

FOREIGN PATENT DOCUMENTS

WO    WO-2019113066 A1 *  6/2019    ............. A61K 35/76

OTHER PUBLICATIONS

Farrar et al., "Genome sequence and analysis of a Propionibacterium acnes bacteriophage," J Bacteriol 189(11):4161-4167, 2007.*
(Continued)

*Primary Examiner* — Rosanne Kosson
(74) *Attorney, Agent, or Firm* — QUARLES & BRADY LLP

(57) ABSTRACT

Provided herein are, inter alia, compositions, systems, and methods for preventing or treating acne. Included are compositions, combinations, systems, and methods comprising at least one *Propionibacterium acnes* bacteriophage, at least one anti-acne compound, and a pharmaceutically acceptable carrier. Also included are compositions, combinations, and systems comprising a *Propionibacterium acnes* bacteriophage and an enzyme. Methods for preventing or treating acne are also provided.

18 Claims, 11 Drawing Sheets
Specification includes a Sequence Listing.

Minocycline

PHIT-101

*P. acnes*    *P. granulosum*
Acne-causing   Commensal

Related U.S. Application Data continuation of application No. 16/606,158, filed as application No. PCT/US2018/028556 on Apr. 20, 2018, now abandoned.

(60) Provisional application No. 62/488,326, filed on Apr. 21, 2017.

(51) Int. Cl.

| | |
|---|---|
| *A61K 8/22* | (2006.01) |
| *A61K 8/23* | (2006.01) |
| *A61K 8/34* | (2006.01) |
| *A61K 8/368* | (2006.01) |
| *A61K 8/66* | (2006.01) |
| *A61K 8/67* | (2006.01) |
| *A61K 8/99* | (2017.01) |
| *A61K 9/00* | (2006.01) |
| *A61K 31/05* | (2006.01) |
| *A61K 31/327* | (2006.01) |
| *A61K 31/60* | (2006.01) |
| *A61K 33/04* | (2006.01) |
| *A61K 35/74* | (2015.01) |
| *A61K 35/741* | (2015.01) |
| *A61K 38/47* | (2006.01) |
| *A61K 45/06* | (2006.01) |
| *A61P 17/10* | (2006.01) |
| *A61Q 19/00* | (2006.01) |

(52) U.S. Cl.
CPC .............. *A61P 17/10* (2018.01); *A61Q 19/00* (2013.01); *C12Y 302/01052* (2013.01); *C12Y 105/01001* (2013.01); *C12Y 111/01* (2013.01); *C12Y 304/21062* (2013.01); *C12Y 304/21064* (2013.01)

(56) References Cited

OTHER PUBLICATIONS

Alignment of instant SEQ ID No. 1 and GenBank Accession No. NC_009541.1, Propionibacterium bacteriophage PA6 of Farrar et al., Mar. 5, 2025.*

* cited by examiner

IL17

TNFα

Skin Microbiome

Genotypic Screen
Multi-locus

Phenotypic          Phenotypic
Marker 1            Marker 2

Immunogenic Potential

COMPOSITIONS COMPRISING *PROPIONIBACTERIUM ACNES* BACTERIOPHAGES FOR TREATING ACNE

CROSS-REFERENCE TO RELATED APPLICATIONS

This application is a divisional of U.S. application Ser. No. 17/819,050, filed Aug. 11, 2022, which is a continuation of U.S. application Ser. No. 16/606,158, filed Sep. 24, 2021, which is a U.S. national phase application of International Patent Application No. PCT/US18/28556 filed Apr. 20, 2018, which in turn claims the benefit of U.S. Provisional Application No. 62/488,326, filed Apr. 21, 2017. The entire content of each of the above-referenced applications is hereby incorporated by reference.

GOVERNMENT SUPPORT

This invention was made with government support under Grant No. 1R43AR068172-01 awarded by the National Institutes of Health. The government has certain rights in the invention.

INCORPORATION-BY-REFERENCE OF SEQUENCE LISTING

A Sequence Listing accompanies this application and is submitted as an XML file of the sequence listing named "177601.00022.xml" which is 87,200 bytes in size and was created on Aug. 8, 2022. The sequence listing is electronically submitted via Patent Center with the application and is incorporated herein by reference in its entirety.

BACKGROUND

Acne is a nearly universal condition that affects more than 80% of all people worldwide. This chronic skin condition is complex but the main etiological agent is *Propionibacterium acnes* whose overgrowth leads to inflammation that causes pimples. Despite a clear need for innovation, there has not been a novel acne drug in over 30 years. Current treatments including benzoyl peroxide and antibiotics are quite ineffective, and the most effective treatment—isotretinoin—is limited to a small set of patients due to dangerous side effects (including birth defects, liver damage, and suicide).

New methods and compositions for treating for acne are needed.

BRIEF SUMMARY

Provided herein are, inter alia, compositions, combinations, systems, and methods for preventing or treating acne.

In an aspect, provided herein is a composition comprising, consisting essentially of, or consisting of at least one *Propionibacterium acnes* bacteriophage, at least one anti-acne compound, and a pharmaceutically acceptable carrier.

In an aspect, provided herein is a composition that includes at least one *Propionibacterium acnes* bacteriophage, no more than one anti-acne compound, and a pharmaceutically acceptable carrier.

In an aspect, provided herein is a composition that includes active ingredients consisting of at least one *Propionibacterium acnes* bacteriophage and no more than one anti-acne compound, and a pharmaceutically acceptable carrier.

In an aspect, provided herein is a composition that includes at least one *Propionibacterium acnes* bacteriophage, at least one anti-acne compound, and a pharmaceutically acceptable carrier, wherein the composition does not comprise a probiotic bacterium.

In an aspect, provided herein is a composition that includes a *Propionibacterium acnes* bacteriophage and an enzyme.

In an aspect, provided herein is a combination comprising, consisting essentially of, or consisting of at least one *Propionibacterium acnes* bacteriophage and at least one anti-acne compound, wherein each of the at least one *Propionibacterium acnes* bacteriophage and the at least one anti-acne compound is in a composition that further includes a pharmaceutically acceptable carrier.

In an aspect, provided herein is a combination that includes a *Propionibacterium acnes* bacteriophage and an enzyme.

In an aspect, provided herein is a method of preventing or treating acne in a subject in need thereof, the method including administering an effective amount of a composition or combination provided herein.

*acnes* as effectively as in liquid culture, but addition of the biofilm degrading enzyme Dispersin greatly increased the bacterial killing to levels similar to liquid culture.

Figure 6:
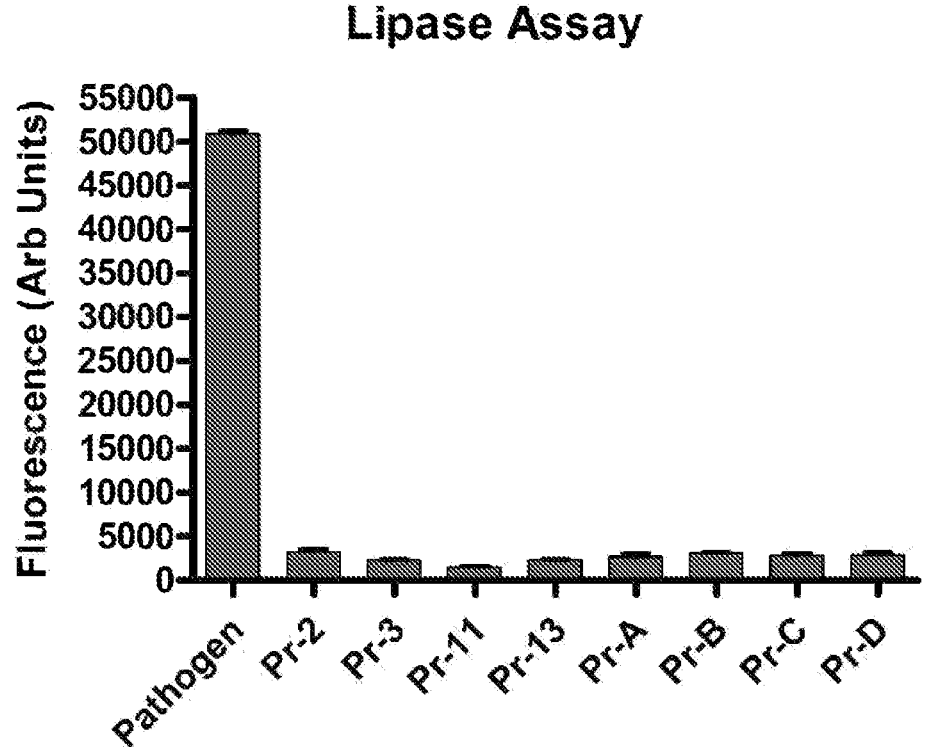

FIG. 6. Probiotic strains produce low levels of lipase in adherent culture. Probiotic *P. acnes* strains with known genotypes were grown under biofilm conditions in a microtiter plate. After 72 hrs of growth, the culture supernatant was filter-sterilized and incubated with 4-MU palmitate at 37 C for 4 hours to determine extracellular lipase production. The lipase production of the probiotic strains (Pr #X) was very low in comparison to pathogen, indicating a lower inflammatory potential.

Figure 7:
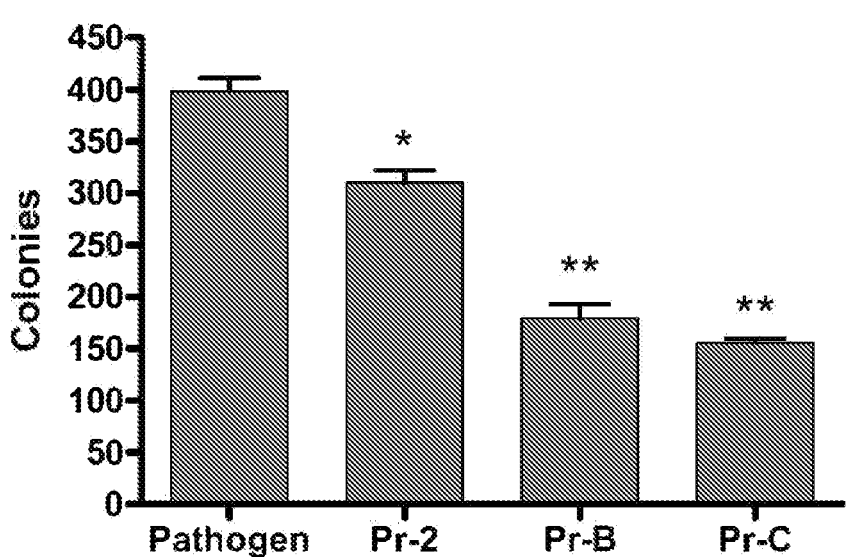
Figure 8A:
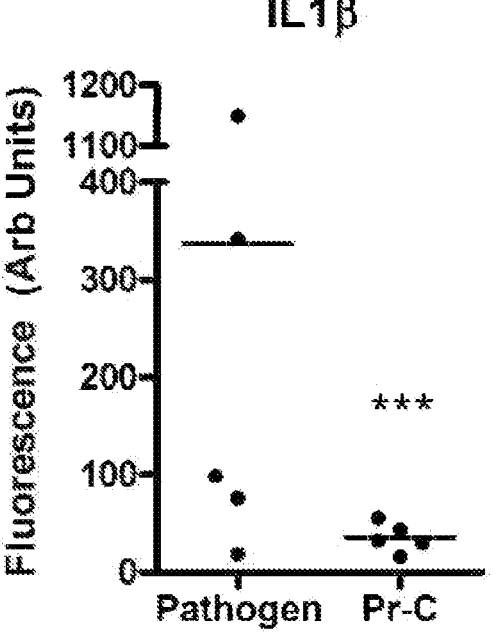
Figure 8B:
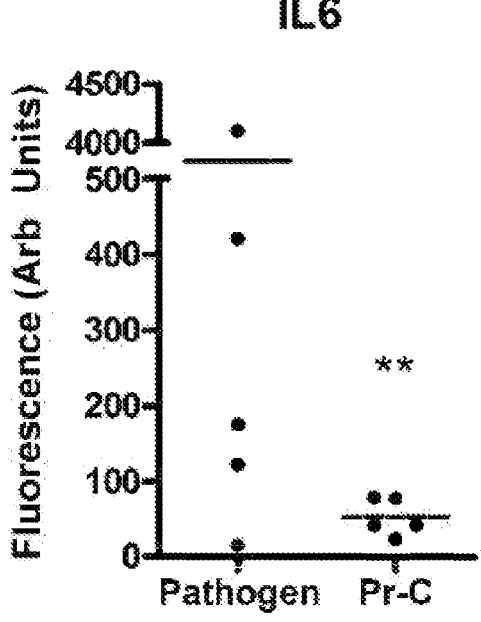
Figure 8C:
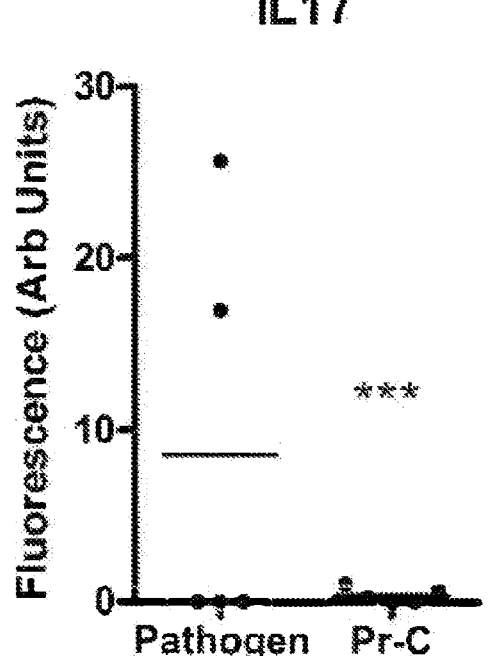
Figure 8D:
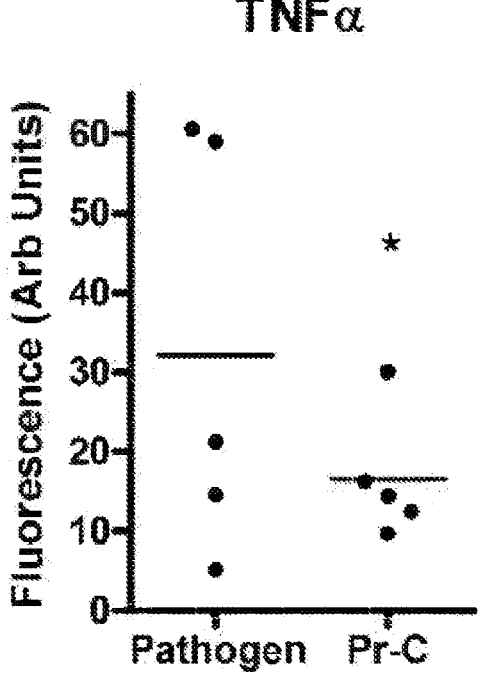

FIG. 7. Probiotic strains adhere significantly less to epithelial cells than pathogenic *P. acnes*. Select probiotic strains were incubated with confluent A-431 epithelial cells (MOI 10). After washing the wells, cells were lifted using 0.1% Tween 80 solution and plated on BHI plates. After anaerobic incubation for 72 hours, colonies were counted. The data show that probiotic strains showed significantly lower binding to epithelial cells (* $p < 0.05$, ** $p < 0.005$).

FIGS. 8A-8D. Lower inflammatory potential of probiotic strain in mouse ear inflammation model. CBA/J mice (5 mice per cohort) were injected with *P. acnes* strains, and cytokine analysis was performed at day 5. The probiotic strain Pr #C showed significantly lower levels (* $p < 0.05$,  $p < 0.01$, * $p < 0.0001$) of inflammatory cytokines IL-1β (FIG. 8A), IL-6 (FIG. 8B), IL-17 (FIG. 8C), and TNFα (FIG. 8D) than the pathogenic strain. Pr-C has the ProII 16S sequence.

Figure 9:
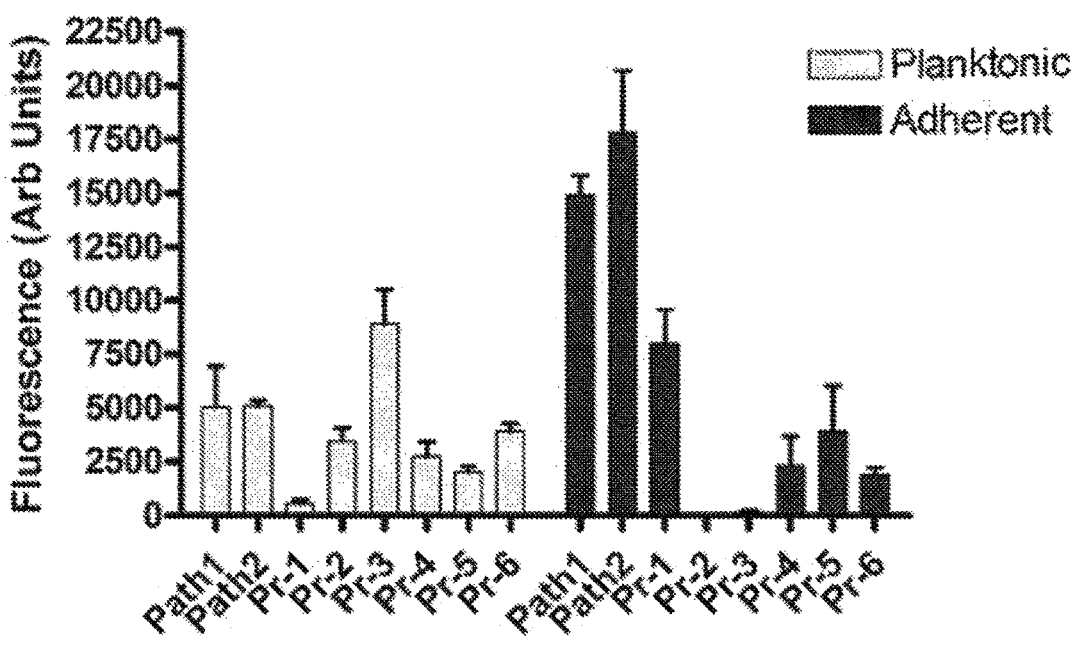

FIG. 9. *P. acnes* strains have different lipase profiles in planktonic and sessile cultures. A set of two pathogenic (Path-1, Path-2) and two probiotic (Pr-1 to Pr-6) *P. acnes* strains were evaluated for lipase production in planktonic (gray bars) and sessile (black bars) cultures. While the lipase production of probiotic strains was not significantly different from the pathogenic strains in liquid (planktonic) culture, their lipase output in adherent culture was consistently lower than corresponding pathogenic cultures. Interestingly, variability in lipase production amongst probiotic strains was observed. The strains with lowest lipase activity were selected.

Figure 10:
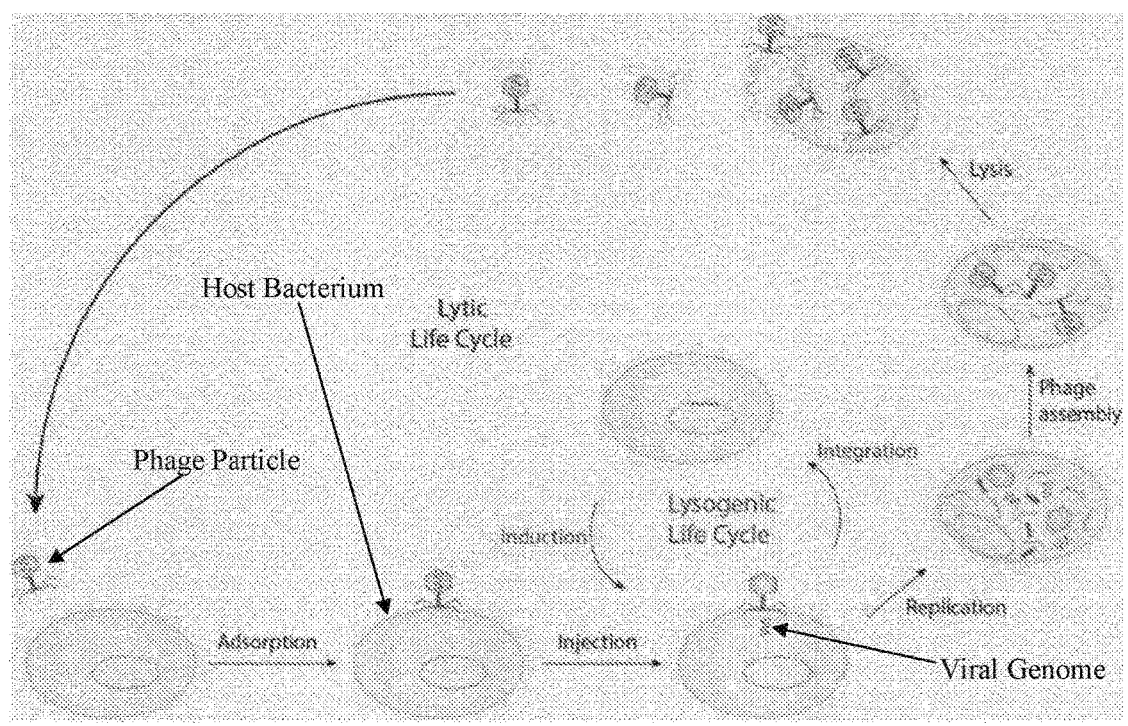

FIG. 10. illustrates life-cycles of exemplary bacteriophages. Anticlockwise from bottom left: A phage particle recognizes and adsorbs onto the surface of the host bacterium. The phage genome is injected into the bacteria. In the lysogenic life cycle, this DNA gets integrated into the bacterial genome and replicates with it for several cycles. In the lytic life cycle, the genome does not integrate and proceeds to hijack the host machinery to replicate its genome and phage structural components. The fully assembled phage then lyses the cell, typically by producing endolysins and holins at the late stage of infection. The liberated phages are now free to seek out and infect a new host bacterium, initiating another lytic cycle.

Figure 11:
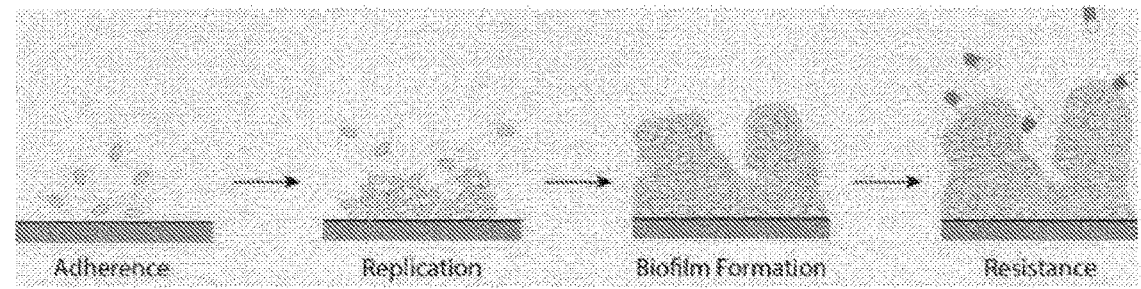

FIG. 11 illustrates the formation of exemplary bacterial biofilms. Bacterial cells land and adhere to a surface with favorable conditions for growth. They replicate to form a colony, until a certain threshold of cell density (quorum) triggers biofilm formation. The biofilm includes a mixture of polysaccharides, proteins, DNA and lipids in varying proportions. The biofilm is a physical barrier that protects the bacterial colony from harsh external conditions and grants resistance to antibiotics, toxins and immune cells.

Figure 12:
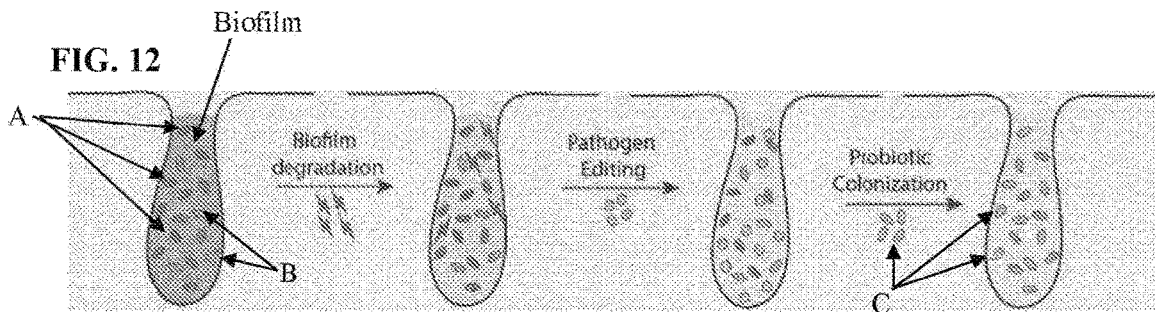

FIG. 12 illustrates an embodiment of three components act in concert; their effects are described sequentially for exposition. An inflamed comedone is typically clogged with the biofilm produced by overgrown *P. acnes* (A), along with commensal skin bacteria (B). The biofilm-degrading enzyme (bolts) breaks down the *P. acnes* biofilm to provide better access for the other components. The bacteriophage (hexagons) then edits or specifically kills the pathogenic *P. acnes* and clears the infection. Finally, the probiotic bacteria (C) colonize the pore and occupy the niche of the pathogen, preventing it from growing back and recalibrating the microbiome to a healthy state.

Figure 13:
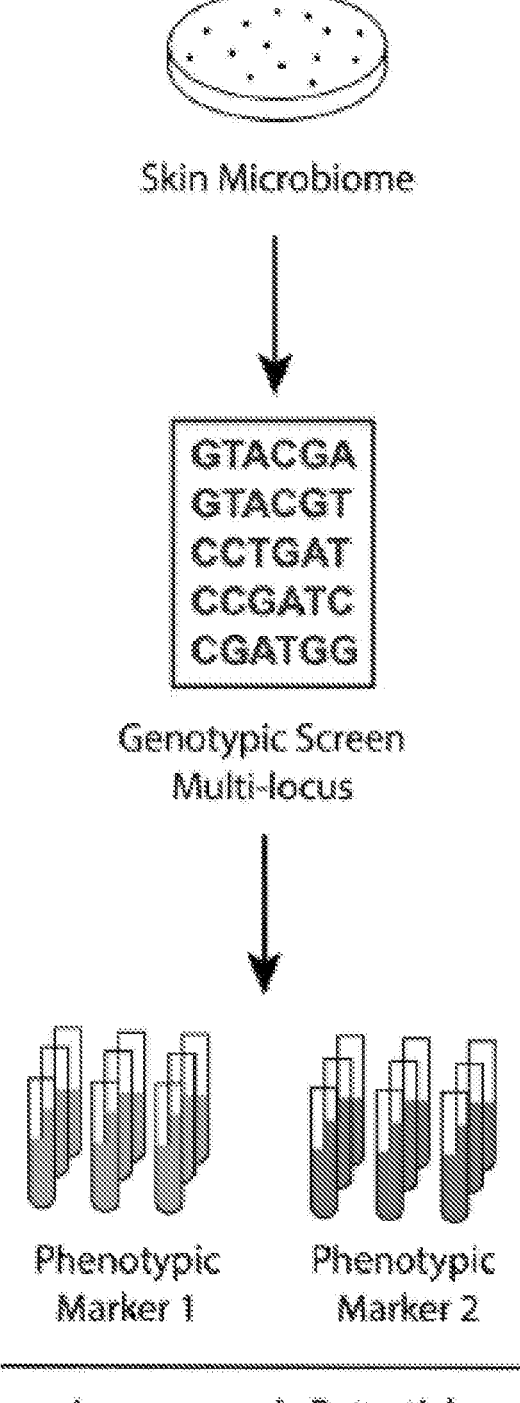

FIG. 13 is a cartoon of a non-limiting probiotic bacterium screening process.

Figure 14:
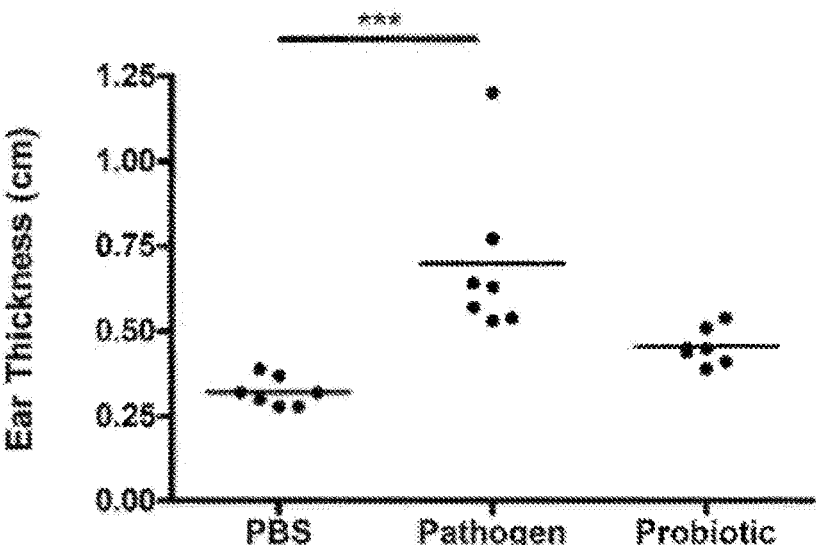

FIG. 14 is a graph showing that the pathogenic strain produces significantly higher ear inflammation than PBS control, while the lead probiotic strain Pr-C induces ear inflammation not significantly different from PBS control.

Figure 15:
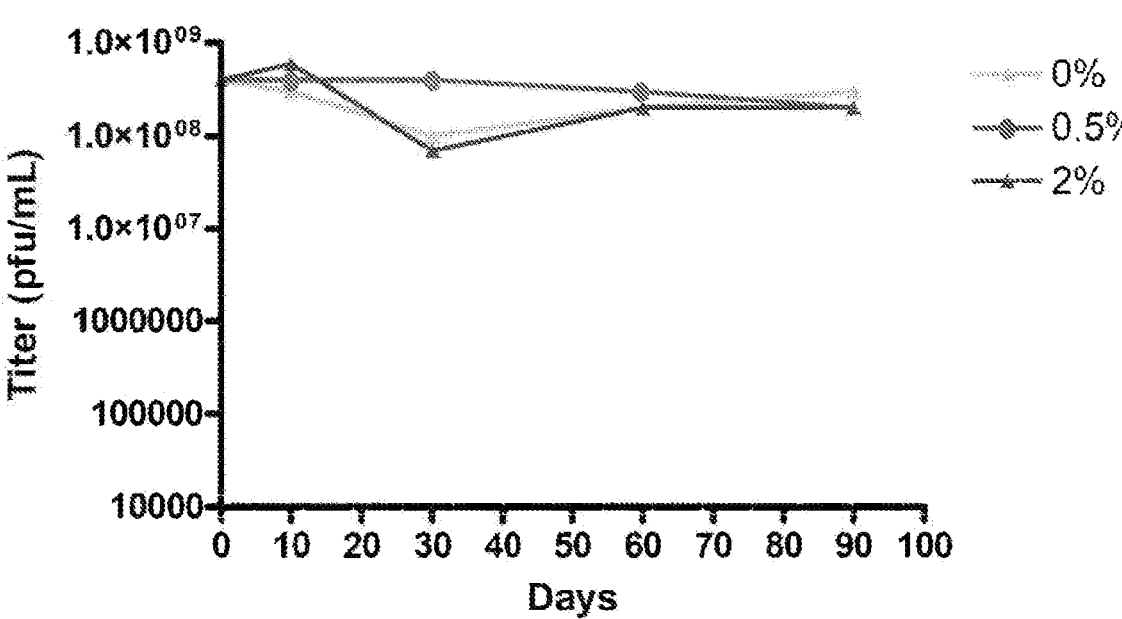

FIG. 15 is a graph showing that a phage remains stable in the presence of low (0.5% w/v) and high (2% w/v) concentrations of salicylic acid.

Figure 16:
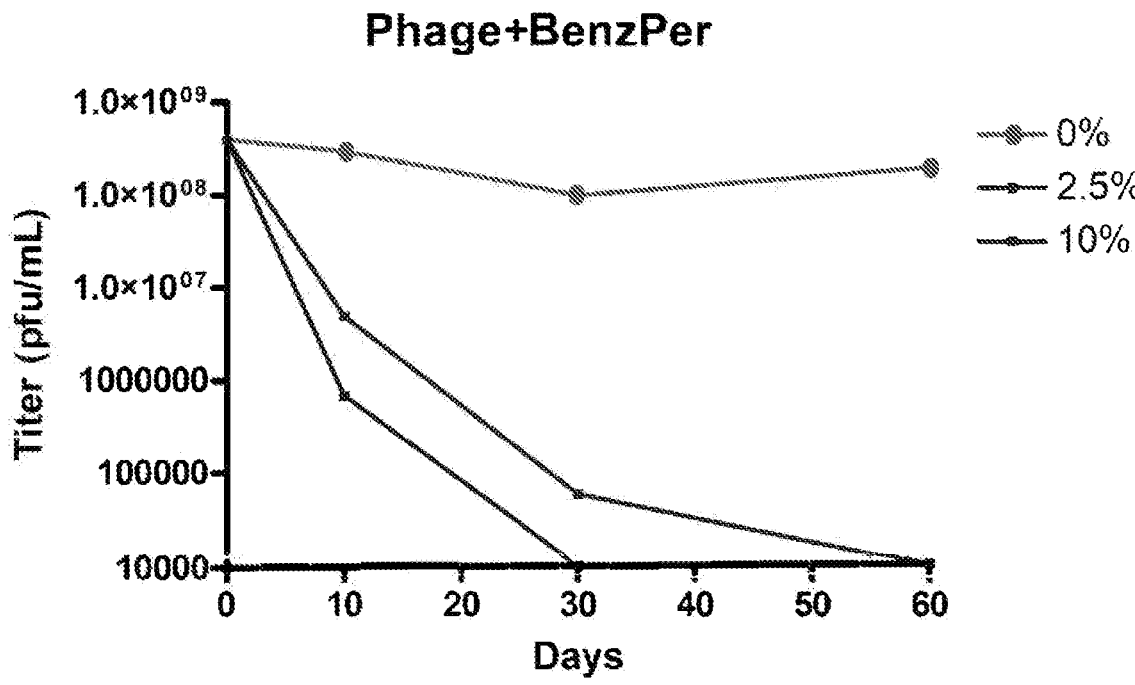

FIG. 16 is a graph showing that a phage loses its viability in the presence of benzoyl peroxide over 60 days. The rate of loss of phage viability is greater at the higher concentration (10% w/v) compared to the lower concentration (2.5% w/v).

DETAILED DESCRIPTION

Provided herein, are, inter alia, compositions, combinations, methods, and systems for treating and preventing acne.

Salicylic acid and benzoyl peroxide are the most commonly used anti-acne agents in over-the-counter (OTC) products. The stability of phages in combination with these anti-acne agents is unknown, especially since phages diverge widely in their stability and response to external physical and chemical factors. The redox properties of benzoyl peroxide and sulfur can potentially cause the degradation of the protein coat of the phage. Previous studies have shown that exposure to peroxide increases the rate of protein degradation by destabilizing the protein and increasing its susceptibility to proteolysis (Fligiel et al. Protein degradation following treatment with hydrogen peroxide. *Am J Pathol* 1984, 115 (3), 418-25; Kocha et al. Hydrogen peroxide-mediated degradation of protein: different oxidation modes of copper- and iron-dependent hydroxyl radicals on the degradation of albumin. *Biochim Biophys Acta* 1997, 1337 (2), 319-26). Salicylic acid is noted for its protein-binding ability (Lee et al. Protein binding of acetylsalicylic acid and salicylic acid in porcine and human serum. *Vet Hum Toxicol* 1995, 37 (3), 224-5; Verbeeck and Cardinal, Plasma protein binding of salicylic acid, phenytoin, chlorpromazine, propranolol and pethidine using equilibrium dialysis and ultracentrifugation. *Arzneimittelforschung* 1985, 35 (6), 903-6), and a high affinity for the protein coat of the capsid or the tail fibers would render the phage unviable.

Surprisingly, a *Propionibacterium acnes* bacteriophage was found to be stable in compositions that include salicylic acid. See, for example, FIG. 15. Thus, salicylic acid is shown to be well tolerated by the phage and is a suitable anti-acne agent for co-formulation. In embodiments, the anti-keratolytic activity of the salicylic acid complements phage activity by enabling deeper penetration of the phage, thereby increasing its killing efficiency. In embodiments, phages as described herein may be combined with salicylic acid in compositions for preventing and treating acne.

While benzoyl peroxide is not suitable for co-formulation with the phage tested (see FIG. 16) for formulations that will be stored for more than, e.g., a few days, benzoyl peroxide can be used along with a phage product as part of an anti-acne combination (e.g., a kit). In embodiments, the benzoyl peroxide is an active ingredient in a cleanser, which is applied to the skin and washed off prior to the application of a comprising the phage composition/formulation. In embodiments, the anti-keratolytic and transient antibacterial action of the benzoyl peroxide complements the specific deeper and targeted killing of *P. acnes* by the bacteriophage.

In embodiments, a *Propionibacterium acnes* bacteriophage and an anti-acne compound (such as salicylic acid and/or sulfur) are in a single composition that is topically administered to the skin of a subject. In embodiments, a kit that includes a *Propionibacterium acnes* bacteriophage and an anti-acne compound (e.g. in separate containers, such as bottles) is provided. In embodiments, a *Propionibacterium acnes* bacteriophage is in one composition and an anti-acne compound (such as benzoyl peroxide, salicylic acid, and/or sulfur) is in another composition, and each composition is topically administered to the skin of a subject. In embodiments, the *Propionibacterium acnes* bacteriophage is administered to the subject, and then the anti-acne compound is administered to the subject. In embodiments, the anti-acne compound is administered to the subject, and then the *Propionibacterium acnes* bacteriophage is administered to the subject. In embodiments, the subject's face is washed between when the anti-acne compound and the *Propionibacterium acnes* bacteriophage (in either order) are topically administered to the face of the subject.

In embodiments, the effective dose of the anti-acne compound (such as benzoyl peroxide, salicylic acid, or sulfur) when used in combination with the *Propionibacterium acnes* bacteriophage is less than would be required if the anti-acne compound was used alone. In embodiments, the effective dose of the anti-acne compound (such as benzoyl peroxide, salicylic acid, or sulfur) when used in combination with the *Propionibacterium acnes* bacteriophage is less than 90%, 80%, 70%, 60%, 50%, 40%, 30%, 20%, or 10% less than the dose that would be required if the anti-acne compound was used alone.

Definitions

The following definitions are included for the purpose of understanding the present subject matter and for constructing the appended patent claims. The abbreviations used herein have their conventional meanings within the chemical and biological arts.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure As used herein a "*Propionibacterium acnes* bacteriophage" is a bacteriophage that infects, replicates within, and kills *P. acnes* cells. In embodiments, a *P. acnes* bacteriophage is a lytic *P. acnes* bacteriophage. In embodiments, a *P. acnes* bacteriophage is capable of lysing a *P. acnes* bacterium and incapable of lysing any bacterium which is not *P. acnes*. In embodiments, a *P. acnes* bacteriophage is incapable of sustaining lysogeny in a bacterium. In embodiments, the use of a bacteriophage that can lyse *P. acnes* but is incapable of sustaining lysogeny has the advantage that the bacteriophage cannot lie dormant within a bacterium, but must lyse the bacterium and hence kill it. In embodiments, a *P. acnes* bacteriophage lacks the ability to express at least one gene necessary for sustaining lysogeny. The term "lacks the ability to express at least one gene necessary for sustaining lysogeny" is intended to indicate that the *P. acnes* bacteriophage lacks the ability to produce a fully functional protein product necessary to sustain lysogeny, for example, as the result of one or more point mutations or full or partial deletions of the genome. In embodiments, the *P. acnes* bacteriophage has a genome that lacks all or part of at least one gene necessary for sustaining lysogeny (e.g., artificially or naturally, e.g., the strain is or is derived from a strain that lacks all or part of at least one gene necessary for sustaining lysogeny). In embodiments, the *P. acnes* bacteriophage may comprise defects (e.g. mutations, insertions or deletions) in the genome in non-coding regions that may, nonetheless, affect the ability of the phage to sustain lysogeny, for example defects in the genome integration site(s) (e.g. a /att/site) or in a repressor binding site. In embodiments, a *P. acnes* bacteriophage is naturally occurring and isolated, with the added advantage that artificial mutations need not be introduced into the bacteriophage. In embodiments, a *P. acnes* bacteriophage is capable of lysing a plurality of strains of the *P. acnes* bacterium. In embodiments, a *P. acnes* bacteriophage is capable of lysing at least about 5, 10, 15, 20, 25, 30 or more strains of the *P. acnes* bacterium. Non-limiting examples of *P. acnes* bacteriophages are disclosed herein. In embodiments, the *P. acnes* bacteriophage has a genome having sequence identity of at least about 80%, 81%, 82%, 83%, 84%, 85%, 86%, 87%, 88%, 89%, 90%, 95%, 99%, 99.1%, 99.2%, 99.3%, 99.4%, 99.5%, 99.6%, 99.7%, 99.8%, 99.9% with SEQ ID NO: 1. In embodiments, a *P. acnes* bacteriophage has a genome having the sequence of SEQ ID NO: 1, or includes the sequence of SEQ ID NO: 1. In embodiments, the genome of the *P. acnes* bacteriophage has no insertions or deletions compared to SEQ ID NO: 1. In embodiments, the genome of the *P. acnes* bacteriophage has no insertions or deletions, and only conservative substitutions compared to SEQ ID NO: 1. In embodiments, the *P. acnes* bacteriophage is one of the following exemplary isolates of *P. acnes* bacteriophages that have been deposited under the terms of the Budapest Treaty at The National Collection of Industrial, Marine and Food Bacteria (NCIMB), Ferguson Building, Craibstone Estate, Bucksbum, Aberdeen, AB21 9YA, United Kingdom, under the following accession numbers: Accession no. NCIMB 41332 (isolate PA6); Accession no. NCIMB 41334 (isolate 1874); Accession no. NCIMB 41333 (isolate 1878); Accession no. NCIMB 41335 (isolate 1905); Accession no. NCIMB 41349 (isolate 1894); Accession no. NCIMB 41350 (isolate 103609); Accession no. NCIMB 41351 (isolate 103672). In embodiments, a non-limiting example of a host bacterium, *P. acnes*, AT1 has been deposited as NCIMB 41336. In embodiments, a *P. acnes* bacteriophage has a genome having sequence identity of at least about 80%, 81%, 82%, 83%, 84%, 85%, 86%, 87%, 88%, 89%, 90%, 95%, or 99% with the genome of the bacteriophage deposited under Accession No. NCIMB 41349. In embodiments, a *P. acnes* bacteriophage has a genome having sequence identity of at least 87% with the genome of the bacteriophage deposited under Accession No. NCIMB 41350. In embodiments, a *P. acnes* bacteriophage has a genome having sequence identity of at least 88% with the genome of the bacteriophage deposited under Accession No. NCIMB 41351. Additional non-limiting descriptions relating to *P. acnes* bacteriophages are provided in U.S. Pat. No. 9,068, 159 B2, issued Jun. 30, 2015, the entire content of which is incorporated herein by reference. The terms "phage" and "bacteriophage" are used interchangeably herein.

As used herein, "degrading" a biofilm means cleaving a covalent bond of at least one compound that forms part of a biofilm (e.g., by enzymatic activity). Non-limiting examples of compounds that may form a part of a biofilm include polymers, glycosides, proteins, polysaccharides, and nucleic acids. As used herein, a "*P. acnes* biofilm degrading enzyme" is an enzyme that degrades at least one compound that forms part of a *P. acnes* biofilm.

The enzymes as provided herein include any naturally occurring forms, homologs, isoforms or variants that maintain the enzymatic activity (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form.

The term "isolated," when applied to a bacterium or bacteriophage, refers to a bacterium or bacteriophage that has been (1) separated from at least some of the components with which it was associated when initially produced (whether in nature or in an experimental setting), and/or (2) produced, prepared, purified, and/or manufactured by the hand of man, e.g. using artificial culture conditions such as (but not limited to) growing on a plate and/or in a fermenter. Isolated bacteria include those bacteria that are cultured, even if such cultures are not monocultures. In embodiments, the isolated bacteria are bacteria that are cultured as a monoculture (e.g., on a plate or in liquid culture such as in a fermenter). Isolated bacteria and bacteriophages may be separated from at least about 10%, about 20%, about 30%, about 40%, about 50%, about 60%, about 70%, about 80%, about 90%, about 95%, about 96%, about 97%, about 99% or more of the other components with which they were initially associated (e.g., by weight). In embodiments, isolated bacteria are more than about 80%, about 85%, about 90%, about 91%, about 92%, about 93%, about 94%, about 95%, about 96%, about 97%, about 98%, about 99%, or more than about 99% pure (e.g., by weight). In embodiments, isolated bacteriophages are more than about 80%, about 85%, about 90%, about 91%, about 92%, about 93%, about 94%, about 95%, about 96%, about 97%, about 98%, about 99%, or more than about 99% pure (e.g., by weight). In embodiments, a composition provided herein includes one or more isolated bacteriophages. In embodiments, a composition provided herein includes an isolated bacteriophage. In embodiments, a bacteriophage that is administered is an isolated bacteriophage. In embodiments, a composition provided herein includes one or more isolated bacteria. In embodiments, a composition provided herein includes an isolated bacterium. In embodiments, a bacterium that is administered is an isolated bacterium.

A "control" sample or value refers to a sample that serves as a reference, usually a known reference, for comparison to a test sample. For example, a test sample can be taken from a test condition, e.g., in the presence of a test compound (e.g., enzyme) or phage, and compared to samples from known conditions, e.g., in the absence of the test compound, phage, or bacterium (negative control), or in the presence of a known compound, phage, or bacterium (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life, the degradation of a biofilm or a component thereof, or bacterial cell lysis) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. Polynucleotides are polymers of any length, including longer lengths, e.g., 200, 300, 500, 1000, 2000, 3000, 5000, 7000, 10000, 20000, 30000, 40000 etc. Polynucleotides and oligonucleotides will generally contain phosphodiester bonds, although in some cases, nucleic acid analogs are included that may have alternate backbones, that include, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The term "bp" and the like refer, in the usual and customary sense, to the indicated number of base pairs.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. In embodiments, the percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire nucleic acid or polypeptide sequence or individual portions or domains of a nucleic acid or polypeptide), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. In embodiments, the identify exists over a region that is about or at least about 20, 50, 100, 1000, 2500, 5000, 7500, 10000, 15000, 20000, 25000, or 30000 amino acids or nucleotides in length to about, less than about, or at least about 31000, 32000, 33000, 34000 or 35000 amino acids or nucleotides in length. Optionally, the identity exists over a region that is at least about 10 to about 100, about 20 to about 75, about 30 to about 50 amino acids or nucleotides in length. Optionally, the identity exists over a region that is at least about 50 amino acids in length, or more preferably over a region that is 100 to 500 or 1000 or more amino acids in length. Included herein are phages comprising nucleic acids (e.g., a genome or a portion thereof) having sequences that are substantially identical to any of SEQ ID NOs: 1, 11, 13, 15, 17, 19, 21, 23, 25, or 27. Non-limiting examples of phages provided herein comprise genomes having sequences that are substantially identical to SEQ ID NO: 1.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions in which a sequence may be compared to a reference sequence of the same number of contiguous positions after the two sequences are optimally aligned. In embodiments, a comparison window includes about or at least about 20, 50, 100, 1000, 2500, 5000, 7500, 10000, 15000, 20000, 25000, or 30000 to about, less than about, or at least about 31000, 32000, 33000, 34000 or 35000 contiguous positions. In embodiments, a comparison window includes about or at least about 20 to about, less than about, or at least about 31000 contiguous positions. In embodiments, a comparison window includes about or at least about 25000 to about, less than about, or at least about 31000 contiguous positions. In embodiments, a comparison window includes about or at least about 26000 to about, less than about, or at least about 31000 contiguous positions. In embodiments, a comparison window includes about or at least about 27000 to about, less than about, or at least about 31000 contiguous positions. In embodiments, a comparison window includes about or at least about 28000 to about, less than about, or at least about 31000 contiguous positions. In embodiments, a comparison window includes about or at least about 29000 to about, less than about, or at least about 31000 contiguous positions. In embodiments, a comparison window includes about or at least about 30000 to about, less than about, or at least about 31000 contiguous positions. In embodiments, a comparison includes about 20 to about 600, about 50 to about 200, or about 100 to about 150 contiguous positions. In embodiments, the comparison window is the entire length of a reference sequence, such as the sequence of a bacteriophage genome. Methods of alignment of sequences for comparison are well-known in the art. In embodiments, optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An example of algorithms suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. As will be appreciated by one of skill in the art, the software for performing BLAST analyses is publicly available through the website of the National Center for Biotechnology Information (NCBI). In embodiments, BLAST and BLAST 2.0 are used, with the parameters described herein, to determine percent sequence identity for the nucleic acids and proteins. In embodiments, a BLAST algorithm involves first identifying high scoring sequence pairs (HSPs) by identifying short words of length W in the query sequence, which either match or satisfy some positive-valued threshold score T when aligned with a word of the same length in a database sequence. In embodiments, T is referred to as the neighborhood word score threshold (Altschul et al., supra). In embodiments, these initial neighborhood word hits act as seeds for initiating searches to find longer HSPs containing them. In embodiments, the word hits are extended in both directions along each sequence for as far as the cumulative alignment score can be increased. In embodiments, cumulative scores are calculated using, for nucleotide sequences, the parameters M (reward score for a pair of matching residues; always >0) and N (penalty score for mismatching residues; always <0). In embodiments, for amino acid sequences, a scoring matrix is used to calculate the cumulative score. In embodiments, extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. In embodiments, the BLAST algorithm parameters W, T, and X determine the sensitivity and speed of the alignment. In embodiments, the NCBI BLASTN or BLASTP program is used to align sequences. In embodiments, the BLASTN or BLASTP program uses the defaults used by the NCBI. In embodiments, the BLASTN program (for nucleotide sequences) uses as defaults: a word size (W) of 28; an expectation threshold (E) of 10; max matches in a query range set to 0; match/mismatch scores of 1, −2; linear gap costs; the filter for low complexity regions used; and mask for lookup table only used. In embodiments, the BLASTP program (for amino acid sequences) uses as defaults: a word size (W) of 3; an expectation threshold (E) of 10; max matches in a query range set to 0; the BLOSUM62 matrix (see Henikoff & Henikoff, Proc. Natl. Acad. Sci. USA 89:10915 (1992)); gap costs of existence: 11 and extension: 1; and conditional compositional score matrix adjustment.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions to a peptide, polypeptide, or protein sequence which alters a single amino acid is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "disease" refers to any deviation from the normal health of a mammal and includes a state when disease symptoms are present, as well as conditions in which a deviation (e.g., dysbiosis, infection, gene mutation, genetic defect, etc.) has occurred, but symptoms are not yet manifested. In embodiments, the disease is acne. In embodiments, the disease includes dermal dysbiosis. In embodiments, methods, compositions, systems, phages, and probiotic bacteria provided herein are suitable for use in a subject that is a member of the Vertebrate class, Mammalia, including, without limitation, primates (such as humans), livestock, work animals, and domestic pets (e.g., a companion animal). In embodiments, a subject is a human subject. As used herein, a "symptom" of a disease includes and clinical or laboratory manifestation associated with the disease, and is not limited to what a subject can feel or observe.

As used herein, the term "dermal dysbiosis" means a difference in the skin microbiota compared to a healthy or general population. In embodiments, the dysbiosis is on the surface of the skin, within skin (e.g., within a skin region or layer of skin cells), within a gland, and/or within a pore of the skin. In embodiments, the dysbiosis is within sweat and/or sebum. In embodiments, the skin is on the face (e.g., the forehead, one or more cheeks, the nose, or the chin of a subject). In embodiments, the skin is on the shoulders, chest, or back. In embodiments, dermal dysbiosis includes a change in microbiota commensal species diversity as compared to a healthy or general population and may include decrease of beneficial microorganisms and/or increase of pathobionts (pathogenic or potentially pathogenic microorganisms) and/or decrease of overall microbiota species diversity. Many factors can lead to dysbiosis, including hormonal changes (e.g., during adolescence), infrequent washing, cosmetic use, antibiotic use, psychological and physical stress, radiation, and dietary changes.

In embodiments, compositions are administered to a subject suffering from acne in a "therapeutically effective dose." Amounts effective for this use may depend upon the severity of the disease and the general state of the patient's health. Single or multiple administrations of the compositions may be administered depending on the dosage and frequency as required and tolerated by the patient. A "patient" or "subject" includes both humans and other animals, particularly mammals. Thus the methods are applicable to both human therapy and veterinary applications.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the bacteriophages, probiotic bacteria, and/or compounds of the invention. One of skill in the art will recognize that other pharmaceutical excipients are useful in the present invention.

The term "contacting" may include allowing two species to react, interact, or physically touch, wherein the two species may be, for example, an enzyme as described herein and a biofilm that includes a substrate of the enzyme. In another example, the two species may be a bacteriophage and a cell of a species that the bacteriophage infects. In embodiments contacting includes, for example, allowing a bacteriophage as described herein to interact with a *P. acnes* cell. In embodiments contacting includes, for example, allowing an enzyme as described herein to interact with a *P. acnes* biofilm.

"Patient" or "subject in need thereof" refers to a living member of the animal kingdom suffering from or who may suffer from the indicated disorder. In embodiments, the subject is a member of a species that includes individuals who naturally suffer from the disease. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer. In embodiments, the subject is a human.

The terms "subject," "patient," "individual," etc. are not intended to be limiting and can be generally interchanged. That is, an individual described as a "patient" does not necessarily have a given disease, but may be merely seeking medical advice.

As used herein the abbreviation "sp." for species means at least one species (e.g., 1, 2, 3, 4, 5, or more species) of the indicated genus. The abbreviation "spp." for species means 2 or more species (e.g., 2, 3, 4, 5, 6, 7, 8, 9, 10 or more) of the indicated genus. In embodiments, methods and compositions provided herein comprise a single species within an indicated genus or indicated genera, or 2 or more (e.g., a plurality that includes more than 2) species within an indicated genus or indicated genera. In embodiments, 1, 2, 3, 4, 5, or more or all or the indicated species is or are isolated. In embodiments, the indicated species are administered together. In embodiments, each of the indicated species is present in a single composition that includes each of the species. In embodiments, each of the species is administered concurrently, e.g., within about 1, 2, 3, 4, 5, 6, 7, 8, 9, 10, 30, or 60, 1-5, 1-10, 1-30, 1-60, or 5-15 seconds or minutes of each other.

In this disclosure, "comprises," "comprising," "containing," and "having" and the like can have the meaning ascribed to them in U.S. Patent law and can mean "includes," "including," and the like. Thus, the transitional term "comprising," which is synonymous with "including," "containing," or "characterized by," is inclusive or open-ended and does not exclude additional, unrecited features, integers, steps, operations, elements, and/or components. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. By contrast, the transitional phrase "consisting of" excludes any feature, integer, element, step, operation, component, and/or ingredient not specified.

As used herein, the term "about" in the context of a numerical value or range means ±10% of the numerical value or range recited or claimed, unless the context requires a more limited range.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," herein and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

As used in the description herein and throughout the claims that follow, the meaning of "a," "an," and "the" includes plural reference unless the context clearly dictates otherwise.

As used herein, "treating" or "treatment" of a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean inhibiting the progression of the condition, disorder or disease, slowing the progression of the condition, disorder or disease temporarily, although in some instances, it involves halting the progression of the condition, disorder or disease permanently. In the case of treating acne, the terms can refer to reducing, e.g., dermal dysbiosis and/or the number or size of cystic lesions, whiteheads (closed plugged pores), blackheads (open plugged pores—in which oil exposed to the air has a dark color, e.g., brown or black), mall red, tender bumps (papules), pimples (pustules; papules with pus at their tips), large, solid, painful lumps beneath the surface of the skin (nodules).

As used herein, the terms "treat" and "prevent" are not intended to be absolute terms. In embodiments, treatment can refer to a 10%, 20%, 30%, 40%, 50%, 60%, 70%, 80%, 90%, or 100% reduction in the severity of an established disease, condition, or symptom of the disease or condition. In embodiments, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. In embodiments, references to decreasing, reducing, or inhibiting include a change of 10%, 20%, 30%, 40%, 50%, 60%, 70%, 80%, 90% or greater as compared to a control level and such terms can include but do not necessarily include complete elimination. Treatment can refer to any delay in onset, amelioration of symptoms, improvement in patient skin appearance, etc. The effect of treatment can be compared to an individual or pool of individuals not receiving the treatment, or to the same patient prior to treatment or at a different time during treatment. In embodiments, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques. In embodiments, treatment is effective to reduce at least one symptom of acne. In embodiments, treatment is effective to reduce the level of pimples (pustules) on the face, forehead, chest, back, and/or shoulders of the subject. In embodiments, treatment is effective to reduce the level of whiteheads (closed plugged pores) on the face, forehead, chest, back, and/or shoulders of the subject. In embodiments, treatment is effective to reduce the level of blackheads (open plugged pores) on the face, forehead, chest, back, and/or shoulders of the subject. In embodiments, treatment is effective to reduce the level of papules on the face, forehead, chest, back, and/or shoulders of the subject. In embodiments, treatment is effective to reduce the level of solid, painful lumps beneath the surface of the skin (nodules) on the face, forehead, chest, back, and/or shoulders of the subject. In embodiments, treatment is effective to reduce the level of cystic lesions on the face, forehead, chest, back, and/or shoulders of the subject. In embodiments, the level (e.g., number) is reduced compared to before treatment has begun. In embodiments, the level (e.g., number) is reduced compared to a corresponding subject who is afflicted with *acnes* but who has not received treatment. In embodiments, the level (e.g., number) is reduced compared to a corresponding subject who is afflicted with *acnes* but who has not received treatment comprising a bacteriophage.

The terms "effective amount," "effective dose," "therapeutically effective amount," etc. refer to the amount of an agent that is sufficient to ameliorate a disorder, as described herein. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "diagnosis" refers to a relative probability a subject has a given metabolic disorder. Symptoms and diagnostic criteria are summarized herein. Similarly, the term "prognosis" refers to a relative probability that a certain future outcome may occur in the subject. For example, in the context of the present invention, prognosis can refer to the likelihood that an individual will develop acne. Prognosis can also refer to the likely severity of the disease (e.g., severity of symptoms, rate of functional decline, etc.). The terms are not intended to be absolute, as will be appreciated by any one of skill in the field of medical diagnostics.

Compositions and Combinations Comprising Bacteriophages

In an aspect, provided herein is a composition comprising, consisting essentially of, or consisting of at least one *P. acnes* bacteriophage, at least one anti-acne compound, and a pharmaceutically acceptable carrier.

In an aspect, provided herein is a composition that includes at least one *Propionibacterium acnes* bacteriophage, no more than one anti-acne compound, and a pharmaceutically acceptable carrier.

In an aspect, provided herein is a composition that includes active ingredients consisting of at least one *Propionibacterium acnes* bacteriophage and no more than one anti-acne compound, and a pharmaceutically acceptable carrier.

In an aspect, provided herein is a composition that includes at least one *P. acnes* bacteriophage, at least one anti-acne compound, and a pharmaceutically acceptable carrier, wherein the composition does not comprise a probiotic bacterium.

In embodiments, the at least one anti-acne compound is benzoyl peroxide. In embodiments, the benzoyl peroxide is present at a concentration of 2.5% to 10% (weight/volume). In embodiments, the benzoyl peroxide is present at a concentration of less than 2.5% but greater than about 0.1%, 0.5%, 1%, 1.5%, or 2% (weight/volume). In embodiments, the benzoyl peroxide is present at a concentration of 2.5% to 10%, e.g., about 2.5%, 3%, 3.5%, 4%, 4.5%, 5%, 5.5%, 6%, 6.5%, 7%, 7.5%, 8%, 8.5%, 9%, 9.5%, or 10% (weight/volume). In embodiments, the benzoyl peroxide is present at a concentration of less than 2.5% but greater than about 0.1%, 0.5%, 1%, 1.5%, or 2% (weight/volume).

In embodiments, the at least one anti-acne compound is salicylic acid. In embodiments, the salicylic acid is present at a concentration of 0.5% to 2% (weight/volume). In embodiments, the salicylic acid is present at a concentration of less than 0.5% but greater than about 0.1% (weight/volume). In embodiments, the salicylic acid is present at a concentration of 0.5% to 2%, e.g., about 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (weight/volume). In embodiments, the salicylic acid is present at a concentration of less than 0.5% but greater than about 0.1% (weight/volume).

In embodiments, the at least one anti-acne compound is sulfur. In embodiments, the sulfur is present at a concentration of 3% to 10% (weight/volume). In embodiments, the sulfur is present at a concentration of less than 3% but greater than about 0.1%, 0.5%, 1%, 1.5%, 2%, or 2.5% (weight/volume). In embodiments, the sulfur is present at a concentration of 3% to 10%, e.g., about 3%, 3.5%, 4%, 4.5%, 5%, 5.5%, 6%, 6.5%, 7%, 7.5%, 8%, 8.5%, 9%, 9.5%, or 10% (weight/volume). In embodiments, the sulfur is present at a concentration of less than 3% but greater than about 0.1%, 0.5%, 1%, 1.5%, 2%, or 2.5% (weight/volume). In embodiments, resorcinol is present at a concentration of 2% and sulfur is present at a concentration of 3% to 8% (e.g., about 2.5%, 3%, 3.5%, 4%, 4.5%, 5%, 5.5%, 6%, 6.5%, 7%, 7.5%, or 8%) (weight/volume).

In embodiments, the at least one anti-acne compound is resorcinol and sulfur. In embodiments, the resorcinol is present at a concentration of 2% and sulfur is present at a concentration of 3% to 8% (weight/volume). In embodiments, resorcinol is present at a concentration of 2% and sulfur is present at a concentration of 3% to 8% (e.g., about 2.5%, 3%, 3.5%, 4%, 4.5%, 5%, 5.5%, 6%, 6.5%, 7%, 7.5%, or 8%) (weight/volume).

In embodiments, the at least one anti-acne compound includes resorcinol monoacetate and sulfur. In embodiments, the resorcinol monoacetate is present at a concentration of 3% and sulfur is present at a concentration of 3% to 8% (weight/volume). In embodiments, resorcinol monoacetate is present at a concentration of 3% and sulfur is present at a concentration of 3% to 8% (e.g., about 2.5%, 3%, 3.5%, 4%, 4.5%, 5%, 5.5%, 6%, 6.5%, 7%, 7.5%, or 8%) (weight/volume).

In embodiments, the *P. acnes* bacteriophage is present in an amount of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ plaque forming units (pfu). In embodiments, the *P. acnes* bacteriophage is present in an amount of about $1\times10^6$ to $1\times10^{11}$ pfu. In embodiments, the *P. acnes* bacteriophage is present in an amount of about $1\times10^6$ to $1\times10^8$, about $1\times10^8$ to $1\times10^9$, about $1\times10^9$ to $1\times10^{10}$, about $1\times10^9$ to $1\times10^{11}$ or about $1\times10^{10}$ to $1\times10^{11}$ pfu.

In embodiments, a probiotic bacterium is present in an amount of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ colony forming units (cfu). In embodiments, the probiotic bacterium is present in an amount of about $1\times10^6$ to $1\times10^{11}$ cfu. In embodiments, the probiotic bacterium is present in an amount of about $1\times10^6$ to $1\times10^8$, about $1\times10^8$ to $1\times10^9$, about $1\times10^9$ to $1\times10^{10}$, about $1\times10^9$ to $1\times10^{11}$ or about $1\times10^{10}$ to $1\times10^{11}$ cfu.

In embodiments, the anti-acne compound is an antibiotic, a retinoid, or an alpha-hydroxy acid.

In an aspect, provided herein is a composition that includes a *P. acnes* bacteriophage and an enzyme.

In an aspect, provided herein is a combination comprising, consisting essentially of, or consisting of at least one *P. acnes* bacteriophage, at least one anti-acne compound, wherein each of the at least one *P. acnes* bacteriophage and the at least one anti-acne compound is in a composition that further includes a pharmaceutically acceptable carrier.

In an aspect, provided herein is a combination that includes a *P. acnes* bacteriophage and an enzyme.

In embodiments, the *P. acnes* bacteriophage has a linear double stranded DNA genome.

In embodiments, the *P. acnes* bacteriophage is within the bacteriophage family Siphoviridae.

In embodiments, the bacteriophage is a wild-type bacteriophage. In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genomic sequence of a wild-type *P. acnes* bacteriophage. A non-limiting example of an genomic sequence for a wild-type *P. acnes* bacteriophage is as follows:

```
                                                        (SEQ ID NO: 1)
  1  AGTGAAATAC CTCCCTTTTG TGGTTTTGTC TGTTTGTCGA CTTTTTGTGT TGGTGGTGAG

61  TGTTGTGCAG CCTGAGCTTC CTGAGTCTCG TGAGTGGTGT GGGGAGACGC GTCGTTGGTG

121  GCGTGTGTGG GGTGAGGATA GTCGCGCGCC GTATGTGTCT GATGAGGAGT GGTTGTTTCT

181  TATGGATGCT GCGGTGATTC ATGATTGTGT GTGGCGTGAG GGTCGCGCGG ATTTGGTGGC

241  TTCGCTTCGT GCGCATGTGA AGGCTTTTAT GGGCATGTTG GATAGGTATT CGGTTGATGT

301  GGCGTCTGGT GGCCGTGGTG GGGGTTCTGC TGTGGCGATG ATTGACCGGT ATAGGAAGCG

361  TAGGGGGGCT TGAGTAGGTG TCTGGTGTTG TTGGGTCTCA GGTTCCTCGT CACCGTGTGG

421  CTGCGGCGTA TTCGGTGTCT GCTGGGGGTG ATGCTGGGGA GCTTGGTCGT GCGTATGGGT

481  TGACGCCTGA TCCGTGGCAG CAGCAGGTGT TGGATGATTG GCTGGCTGTC GGTAGCAATG

541  GCAGGCTTGC TTCTGGTGTG TGTGGGGTGT TTGTTCCGCG GCAGAATGGC AAGAATGCTA

601  TTTTGGAGAT TGTGGAGTTG TTTAAGGCGA CTATTCAGGG TCGCCGTATT TTGCATACGG

661  CTCACGAGTT GAAGTCGGCT CGTAAGGCGT TTATGCGGTT GAGGTCGTTT TTTGAGAATG

721  AGCGGCAGTT TCCTGACTTG TATCGTATGG TGAAGTCGAT TCGTGCGACG AATGGTCAGG

781  AGGCTATTGT GTTGCATCAT CCGGATTGTG CCACTTTTGA GAAGAAGTGT GGCTGCAGCG
```

-continued

```
 841 GTTGGGGTTC GGTTGAGTTT GTGGCTCGTA GCCGGGGTTC GGCTCGCGGG TTTACGGTTG

901 ATGATTTGGT GTGTGATGAG GCTCAGGAGT TGTCGGATGA GCAGTTGGAG GCTTTGCTTC

961 CTACGGTAAG TGCTGCCCCG TCTGGTGATC CGCAGCAGAT TTTCCTTGGT ACGCCGCCTG

1021 GGCCGTTGGC TGATGGTTCT GTGGTGTTGC GTTTGCGTGG GCAGGCGCTT GGTGGCGGTA

1081 AAAGGTTTGC GTGGACGGAG TTTTCGATTC CTGACGAGTC TGATCCGGAT GATGTGTCGC

1141 GGCAGTGGCG GAAGTTGGCG GGGGATACGA ATCCGGCGTT GGGGCGTCGC CTGAATTTTG

1201 GGACCGTAAG CGATGAGCAT GAGTCGATGT CTGCTGCCGG TTTTGCTCGG GAGCGGCTTG

1261 GCTGGTGGGA TCGTGGCCAG TCTGCTGCGT CTGTGGTTCC TGCTGATAAG TGGGCTCAGT

1321 CTGCGGTGGA TGAGGCGAGT CTGGTTGGCG GGAAAGTGTT TGGTGTCTCG TTTTCTCGTT

1381 CTGGGGATCG GGTTGCTTTG GCGGGTGCCG GCAAGACTGA TGCTGGGGTT CATGTTGAGG

1441 TTATTGATGG GCTGTCGGGA ACGATTGTTG ATGGTGTGGG CCGGTTGGCT GACTGGTTGG

1501 CGGTTCGTTG GGGTGATACT GACCGGATCA TGGTTGCCGG GTCTGGTGCG GTGTTGTTGC

1561 AGAAGGCGTT GACGGATCGT GGTATTCCGG GCCGTGGCGT GGTGGTTGCT GATACTGGCG

1621 TTTATGTGGA GGCTTGTCAG GCGTTTCTTG AGGGTGTCAG GTCGGGTGTG ATCAGTCATC

1681 CTCGTGCTGA TTCTCGCCGT GACATGTTGG ATATTGCTGT GAGGTCGGCT GTGCAGAAGC

1741 GTAAGGGGTC TGCGTGGGGT TGGGGTTCCT CGTTTAAGGA TGGTTCTGAG GTTCCTTTGG

1801 AGGCTGTGTC TTTGGCGTTT TTGGGGGCTA AACGTGTTCG TCGTGGCCGT CGGGAGCGTA

1861 GTGGTAGGAA GCGGGTGTCT GTGGTATGAA CTCGGATGAG TTGGCTCTGA TTGAGGGCAT

1921 GTACGATCGT ATCCAAAGGT TGTCTTCGTG GCATTGTTGT ATTGAGGGCT ACTATGAGGG

1981 CTCTAATCGG GTGCGTGACC TTGGTGTGGC TATTCCGCCG GAGTTGCAGC GTGTGCAGAC

2041 TGTGGTGTCG TGGCCTGGTA TAGCTGTGGA TGCTTTGGAG GAGCGTCTGG ATTGGCTTGG

2101 CTGGACTAAT GGTGACGGCT ACGGCCTTGA TGGTGTGTAT GCTGCGAATC GGCTTGCTAC

2161 GGCGTCGTGT GATGTGCATT TGGATGCGCT GATTTTTGGG TTGTCGTTTG TTGCGATCAT

2221 TCCTCATGGT GATGGTACGG TGTCGGTTCG TCCGCAGTCA CCAAAGAATT GTACGGGCAA

2281 GTTTTCGGCT GACGGGTCTC GTTTGGATGC GGGTTTGGTG GTGCAGCAGA CGTGTGATCC

2341 TGAGGTTGTT GAGGCTGAGC TTTTGCTTCC TGATGTGATT GTTCAGGTGG AGCGGCGGGG

2401 TTCGCGTGAA TGGGTTGAGG TGGATCGTAT ACCGAATGTG TTGGGTGCGG TTCCGTTGGT

2461 GCCTATTGTG AATCGTCGCC GTACTTCTAG GATTGATGGC CGTTCGGAGA TTACGAGGTC

2521 TATTAGGGCT TACACGGATG AGGCTGTGCG CACACTGTTG GGGCAGTCTG TGAATCGTGA

2581 TTTTTATGCG TATCCTCAGC GTTGGGTGAC TGGCGTGAGC GCGGATGAGT TTTCGCAGCC

2641 TGGCTGGGTC CTGTCGATGG CTTCTGTGTG GGCTGTGGAT AAGGATGATG ACGGTGACAC

2701 TCCGAATGTG GGGTCGTTTC CTGTCAATAG TCCTACACCG TATTCGGATC AGATGAGACT

2761 GTTGGCGCAG TTGACTGCGG GTGAGGCGGC TGTTCCGGAA CGCTATTTCG GGTTTATCAC

2821 GTCTAACCCA CCTAGTGGGG AGGCTTTGGC TGCCGAGGAA TCTCGGCTTG TGAAGCGTGC

2881 TGAGCGGCGT CAAACGTCGT TTGGTCAGGG TTGGCTGTCG GTTGGTTTTT TGGCTGCCAA

2941 GGCGTTGGAT TCTCGTGTTG ATGAGGCCGA TTTTTTTGGT GATGTTGGTT TGCGTTGGCG

3001 TGATGCTTCG ACGCCTACCC GGGCGGCTAC GGCTGATGCT GTGACGAAGC TTGTTGGTGC

3061 CGGTATTTTG CCTGCTGATT CTCGTACGGT GTTGGAGATG TTGGGGCTTG ATGATGTGCA

3121 GGTTGAGGCT GTGATGCGTC ATCGTGCTGA GTCGTCTGAC CCGTTGGCGG TGCTTGCTGG

3181 GGCTATATCG CGTCAAACTA ACGAGGTATG ATAGGCGATG GCTTCGGGGG TTGAGGCGAG
```

-continued

```
3241 GCTTGCGGCG ACTGAGTATC AGCGTGAGGC GGTCAGGTTT GCTGGGAAGT ATGCGGGCTA

3301 TTATTCTGAG CTTGGTCGTT TGTGGCGTGC CGGCAGGATG AGTGACACGC AGTATGTGCG

3361 TTTGTGTGTG GAGTTGGAGC GTGCCGGCCA TGATGGTTCG GCATCGTTGG CTGCCAGGTT

3421 TGTGTCGGAT TTTCGCCGGT TGAATGGTGT GGATCCGGGT TTGATTGTGT ATGACGAGTT

3481 TGATGCTGCG GCGGCTTTGG CTAGGTCTAT TTCGACCACG AAGATTCTTG AGAGTGACCC

3541 GGATAGGGCG AATGACACGA TTGATGCGAT GGCGGCGGGT TTTGATCGGG CTGTTATGAA

3601 TGCTGGCCGT GACACGGTTG AGTGGTCTGC GGGTGCGCAG GGTAGGTCGT GGCGTCGGGT

3661 GACGGATGGT GATCCGTGTG CTTTTTGTGC CATGTTGGCT ACGAGGTCGG ATTATACGAC

3721 AAAAGAGAGG GCACTTACTA CTGGACATAC TCGGCGTCAT AAGCGTGGTG GTAAGCGTCC

3781 GTTTGGTTCG AAGTATCATG ATCATTGTGG TTGTACGGTG GTTGAGGTTG TTGGCCCTTG

3841 GGAACCAAAT AGGGCTGATG CCGAGTATCA GAGGACGTAT GAGAAGGCCT GTGAGTGGGT

3901 TGATGATCAT GGGTTGCAGC AATCGCCTGG CAATATTTTG AAGGCTATGC GTACTGTTGG

3961 CGACATGAGA TAATTTGATG TGGTTTCCGG TTGTGCGCCG CCGGTTATTG GTGCACAGGG

4021 TTGTCTCCCG CACGGGGGTC AACAATATTG TGTTGTTTTC CGCAAGGAGT GTAGGGTTAG

4081 GCTATGGCCG ATCAGAGTGT TGAGGAACAG AATGTTGACA ATGATGTTGT GGAGTCCGGA

4141 AAGGATAACG GCATTGTTGA TACAGTAAAA GACGATGGCG GGCAGGAGGT AGCCGACAAT

4201 CAGTTGAAGA ATGAAGGCGA GGGTAAATCG CCGGGGACTG ATTGGAAGGC TGAGGCCCGT

4261 AAGTGGGAGT CTCGTGCTAA AAGTAATTTT GCCGAGTTGG AGAAGCTTCG CGCCTCGGAT

4321 GGTGATGCGG GGTCTACGAT TGATGAGCTT CGCCGCAAGA ATGAGGAACT CGAAGACCGG

4381 ATCAATGGGT TTGTTCTTGA GGGTGTGAAG CGCGAGGTGG CTGCCGAGTG TGGCCTGTCG

4441 GGTGATGCTG TCGCTTTCTT GTCGGGTGGC GATAAGGAGT CGCTTGCCGA GTCTGCGAAA

4501 GCTTTGAAGG GTTTGATCGA CCATAGTAGT GGTGGCGCGG GTGTGCGCCG TCTTGCGGGG

4561 AGTGCCCCCG TTGATGATGT TAAACGACGT GAGGGTGTCG CGTTTGTGGA TGCTCTTGTC

4621 AATAATTCTA GGAGATGATT TGTGATGGCT GACGATTTTC TTTCTGCAGG GAAGCTTGAG

4681 CTTCCTGGTT CTATGATTGG TGCGGTTCGT GACCGTGCTA TCGATTCTGG TGTTTTGGCG

4741 AAGCTTTCGC CGGAGCAGCC GACTATTTTC GGGCCTGTGA AGGGTGCCGT GTTTAGTGGT

4801 GTTCCTCGCG CCAAGATTGT TGGTGAGGGC GAGGTTAAGC CTTCCGCGTC TGTTGATGTT

4861 TCGGCGTTTA CTGCGCAGCC TATCAAGGTT GTGACTCAGC AGCGTGTCTC GGATGAGTTT

4921 ATGTGGGCTG ATGCTGATTA CCGTCTGGGT GTGCTTCAGG ATCTGATTTC CCCGGCTCTT

4981 GGTGCTTCGA TTGGTCGCGC CGTGGATCTG ATTGCTTTCC ATGGTATTGA TCCTGCCACT

5041 GGTAAAGCGG CTTCCGCTGT GCATACTTCG CTGAATAAGA CGAAGAATAT TGTTGATGCC

5101 ACGGATTCTG CTACGGCTGA TCTTGTTAAG GCTGTCGGCC TGATTGCTGG TGCTGGTTTG

5161 CAGGTTCCTA ACGGGGTTGC TTTGGATCCG GCGTTCTCGT TTGCGCTGTC TACTGAGGTG

5221 TATCCGAAGG GGTCTCCGCT TGCCGGTCAG CCTATGTATC CTGCCGCCGG GTTTGCCGGT

5281 TTGGATAATT GGCGCGGGCT GAATGTTGGT GCTTCTTCGA CTGTTTCTGG CGCCCCGGAG

5341 ATGTCGCCTG CCTCTGGCGT TAAGGCTATT GTTGGTGATT CTCTCGTGT TCATTGGGGT

5401 TTCCAGCGTA ACTTCCCGAT CGAGCTTATC GAGTATGGTG ACCCGGATCA GACTGGGCGT

5461 GACTTGAAGG GCCATAATGA GGTTATGGTT CGTGCCGAGG CTGTCCTGTA TGTTGCGATT

5521 GAGTCGCTTG ATTCGTTTGC TGTTGTGAAG GAGAAGGCTG CCCCGAAGCC TAATCCGCCG

5581 GCCGAGAACT GATTCATTTG TTGCGGTGAT GTTTTCTATG TGCAGGGGGT GGTGTTGATG

5641 GGTATCATTT TGAAGCCTGA GGATATTGAG CCTTTCGCCG ATATTCCTAG AGAGAAGCTT
```

-continued

```
5701 GAGGCGATGA TTGCCGATGT GGAGGCTGTG GCTGTCAGTG TCGCCCCCTG TATCGCTAAA

5761 CCGGATTTCA AATACAAGGA TGCCGCTAAG GCTATTCTGC GCAGGGCCCT GTTGCGCTGG

5821 AATGATACCG GGGTTTCGGG TCAGGTGCAG TACGAGTCTG CGGGCCCGTT TGCTCAGACT

5881 ACACGGTCGA ATACTCCCAC GAATTTGTTG TGGCCTTCTG AGATTGCCGC GTTGAAGAAG

5941 TTGTGTGAGG GTGATGGTGG GGCTGGTAAA GCGTTCACTA TTACACCGAC CATGAGGAGT

6001 AGTGTGAATC ATTCTGAGGT GTGTTCCACG GTGTGGGGTG AGGGTTGCTC GTGCGGATCT

6061 GATATTAACG GCTATGCTGG CCCTTTGTGG GAGATATGAT ATGACCGGTT TTCCTTACGG

6121 TGAAACGGTT GTGATGCTTC AACCGACTGT TCGTGTCGAT GATCTTGGCG ACAAGGTGGA

6181 AGACTGGTCT AAGCCTGTCG AGACTGTGTA CCATAACGTG GCCATCTATG CTTCCGTTTC

6241 GCAGGAGGAT GAGGCTGCCG GCCGTGACTC TGACTATGAG CATTGGTCGA TGCTTTTCAA

6301 GCAGCCTGTT GTGGGTGCCG GTTATCGTTG CCGGTGGCGT ATTCGGGGTG TGGTTTGGGA

6361 GGCGGACGGG TCTCCTATCG TGTGGCATCA TCCGATGTCT GGTTGGGATG CTGGTACGCA

6421 GGTTAATGTG AAGCGTAAGA AGGGCTGATG GGTTGTGGCT CAGGATGTGA ATGTGAAGCT

6481 GAACTTGCCG GGTATTCGTG AGGTGTTGAA GTCTTCTGGG GTGCAGTCGA TGTTGGCTGA

6541 GCGTGGCGAG CGGGTGAGGC GTGCGGCTTC GGCGAATGTT GGCGGTAATG CTTTTGATAG

6601 GGCCCAATAC CGTAGTGGTT TGTCGTCGGA GGTGCAGGTT CACCGTGTGG AGGCTGTGGC

6661 GAGGATTGGC ACCACCTATA AGGGTGGGAA GCGTATTGAG GCGAAGCATG GCACGTTGGC

6721 GAGGTCGATT GGGGCTGCGT CGTGATCGTT TACGGTGATC CGCGTGTGTG GGCTAAACGT

6781 GTGCTCAAGG ATGATGGCTG GCTGTCCGAT ATACCCTGTG TGGGGACGGT GCCTGACGAT

6841 TTCAGCGGTG ACCTGATTTG GTTGGCGTTG GATGGCGGCC CACAGTTGCA TGTTCGCGAG

6901 CAGGTGTTTT TGCGGGTGAA CGTGTTTTCT GATATGCCTG ATCGTGCCAT GTCGCTAGCC

6961 AGGCGGGTTG AGGCTGTCCT TGTAGACGGT GTGGACGGTG ACCCGGTGGT GTTTTGTCGA

7021 CGGTCTACTG GCCCTGATTT GCTGGTTGAT GGTGCACGTT TTGATGTGTA TTCGCTGTTT

7081 GAGCTGATAT GCAGGCCTGT CGAATCCGAG TAAACGTTTT GTTTTGATAT TGTTGTTTGT

7141 TTTTTGTTTG ATATTGTTTT TGGGGGTTAT GATGGCTGGA ACACGTAAAG CGTCTAATGT

7201 TCGTTCCGCG GTTACGGGTG ACGTCTATAT TGGTAAAGCT CATGCCGGTG ACACTATTGA

7261 TGGTGTGAAG ACGGTTCCTG ACGGGCTTAC AGCTTTAGGG TATCTGTCTG ATGACGGGTT

7321 TAAGATTAAA CCGGAGCGTA AAACGGATGA TTTGAAGGCT TGGCAGAATG CGGATGTTGT

7381 TCGCACTGTG GCTACGGAAT CGTCTATCGA GATTTCTTTC CAGCTGATCG AGTCTAAGAA

7441 GGAGGTTATC GAGCTGTTTT GGCAGTCGAA GGTTACTGCC GGAGCCGATT CGGGTTCGTT

7501 CGATATTTCT CCTGGTGCCA CGACGGGTGT TCATGCCCTG TTGATGGATA TTGTTGATGG

7561 CGATCAGGTT ATTCGCTACT ATTTCCCTGA GGTTGAGTTG ATCGATCGTG ACGAGATTAA

7621 GGGTAAGAAT GGCGAGGTGT ATGGGTATGG TGTGACGTTG AAGGCGTATC CTGCCCAGAT

7681 TAATAAGAAG GGTGATGCGG TGTCTGGTCG GGGGTGGATG ACGGCTTTAA AAGCTGATAC

7741 TCCTCCGACT CCTCCTCCGG CCCCGAATCC TCCGAAGCCT GAGCCGGATC CGAATCCGCC

7801 GTCTAATAAC TGATACACAT AGTTTGAGGG ATTGTTGATA GATGAGTGAC ACGGGTTACA

7861 CGTTGAAGAT TGGTGACCGT AGCTGGGTGT TGGCGGATGC GGAGGAGACG GCTCAGGCTG

7921 TTCCTGCCCG CGTTTTCCGT CGTGCTGCTA AGATTGCCCA GTCGGGTGAG TCTGCGGATT

7981 TCGCCCAGGT TGAGGTGATG TTTTCTATGT TGGAGGCTGC CGCCCCGGCT GACGCGGTGG

8041 AGGCCCTGGA GGGGCTTCCT ATGGTTCGTG TGGCCGAGAT TTTCCGCCAG TGGATGGAAT
```

-continued

```
 8101 ACAAGCCTGA CGGTAAGGGT GCCTCGCTGG GGGAATAGTT TGGCTCCACG GCCTGATTGA

8161 TGATTATCGT GGGGCCATCG AATACGATTT CCGCACCAAG TTTGGTGTTT CTGTTTATAG

8221 TGTTGGTGGC CCGCAGATGT GTTGGGGTGA GGCTGTCCGG CTGGCTGGCG TGTTGTGTAC

8281 CGATACGTCT AGCCAGTTGG CGGCCCACCT GAATGGTTGG AAGCGCCCGT TTGAGTGGTG

8341 CGAGTGGGCT GTGTTGGACA TGCTGGATCA TTACAGGTCT GCTAATAGTG AGGGGCAGCC

8401 GGAGCCTGTG GCGAGGCCTA CGGATGAGCG TAGGGCCCGG TTTACGTCTG GGCAGGTGGA

8461 CGATATTTTG GCGCGTGTTC GTGCTGGTGG CGGGGTGTCT CGCGAGATTA ATATTATGGG

8521 GTGAATAGTG TATGTCTGGT GAGATTGCTT CCGCATATGT GTCGTTGTAT ACGAAGATGC

8581 CTGGTTTGAA GGCGGATGTT GGTAAACAGC TTTCTGGGGT GATGCCTGCT GAGGGTCAGC

8641 GTTCGGGTAG TTTGTTTGCT AAGGGAATGA AGTTGGCTCT TGGTGGTGCG GCGATGATGG

8701 GTGCCATCAA TGTTGCTAAG AAGGGCCTCA AGTCGATTTA TGATGTGACT ATTGGTGGCG

8761 GTATTGCTAG GGCGATGGCT ATTGATGAGG CTCAGGCTAA GTTGACTGGT TTGGGTCATA

8821 CGTCTTCTGA CACGTCTTCG ATTATGAATT CGGCTATTGA GGCTGTTACT GGTACGTCGT

8881 ATGCGTTGGG GGATGCGGCG TCTACGGCTG CGGCGTTGTC TGCTTCGGGT GTGAAGTCTG

8941 GCGGGCAGAT GACGGATGTG TTGAAGACTG TCGCCGATGT GTCTTATATT TCGGGTAAGT

9001 CGTTTCAGGA TACGGGCGCT ATTTTTACGT CTGTGATGGC TCGCGGTAAG TTGCAGGGCG

9061 ATGACATGTT GCAGCTTACT ATGGCGGGTG TTCCTGTCCT GTCTTTGCTT GCCAGGCAGA

9121 CTGGTAAAAC GTCTGCTGAG GTGTCGCAGA TGGTGTCAAA GGGGCAGATT GATTTTAACA

9181 CGTTTGCGGC TGCGATGAAG CTTGGCATGG GTGGTGCTGC GCAGGCGTCT GGTAAGACGT

9241 TTGAGGGCGC TATGAAGAAT GTTAAGGGCG CCCTGGGTTA TCTTGGTGCT ACGGCTATGG

9301 CCCCGTTTCT TAACGGGTTG CGGCAGATTT TTGTTGCGTT GAATCCGGTT ATCAAGTCTG

9361 TCACGGATTC CGTGAAGCCG ATGTTTGCTG CCGTCGATGC TGGTATTCAG CGTATGATGC

9421 CGTCTATTTT GGCGTGGATT AACCGTATGC CGGCTATGAT CACTCGAATG AATGCACAGA

9481 TGCGCGCCAA GGTGGAGCAG TTGAAGGGCG TTTTTGCAAG GTTGCATTTG CCTGTTCCTA

9541 AGGTGAATTT GGGTGCCATG TTTGCTGGCG GCACCGCAGT GTTCGGTATT GTTGCTGCGG

9601 GTGTTGGGAA GCTTGTCGCG GGGTTTGCCC CGTTGGCGGT GTCGTTGAAG AATCTGTTGC

9661 CGTCGTTTGG TGCTTTGAGG GGTGCCGCCG GGGGGCTTGG TGGCGTGTTT CGCGCCTTGG

9721 GTGGCCCTGT TGGTATTGTG ATCGGCTTGT TTGCTGCCAT GTTTGCTACG AACGCCCAGT

9781 TCCGTGCCGC TGTTATGCAG CTTGTGGGGG TGGTTGGCCG GGCTTTGGGG CAGATTATGG

9841 TCGCCTTGCA GCCATTGTTC GGGATTGTTG CTGGCGTGGT TGCCAGGTTG GCTCCCGTTT

9901 TTGGCCAGAT TATTGGTATG GTTGCTGGTT TGGCTGCCCG CTGGTGCCT GTTATTGGTA

9961 TGCTTATTGC CCGGCTGGTT CCTGTTATCA CCCAGATTAT TGGTATGGTA ACCCAGGTTG

10021 CTGCCATGTT GTTGCCTATG CTGATGCCGG TTATTCAGGC TGTTGTTGCT GTGATACGGC

10081 AGGTTATTGG TGTGGTCATG CAGTTGATAC CTGTTTTGAT GCCGGTTGTG CAGCAGATTT

10141 TGGGTGCTGT CATGTCTGTT TTGCCGCCGA TTGTTGGTTT GATACGGTCG CTGATACCGG

10201 TGATCATGTC GATTATGCGT GTGGTGGTGC AGGTTGTTGG TGCCGTGCTA CAGGTGGTGG

10261 CCCGTATTAT TCCGGTTGTT ATGCCGATTT ATGTTTCGGT GATTGGATTC ATTGCCAAGA

10321 TTTATGCTGC GGTTATCGTT TTTGAGGCTA AGGTTATTGG CGCTATTCTT CGTACTATTA

10381 CGTGGATTGT GAATCATTCA GTGTCTGGCG TGAGGTCTAT GGGCACGGCC ATCCAGAATG

10441 GCTGGAATCA TATCAAATCG TTTACGTCGG CGTTTATTAA CGGTTTCAAG TCGATCATTT

10501 CTGCCGGTGT TGCCGCGGTT GTGGGGTTTT TTACGCGGCT TGGTTTGTCG GTTGCCTCCC
```

-continued

```
10561 ATGTGAGGTC TGGTTTTAAC GCGGCCCGTG GTGCTGTTTC TTCTGCGATG AATGCTATTC

10621 GGAGTGTTGT GTCTTCGGTG GCGTCTGCTG TTGGCGGGTT TTTCGGGTCG ATGGCGTCTA

10681 GGGTTCGTAG TGGTGCTGTG CGCGGGTTTA ATGGTGCCCG GAGTGCGGCT TCTTCTGCTA

10741 TGCATGCTAT GGGGTCTGCG GTGTCTAACG GTGTGCATGG TGTGCTGGGG TTTTTCCGGA

10801 ATTTGCCTGG CAATATTAGG GGCGCCTTGG GTAGTATGGG GTCCCTGTTG GTGTCGGCTG

10861 GCCGTGATGT GGTGTCTGGT TTGGGTAACG GTATCCGGAA TGCTTTGAGT GGCCTGTTGG

10921 ATACGGTGCG TAACATGGGT TCCCAGATTG CGAACGCGGC GAAGTCTGCG CTGGGTATTC

10981 ATTCCCCGTC TCGGGTGTTT CGTGACGAGG TTGGCCGTCA GGTTGTTGCC GGTTTGGCTG

11041 AGGGGATCAC CGGGAATGCT GGTTTGGCGT TGGATGCGAT GTCTGGTGTG GCTGGCCGTC

11101 TTCCGGATGC TGTGGATGCC CGGTTTGGTG TGCGATCGTC TGTGGGCTCG TTTACCCCGT

11161 ACGACCGGTA TCGGCGTGCG AACGAGAAGA GTGTTGTGGT GAATGTGAAC GGACCCACGT

11221 ATGGGGATCC TGCCGAGTTT GCGAAGCGGA TTGAGCGTCA GCAGCGTGAC GCTTTGAATG

11281 CGTTGGCTTA CGTGTGATCG AGGGGGTGTT GTGCATGTTT ATTCCTGACC CGTCTGATCG

11341 TGCCGGTTTG ACTGTGGATT GGACTATGTT TCCGTTGGTG GGTAATGCTC CGGAGCGTGT

11401 GCTTCATTTG ACGGATTATA CGGGGTCGTC TCCGGTCATG TTGTTGAATG ATTCGTTGCG

11461 CGGCCTGGGT ATGCCTGAGG TGGAGCAGTT TTCTCAAACG CATGTTGGTG TGCATGGTTC

11521 GGAGTGGCGC GGGTTTAATG TGAAGCCTCG CGAGGTGACT TTGCCGGTGT TGGTGTCGGG

11581 TGTTGACCCG GATCCGGTGG GCGGGTTTCG TGACGGTTTT TTGAAGGCGT ATGACGCGTT

11641 GTGGTCTGCG TTTCCTCCGG GCGAGGTGGG GGAGTTGTCT GTGAAGACTC CTGCCGGTCG

11701 TGAGCGTGTG TTGAAGTGCC GGTTTGATTC GGCTGATGAC ACGTTTACGG TTGATCCGGT

11761 GAACCGTGGC TATGCGCGCT ATCTGTTGCA TTTGACAGCT TATGATCCGT TTTGGTATGG

11821 GGATGAGCAA AAGTTTCGTT TTAGTAACGC GAAGTTGCAG GATTGGTTGG GTGGCGGCCC

11881 TGTCGGCAAG AAGGGTACCG CGTTTCCTGT GGTGTTAACA CCGGGTGTGG GCTCGGGCTG

11941 GGATAACCTG TCTAATAAGG GTGATGTGCC TGCGTGGCCT GTGATTCGTG TTGAGGGTCC

12001 TTTGGAGTCG TGGTCTGTGC AGATTGATGG TTTGCGTGTG TCTTCGGACT ATCCGGTCGA

12061 GGAGTTTGAT TGGATCACTA TTGATACGGA TCCTCGCCAG CAGTCTGCGT TGTTGAACGG

12121 GTTTGAGGAT GTGATGGATC GTTTGACAGA GTGGGAGTTT GCGCCTATCC CGCCTGGCGG

12181 TTCTAAGAGT GTGAATATTG AGATGGTTGG TTTGGGTGCT ATTGTTGTGT CGGTGCAGTA

12241 CAGGTTTTTG AGGGCTTGGT GAATAGTTGA TGGCTGGTCT TGTTCCGCAT GTAACATTGT

12301 TTACACCTGA TTATCGCCGT GTGGCGCCTA TCAATTTTTT TGAGTCGTTG AAGTTGTCGT

12361 TGAAGTGGAA TGGTTTGTCG ACTTTGGAGT TGGTGGTGTC GGGGGATCAT TCGAGGCTTG

12421 ACGGGTTGAC GAAGCCGGGT GCGCGGCTGG TTGTTGATTA TGGTGGTGGC CAGATTTTTT

12481 CTGGGCCTGT GCGTAAAGTG CATGGTGTGG GTCCGTGGCG TTCTTCCCGT GTGACTATAA

12541 CGTGTGAGGA TGATATTCGG CTGTTGTGGC GTATGTTGAT GTGGCCTGTG AATTATCGTC

12601 CTGGTTTGGT TGGTATGGAG TGGCGTGCGG ACAGGGATTA TGCCCACTAT TCGGGTGCGG

12661 CTGAGTCGGT TGCTAAGCAG GTGTTGGGGG ATAATGCTTG GCGTTTTCCG CCTGGTTTGT

12721 TTATGAACGA TGATGAGAGT CGTGGCCGCT ATATTAAGGA TTTTCAGGTG CGGTTTCACG

12781 TGTTTGCCGA TAAGTTGTTG CCGGTGTTGT CGTGGGCTCG GATGACTGTC ACGGTGAACC

12841 AGTTTGAGAA TGCGAAGTTT GATCAGCGTG GTTTGTTGTT TGATTGTGTG CCTGCTGTGA

12901 CCCGGACGCA TGTGTTGACT GCCGAGTCTG GTTCGATTGT GTCGTGGGAG TATGTGCGTG
```

-continued

```
12961 ACGCCCCGAA GGCTACTTCG GTGGTGGTTG GTGGCCGCGG CGAGGGCAAA GATCGGCTGT

13021 TTTGCGAGGA TGTTGATTCG ATGGCCGAGG ATGACTGGTT TGATCGTGTC GAGGTGTTTA

13081 AGGATGCCCG TAACACGGAT TCCGAGAATG TGCATCTTAT TGATGAGGCT GAGCGGGTGT

13141 TGTCCGAGTC GGGGGCTACG TCGGGGTTTA AGATCGAGTT GGCTGAGTCG GATGTGTTGC

13201 GGTTTGGGCC TGGCCGCCTG ATGCCGGGTG ATCTTATCTA TGTGGATGTG GGCTCGGGGC

13261 CTATTGCGGA GATTGTGCGC CAGATTGATG TGGAGTGTGA TTCGCCTGGT GATGGGTGGA

13321 CGAAGGTGAC TCCGGTTGCT GGGGATTATG AGGATAATCC GTCGGCGCTG TTGGCTCGCC

13381 GTGTGGCTGG TTTGGCTGCG GGTGTGCGGG ATTTGCAAAA ATTCTAATTG TTAGGGGTTT

13441 GTTGTGGGTA TTGTGTGTAA AGGGTTTGAT GGTGTGTTGA CCGAGTATGA TTGGGCTCAA

13501 ATGTCTGGTC TGATGGGTAA TATGCCGTCC GTGAAAGGGC CGGATGATTT TCGTGTCGGC

13561 ACTACGATTC AGGGTTCCAC GGTGTTGTGT GAGGTCCTGC CGGGGCAGGC TTGGGCTCAC

13621 GGGGTGATGT GCACGTCGAA TGCTGTTGAG ACGGTGACAG GTCAGCTTCC GGGCCCGGGT

13681 GAGACCCGCT ACGACTATGT TGTCCTGTCG CGGGATTGGC AGGAGAATAC GGCCAAGTTG

13741 GAGATTGTTC CTGGGGGGCG TGCGGAGCGT GCCCGTGACG TGTTGCGTGC GGAGCCTGGC

13801 GTGTACCATC AGCAGTTGTT GGCTACTTTG GTGGTGTCGT CTAACGGGTT GCAGCAGCAG

13861 CTTGACAGGA GGGCTATAGC GGCCCGTGTG GCGTTTGGGG AGTCTACTGC ATGTGATCCT

13921 ACCCCTGTGG AGGGTGACCG GGTGATGGTG CCTTCTGGGG CTGTGTTGGC TAATCATGCT

13981 AACGAGTGGA TGCTGTTGTC TCCGCGGATT GAGACGGGCA CTAAGTCGAT CATGTTTGGC

14041 GGGTCTGCTG TGTATGCTTA CACGATTCCG TTTGATCGCC AGTTTGCTAG TCCGCCTGTT

14101 GTGGTGGCGT CTATGGCTAC GGCGGCTGGG GGCACGACCC AGATTGATGT GAAAGCCTAC

14161 AATGTGACTG CCCAAAATTT TAGTTTGGCG TTTATTACGA ATGATGGTTC GAAGCCGAAT

14221 GGTGTGCCTG CGGTGGCTAA TTGGATTGCT GTCGGCGTGT GACTGTACAG GTGTTGTGGC

14281 GGATGGTGTG ATGTTGGGGG GCTGTGGTGT CGTGGTTTAC TCCTGCACTG GTGGCCTCTA

14341 TTTGTACCGC GTTGGCCACG GTTTTGGGTT CTGTTCAGGC TGTCACGTCT AAATCTAGGA

14401 GGCGTTTGCG CCGCCTGTCG GCGCAGGTGG ATGCGATGGA AGAGTATACG TGGGGTGTGC

14461 GGCGCGAGGT GCGAAGGTTT AACGCCGGGC TTCCTGACGA GGTGGAGCCT ATGCATCTCC

14521 CTGATTTGCC CGAGTTTTTG AAAGATACTG TTGATGGTGG AGGTGAGTAG GGTTGAGGGA

14581 GTTGGAGGAG GAGAAGCGGC AGCGCCGCAA TTTTGAGAAG GCTTCACTGG TGTTGCTGTT

14641 TTTGTCGCTT GTGTTATTGG CTGTGGTTGC TGCGGGTGCT TTGCGTTTCG GGGCTGTATC

14701 CTCTGAGCGG GATTCGGAGC AGGCGAGGGC CCAGTCGAAT GGTACAGCCG CCAAGGGTTT

14761 AGCCAGCAGT GTGCGGCAGG TGTGTGCTCA GGGTGGACGG GAGTCTGTGC GGCTTCACCA

14821 GTCTGGTTTG TGTGTGGATG CTCAGCGTGT TGAGCGTAGT GTGCAGGGTG TGCCGGGTCC

14881 TGCCGGTGAG CGCGGCCCGC AAGGCCCGGC AGGTGTGGAC GGCCGGGATG GTGTTAATGG

14941 TTCGGCTGGG CTGGTTGGCC CTGTGGGTCC GCAGGGGTCC CCGGGTTTGA ATGGTGTGAA

15001 AGGTCCTGAC GGGGTTGCCTG GCGCTAACGG TTCGGATGGC CGTGATGGTG TGGACGGTGT

15061 GAACGGCAAT GATGGCGCTG ATGGTCGGGA TGGTTCGGCC GGTGAGCGCG GTGATGTGGG

15121 CCCCTCAGGT CCTGCCGGCC CGCAAGGTGC ACAGGGTGAA CGGGGTGAGC GCGGCCCCGC

15181 CGGTGCGAAT GGCACGAATG GCAAGGACGG TAAGGATGGT GCCGACGGCC GTGATGGGCG

15241 TTCGGTTGTG TCTGTGTACT GTTTCGGTGG CCTGCCAGGT GTGTGAAACCA TCACCTGTGG

15301 TTACCGTGTC ATCCCGTAAA TAGAAGAAGA GGGAAGGGTG TTACTAGTGT TGATTGTGGT

15361 TTTTGGTGGT GGTGTGTGGT GAGATACATT CCTGCAGCGC ATCACTCTGC CGGCTCTAAT
```

-continued

```
15421 AATCCGGTGA ACAGGGTTGT GATTCATGCA ACATGCCCGG ATGTGGGGTT TCCGTCCGCC

15481 TCACGTAAGG GGCGGGCGGT GTCTACAGCA AACTATTTCG CTTCCCCATC GTCTGGTGGT

15541 TCGGCGCATT ATGTGTGTGA TATTGGGGAG ACGGTGCAAT GCTTGTCGGA GTCTACGATT

15601 GGTTGGCATG CCCCGCCGAA TCCGCATTCT TTGGGTATCG AGATTTGCGC GGATGGGGGT

15661 TCGCATGCCT CGTTCCGTGT GCCGGGGCAT GCTTACACTC GGGAGCAGTG GCTTGATCCG

15721 CAGGTGTGGC CTGCCGTTGA GAGGGCGGCG GTGCTGTGTA GACGTTTGTG TGACAAATAT

15781 AATGTTCCGA AAAGGAAACT GTCGGCTGCC GATTTGAAGG CTGGCAGGCG GGGTGTGTGT

15841 GGCCATGTGG ATGTTACGGA TGCGTGGCAT CAGTCGGATC ATGACGATCC TGGGCCGTGG

15901 TTTCCGTGGG ACAAATTTAT GGCCGTCGTC AACGGCGGCA GTGGAGATAG TGGGGAGTTA

15961 ACTGTGGCTG ATGTGAAAGC CTTGCATGAT CAGATTAAAC AATTGTCTGC TCAGCTTACT

16021 GGTTCGGTGA ATAAGCTGCA CCATGATGTT GGTGTGGTTC AGGTTCAGAA TGGTGATTTG

16081 GGTAAACGTG TTGATGCCTT GTCGTGGGTG AAGAATCCTG TGACGGGGAA GCTGTGGCGC

16141 ACTAAGGATG CCCTGTGGAG TGTCTGGTAT TACGTGTTGG AGTGTCGTAG CCGTCTTGAC

16201 AGGCTCGAGT CTGCTGTCAA CGATTTGAAA AAGTGATGGT GGTTTGTTGT GGGTAAACAG

16261 TTTTGGTTAG GTTTGCTAGA GCGGGCGGCT AAGACTTTTG TGCAAACGTT TGTTGCTGTG

16321 TTGGGGGTGA CGGCGGGTGT CACGTATACG GCGGAGTCGT TTCGTGGTTT GCCGTGGGAG

16381 TCTGCGTTGA TTACGGCTAC GGTTGCTGCG GTCCTGTCGG TGGCTACCTC GTTTGGTAGC

16441 CCGTCGTTTG TGGCTGGTAA GCCGAAAACC ACGCCTGTGG ATGCGGGTTT GGTTCCGCCG

16501 GATGATCCCG GAATAGTGGA GCCTCACATG GTGGATGTGT CGGATCCTGG CATGATCGAG

16561 CCTGCAGATG ATGTGGATCT TGGTGTAGGC TATGTGCCGA AACATGCTGC CGAGTCGGAG

16621 GTTGGCACGG TAGAGTCGAC TGTTGCATAA GTGAATATAG ATGTGTGCCC CAGCGGTGCT

16681 GCCACGATTG TGTGGTGGTT GCCGCTGGGG CACTATTTTT GTATATTGCG GTGTGGCTAT

16741 GATTCGTTGC TGTCGATGGT GTCTTCGAGC ATCTGGTACA GGTGGAGGCA GGTAGAGATA

16801 GTTTCGCTGG CCTGGTCGAG AACGTTCCGG CCGATAACAT TTTTGTTGTT GTCGCGGTGG

16861 CGGATGATAG ACCACATGAT CTCGTCGGCT GCCGCCTGCA ATAGTTTTGC CTGGTATGCG

16921 ATTCCAGCGA GCCAGTCTAG TGCTTCCTGG CTTGCATAGG GTGTCTGGTC CTCGCTGTTG

16981 CTTGTGGGGT GTCCTGCACT GTCGCATAGC CACAGGATTT CGCTGCACTC GTCTAGCGTG

17041 TCCTGGTCTA TAGCGAGATC GTCGAGGCTG ACATTGTTGA CGGTAAGGTT CACGTTGTCG

17101 AGGGAGATGG GTACACCGTA CTGGTTTTCG ACACCGTCAA CAATGTTTTC CAATTGCTGC

17161 ATGTTGGTGG GCTGTTGTTG GACGATACGG TGTATCGCTG TGTTGAGGGT GGTGTAGGTG

17221 ATATTGTGTG TGTTGTTCAT CGTGTTATGC CATTCCTTCG TTATCGTCTG GCCTGTAGTA

17281 TGTGCTGTTT GCGTACTCGG TTAACGTCAT CAGTGTTTGG TCTGCCCACT GTTTCACAGT

17341 CTGCCTTGTC ACTCCGAGTC GTTGGGCGGC TGTGGCGTAG GTTTGGTCAT ACCCGTATAC

17401 TTCCCTGAAT GCTGCCAACC GTGCCAAATG TTTTCGCTGT TTGGATGGCT GGCAGGCGAG

17461 GGTGTAGTCG TCGATGGCTA GCTGTAGATC GATCATGGTG GCAATGTTGT TGCCGTGGTG

17521 TTGTGGCGCG GTTGGTGGGG GTGGCATTCC TGGCTCCACA CTGGGTTTCC ATGGGCCTCC

17581 GTTCCAGATC CATTGGGCGG CTTGGATGAT GTCTGCGGTG GTGTAGGTTC GGTTCACTGG

17641 TCATCCCCTG AACAGGTTGT CTGGGTTGCT GGTGCGGATT GTGTCGAATC GTCCGACGCA

17701 GTGGCAGTAG TCGTACATGA GTTTGATAAT GTGTTGGTGG TCTCCCAAAT AGGTGTTTCC

17761 GCTGATGCTG TAGGTGGCTG TGCCGTCTTT ACTAATAGTG TATTTGGCGG TGATGGTTTC
```

-continued

```
17821 GGGGTTTTCG GTGTCGGTGA TGATGGCTGT GGTGGTGGTG CCTACGGTTT GGAGCACGGT

17881 GGTTTGGGTT CCGTCGTCGA TGGTGGTTTT AACCATGAGG TGTGTTCTCC CTTTGTGTTA

17941 GTTGCTGGTT TGGTTGTCGG CTAGATGAAT GATGTCGGGT AAGGGTTTCG GCTGGTCTAA

18001 ATGTTGTGTG GTTTTGTTGG CTAGCCGTTT GGCTACCCTG TAGCACATTT TGGTGTAGTG

18061 TTTGTTGTCT AGGTTGTGGT ATTGTTCCCG CACCGCAATA TATAGCAGGG AGTCTTGGTA

18121 CAGGTCGTCT GCATTGATTG CGGGGTAGTG TGCGGCTGTT TTAGTGCATG CCCGGTTGAG

18181 TGTGCGTAGA TGATGGTCTG TGGCCCACAC CCACGATGCG GTGGTGGCTA GGTCGGCTTT

18241 TGTTGGTCGT CGGCTCATGG CATCTCTTTC ATCTGGCTAT CTGGTAGTTG TTTGGTGTTT

18301 TGTTGTTGAT AGTGTAGCAC ACGAGTCCGG GGTTTCCGGT GGTGCCCGTC TTGTGCCGGT

18361 ACCATGTGGA TTCGCCTTCC ATGGATGGGC ATTGGATGAA GGTGCGTTGT CCTTGTTCGG

18421 AGATTTCTAG GTGGTGCCTG TGTCCGGCCA TGAGGATGTG GGATGTGGTG CCGTTGTGGA

18481 ATTCTTGTCC GCGCCACCAA TCATAGTGTT TGCCGGTGCG CCATTGGTGG CCGTGGGCGT

18541 GTAGTATCCG TGTGCCGGCT ACTTCGACGG TGGTGGTCAT TTCGTCTCGG CTGGGGAAAT

18601 AAAAGTGTAG GTTGGGGTAT TGGTTGGTGA GCTGGTAGGC TTCTGCGATG GCGCGGCAGC

18661 AGTCTACGTC GAAGGAGTCG TCGTAGGTGG TGACTCCTTT GCCGAAGCGT ACGGCTTCTC

18721 CGTGGTTGCC GGGGATGGAT GTGATGGTCA CGTTTTTGCA GTGGTCGAAC ATGTGGATGA

18781 GTTGCATCAT GGCCATGCGG GTGAGCCTGA TTTGTTCCGT CAAGGGGGTT TGTGTGCGCC

18841 AGGCGTTGTT GCCTCCTTGT GACACGTATC CTTCGATCAT GTCGCCGAGG AATGCGATGT

18901 GGACTCGTTC GGGTTTGCCT GCCTGCTGCC AGTAGTGTTT AGCTGATGTG AGGGAGCGCA

18961 GGTAGTCGTC GGCGAAGTGT GATGTTTCCC CGCCGGGGAT GCCTTTGCCG ATTTGGAAGT

19021 CGCCTGCCCC GATGACGAAG GCCGCAGTGC TGTAGTCGGT GCGGGTGTCC TGTTCGGGTT

19081 TTGGGGGTGT CCATTCGGCT AGTTTATCGA CGAGTTCGTC TACAGGGTAG GGGTTTGTTG

19141 CGGGTTGGTG GTCGATGATT TTTTGTACGG ATCTGCCTGT TTCTCCGTTG GGGAGTGTCC

19201 ATTCGGAGAT GCGTGTGCGG CGTACGGTGC CGTTTGCGAG ATCATCGCAG ATGGTGTCTG

19261 CTTCGCTATC GTGGTTGGCT AGCTGGGTGA GTAGCCGGTC TATGTTGTCT ATCACTGGGT

19321 ATCCTCTTCT TGCGGGGTGG TGTTGGCTTG TTTGCGGCGG TAGTCTTTTA TAACGGTGGC

19381 GGAGATGGGG TATCCTGCCT GGGTGAGCTG TTTTGCTAGC CATGAGGCGG GGATGGTTTT

19441 GTCGGCGAGC ACGTCGGCAG CCTTGTTGCC GTAGCGTTGG ATGAGTGTTT CAGTTTTGGT

19501 TGCCATGGTG TCCTATCGGT TGTGTGGTGG GCTGCCATCC TGTGCGGCAG TCGCCGTCGT

19561 GGCCTGGTTT GCGTGTGCAC CACGATACGG TTCTGTCTGT GTGGTTGAGT GTTTTGCCGC

19621 ACATGACGTT TTGTAGATGC TCTGGCAGTG CGCCGTCACC CTGGTTGCTG GTTTGTGTGT

19681 CGAAGAGTGT TTTCTGGTTG GTGAAATGCT CGGACACGGT GCCATTATGT ACGGGTAGTA

19741 TCCATGTTTT CCATTGTTGT TGTAGCCGGG TGTTCCAGTG GAATTGTTTT GCTGCGTTCG

19801 TGGCTTGTTT GATGGTTTTG TAGTAGCCGA CGAGGATGCG CTGGTGTTCA CTGTCGGGAG

19861 GGTTTTGGCC TCGCCAGTAT TGTGCCGCCA CGGCGTAGCG GTTGCTGGCT GTGAAGGCGT

19921 CCCAGCAGTA TTCAATAATG TGTTGTAGTA CACTATCGGG CATGTCTCGT ACTTGGTTTT

19981 CGTCGAGCCA CGCGTCGACA ATGATGTTGC GTATGGCGCG TTTGTCTTTG GTGGTGGGTT

20041 TGAATGCGAT GCTCACAGTA CGGGCCTGTC GTCTTGCATG AAATCATTAA AGGATGATTC

20101 GCTTGCGCGG CGTGCTTGTG TGATTTGCTG GTCAGACCAG TCGGGGTGTT GCTGTTTCAG

20161 ATAGTACCAG TGGCACGCAT TGTAGGTTTC GTCTTGTAGC CGGGTGAGAT GGTTTTCGGT

20221 GATGATTTGT TTCCACATAG TCCATGACAC GTCGAGCCGG TCCAATATTT CCATTGCTGG
```

-continued

```
20281 AATGTTGAAC TGGTTCAGGA AGAGTATTTC GTGGGTGTAG TATTCCTTCT CGTACTGGTC

20341 CCATCCACTT CGGTGCCTGT TGGGCTGGTT TTTGGGGTAG GCTTCCCGGC ATACTTTGTG

20401 CAAATGTTTG GCCATGTCGT CGGGTAGTTT AATGTCAGGG TTGGCGCGGA TCATGGATCG

20461 CATCCCATCA TAGGTGGTGC CCCAGGTGTG CATGATGTAG GTGGGGTCTT CACCATCAGC

20521 CCATTTTTCT GCACAGATGG CGAGGCGGAT GCGTCTCCTG GCTGATTGGC TGGTGTTGCG

20581 CCGGTTGGGG ATGGGGCACG TGTCGAGGGG ATCCATGATG TTTTGGTGTA CCTTTCTTGG

20641 TTTAGGTTGC TTGTGTGGTT TTATTGTAGC ACTGTGTCTA GTGCTTGTGT CAACCCTGTT

20701 TTGCCGGCCT GAAGGTAGGT GTCTGTGACA TCCCCCAGGG TGAGGGGCAC ATGGGTGGCT

20761 TGGGGGAGTG CGGCCTGGAG TGTTTGGGCC ATCTGGTGGC CCGCCTTGTC TGGGTCTGAC

20821 CAGATGTAGA TGTGGTCGTA GCCTTCAAAA AATTTGGTCC AAAAAGTTTG CCACGAGGTT

20881 GCGCCGGGTA GGGCTACGGC TGGCCATCCG CATTGTTCGA GGATCATGGA GTCGAATTCG

20941 CCTTCGCAAA TGTGCATTTC GGCTGCCGGG TTGGCCATGG CGGCCATGTT GTAGATGGAG

21001 CCTGTGTCTC CTGCCGGGGT TAGATATTTG GGGTGGTTGT GGGTTTTGCA ATCATGTTGG

21061 AGTGAGCAGC GGAAACGCAT TTTTCGTATT TCGGCTGGCC CTTCCCAGAC GGGGTACATG

21121 TATGGGATGG TGATGCACTG GTTGTAGTTT TCGTGGCCTT GGATGGGGTC ATTGTCGATG

21181 TATCCAAGGT GGTGGTAGCG GGCTGTTTCT TCGCTGATGC CTCTTGCCGA GAGCAGGTCG

21241 AGTATGTTTT CGAGGTGGGT TTCGTAGCGG GCTGAGGCTT TCTGGATTCG GCGGCGTTCC

21301 GCAATGTTGT AGGGGCGTAT GCTGTCGTAC ATTCGGGTTT TCTTCCTCTA ATCGTTGTTT

21361 CAGTTTGTGG AGTCCGCCTC CGATACCGCA TGTGTGGCAG TACCAGACGC CCTTGTCGAG

21421 GTTGATGCTC ATGGAGGGCT GGTGGTCGTC GTGGAACGGG CAGAGGATGT GTTGCTCGTT

21481 CCGTGACGGG TTGTAGCGTA TCTGGTGGGC GTCTAGGAGG CGGCAGGTGT CAGAGGTGTG

21541 GGAGGAGCTC GTTGAGGGTT GATACCACAT AGGCTTCGCT CCAGGGTTTG TTGCGCTGTT

21601 TCATGATGAC GAGTCCGATG GTGGATTGGT TTTCGCGGTT TCGGTGTGTT TCGTAGTTGC

21661 GTGCCTCCCG GCTGGCTTGT TTCACGAATT CGGCTAGGTG TGCCTGTCCT GCTTTGGCTT

21721 CGATCACATA GGTTTTGTTG CCGGTTGTGA GGATGAGGTC GCCTTCGTCT TCTTTACCGT

21781 TGAGGTGGAG GCGTTCTATA TCATAGCCGG TGTCGCGTAG CTGGTGGAGG AGTCTTGTTT

21841 CCCATTCGGC GCCGGCTCGG CGGTTGCGTG CCTGTTGTGT TGACATGATA GTCCTTTATG

21901 TTCTTGTGTC ATGTTCCAGG GCTGTTTTTC TACTAGGGGC CCGAAGAATG TGTATTCGGG

21961 GTAGGCTCGT AGTCGTTCGT ATTTTGTTCC GTCTGGGCTG GATTTGCCGG TTCTCTGTTT

22021 CAGGACGGCG ATGCGTGCCT CGGCGGGGAT GGTGAGGCCG TTGCCGTTGT CTTCGCCACC

22081 ATACAGGGAG ACTCCCAATA TGAGTTGTGG TTTTTCGGAG AGGCCGTTTT TGATTTCCCG

22141 CCTAGCTGGG GGGTGTTCGA TGTCGGTGCC GGTTTTGTCG GTTGCGTGGT GGGTGACGAT

22201 GATGGTGGAG CCAGTATCTC TACCTAAGGC TGTGATCCAT TGCATGGCTT CTTGCTGTGC

22261 CTGATAGTCG GATTCGCAGT CTTGGATGTC CATCAGGTTG TCTATAACAA TAATGGGTGG

22321 GAAGGTGTTC CACATTTCCA TGTAGGCTTG CAGTTCCATG GTGATGTCTG TCCATGTGAT

22381 GGGTGACTGG AATGAGAAGG TGATGTGTCC GCCGTGGTGG ATGCTGTCTC GATAGTATTC

22441 TGGCCCGTAG TTGTCGATGT TGTGTTGTAT CTGTTGGGTG GTGTGTGGG TGTTGAGTGA

22501 GATGATTCGT GTGGAGGCCT CCCAGGGTGT CATGTCCCCT GATATGTAGA GGGCTGGCTG

22561 GTTGAGCATC GCGGTGATGA ACATGGCTAG CCCTGATTTT TGGCTGCCGG ACCGCCCCGC

22621 GATCATGACC AAATCCCCTT TGTGGATGTG CATGTCCAGG TTGTCATACA AGGGTGCTAG
```

-continued

```
22681 TTGGGGTATG CGGGGCAGTT CGGCGGCTGT TTGGGAGGCC CTCTCGAAGG ATCTTTGGAG

22741 AGAGAGCATC GGGACCTTAA TCTATCTGTT GGTTGGGTGT GTTTTGGTGG TCAGATGGAG

22801 TCGATGTCGA TGTCAGCATC GGCGGGGGCT GTGGTGTCGT CTAGCTGGCC GTTGTCGCGT

22861 TTGTCTACAT ATTCGGCAAC CTTATCGTAG ATGGCGTCGT CGAGGGGTTT GAGGACGACC

22921 GCGTTGAACC CGTTTTTGGT GCGCACGGTG GCAAGTTTGA AGGCTTGTTC TTCGCCGAGA

22981 TATGCTTCTA GGTCGCGGAT CATGGAGTGT GGGCGGTCGT TGTTGCCGCG TGCTTTTTCG

23041 ATGATGGCGT TGGGGATGGT TTCTGGGGTG CCGTTGTTGA GATCCTGGAG GGTGTGGAAG

23101 ATTGTGACAT CAGCGTAGAT GCGGTCTGCG ACCTGTCCAC CGTAGCCTTC GGTGTTGTGT

23161 TCTACGTCGC GGATTTTGAA GGCGATGGCG GTGGCGTCCT GGTTTCGGGA GGGGTTGAAG

23221 AAGGTGCTGT TGCTGTTGTT GTGGTAGTTG GCGAGTGCCA TGATTGTGTT ATCCTTTACT

23281 GTTGTGTCTG TTTTTGTTGT CTTATATTGG TTTATCGGGT GAGGCTGTTT CGTTTGCTGC

23341 GGAAAGCCTC GGAAACGTCA CTGTTACTGG TGATGGTCTT CTTGTACTGT TTGAGTAGGT

23401 CTGCTAGCTG TGTCTTGCTG GTGGCTTTGT TTATCCGGTC GATGATGATG TCGTTTTCCT

23461 GTGATGCGAT TTTGTTGACG TAGTCTTTGG CGGCTTTATC GTATCGGTCT TGAAGCAGGA

23521 TTGCTGCGCT AGCGATGAGG GTTGCGAGAT CCCAGTCTTT GGATACGGTT TCGTCTTTCA

23581 ATCCTCCTAG CAGATCAATA ATGGATTGTT TGATGTCTTC TGCGGTGTCT CCGCGGATGA

23641 CTGTCCATGG GGCGGCATAG TCGCCACCGT ATTTGAGTGT GATAGTTAGT TTTCCGCTGT

23701 CTGTGGTGTG CTCGTCGGTC ACGTGTTTTC CTTTTCGTTG TTTTCGGCTT CTGGTGGCTG

23761 TACGGTGGTT TCTATCGGGT ATCTGTAGGC GTCTTTCCCG TTGACGGCCC AGCAGGCGTC

23821 CTTGACGGGG CATCCTTTGC AGAGTGTGGT GACGTGGGGT ACGAAGATGC CTTGGCTGAT

23881 TCCTTTCATT GCTTGACTGT ACATGGATGA TACATGCCGG TAGGTGTTGT TGTCAAGATC

23941 AATGAGTTCG GTTGCTGTGC CCTGCTCGAC TGATTGCTCG TCTCCCTTGG TGGTGGCGGG

24001 TGTCCAAAAC ATGCCTTTCG TCACATGGAT GCCGTGTTGG GCGAGCATGT ACCGGTATGT

24061 GTGCAGCTGC ATACTGTCTG CGGGTAGGCG TCCGGTTTTG AGGTCCAAAA TGAAGGTTTC

24121 GCCGGTGTCG GTGTCGGTGA ATACCCGGTC AATATATCCG ACTATTTTTG TGTCATCGTC

24181 GAGGGTGGTT TCTACCGGGT ATTCGATGCC TGGCTGGCCG TCAATAACAG CGGTGGCGTA

24241 TTCTGGGTGG TTGCGCCTCC ATGTTTTCCA GCGGTCCACA AAGGTGGGGC CGTACATCAT

24301 CCACCAATTG TAGTCTTTCT TGTGTGGCCC GCCTGACTCG CACATGTTTT TGCATATTCT

24361 GCCGGAGGGC TTTATGTTTG TGCCTTCGGA TTCGGCGAGG GCGATTTGGG TGTCGAAAAT

24421 GTTTGTGAAG GATGAGAGTT TGTCTGGCAG TGCAGGGTAT TCGGCGGGGT TGTACAGGTG

24481 TAGGTCGTAT TGTTCGGTGA TGTGGTGTAT GGCGCTTCCG GCGATGGTGG CGTACCAGGT

24541 GTGGTGTTGG GCGTGGTAGC CGTGTGCTAG GCGCCATTTT TCGCCGCATT CGGCCCACTG

24601 TGTGAGTGAA CTGTAGGAGA TGTGGCCTGG ATGGTTGATG GTTTTCGGGT ATTGTGCTAG

24661 GGGCATTACT TGTCGCCTTT GTGGGTGTTC CATGGGTTGC GGGTGTCTTT GCCGGCGTGG

24721 TGTTGCTGGT AGGCGAGGAG TGCGAGGCAG TGCCAGGCAG CGTGTGCCAG ATGCGGCAAA

24781 TGTGATTCGT TGTCGAGGTT GTTGCCTTGC TGCCATGATA ACAGGTGCCG GTAGAGGGCG

24841 TCGACACTGT GGCTCCACGG GTATCCTCCG GTCCAGTTGT TGTCGCCGTA CTTGGTGGCA

24901 CCGTAGCCTG CCACGGAGCC TAGGGCGTGC AAGGCTGCGG GGTCGATGAG GGAGAGCCTG

24961 CAGAGTTTCA ATTCTTTTCG GGCACCGCTG TTGGGGTCGG TGTACATGCT GGTGGGCTCA

25021 TCCATGGTGT GTGTGCTCCT TAAGCGTGGG TTACTGGTTA TTGTCGTGGG CGAGTGCTAC

25081 GGCGAGAATA ATGATGGCGA GGGTTTCAGC GATCAGTATG GGTGTTGTGA TCATTTAGTG
```

-continued

```
25141 TCTCGGGGAT TATTGGTGAG TGTTGATGCA CCTAGGAGGG TGGCGAGGGC GCATGCGGCG

25201 ATGGTGGCGA GGGCTGCCTT GTGTGGGGTG CCGGTTGCGT ACATCCATGT GATGATGCCG

25261 CCTTGGATCC AGGCTAGACT GGTGAAGAAC GTTTCGTAAC TGTGTAGCTC AATGTTGTTG

25321 TTGGGTGTGT TCATGCTTGC TCCTGAAGAA TGGTGTTGAT GGTTTTATAA ATGTTGTACA

25381 GGTCGGTTTC GATAGATAAC AGTTGGTTGA TTTGGTGGTC GAGATCAATG TCTGGGTTGA

25441 GGGTGTCGAT GCGGGCGGCG ATATCGGTGG CGGTGCGTAG GCTTACTGCT GCACCGTGGA

25501 TGATGTGGCA CATGTCGGTG AGGCCGACTT TGGCGATATA GTGTGACATG AGAGGCATAA

25561 TAGGTGTGCT GTCTTTCTGG TCAGCGTGAA GGGTTGATGG ACATATCCTC TACCTGTGGT

25621 TTGTCTTCGG TGCCGGAGAC TTGGCAGAAG ACTTTCACAT GCGTCTTGGA TGCTCCGGCC

25681 TGTTTGGCGG TGGCACCGTA GGCGATAGTA AAGGTGTCTT TGTGGGCGCC GATGACTTTG

25741 TGTAGGAAGA GGTCGATGTC GGGGTTGCCG TTCCATTTGA CACCGTTTTC TGCGGCTGTC

25801 TGGGTGGCTT TCTGATTGCA GGCGTGTGCG GCGGTGATCA TGGTGAGACC CTTGCTGGTT

25861 TCTTCACCCC TTGCTTGGGC TTGCCGGTGG GCTTTGGCCT GCTCGGCTTG TAGGGAGCGG

25921 ACTGCTGCGG CCTGGCGGGC CTTCTTCTCA GCCTTGCGCT GCTGGACGGT TTTGGGTGTC

25981 CATTCGGTGT TGGCTGTGGT TACCTGTGGT GCGGGTTGTG AGGCGAGTGG CGGATTGTCG

26041 TCTGGGGCTG GCATGAAGGA TGCTGCGGCA ATAATGGCGA CTGTGGCGCC TGCGATGGTG

26101 TAGCCTGTTT TCTTGTTCAT GATTTTATGT TCCCCTTTCC GGGGTGTTGT TCGTTGCTGA

26161 CATGGTTAAT ACTTTCAGCG GCTGGGCCCA CTGTCAAGGC TGCGCTCAGT TTGTGTGAGC

26221 GTTTCTTGTG TGGCTAGGGG TGATGGCTTC TTTCGCCCAA TAGGATGTGC CACCGCTGGT

26281 CCAGTATCCG AGTTTGTTGC GCTGCATGCC CTTGGCGTCC ATCTCGTCGA TAGTGAGGCA

26341 CCTGCGGCGA TTGGGGCCTG TCTTGACCCC GTGGTCGCCT GTCCGGTGCA TGTCGCCTGA

26401 GGTGGTACTC GTGAATGTTT CATGGCAGAT GGTACAGTGC TCTGGTCGAT ATCCGGTGAT

26461 TGTGCTATCG CACTTGTGGC ATGTCCATTC CATGATTGCT CCTATTTTCC ATTATAAGAC

26521 TTCCTGTAGT GCCATTTTAG CGCCTTGCGG GTCTTGGGGG TACAACTATA TAGGTCAGGT

26581 GTTTCTAGGC GATTCTAGGC TCATTGTGTG TGGCTGGGGT TTTATCGGGC ACACAGGGTG

26641 AGCAGGTGGC CAACATTGAT GCGGGTCACA TTCCAGTAGA GTTGCGTGGC TTCCCCACTG

26701 GTGAGCGGCT TCCACTCGTC ATGGCTGAAC ACGGTGCCAT CGGATGCGAT GAACGTGTTG

26761 GGGCGTAGCT TGTGGAGTTC GGCTTCCACG CTCTGCCGGT AGGCTTCGGC GAGGCCCTCA

26821 AAATCCATGT GGTCGCAGGG GAGGTTTTCG AGGCGTGTCA GGTCGAAGGG TGTGGGGCAG

26881 TCGTAGCTGG CGGGGGTGTA GAGCTGGGTG AAGTGGTTGG CGATCTTCTG CATCATGATT

26941 CCTTTTCTGA TGATGGTGTG TTGAGGGTTT ATCGGGTGGA TGCGACAAGG ATGGCGTCTA

27001 CATCGATCAT GTCGATGAGA TCGTGGAGTT CCTCGGCCTC GTTCTCAGTG AGTGGCTGCC

27061 AGGCGTAGTC GCCGTATACG GCGCCGTCGA GGGTGACAGT CCACGGGGGC CGGATGAGTC

27121 GTATGGCTTC TTGTACTTTA GCGTGGTACA TGCGGCGCAC CATATCCAGA TCGATGTCGT

27181 CTGAATGGTT TCCGGTGAGG CTGTGGAGGC TGAGCGGGTC GATGTCTGTC TGCCTGTAGA

27241 GGGATGTGAA GGATGGGGTG ATGAGTGTGC CATCCATGAG TGTGCTCCTT TCGGTGGTTG

27301 TAGGGGTTGT TGTGGTTTCT AGAGTGTGCG GGCTGCGACC CCACAGTCAA GGTGTCGCTC

27361 AAACTCAGTG AGCGTTTCAT ATGGGTGTGT TGGGTGTGAC AGATGTCACT TAAGCCTTGA

27421 TGGCCTCTCT CAGCGCCTCA AATCTTCTAG GGTAGGATT ATGAAGGGTT GGCCCTGCTG

27481 ATCGATTCTA GGCCCCATAC AGGGCGTCTG AGGGGTGTGT CTGAGTGATA GTGGGTGTGG
```

```
                              -continued
27541 CAGATGATCT AGCGAGTCAA GGTGCCGAGC TGAGACATAA GATCTATCAT CTAGGTGTGT

27601 GAGATGTATC ACATCCTCCC GGCTTGGTGT GCACCCTCAA GGCCACCCAG TCGATCTGAC

27661 GTGGAGGGTG TAGCCCAGAA ATACTGTTTA AAGCCTTCAC ACGGCGCCTA GGAGCGCCTT

27721 ACAGGGTGGG GGCTAGGTAT TTATACCCCC AGCACATTCT GATCGATTCT AGACGCCTAC

27781 AGGAGCCCGA TACACGATCA GCCATCCAGA CGCAGATCAT CAGCACCTAT CATGGTTAGC

27841 TAAGCCTCAA CTATGTGGAC AGTGTTGGTT ACTGTGGGGG AAGAAGGACA CGGTAAAAGA

27901 AAGAGGGGGA GTATCAGCTT TAAAGCCTTA AGGTCTTAGC GCTTAGCACC GATGGTCTTA

27961 GCAGTTAGCA CCGAGCCCCC TCAAGGGCTC GGCATCAGCC CGAACAGGCA CAGCCATGAA

28021 AGGAGTACAC GCCATCAGGG AAGGCTTTCG AGTACGAGGA GCCTCAGCGA CGAGTACTCG

28081 AAAGCCTGAG GGAACACCCA TCAGCACTGA TGAGCCTAGC GTATTCGGAA AGGACACAAG

28141 AGTGAAGTGT GACAGCTGTC CGGGAGTGAA CCCCGTTCTG ACTAGGGGTT TCAGCCTTAA

28201 CCACCCTCAA AGGTTACAAG ACTCTAAGAA AATTTAAGGA AAAGTTTAGG TTTAATTTTT

28261 GGACCTTTAC TACCAAAAAC ACCCGTTTAC AGCCCTCAAA CCCGCCTATA GAGCCAAAAC

28321 CACCAGTTTG ACTCATCCCA GGTGGGGTAT GATAGGCTGG ACAGGTAGCC AGCTGGACGC

28381 AAGGCCGGAA AGTGCTAACG CACTTTCCAA CCTCGCTTAC CATCAGTCTA CCAAACACTT

28441 AAAGACCTAA GGGCTTAGCG CTAAGGTGCT GATAGCTTAG CACCGAGCCC CCTCAAGGGC

28501 TCGGCATCAG TCTTAAAGCC TTAAATACTT AAAGTAACTA TAAAACTTTA AAAGCTTAAC

28561 ACTTAAGGAT ATAAACTTTA CATCAGTGTT TAAGACTTAA AAACTTAAAA TAACTATTAA

28621 GACTTAAAGT AACTATAAAA CATTAAAGAC CTTAAGTACT TAAAGTTAAC CATCAGTCTT

28681 AAACTTTACT ATGATAACCT ATAAGTCTTA AAGCTTATAG GTATAATAAT ATAATATAAG

28741 TATTAAAGCT TATAAGTTAT AAAAGTTTTA GAAGAGTTAA AGGGTTAACT TCTTTACTTC

28801 TCTTCTCTCT TTGGTTCTTT CTCTCTTCTC TTCTTTTCTT CATCGGGGGA GAAGAGGAAC

28861 CTTTAACGTC AACGCTGATG GACTTTTCGC CGTGTGTCTC GTGTGCTTCT GGTCGCAAGC

28921 TCCCATCGCA CACTCCCCAC ACTCTTTCAC CTGTGTCCCT TTCAGGCTTA GCGTGTTCAG

28981 CTGAAGGCGT ACAGCGTGTC ACGCTTAAAC CCTTAACACC AGGTAAGACT TAAAGTGCAT

29041 ATTATAAGTA GAAGACTTTA AAACCTTAAG GGTGTTCCTG CTTAGCCTGT GTCCTTTAAC

29101 GCTAGGCGCT AAGCCGTGAA ACGTGAACAC CCATCCACCC CTCTTCTTTT TACCGTGTCC

29161 TTCTTCTTTT GACACCGCTG GGGGGCGATG TGATCTTTTT AACATGCCAG GGGGTGCGGG

29221 TAGAAAACAA CCACCCCACC ACAAACAGAA CACCCCCTCA AACGCACAAA ACAGCCCCCA

29281 GGATCGATGA ACAGGGCAAG GGCAAGGTAT TCATACCCCC AGACGATTCC AGGCCGTTAG

29341 AGAGGCAAAT AAGACCCGTA CAGGGCTAGG TGAGGAATAG ACACATCATG GCACGCACCA

29401 ATCGCACAGC TAGCCAAGCC CACCGACGCT GGCGGCAACG ACTCATCACC CAAGCCCAAC

29461 AACAAGGCCA AACCGAATGC CCACTCTGCG GAGTCACCAT CACCTGGGAC ACACACGACC

29521 TACCAACCAG CCCCGAAGCC GACCACATCA CACCCGTCAG CAGGGGAGGA CTCAACACCC

29581 TCGACAACGG GCAAATCATC TGCAGAACAT GCAACAGAAG CAAAGGCAAT CGCAGCGAAC

29641 CAAACATCAA ATTCCAACAA CAAACCACAA AAACATTGAT TCCATGGTGA CAAACCCGCC

29701 AACCCCCACC GGGGACACCC CCTGCACAGG CGTGCAAGAC CTCGTACGGC TT
```

In embodiments, the bacteriophage is a bacteriophage as deposited under Accession No. NCIMB 41349, 41350, or 41351. In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genome of the bacteriophage deposited under Accession No. NCIMB 41349. In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genome of the bacteriophage deposited under Accession No. NCIMB 41350. In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genome of the bacteriophage deposited under Accession No. NCIMB 41351.

In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the nucleotide sequence of SEQ ID NO: 1. In embodiments, the bacteriophage has a genome with a nucleotide sequence that is identical to the nucleotide sequence of SEQ ID NO: 1.

In embodiments, the genome of the bacteriophage encodes, from the 5' to the 3' end, a small terminase, a large terminase, a portal protein, gp4, a scaffold protein, a major head protein, gp7, gp8, gp9, gp10, a major tail protein, gp12, gp13, a tape measure protein, a minor tail subunit, optionally a protease, gp17, gp18, a tail protein, an amidase, a holin, gp22, gp23, a sigma factor, gp25, gp26, gp27, gp28, gp29, gp30, a DNA primase, a DNA primase 2, gp33, a DNA helicase, gp35, gp36, an exonuclease, gp38, gp39, gp40, gp41, gp42, gp43, gp44, gp45, gp46, gp47, and gp48.

In embodiments, the composition further includes a *P. acnes* biofilm degrading enzyme.

In embodiments, the enzyme is an anti-aging enzyme. In embodiments, the anti-aging enzyme is a superoxide dismutase or a peroxidase.

In embodiments, the enzyme is a *P. acnes* biofilm degrading enzyme. In embodiments, the enzyme is a glycosidase, a protease, a DNAse, or a restriction endonuclease. In embodiments, the enzyme is a glycosidase. In embodiments, the glycosidase is a glycoside hydrolase. In embodiments, the enzyme catalyzes the hydrolysis of linear polymers of N-acetyl-D-glucosamines. In embodiments, the enzyme is a β-hexosaminidase. In embodiments, the enzyme hydrolyzes β-1,6-glycosidic linkages of acetylglucosamine polymers. In embodiments, the enzyme is a DNAse I, a restriction endonuclease, papain, bromelain, Trypsin, Proteinase K, Subtilisin, serratiopeptidase, dispersin, alginate lyase, amylase, or cellulase. In embodiments, the enzyme is Dispersin B. In embodiments, the enzyme is a protease, and the protease is proteinase K or subtilisin.

In embodiments, the enzyme is a dispersin. In embodiments, the enzyme is Dispersin B. In embodiments, the enzyme is a naturally occurring form, homolog, isoform or variant of a dispersin (such as Dispersin B) that maintains the enzymatic activity (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes Dispersin B is as follows:

(SEQ ID NO: 11)
ATGAATTGTTGCGTAAAAGGCAATTCCATATATCCGCAAAAAACAAGTAC

44
-continued

CAAGCAGACCGGATTAATGCTGGACATCGCCCGACATTTTTATTCACCCG

AGGTGATTAAATCCTTTATTGATACCATCAGCCTTTCCGGCGGTAATTTT

CTGCACCTGCATTTTTCCGACCATGAAAACTATGCGATAGAAAGCCATTT

ACTTAATCAACGTGCGGAAAATGCCGTGCAGGGCAAAGACGGTATTTATA

TTAATCCTTATACCGGAAAGCCATTCTTGAGTTATCGGCAACTTGACGAT

ATCAAAGCCTATGCTAAGGCAAAAGGCATTGAGTTGATTCCCGAACTTGA

CAGCCCGAATCACATGACGGCGATCTTTAAACTGGTGCAAAAAGACAGAG

GGGTCAAGTACCTTCAAGGATTAAAATCACGCCAGGTAGATGATGAAATT

GATATTACTAATGCTGACAGTATTACTTTTATGCAATCTTTAATGAGTGA

GGTTATTGATATTTTTGGCGACACGAGTCAGCATTTTCATATTGGTGGCG

ATGAATTTGGTTATTCTGTGGAAAGTAATCATGAGTTTATTACGTATGCC

AATAAACTATCCTACTTTTTAGAGAAAAAAGGGTTGAAAACCCGAATGTG

GAATGACGGATTAATTAAAAATACTTTTGAGCAAATCAACCCGAATATTG

AAATTACTTATTGGAGCTATGATGGCGATACGCAGGACAAAAATGAAGCT

GCCGAGCGCCGTGATATGCGGGTCAGTTTGCCGGAGTTGCTGGCGAAAGG

CTTTACTGTCCTGAACTATAATTCCTATTATCTTTACATTGTTCCGAAAG

CTTCACCAACCTTCTCGCAAGATGCCGCCTTTGCCGCCAAAGATGTTATA

AAAAATTGGGATCTTGGTGTTTGGGATGGACGAAACACCAAAAACCGCGT

ACAAAATACTCATGAAATAGCCGGCGCAGCATTATCGATCTGGGGAGAAG

ATGCAAAAGCGCTGAAAGACGAAACAATTCAGAAAAACACGAAAAGTTTA

TTGGAAGCGGTGATTCATAAGACGAATGGGGATGAGTGA

A non-limiting example of a Dispersin B amino acid sequence is as follows:

(SEQ ID NO: 12)
MNCCVKGNSIYPQKTSTKQTGLMLDIARHFYSPEVIKSFIDTISLSGGNF

LHLHFSDHENYAIESHLLNQRAENAVQGKDGIYINPYTGKPFLSYRQLDD

IKAYAKAKGIELIPELDSPNHMTAIFKLVQKDRGVKYLQGLKSRQVDDEI

DITNADSITFMQSLMSEVIDIFGDTSQHFHIGGDEFGYSVESNHEFITYA

NKLSYFLEKKGLKTRMWNDGLIKNTFEQINPNIEITYWSYDGDTQDKNEA

AERRDMRVSLPELLAKGFTVLNYNSYYLYIVPKASPTFSQDAAFAAKDVI

KNWDLGVWDGRNTKNRVQNTHEIAGAALSIWGEDAKALKDETIQKNTKSL

LEAVIHKTNGDE

In embodiments, the enzyme is an alginate lyase. In embodiments, the enzyme is a naturally occurring form, a homolog, an isoform or a variant of an alginate lyase that maintains the enzymatic activity of the alginate lyase (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes an alginate lyase is as follows:

```
                                    (SEQ ID NO: 13)
ATGAAAACGTCCCACCTGATCCGTATCGCCCTGCCCGGTGCCCTCGCCGC

GGCATTGCTCGCCAGCCAGGTCAGCCAGGCCGCCGACCTGGTACCCCCGC

CCGGCTACTACGCGGCGGTCGGCGAGCGCAAGGGCAGCGCCGGCAGCTGC

CCCGCGGTGCCGCCGCCGTATACCGGCAGCCTGGTCTTCACCAGCAAGTA

CGAAGGCTCCGATTCGGCGCGGGCGACCCTCAACGTCAAGGCGGAGAAGA

CCTTCCGCTCGCAGATCAAGGACATCACCGACATGGAGCGCGGCGCCACC

AAGCTGGTCACCCAGTACATGCGCAGCGGCCGCGACGGCGACCTGGCCTG

CGCACTGAACTGGATGAGCGCCTGGGCCCGCGCCGGCGCCCTGCAGAGCG

ACGACTTCAACCACACCGGCAAGTCCATGCGCAAATGGGCGCTGGGCAGC

CTCTCCGGCGCCTACATGCGCCTGAAGTTCTCCAGCTCGCGGCCGCTCGC

GGCCCACGCCGAGCAGAGCCGGGAAATCGAGGACTGGTTCGCCCGGCTCG

GCACCCAGGTAGTCCGCGACTGGAGCGGCCTGCCGCTGAAGAAGATCAAC

AACCATTCCTACTGGGCGGCCTGGTCGGTGATGTCCACCGCGGTGGTGAC

CAACCGCCGCGACCTCTTCGACTGGGCGGTGAGCGAGTTCAAGGTCGCCG

CCAACCAGGTCGACGAGCAGGGCTTCCTGCCCAACGAACTCAAGCGCCGC

CAGCGCGCCCTCGCCTACCACAACTATGCGCTGCCACCGCTGGCGATGAT

CGCCGCGTTCGCCCAGGTCAACGGCGTCGACCTGCGCCAGGAGAACCACG

GCGCCCTGCAGCGCCTGGCCGAGCGGGTGATGAAGGGAGTCGACGACGAG

GAAACCTTCGAGGAGAAGACCGGCGAGGACCAGGACATGACCGACCTCAA

GGTCGACAACAAGTACGCCTGGCTGGAGCCCTACTGCGCCCCTCTACCGCT

GCGAGCCGAAGATGCTCGAGGCGAAGAAGGACCGCGAGCCGTTCAACAGT

TTCCGCCTCGGCGGCGAAGTGACGCGGGTGTTCAGCCGCGAAGGGGGAAG

TTG
```

A non-limiting example of an alginate lyase amino acid sequence is as follows:

```
                                    (SEQ ID NO: 14)
MKTSHLIRIALPGALAAALLASQVSQAADLVPPPGYYAAVGERKGSAGSC

PAVPPPYTGSLVFTSKYEGSDSARATLNVKAEKTFRSQIKDITDMERGAT

KLVTQYMRSGRDGDLACALNWMSAWARAGALQSDDFNHTGKSMRKWALGS

LSGAYMRLKFSSSRPLAAHAEQSREIEDWFARLGTQVVRDWSGLPLKKIN

NHSYWAAWSVMSTAVVTNRRDLFDWAVSEFKVAANQVDEQGFLPNELKRR

QRALAYHNYALPPLAMIAAFAQVNGVDLRQENHGALQRLAERVMKGVDDE

ETFEEKTGEDQDMTDLKVDNKYAWLEPYCALYRCEPKMLEAKKDREPFNS

FRLGGEVTRVFSREGGS
```

In embodiments, the enzyme is an amylase. In embodiments, enzyme is a naturally occurring form, a homolog, an isoform or a variant of an amylase that maintains the enzymatic activity of the amylase (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes an amylase is as follows:

```
                                    (SEQ ID NO: 15)
ATGAAACAACAAAAACGGCTTTACGCCCGATTGCTGACGCTGTTATTTGC

GCTCATCTTCTTGCTGCCTCATTCTGCAGCAGCGGCGGCAAATCTTAATG

GGACGCTGATGCAGTATTTTGAATGGTACATGCCCAATGACGGCCAACAT

TGGAAGCGTTTGCAAAACGACTCGGCATATTTGGCTGAACACGGTATTAC

TGCCGTCTGGATTCCCCCGGCATATAAGGGAACGAGCCAAGCGGATGTGG

GCTACGGTGCTTACGACCTTTATGATTTAGGGGAGTTTCATCAAAAAGGG

ACGGTTCGGACAAAGTACGGCACAAAAGGAGAGCTGCAATCTGCGATCAA

AAGTCTTCATTCCCGCGACATTAACGTTTACGGGGATGTGGTCATCAACC

ACAAAGGCGGCGCTGATGCGACCGAAGATGTAACCGCGGTTGAAGTCGAT

CCCGCTGACCGCAACCGCGTAATTTCAGGAGAACACCTAATTAAAGCCTG

GACACATTTTCATTTTCCGGGGCGCGGCAGCACATACAGCGATTTTAAAT

GGCATTGGTACCATTTTGACGGAACCGATTGGGACGAGTCCCGAAAGCTG

AACCGCATCTATAAGTTTCAAGGAAAGGCTTGGGATTGGGAAGTTTCCAA

TGAAAACGGCAACTATGATTATTTGATGTATGCCGACATCGATTATGACC

ATCCTGATGTCGCAGCAGAAATTAAGAGATGGGGCACTTGGTATGCCAAT

GAACTGCAATTGGACGGTTTCCGTCTTGATGCTGTCAAACACATTAAATT

TTCTTTTTTGCGGGATTGGGTTAATCATGTCAGGGAAAAAACGGGGAAGG

AAATGTTTACGGTAGCTGAATATTGGCAGAATGACTTGGGCGCGCTGGAA

AACTATTTGAACAAAACAAATTTTAATCATTCAGTGTTTGACGTGCCGCT

TCATTATCAGTTCCATGCTGCATCGACACAGGGAGGCGGCTATGATATGA

GGAAATTGCTGAACGGTACGGTCGTTTCCAAGCATCCGTTGAAATCGGTT

ACATTTGTCGATAACCATGATACACAGCCGGGGCAATCGCTTGAGTCGAC

TGTCCAAACATGGTTTAAGCCGCTTGCTTACGCTTTTATTCTCACAAGGG

AATCTGGATACCCTCAGGTTTTCTACGGGGATATGTACGGGACGAAAGGA

GACTCCCAGCGCGAAATTCCTGCCTTGAAACACAAAATTGAACCGATCTT

AAAAGCGAGAAAACAGTATGCGTACGGAGCACAGCATGATTATTTCGACC

ACCATGACATTGTCGGCTGGACAAGGGAAGGCGACAGCTCGGTTGCAAAT

TCAGGTTTGGCGGCATTAATAACAGACGGACCCGGTGGGGCAAAGCGAAT

GTATGTCGGCCGGCAAAACGCCGGTGAGACATGGCATGACATTACCGGAA

ACCGTTCGGAGCCGGTTGTCATCAATTCGGAAGGCTGGGGAGAGTTTCAC

GTAAACGGCGGGTCGGTTTCAATTTATGTTCAAAGATAG
```

A non-limiting example of an amylase amino acid sequence is as follows:

```
                                    (SEQ ID NO: 16)
MKQQKRLYARLLTLLFALIFLLPHSAAAAANLNGTLMQYFEWYMPNDGQH

WKRLQNDSAYLAEHGITAVWIPPAYKGTSQADVGYGAYDLYDLGEFHQKG

TVRTKYGTKGELQSAIKSLHSRDINVYGDVVINHKGGADATEDVTAVEVD

PADRNRVISGEHLIKAWTHFHFPGRGSTYSDFKWHWYHFDGTDWDESRKL
```

-continued

NRIYKFQGKAWDWEVSNENGNYDYLMYADIDYDHPDVAAEIKRWGTWYAN

ELQLDGFRLDAVKHIKFSFLRDWVNHVREKTGKEMFTVAEYWQNDLGALE

NYLNKTNFNHSVFDVPLHYQFHAASTQGGGYDMRKLLNGTVVSKHPLKSV

TFVDNHDTQPGQSLESTVQTWFKPLAYAFILTRESGYPQVFYGDMYGTKG

DSQREIPALKHKIEPILKARKQYAYGAQHDYFDHHDIVGWTREGDSSVAN

SGLAALITDGPGGAKRMYVGRQNAGETWHDITGNRSEPVVINSEGWGEFH

VNGGGVSIYVQR

In embodiments, the enzyme is a cellulase. In embodiments, enzyme is a naturally occurring form, a homolog, an isoform or a variant of a cellulase that maintains the enzymatic activity of the cellulase (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes a cellulase is as follows:

```
                                        (SEQ ID NO: 17)
ATGAAGTTTCAGAGCACTTTGCTTCTTGCCGCCGCGGCTGGTTCCGCGTT

GGCTGTGCCTCATGGCTCCGGACATAAGAAGAGGGCGTCTGTGTTTGAAT

GGTTCGGATCGAACGAGTCTGGTGCTGAATTTGGGACCAATATCCCAGGC

GTCTGGGGAACCGACTACATCTTCCCCGACCCCTCGACCATCTCTACGTT

GATTGGCAAGGGAATGAACTTCTTCCGCGTCCAGTTCATGATGGAGAGGT

TGCTTCCTGACTCGATGACTGGTTCATACGACGAGGAGTATCGGCCAAC

TTGACGACTGTGGTGAAAGCGGTCACGGATGGAGGCGCGCATGCGCTCAT

CGACCCTCATAACTATGGCAGATACAACGGGGAGATCATCTCCAGTACAT

CGGATTTCCAGACTTTCTGGCAGAATCTGGCGGGCCAGTACAAAGATAAC

GACTTGGTCATGTTTGATACCAACAACGAATACTACGACATGGACCAGGA

TCTCGTGCTGAATCTCAACCAAGCAGCCATTAACGGCATCCGCGCTGCAG

GTGCAAGCCAGTACATTTTCGTCGAAGGCAACTCCTGGACCGGAGCTTGG

ACATGGGTCGATGTCAACGATAATATGAAGAATTTGACCGACCCAGAAGA

CAAGATCGTCTATGAAATGCACCAGTACCTAGACTCCGACGGTTCCGGCA

CTTCGGAGACCTGTGTCTCCGGGACAATCGGAAAGGAGCGGATCACTGAT

GCTACACAGTGGCTCAAGGACAATAAGAAGGTCGGCTTCATCGGCGAATA

TGCCGGGGGGTCCAATGATGTGTGTCGGAGTGCCGTGTCCGGGATGCTAG

AGTACATGGCGAACAACACCGACGTATGGAAGGGTGCGTCGTGGTGGGCA

GCCGGGCCATGGTGGGGAGACTACATTTTCAGCCTGGAGCCCCCAGATGG

AACTGCTTACACGGGTATGCTGGATATCCTGGAGACGTATCTCTGA
```

A non-limiting example of a cellulase amino acid sequence is as follows:

```
                                        (SEQ ID NO: 18)
MKFQSTLLLAAAAGSALAVPHGSGHKKRASVFEWFGSNESGAEFGTNIPG

VWGTDYIFPDPSTISTLIGKGMNFFRVQFMMERLLPDSMTGSYDEEYLAN
```

-continued

LTTVVKAVTDGGAHALIDPHNYGRYNGEIISSTSDFQTFWQNLAGQYKDN

DLVMFDTNNEYYDMDQDLVLNLNQAAINGIRAAGASQYIFVEGNSWTGAW

TWVDVNDNMKNLTDPEDKIVYEMHQYLDSDGSGTSETCVSGTIGKERITD

ATQWLKDNKKVGFIGEYAGGSNDVCRSAVSGMLEYMANNTDVWKGASWWA

AGPWWGDYIFSLEPPDGTAYTGMLDILETYL

In embodiments, the enzyme is proteinase K. In embodiments, the enzyme is a naturally occurring form, a homolog, an isoform or a variant of proteinase K that maintains the enzymatic activity of proteinase K (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes proteinase K is as follows:

```
                                        (SEQ ID NO: 19)
ATGCGTTTGTCTGTTCTTCTGAGTCTTCTTCCCCTCGCTCTCGGCGCTCC

TGCCGTTGAGCAGCGCTCCGAGGCTGCTCCTCTGATCGAGGCCCGCGGCG

AGATGGTTGCCAACAAGTACATTGTCAAGTTCAAGGAGGGTAGCGCTCTT

TCTGCTCTCGATGCTGCCATGGAGAAGATTTCTGGCAAGCCCGACCACGT

CTACAAGAACGTCTTCAGTGGTTTCGCTGCGACCCTTGACGAGAACATGG

TTCGGGTTCTCCGCGCCCATCCCGATGTTGAGTACATTGAGCAGGATGCT

GTTGTCACCATCAACGCTGCGCAGACCAACGCTCCCTGGGGCCTTGCTCG

CATCTCCAGCACCAGCCCCGGTACCTCTACTTACTACTATGACGAATCTG

CCGGCCAAGGCTCCTGCGTCTACGTGATTGACACCGGTATCGAGGCATCG

CACCCCGAGTTTGAGGGTCGTGCCCAGATGGTCAAGACCTACTACTACTC

CAGTCGCGACGGTAACGGTCACGGCACTCACTGCGCTGGTACCGTTGGCT

CCCGAACCTACGGTGTCGCCAAGAAGACCCAGCTCTTTGGTGTCAAGGTC

CTCGATGACAACGGCAGTGGCCAGTACTCCACCATCATCGCCGGTATGGA

CTTTGTTGCCAGCGACAAGAACAACCGCAACTGCCCCAAAGGTGTCGTTG

CCTCCTTGTCCCTTGGCGGTGGTTACTCCTCCTCCGTGAACAGCGCCGCT

GCCAGGCTCCAGAGCTCTGGTGTCATGGTCGCCGTCGCTGCCGGTAACAA

CAACGCTGACGCCCGCAACTACTCCCCTGCTTCTGAGCCCTCGGTCTGCA

CTGTCGGTGCTTCTGACCGCTACGACAGACGCTCCAGCTTCTCCAACTAC

GGCAGCGTTTTGGACATCTTTGGCCCTGGTACCAGCATTCTCTCCACCTG

GATCGGCGGCAGCACCCGCTCCATCTCTGGAACTTCCATGGCTACTCCCC

ACGTTGCCGGTCTCGCTGCCTACCTCATGACTCTTGGAAAGACTACCGCC

GCCAGCGCTTGCCGATACATTGCCGACACCGCCAACAAGGGCGACTTGAG

CAACATTCCCTTCGGCACTGTCAACCTGCTTGCCTACAACAACTACCAGG

CTTAA
```

A non-limiting example of a proteinase K amino acid sequence is as follows:

A non-limiting example of a subtilisin amino acid sequence is as follows:

(SEQ ID NO: 20)
MRLSVLLSLLPLALGAPAVEQRSEAAPLIEARGEMVANKYIVKFKEGSAL

SALDAAMEKISGKPDHVYKNVFSGFAATLDENMVRVLRAHPDVEYIEQDA

VVTINAAQTNAPWGLARISSTSPGTSTYYYDESAGQGSCVYVIDTGIEAS

HPEFEGRAQMVKTYYYSSRDGNGHGTHCAGTVGSRTYGVAKKTQLFGVKV

LDDNGSGQYSTIIAGMDFVASDKNNRNCPKGVVASLSLGGGYSSSVNSAA

ARLQSSGVMVAVAAGNNNADARNYSPASEPSVCTVGASDRYDRRSSFSNY

GSVLDIFGPGTSILSTWIGGSTRSISGTSMATPHVAGLAAYLMTLGKTTA

ASACRYIADTANKGDLSNIPFGTVNLLAYNNYQA

In embodiments, the enzyme is subtilisin. In embodiments, the enzyme is a naturally occurring form, a homolog, an isoform or a variant of subtilisin that maintains the enzymatic activity of subtilisin (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes subtilisin is as follows:

(SEQ ID NO: 21)
ATGATGAGGAAAAAGAGTTTTTGGCTTGGGATGCTGACGGCCTTCATGCT

CGTGTTCACGATGGCATTCAGCGATTCCGCTTCTGCTGCTCAACCGGCGA

AAAATGTTGAAAAGGATTATATTGTCGGATTTAAGTCAGGAGTGAAAACC

GCATCTGTCAAAAAGGACATCATCAAAGAGAGCGGCGGAAAAGTGGACAA

GCAGTTTAGAATCATCAACGCGGCAAAAGCGAAGCTAGACAAAGAAGCGC

TTAAGGAAGTCAAAAATGATCCGGATGTCGCTTATGTGGAAGAGGATCAT

GTGGCCCATGCCTTGGCGCAAACCGTTCCTTACGGCATTCCTCTCATTAA

AGCGGACAAAGTGCAGGCTCAAGGCTTTAAGGGAGCGAATGTAAAAGTAG

CCGTCCTGGATACAGGAATCCAAGCTTCTCATCCGGACTTGAACGTAGTC

GGCGGAGCAAGCTTTGTGGCTGGCGAAGCTTATAACACCGACGGCAACGG

ACACGGCACACATGTTGCCGGTACAGTAGCTGCGCTTGACAATACAACGG

GTGTATTAGGCGTTGCGCCAAGCGTATCCTTGTACGCGGTTAAAGTACTG

AATTCAAGCGGAAGCGGAACTTACAGCGGCATTGTAAGCGGAATCGAGTG

GGCGACGACAAACGGCATGGATGTTATCAACATGAGTCTTGGAGGACCAT

CAGGCTCAACAGCGATGAAACAGGCGGTTGACAATGCATATGCAAGAGGG

GTTGTCGTTGTGGCGGCTGCTGGGAACAGCGGATCTTCAGGAAACACGAA

TACAATCGGCTATCCTGCGAAATACGACTCTGTCATCGCAGTTGGCGCGG

TAGACTCTAACAGCAACAGAGCTTCATTTTCCAGCGTCGGAGCAGAGCTT

GAAGTCATGGCTCCTGGCGCAGGCGTGTACAGCACTTACCCAACCAGCAC

TTATGCAACATTGAACGGAACGTCAATGGCTTCTCCTCATGTAGCGGGAG

CAGCAGCTTTGATCTTGTCAAAACATCCGAACCTTTCAGCTTCACAAGTC

CGCAACCGTCTCTCCAGTACGGCGACTTATTTGGGAAGCTCCTTCTACTA

TGGAAAAGGTCTGATCAATGTCGAAGCTGCCGCTCAATAA

A non-limiting example of a subtilisin amino acid sequence is as follows:

(SEQ ID NO: 22)
MMRKKSFWLGMLTAFMLVFTMAFSDSASAAQPAKNVEKDYIVGFKSGVKT

ASVKKDIIKESGGKVDKQFRIINAAKAKLDKEALKEVKNDPDVAYVEEDH

VAHALAQTVPYGIPLIKADKVQAQGFKGANVKVAVLDTGIQASHPDLNVV

GGASFVAGEAYNTDGNGHGTHVAGTVAALDNTTGVLGVAPSVSLYAVKVL

NSSGSGSYSGIVSGIEWATTNGMDVINMSLGGASGSTAMKQAVDNAYAKG

VVVVAAAGNSGSSGNTNTIGYPAKYDSVIAVGAVDSNSNRASFSSVGAEL

EVMAPGAGVYSTYPTNTYATLNGTSMASPHVAGAAALILSKHPNLSASQV

RNRLSSTATYLGSSFYYGKGLINVEAAAQ

In embodiments, the enzyme is trypsin. In embodiments, the enzyme is a naturally occurring form, a homolog, an isoform or a variant of trypsin that maintains the enzymatic activity of trypsin (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes trypsin is as follows:

(SEQ ID NO: 23)
ATCGTCGGGGGCTACACCTGCGCAGAGAATTCCGTCCCTTACCAGGTGTC

CCTGAATGCTGGCTACCACTTCTGCGGGGGCTCCCTCATCAATGACCAGT

GGGTGGTGTCCGCGGCTCACTGCTACCAGTACCACATCCAGGTGAGGCTG

GGAGAATACAACATTGATGTCTTGGAGGGTGGTGAGCAGTTCATCGATGC

GTCCAAGATCATCCGCCACCCCAAGTACAGCAGCTGGACTCTGGACAATG

ACATCCTGCTGATCAAACTCTCCACGCCTGCGGTCATCAATGCCCGGGTG

TCCACCTTGCTGCTGCCCAGTGCCTGTGCTTCCGCAGGCACAGAGTGCCT

CATCTCCGGCTGGGGCAACACCCTGAGCAGTGGCGTCAACTACCCGGACC

TGCTGCAATGCCTGGTGGCCCCGCTGCTGAGCCACGCCGACTGTGAAGCC

TCATACCCTGGACAGATCACTAACAACATGATCTGCGCTGGCTTCCTGGA

AGGAGGCAAGGATTCCTGCCAGGGTGACTCTGGCGGCCCTGTGGCTTGCA

ACGGACAGCTCCAGGGCATTGTGTCCTGGGGCTACGGCTGTGCCCAGAAG

GGCAAGCCTGGGGTCTACACCAAGGTCTGCAACTACGTGGACTGGATTCA

GGAGACCATCGCCGCCAAC

A non-limiting example of a trypsin amino acid sequence is as follows:

(SEQ ID NO: 24)
IVGGYTCGANTVPYQVSLNSGYHFCGGSLINSQWVVSAAHCYKSGIQVRL

GEDNINVVEGNEQFISASKSIVHPSYNSNTLNNDIMLIKLKSAASLNSRV

ASISLPTSCASAGTQCLISGWGNTKSSGTSYPDVLKCLKAPILSDSSCKS

-continued

-continued

AYPGQITSNMFCAGYLEGGKDSCQGDSGGPVVCSGKLQGIVSWGSGCAQK

NKPGVYTKVCNYVSWIKQTIASN

In embodiments, the enzyme is serratiopeptidase. In embodiments, the enzyme is a naturally occurring form, a homolog, an isoform or a variant of serratiopeptidase that maintains the enzymatic activity of serratiopeptidase (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes serratiopeptidase is as follows:

(SEQ ID NO: 25)
ATGCAATCTACTAAAAAGGCAATTGAAATTACTGAATCCAGCCTCGCTGC

CGCGACAACCGGTTACGATGCTGTAGACGACCTGCTGCATTATCATGAGC

GGGGTAACGGGATTCAGATTAATGGCAAGGATTCATTTTCTAACGAGCAA

GCTGGGCTGTTTATTACCCGTGAGAACCAAACCTGGAACGGTTACAAGGT

ATTTGGCCAGCCGGTCAAATTAACCTTCTCGTTCCCGGACTATAAGTTCT

CTTCCACCAACGTCGCCGGCGACACCGGGCTGAGCAAGTTCAGCGCGGAA

CAGCAGCAGCAGGCTAAGCTGTCGCTGCAGTCCTGGGCCGACGTCGCCAA

TATCACCTTCACCGAAGTGGCGGCCGGTCAAAAGGCCAATATCACCTTCG

GCAACTACAGCCAGGATCGTCCCGGCCACTATGATTACGGCACCCAGGCC

TACGCCTTCCTGCCGAACACCATTTGGCAGGGCCAGGATTTGGGCGGCCA

GACTTGGTACAACGTAAACCAATCCAACGTGAAGCATCCGGCGACCGAAG

ACTACGGCCGCCAGACGTTCACCCATGAGATTGGCCATGCGCTGGGCCTG

AGCCACCCGGGCGACTACAACGCCGGTGAGGGCAACCCGACCTATAGAGA

TGTCACCTATGCGGAAGATACCCGCCAGTTCAGCCTGATGAGCTACTGGA

GTGAAACCAATACCGGTGGCGACAACGGCGGTCACTATGCCGCGGCTCCG

CTGCTGGATGACATTGCCGCCATTCAGCATCTGTATGGCGCCAACCTGTC

GACCCGCACCGGCGACACCGTGTACGGCTTTAACTCCAATACCGGTCGTG

ACTTCCTCAGCACCACCAGCAACTCGCAGAAAGTGATCTTTGCGGCCTGG

GATGCGGGCGGCAACGATACCTTCGACTTCTCCGGTTACACCGCTAACCA

GCGCATCAACCTGAACGAGAAATGGTTCTCCGACGTGGGCGGCCTGAAGG

GCAACGTGTCGATCGCCGCCGGTGTGACCATTGAGAACGCCATTGGCGGT

TCCGGCAACGACGTGATCGTCGGCAACGCGGCCAATAACGTGCTGAAAGG

CGGCGCGGGTAACGACGTGCTGTTCGGCGGCGGCGGGGCGGATGAATTGT

GGGGCGGTGCCGGCAAAGACATCTTCGTGTTCTCTGCCGCCAGCGATTCC

GCACCGGGCGCTTCAGACTGGATCCGCGACTTCCAGAAAGGGATCGACAA

GATCGACCTGTCGTTCTTCAATAAAGAAGCGCAGAGCAGCGATTTCATTC

ACTTCGTCGATCACTTCAGCGGCACGGCCGGTGAGGCGCTGCTGAGCTAC

AACGCGTCCAGCAACGTGACCGATTTGTCGGTGAACATCGGTGGGCATCA

GGCGCCGGACTTCCTGGTGAAAATCGTCGGCCAGGTAGACGTCGCCACGG

ACTTTATCGTGTAA

A non-limiting example of a serratiopeptidase amino acid sequence is as follows:

(SEQ ID NO: 26)
MQSTKKAIEITESSLAAATTGYDAVDDLLHYHERGNGIQINGKDSFSNEQ

AGLFITRENQTWNGYKVFGQPVKLTFSFPDYKFSSTNVAGDTGLSKFSAE

QQQQAKLSLQSWADVANITFTEVAAGQKANITFGNYSQDRPGHYDYGTQA

YAFLPNTIWQGQDLGGQTWYNVNQSNVKHPATEDYGRQTFTHEIGHALGL

SHPGDYNAGEGNPTYRDVTYAEDTRQFSLMSYWSETNTGGDNGGHYAAAP

LLDDIAAIQHLYGANLSTRTGDTVYGFNSNTGRDFLSTTSNSQKVIFAAW

DAGGNDTFDFSGYTANQRINLNEKWFSDVGGLKGNVSIAAGVTIENAIGG

SGNDVIVGNAANNVLKGGAGNDVLFGGGGADELWGGAGKDIFVFSAASDS

APGASDWIRDFQKGIDKIDLSFFNKEAQSSDFIHFVDHFSGTAGEALLSY

NASSNVTDLSVNIGGHQAPDFLVKIVGQVDVATDFIV

In embodiments, the enzyme is a DNAse. In embodiments, the enzyme is a naturally occurring form, a homolog, an isoform or a variant of a DNAse that maintains the enzymatic activity of the DNAse (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the enzyme is a DNAse I. In embodiments, the DNAse I is bovine pancreatic DNAse I. A non-limiting example of a DNA sequence that encodes a bovine pancreatic DNAse I is as follows:

(SEQ ID NO: 27)
TTGAAGATTGCTGCTTTCAACATTAGAACTTTCGGTGAAACTAAAATGTC

TAACGCTACTTTGGCATCTTACATCGTTAGAATTGTCAGAAGATATGATA

TCGTTTTAATTCAAGAAGTTAGAGACTCTCACTTGGTTGCAGTTGGTAAA

TTGTTAGACTACTTGAACCAAGATGACCCAAACACTTACCACTACGTTGT

TTCTGAACCATTGGGTAGAAACTCTTACAAAGAAAGATACTTATTCTTGT

TCAGACCAAACAAAGTTTCAGTTTTGGATACTTACCAATACGACGACGGT

TGCGAATCTTGTGGTAACGATTCTTTCTCCAGAGAACCTGCTGTTGTTAA

ATTCTCATCACACTCTACCAAGGTTAAAGAGTTCGCTATCGTTGCTTTGC

ATTCTGCTCCTTCTGACGCTGTTGCTGAAATTAACTCTTTGTACGACGTT

TACTTAGATGTTCAACAGAAATGGCACTTGAACGACGTCATGTTGATGGG

TGACTTTAACGCTGATTGCTCTTATGTTACTTCTTCTCAATGGTCTTCAA

TTAGATTGAGAACATCTTCAACTTTCCAATGGTTAATTCCTGATTCCGCT

GATACCACTGCTACTAGTACCAACTGTGCTTACGATAGAATCGTTGTTGC

TGGATCATTATTGCAATCTTCTGTTGTCCCAGGTTCAGCGGCCCCCTTTCG

-continued

```
ATTTCCAAGCTGCATATGGTTTGTCTAATGAAATGGCTTTAGCCATTTCT

GATCACTACCCAGTTGAAGTCACATTGACATAA
```

A non-limiting example of a bovine pancreatic DNAse I amino acid sequence is as follows:

```
                                       (SEQ ID NO: 28)
LKIAAFNIRTFGETKMSNATLASYIVRIVRRYDIVLIQEVRDSHLVAVGK

LLDYLNQDDPNTYHYVVSEPLGRNSYKERYLFLFRPNKVSVLDTYQYDDG

CESCGNDSFSREPAVVKFSSHSTKVKEFAIVALHSAPSDAVAEINSLYDV

YLDVQQKWHLNDVMLMGDFNADCSYVTSSQWSSIRLRTSSTFQWLIPDSA

DTTATSTNCAYDRIVVAGSLLQSSVVPGSAAPFDFQAAYGLSNEMALAIS

DHYPVEVTLT
```

In embodiments, the composition or combination includes a probiotic bacterium.

In embodiments, the probiotic bacterium is a probiotic a *P. sp.*, *Staphylococcus* sp., and/or *Corynebacterium* sp. bacterium.

In embodiments, the probiotic bacterium is a bacterium within the class Betaproteobacteria.

In embodiments, the probiotic bacterium is a probiotic *P. acnes* bacterium.

In embodiments, the *P. acnes* bacterium (a) has a 16S ribosomal DNA (rDNA) sequence with a T992C mutation compared to the KPA171202 type strain 16S rDNA sequence set forth as SEQ ID NO: 2; (b) has a 16S rDNA sequence with a T838C mutation compared to the KPA171202 type strain 16S rDNA sequence set forth as SEQ ID NO: 2; (c) has a 16S rDNA sequence with a C1322T mutation compared to the KPA171202 type strain 16S rDNA sequence set forth as SEQ ID NO: 2; (d) has a 16S rDNA sequence with a C986T mutation compared to the KPA171202 type strain 16S rDNA sequence set forth as SEQ ID NO: 2; (e) has a 16S rDNA sequence that is identical to the sequence of SEQ ID NO: 3; (f) has a 16S rDNA sequence that is identical to the sequence of SEQ ID NO: 4; (g) does not comprise a linear plasmid; (h) does not comprise a plasmid that has a virulence factor; and/or (i) does not have a plasmid that encodes an extrachromosomal lipase and/or a tight adhesion virulence factor.

In embodiments, the *P. acnes* bacterium (a) produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in a planktonic culture; (b) produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in an adherent culture; (c) adheres to epithelial cells at least 50% less than a pathogenic *P. acnes* strain; and/or (d) is less inflammatory than a pathogenic *P. acnes* strain.

In embodiments, the combination or composition includes at least one additional probiotic bacterium. In embodiments, the at least one additional probiotic bacterium includes *Propionibacterium granulosum* and/or *Propionibacterium avidum*.

In embodiments, a pathogenic *P. acnes* strain (a) has a 16S rDNA sequence with a G1058C mutation compared to the KPA171202 type strain 16S rDNA sequence set forth as SEQ ID NO: 2; (b) has a 16S rDNA sequence with a G1058C and an A1201C mutation compared to the KPA171202 type strain 16S rDNA sequence set forth as SEQ ID NO: 2; (c) has a 16S rDNA sequence with a G529A mutation compared to the KPA171202 type strain 16S rDNA sequence set forth as SEQ ID NO: 2; (d) has a 16S rDNA sequence with a G1004A and a T1007C mutation compared to the KPA171202 type strain 16S rDNA sequence set forth as SEQ ID NO: 2; (e) has a 16S rDNA sequence with a G1268A mutation compared to the KPA171202 type strain 16S rDNA sequence set forth as SEQ ID NO: 2; (f) has a 16S rDNA sequence with a T554C and a G1058C mutation compared to the KPA171202 type strain 16S rDNA sequence set forth as SEQ ID NO: 2; (g) has a 16S rDNA sequence that is identical to the sequence of SEQ ID NO: 5; (h) has a 16S rDNA sequence that is identical to the sequence of SEQ ID NO: 6; (i) has a 16S rDNA sequence that is identical to the sequence of SEQ ID NO: 7; (j) has a 16S rDNA sequence that is identical to the sequence of SEQ ID NO: 8; (k) has a 16S rDNA sequence that is identical to the sequence of SEQ ID NO: 9; and/or (1) has a 16S rDNA sequence that is identical to the sequence of SEQ ID NO: 10.

In embodiments, the combination or composition further includes at least one additional *P. acnes* bacteriophage.

In embodiments, the composition or combination includes a pharmaceutically acceptable carrier. In embodiments, the pharmaceutically acceptable carrier includes an emulsion. In embodiments, the emulsion is an oil-in-water emulsion or a water-in-oil emulsion. In embodiments, a combination or combination includes or is in the form of a cream, lotion, suspension, or aqueous solution.

In embodiments, a composition that includes a bacteriophage is provided. In embodiments, the composition is formulated for topical application to the skin (i.e., the composition is a topical composition). In embodiments, the composition is a pharmaceutical composition.

In an aspect, there is provided a pharmaceutical composition including a wild-type *P. acnes* bacteriophage and an isolated probiotic *P. acnes* bacterium. In embodiments, the composition further includes a pharmaceutically acceptable carrier.

In an aspect, there is provided a pharmaceutical composition including a bacteriophage and/or an isolated probiotic *P. acnes* bacterium and a pharmaceutically acceptable carrier.

In embodiments, the pharmaceutical composition is formulated for topical administration to the skin. In embodiments, the pharmaceutically acceptable carrier includes an emulsion. In embodiments, the emulsion is an oil-in-water emulsion or a water-in-oil emulsion.

In embodiments, the pharmaceutical composition is in the form of a cream, lotion, suspension, or aqueous solution.

In embodiments, a composition or combination includes at least about 2, 3, 4, 5, 6, 7, 8, 9, or 10 *P. acnes* bacteriophages. In embodiments, the *P. acnes* bacteriophages include more than one type of *P. acnes* bacteriophage.

In embodiments, a combination or composition including an isolated probiotic *P. acnes* bacterium may further comprise at least one additional bacterium.

In embodiments, a *P. acnes* bacterium has a 16S rDNA sequence that includes a T992C, T838C, C1322T, and/or a C986T mutation compared to the KPA171202 type strain 16S rDNA sequence set forth as SEQ ID NO: 2. In embodiments, the *P. acnes* bacterium includes a 16S rDNA sequence with a T838C and a C1322T mutation compared to the KPA171202 type strain 16S rDNA sequence set forth as SEQ ID NO: 2. In embodiments, the *P. acnes* bacterium is the ProI strain. In embodiments, the *P. acnes* bacterium includes a 16S rDNA sequence with a C986T and a T992C mutation compared to the KPA171202 type strain 16S rDNA sequence set forth as SEQ ID NO: 2. In embodiments, the *P. acnes* bacterium is the ProII strain. In embodiments, the *P. acnes* bacterium: (a) includes a 16S rDNA sequence with a T992C mutation compared to the KPA171202 type strain 16S rDNA sequence set forth as SEQ ID NO: 2; (b) includes a 16S rDNA sequence with a T838C mutation compared to the KPA171202 type strain 16S rDNA sequence set forth as SEQ ID NO: 2; (c) includes a 16S rDNA sequence with a C1322T mutation compared to the KPA171202 type strain 16S rDNA sequence set forth as SEQ ID NO: 2; (d) includes a 16S rDNA sequence with a C986T mutation compared to the KPA171202 type strain 16S rDNA sequence set forth as SEQ ID NO: 2; (e) includes a 16S rDNA sequence that is identical to the sequence of SEQ ID NO: 3; (f) includes a 16S rDNA sequence that is identical to the sequence of SEQ ID NO: 4; (g) does not comprise a linear plasmid; (h) does not include a plasmid that includes a virulence factor; and/or (i) does not include a plasmid that encodes an extrachromosomal lipase and/or a tight adhesion virulence factor. In embodiments, the *P. acnes* bacterium has a 16S rDNA sequence that is identical to the sequence of SEQ ID NO: 3 or 4.

In embodiments, the *P. acnes* bacterium: (a) produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in a planktonic culture; (b) produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in an adherent culture; (c) adheres to epithelial cells at least 50% less than a pathogenic *P. acnes* strain; and/or (d) is less inflammatory than a pathogenic *P. acnes* strain. In embodiments, the pathogenic *P. acnes* strain (a) has a 16S rDNA sequence with a G1058C mutation compared to the KPA171202 type strain 16S rDNA sequence set forth as SEQ ID NO: 2; (b) has a 16S rDNA sequence with a G1058C and an A1201C mutation compared to the KPA171202 type strain 16S rDNA sequence set forth as SEQ ID NO: 2; (c) has a 16S rDNA sequence with a G529A mutation compared to the KPA171202 type strain 16S rDNA sequence set forth as SEQ ID NO: 2; (d) has a 16S rDNA sequence with a G1004A and a T1007C mutation compared to the KPA171202 type strain 16S rDNA sequence set forth as SEQ ID NO: 2; (e) has a 16S rDNA sequence with a G1268A mutation compared to the KPA171202 type strain 16S rDNA sequence set forth as SEQ ID NO: 2; (f) has a 16S rDNA sequence with a T554C and a G1058C mutation compared to the KPA171202 type strain 16S rDNA sequence set forth as SEQ ID NO: 2; (g) has a 16S rDNA sequence that is identical to the sequence of SEQ ID NO: 5; (h) has a 16S rDNA sequence that is identical to the sequence of SEQ ID NO: 6; (i) has a 16S rDNA sequence that is identical to the sequence of SEQ ID NO: 7; 0) has a 16S rDNA sequence that is identical to the sequence of SEQ ID NO: 8; (k) has a 16S rDNA sequence that is identical to the sequence of SEQ ID NO: 9; and/or (1) has a 16S rDNA sequence that is identical to the sequence of SEQ ID NO: 10.

SEQ ID NO: 2 is the 16S rDNA sequence for the KPA171202 type strain, and is as follows:

```
   1 TTTTTCATTG GAGAGTTTGA TCCTGGCTCA GGACGAACGC TGGCGGCGTG CTTAACACAT

61 GCAAGTCGAA CGGAAAGGCC CTGCTTTTGT GGGGTGCTCG AGTGGCGAAC GGGTGAGTAA

121 CACGTGAGTA ACCTGCCCTT GACTTTGGGA TAACTTCAGG AAACTGGGGC TAATACCGGA

181 TAGGAGCTCC TGCTGCATGG TGGGGGTTGG AAAGTTTCGG CGGTTGGGGA TGGACTCGCG

241 GCTTATCAGC TTGTTGGTGG GGTAGTGGCT TACCAAGGCT TTGACGGGTA GCCGGCCTGA

301 GAGGGTGACC GGCCACATTG GGACTGAGAT ACGCCCAGA CTCCTACGGG AGGCAGCAGT

361 GGGGAATATT GCACAATGGG CGGAAGCCTG ATGCAGCAAC GCCGCGTGCG GGATGACGGC

421 CTTCGGGTTG TAAACCGCTT TCGCCTGTGA CGAAGCGTGA GTGACGGTAA TGGGTAAAGA

481 AGCACCGGCT AACTACGTGC CAGCAGCCGC GGTGATACGT AGGGTGCGAG CGTTGTCCGG

541 ATTTATTGGG CGTAAAGGGC TCGTAGGTGG TTGATCGCGT CGGAAGTGTA ATCTTGGGGC

601 TTAACCCTGA GCGTGCTTTC GATACGGGTT GACTTGAGGA AGGTAGGGGA GAATGGAATT

661 CCTGGTGGAG CGGTGGAATG CGCAGATATC AGGAGGAACA CCAGTGGCGA AGGCGGTTCT

721 CTGGGCCTTT CCTGACGCTG AGGAGCGAAA GCGTGGGGAG CGAACAGGCT TAGATACCCT

781 GGTAGTCCAC GCTGTAAACG GTGGGTACTA GGTGTGGGGT CCATTCCACG GGTTCCGTGC

841 CGTAGCTAAC GCTTTAAGTA CCCCGCCTGG GGAGTACGGC CGCAAGGCTA AAACTCAAAG

901 GAATTGACGG GGCCCCGCAC AAGCGGCGGA GCATGCGGAT TAATTCGATG CAACGCGTAG

961 AACCTTACCT GGGTTTGACA TGGATCGGGA GTGCTCAGAG ATGGGTGTGC CTCTTTTGGG

1021 GTCGGTTCAC AGGTGGTGCA TGGCTGTCGT CAGCTCGTGT CGTGAGATGT TGGGTTAAGT

1081 CCCGCAACGA GCGCAACCCT TGTTCACTGT TGCCAGCACG TTATGGTGGG GACTCAGTGG

1141 AGACCGCCGG GGTCAACTCG GAGGAAGGTG GGGATGACGT CAAGTCATCA TGCCCCTTAT
```

-continued

```
1201 GTCCAGGGCT TCACGCATGC TACAATGGCT GGTACAGAGA GTGGCGAGCC TGTGAGGGTG

1261 AGCGAATCTC GGAAAGCCGG TCTCAGTTCG GATTGGGGTC TGCAACTCGA CCTCATGAAG

1321 TCGGAGTCGC TAGTAATCGC AGATCAGCAA CGCTGCGGTG AATACGTTCC CGGGGCTTGT

1381 ACACACCGCC CGTCAAGTCA TGAAAGTTGG TAACACCCGA AGCCGGTGGC CTAACCGTTG

1441 TGGGGGAGCC GTCGAAGGTG GGACTGGTGA TTAGGACTAA GTCGTAACAA GGTAGCCGTA

1501 CCGGAAGGTG CGGCTGGATC ACCTCCTTTC TAAGGAG
```

SEQ ID NO: 3 is the 16S rDNA sequence for the ProI
probiotic strain, and is as follows:
Nucleotides 838 . . . 838
    ProI Mutation T838C                               15
Nucleotides 1322 . . . 1322
    ProI Mutation C1322T

```
   1 TTTTTCATTG GAGAGTTTGA TCCTGGCTCA GGACGAACGC TGGCGGCGTG CTTAACACAT

61 GCAAGTCGAA CGGAAAGGCC CTGCTTTTGT GGGGTGCTCG AGTGGCGAAC GGGTGAGTAA

121 CACGTGAGTA ACCTGCCCTT GACTTTGGGA TAACTTCAGG AAACTGGGGC TAATACCGGA

181 TAGGAGCTCC TGCTGCATGG TGGGGGTTGG AAAGTTTCGG CGGTTGGGGA TGGACTCGCG

241 GCTTATCAGC TTGTTGGTGG GGTAGTGGCT TACCAAGGCT TTGACGGGTA GCCGGCCTGA

301 GAGGGTGACC GGCCACATTG GGACTGAGAT ACGGCCCAGA CTCCTACGGG AGGCAGCAGT

361 GGGGAATATT GCACAATGGG CGGAAGCCTG ATGCAGCAAC GCCGCGTGCG GGATGACGGC

421 CTTCGGGTTG TAAACCGCTT TCGCCTGTGA CGAAGCGTGA GTGACGGTAA TGGGTAAAGA

481 AGCACCGGCT AACTACGTGC CAGCAGCCGC GGTGATACGT AGGGTGCGAG CGTTGTCCGG

541 ATTTATTGGG CGTAAAGGGC TCGTAGGTGG TTGATCGCGT CGGAAGTGTA ATCTTGGGGC

601 TTAACCCTGA GCGTGCTTTC GATACGGGTT GACTTGAGGA AGGTAGGGGA GAATGGAATT

661 CCTGGTGGAG CGGTGGAATG CGCAGATATC AGGAGGAACA CCAGTGGCGA AGGCGGTTCT

721 CTGGGCCTTT CCTGACGCTG AGGAGCGAAA GCGTGGGGAG CGAACAGGCT TAGATACCCT

781 GGTAGTCCAC GCTGTAAACG GTGGGTACTA GGTGTGGGGT CCATTCCACG GGTTCCGCGC

841 CGTAGCTAAC GCTTTAAGTA CCCCGCCTGG GGAGTACGGC CGCAAGGCTA AAACTCAAAG

901 GAATTGACGG GGCCCCGCAC AAGCGGCGGA GCATGCGGAT TAATTCGATG CAACGCGTAG

961 AACCTTACCT GGGTTTGACA TGGATCGGGA GTGCTCAGAG ATGGGTGTGC CTCTTTTGGG

1021 GTCGGTTCAC AGGTGGTGCA TGGCTGTCGT CAGCTCGTGT CGTGAGATGT TGGGTTAAGT

1081 CCCGCAACGA GCGCAACCCT TGTTCACTGT TGCCAGCACG TTATGGTGGG GACTCAGTGG

1141 AGACCGCCGG GGTCAACTCG GAGGAAGGTG GGGATGACGT CAAGTCATCA TGCCCCTTAT

1201 GTCCAGGGCT TCACGCATGC TACAATGGCT GGTACAGAGA GTGGCGAGCC TGTGAGGGTG

1261 AGCGAATCTC GGAAAGCCGG TCTCAGTTCG GATTGGGGTC TGCAACTCGA CCTCATGAAG

1321 TTGGAGTCGC TAGTAATCGC AGATCAGCAA CGCTGCGGTG AATACGTTCC CGGGGCTTGT

1381 ACACACCGCC CGTCAAGTCA TGAAAGTTGG TAACACCCGA AGCCGGTGGC CTAACCGTTG

1441 TGGGGGAGCC GTCGAAGGTG GGACTGGTGA TTAGGACTAA GTCGTAACAA GGTAGCCGTA

1501 CCGGAAGGTG CGGCTGGATC ACCTCCTTTC TAAGGAG
```

SEQ ID NO: 4 is the 16S rDNA sequence for the ProII probiotic strain, and is as follows:

Nucleotides 986 . . . 986
    ProII Mutation C986T
Nucleotides 992 . . . 992
    ProII Mutation T992C

```
   1  TTTTTCATTG GAGAGTTTGA TCCTGGCTCA GGACGAACGC TGGCGGCGTG CTTAACACAT

61  GCAAGTCGAA CGGAAAGGCC CTGCTTTTGT GGGGTGCTCG AGTGGCGAAC GGGTGAGTAA

121  CACGTGAGTA ACCTGCCCTT GACTTTGGGA TAACTTCAGG AAACTGGGGC TAATACCGGA

181  TAGGAGCTCC TGCTGCATGG TGGGGGTTGG AAAGTTTCGG CGGTTGGGGA TGGACTCGCG

241  GCTTATCAGC TTGTTGGTGG GGTAGTGGCT TACCAAGGCT TTGACGGGTA GCCGGCCTGA

301  GAGGGTGACC GGCCACATTG GGACTGAGAT ACGGCCCAGA CTCCTACGGG AGGCAGCAGT

361  GGGGAATATT GCACAATGGG CGGAAGCCTG ATGCAGCAAC GCCGCGTGCG GGATGACGGC

421  CTTCGGGTTG TAAACCGCTT TCGCCTGTGA CGAAGCGTGA GTGACGGTAA TGGGTAAAGA

481  AGCACCGGCT AACTACGTGC CAGCAGCCGC GGTGATACGT AGGGTGCGAG CGTTGTCCGG

541  ATTTATTGGG CGTAAAGGGC TCGTAGGTGG TTGATCGCGT CGGAAGTGTA ATCTTGGGGC

601  TTAACCCTGA GCGTGCTTTC GATACGGGTT GACTTGAGGA AGGTAGGGGA GAATGGAATT

661  CCTGGTGGAG CGGTGGAATG CGCAGATATC AGGAGGAACA CCAGTGGCGA AGGCGGTTCT

721  CTGGGCCTTT CCTGACGCTG AGGAGCGAAA GCGTGGGGAG CGAACAGGCT TAGATACCCT

781  GGTAGTCCAC GCTGTAAACG GTGGGTACTA GGTGTGGGGT CCATTCCACG GGTTCCGTGC

841  CGTAGCTAAC GCTTTAAGTA CCCCGCCTGG GGAGTACGGC CGCAAGGCTA AAACTCAAAG

901  GAATTGACGG GGCCCCGCAC AAGCGGCGGA GCATGCGGAT TAATTCGATG CAACGCGTAG

961  AACCTTACCT GGGTTTGACA TGGATTGGGA GCGCTCAGAG ATGGGTGTGC CTCTTTTGGG

1021  GTCGGTTCAC AGGTGGTGCA TGGCTGTCGT CAGCTCGTGT CGTGAGATGT TGGGTTAAGT

1081  CCCGCAACGA GCGCAACCCT TGTTCACTGT TGCCAGCACG TTATGGTGGG GACTCAGTGG

1141  AGACCGCCGG GGTCAACTCG GAGGAAGGTG GGGATGACGT CAAGTCATCA TGCCCCTTAT

1201  GTCCAGGGCT TCACGCATGC TACAATGGCT GGTACAGAGA GTGGCGAGCC TGTGAGGGTG

1261  AGCGAATCTC GGAAAGCCGG TCTCAGTTCG GATTGGGGTC TGCAACTCGA CCTCATGAAG

1321  TCGGAGTCGC TAGTAATCGC AGATCAGCAA CGCTGCGGTG AATACGTTCC CGGGGCTTGT

1381  ACACACCGCC CGTCAAGTCA TGAAAGTTGG TAACACCCGA AGCCGGTGGC CTAACCGTTG

1441  TGGGGGAGCC GTCGAAGGTG GGACTGGTGA TTAGGACTAA GTCGTAACAA GGTAGCCGTA

1501  CCGGAAGGTG CGGCTGGATC ACCTCCTTTC TAAGGAG
``` less than about 20% of the level of lipase that is produced by a pathogenic *P. acnes* strain when grown in a planktonic culture. In embodiments, the *P. acnes* bacterium produces less than about 30% of the level of lipase that is produced by a pathogenic *P. acnes* strain when grown in a planktonic culture. In embodiments, the *P. acnes* bacterium produces In embodiments, the *P. acnes* bacterium produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in a planktonic culture. In embodiments, the *P. acnes* bacterium produces about 1-5%, 1-10%, 1-20%, 1-30%, 5-50%, 5-40%, 5-30%, 5-20%, 5-10%, 10-50%, 10-40%, 10-30%, 10-20%, 20-50%, 20-40%, or 20-30% of the level of lipase that is produced by a pathogenic *P. acnes* strain when grown in a planktonic culture. In embodiments, the *P. acnes* bacterium produces less than about 5% of the level of lipase that is produced by a pathogenic *P. acnes* strain when grown in a planktonic culture. In embodiments, the *P. acnes* bacterium produces less than about 10% of the level of lipase that is produced by a pathogenic *P. acnes* strain when grown in a planktonic culture. In embodiments, the *P. acnes* bacterium produces less than about 40% of the level of lipase that is produced by a pathogenic *P. acnes* strain when grown in a planktonic culture. In embodiments, the *P. acnes* bacterium produces less than about 50% of the level of lipase that is produced by a pathogenic *P. acnes* strain when grown in a planktonic culture. In embodiments, the *P. acnes* bacterium produces less than about 1%, 5%, 10%, 15%, 20%, 25%, 30%, 3%, 40%, 45%, 50%, 55%, 60%, 65%, 70%, 75%, 80%, 85%, 90% or 95% of the level of lipase that is produced by a pathogenic *P. acnes* strain when grown in an adherent culture. In embodiments, the *P. acnes* bacterium produces less than about 5% of the level of lipase that is produced by a pathogenic *P. acnes* strain when grown in an adherent culture. In embodiments, the *P. acnes* bacterium produces less than about 10% of the level of lipase that is produced by a pathogenic *P. acnes* strain when grown in an adherent culture. In embodiments, the *P. acnes* bacterium produces less than about 20% of the level of lipase that is produced by a pathogenic *P. acnes* strain when grown in an adherent culture. In embodiments, the *P. acnes* bacterium produces less than about 30% of the level of lipase that is produced by a pathogenic *P. acnes* strain when grown in an adherent culture. In embodiments, the *P. acnes* bacterium produces less than about 40% of the level of lipase that is produced by a pathogenic *P. acnes* strain when grown in an adherent culture. In embodiments, the *P. acnes* bacterium produces less than about 50% of the level of lipase that is produced by a pathogenic *P. acnes* strain when grown in an adherent culture. In embodiments, the *P. acnes* bacterium produces about 1-5%, 1-10%, 1-20%, 1-30%, 5-50%, 5-40%, 5-30%, 5-20%, 5-10%, 10-50%, 10-40%, 10-30%, 10-20%, 20-50%, 20-40%, or 20-30% of the level of lipase that is produced by a pathogenic *P. acnes* strain when grown in an adherent culture. In embodiments, the lipase is extracellular lipase.

In embodiments, the level of lipase produced by a *P. acnes* bacterium (e.g., a probiotic or a pathogenic *P. acnes* bacterium, such as for comparison) is the level of lipase in culture supernatant. In embodiments, the culture supernatant is filtered. In embodiments, the culture supernatant is from a liquid (planktonic) culture. In embodiments, the culture supernatant is from an adherent culture. Non-limiting examples of methods for detecting a level of lipase include absorbance, Bradford protein assays, Biuret test derived assays, fluorescamine, amino black, colloidal gold, nitrogen detection, High-performance liquid chromatography (HPLC), Liquid chromatography-mass spectrometry (LC/MS), enzyme-linked immunosorbent assay (ELISA), protein immunoprecipitation, immunoelectrophoresis, and Western blot.

In embodiments, the *P. acnes* bacterium adheres to epithelial cells at least about 1%, 5%, 10%, 15%, 20%, 25%, 30%, 35%, 40%, 45%, 50%, 55%, 60%, 65%, 70%, 75%, 80%, 85%, 90% or 95% less than a pathogenic *P. acnes* strain. In embodiments, the *P. acnes* bacterium adheres to epithelial cells at least about 50% less than a pathogenic *P. acnes* strain. In embodiments, the *P. acnes* bacterium adheres to epithelial cells at least about 60% less than a pathogenic *P. acnes* strain. In embodiments, the *P. acnes* bacterium adheres to epithelial cells at least about 70% less than a pathogenic *P. acnes* strain. In embodiments, the *P. acnes* bacterium adheres to epithelial cells at least about 80% less than a pathogenic *P. acnes* strain. In embodiments, the *P. acnes* bacterium adheres to epithelial cells at least about 90% less than a pathogenic *P. acnes* strain. In embodiments, the *P. acnes* bacterium adheres to epithelial cells 1-5%, 1-10%, 1-20%, 1-30%, 5-50%, 5-40%, 5-30%, 5-20%, 5-10%, 10-50%, 10-40%, 10-30%, 10-20%, 20-50%, 20-40%, 20-30%, 50-60, 50-70, 50-80, 50-90, 60-80, 70-90 less than a pathogenic *P. acnes* strain.

In embodiments, adherence of a *P. acnes* bacterium (e.g., a probiotic or a pathogenic *P. acnes* bacterium, such as for comparison) to epithelial cells is determined using A-432 epithelial cells. In embodiments, the epithelial cells are confluent on a tissue culture plate or flask. In embodiments, adherence is detected by determining a number of colonies that are formed by *P. acnes* bacteria that have adhered to cultured epithelial cells.

In embodiments, the *P. acnes* bacterium is less inflammatory than a pathogenic *P. acnes* strain.

In embodiments, a *P. acnes* bacterium is less inflammatory than a pathogenic *P. acnes* strain if a lower level of an inflammatory cytokine (e.g., at least about 10%, 20%, 30%, 40%, 50%, 60%, 70%, 80%, or 90% less) is released by an immune cell that contacts the *P. acnes* bacterium or a compound produced by the *P. acnes* bacterium compared to a bacterium of the pathogenic *P. acnes* strain or a compound produced by the bacterium of the pathogenic *P. acnes* strain. In embodiments, a *P. acnes* bacterium is less inflammatory than a pathogenic *P. acnes* strain if a lower level of an inflammatory cytokine is released in tissue (such as skin tissue) that is contacted with *P. acnes* bacterium. In embodiments, the tissue is skin tissue. In embodiments, the tissue is ear tissue, e.g., of a mouse. In embodiments, the inflammatory cytokine is IL-10, IL-6, IL-17, or TNFα, or any combination thereof.

In embodiments, the pathogenic *P. acnes* strain (a) has a 16S rDNA sequence with a G1058C mutation compared to the KPA171202 type strain 16S rDNA sequence set forth as SEQ ID NO: 2; (b) has a 16S rDNA sequence with a G1058C and an A1201C mutation compared to the KPA171202 type strain 16S rDNA sequence set forth as SEQ ID NO: 2; (c) has a 16S rDNA sequence with a G529A mutation compared to the KPA171202 type strain 16S rDNA sequence set forth as SEQ ID NO: 2; (d) has a 16S rDNA sequence with a G1004A and a T1007C mutation compared to the KPA171202 type strain 16S rDNA sequence set forth as SEQ ID NO: 2; (e) has a 16S rDNA sequence with a G1268A mutation compared to the KPA171202 type strain 16S rDNA sequence set forth as SEQ ID NO: 2; (f) has a 16S rDNA sequence with a T554C and a G1058C mutation compared to the KPA171202 type strain 16S rDNA sequence set forth as SEQ ID NO: 2; (g) has a 16S rDNA sequence that is identical to the sequence of SEQ ID NO: 5; (h) has a 16S rDNA sequence that is identical to the sequence of SEQ ID NO: 6; (i) has a 16S rDNA sequence that is identical to the sequence of SEQ ID NO: 7; (j) has a 16S rDNA sequence that is identical to the sequence of SEQ ID NO: 8; (k) has a 16S rDNA sequence that is identical to the sequence of SEQ ID NO: 9; and/or (1) has a 16S rDNA sequence that is identical to the sequence of SEQ ID NO: 10.

SEQ ID NO: 5 is as follows (mutations compared to the 16S sequence of the type strain KPA171202 are underlined):

```
AGAGTTTGATCCTGGCTCAGGACGAACGCTGGCGGCGTGCTTAACACATG

CAAGTCGAACGGAAAGGCCCTGCTTTTGTGGGGTGCTCGAGTGGCGAACG

GGTGAGTAACACGTGAGTAACCTGCCCTTGACTTTGGGATAACTTCAGGA

AACTGGGGCTAATACCGGATAGGAGCTCCTGCTGCATGGTGGGGGTTGGA

AAGTTTCGGCGGTTGGGGATGGACTCGCGGCTTATCAGCTTGTTGGTGGG

GTAGTGGCTTACCAAGGCTTTGACGGGTAGCCGGCCTGAGAGGGTGACCG

GCCACATTGGGACTGAGATACGGCCCAGACTCCTACGGGAGGCAGCAGTG

GGGAATATTGCACAATGGGCGGAAGCCTGATGCAGCAACGCCGCGTGCGG

GATGACGGCCTTCGGGTTGTAAACCGCTTTCGCCTGTGACGAAGCGTGAG

TGACGGTAATGGGTAAAGAAGCACCGGCTAACTACGTGCCAGCAGCCGCG

GTGATACGTAGGGTGCGAGCGTTGTCCGGATTTATTGGGCGTAAAGGGCT

CGTAGGTGGTTGATCGCGTCGGAAGTGTAATCTTGGGGCTTAACCCTGAG

CGTGCTTTCGATACGGGTTGACTTGAGGAAGGTAGGGGAGAATGGAATTC

CTGGTGGAGCGGTGGAATGCGCAGATATCAGGAGGAACACCAGTGGCGAA

GGCGGTTCTCTGGGCCTTTCCTGACGCTGAGGAGCGAAAGCGTGGGGAGC

GAACAGGCTTAGATACCCTGGTAGTCCACGCTGTAAACGGTGGGTACTAG
```

GTGTGGGGTCCATTCCACGGGTTCCGTGCCGTAGCTAACGCTTTAAGTAC

CCCGCCTGGGGAGTACGGCCGCAAGGCTAAAACTCAAAGGAATTGACGGG

GCCCCGCACAAGCGGCGGAGCATGCGGATTAATTCGATGCAACGCGTAGA

ACCTTACCTGGGTTTGACATGGATCGGGAGTGCTCAGAGATGGGTGTGCC

TCTTTTGGGGTCGGTTCACAGGTGGTGCATGCCTGTCGTCAGCTCGTGTC

GTGAGATGTTGGGTTAAGTCCCGCAACGAGCGCAACCCTTGTTCACTGTT

GCCAGCACGTTATGGTGGGGACTCAGTGGAGACCGCCGGGGTCAACTCGG

AGGAAGGTGGGGATGACGTCAAGTCCTCATGCCCCTTATGTCCAGGGCTT

CACGCATGCTACAATGGCTGGTACAGAGAGTGGCGAGCCTGTGAGGGTGA

GCGAATCTCGGAAAGCCGGTCTCAGTTCGGATTGGGGTCTGCAACTCGAC

CTCATGAAGTCGGAGTCGCTAGTAATCGCAGATCAGCAACGCTGCGGTGA

ATACGTTCCCGGGGCTTGTACACACCGCCCGTCAAGTCATGAAAGTTGGT

AACACCCGAAGCCGGTGGCCTAACCGTTGTGGGGGAGCCGTCGAAGGTGG

GACTGGTGATTAGGACTAAGTCGTAACAAGGTAGCCGTACCGGAAGGTGC

GGCTGGATCACCTCCTTTCTAAGGA

SEQ ID NO: 6 is as follows (a mutation compared to the 16S sequence of the type strain KPA171202 is underlined):

AGAGTTTGATCCTGGCTCAGGACGAACGCTGGCGGCGTGCTTAACACATG

CAAGTCGAACGGAAAGGCCCTGCTTTTGTGGGGTGCTCGAGTGGCGAACG

GGTGAGTAACACGTGAGTAACCTGCCCTTGACTTTGGGATAACTTCAGGA

AACTGGGGCTAATACCGGATAGGAGCTCCTGCTGCATGGTGGGGGTTGGA

AAGTTTCGGCGGTTGGGGATGGACTCGCGGCTTATCAGCTTGTTGGTGGG

GTAGTGGCTTACCAAGGCTTTGACGGGTAGCCGGCCTGAGAGGGTGACCG

GCCACATTGGGACTGAGATACGGCCCAGACTCCTACGGGAGGCAGCAGTG

GGGAATATTGCACAATGGGCGGAAGCCTGATGCAGCAACGCCGCGTGCGG

GATGACGGCCTTCGGGTTGTAAACCGCTTTCGCCTGTGACGAAGCGTGAG

TGACGGTAATGGGTAAAGAAGCACCGGCTAACTACGTGCCAGCAGCCGCG

GTGATACGTAGGGTGCGAGCGTTGTCCGGATTTATTGGGCGTAAAGGGCT

CGTAGGTGGTTGATCGCGTCGGAAGTGTAATCTTGGGGCTTAACCCTGAG

CGTGCTTTCGATACGGGTTGACTTGAGGAAGGTAGGGGAGAATGGAATTC

CTGGTGGAGCGGTGGAATGCGCAGATATCAGGAGGAACACCAGTGGCGAA

GGCGGTTCTCTGGGCCTTTCCTGACGCTGAGGAGCGAAAGCGTGGGGAGC

GAACAGGCTTAGATACCCTGGTAGTCCACGCTGTAAACGGTGGGTACTAG

GTGTGGGGTCCATTCCACGGGTTCCGTGCCGTAGCTAACGCTTTAAGTAC

CCCGCCTGGGGAGTACGGCCGCAAGGCTAAAACTCAAAGGAATTGACGGG

GCCCCGCACAAGCGGCGGAGCATGCGGATTAATTCGATGCAACGCGTAGA

ACCTTACCTGGGTTTGACATGGATCGGGAGTGCTCAGAGATGGGTGTGCC

TCTTTTGGGGTCGGTTCACAGGTGGTGCATGCCTGTCGTCAGCTCGTGTC

GTGAGATGTTGGGTTAAGTCCCGCAACGAGCGCAACCCTTGTTCACTGTT

GCCAGCACGTTATGGTGGGGACTCAGTGGAGACCGCCGGGGTCAACTCGG

AGGAAGGTGGGGATGACGTCAAGTCATCATGCCCCTTATGTCCAGGGCTT

CACGCATGCTACAATGGCTGGTACAGAGAGTGGCGAGCCTGTGAGGGTGA

GCGAATCTCGGAAAGCCGGTCTCAGTTCGGATTGGGGTCTGCAACTCGAC

CTCATGAAGTCGGAGTCGCTAGTAATCGCAGATCAGCAACGCTGCGGTGA

ATACGTTCCCGGGGCTTGTACACACCGCCCGTCAAGTCATGAAAGTTGGT

AACACCCGAAGCCGGTGGCCTAACCGTTGTGGGGGAGCCGTCGAAGGTGG

GACTGGTGATTAGGACTAAGTCGTAACAAGGTAGCCGTACCGGAAGGTGC

GGCTGGATCACCTCCTTTCTAAGGA

SEQ ID NO: 7 is as follows (a mutation compared to the 16S sequence of the type strain KPA171202 is underlined):

AGAGTTTGATCCTGGCTCAGGACGAACGCTGGCGGCGTGCTTAACACATG

CAAGTCGAACGGAAAGGCCCTGCTTTTGTGGGGTGCTCGAGTGGCGAACG

GGTGAGTAACACGTGAGTAACCTGCCCTTGACTTTGGGATAACTTCAGGA

AACTGGGGCTAATACCGGATAGGAGCTCCTGCTGCATGGTGGGGGTTGGA

AAGTTTCGGCGGTTGGGGATGGACTCGCGGCTTATCAGCTTGTTGGTGGG

GTAGTGGCTTACCAAGGCTTTGACGGGTAGCCGGCCTGAGAGGGTGACCG

GCCACATTGGGACTGAGATACGGCCCAGACTCCTACGGGAGGCAGCAGTG

GGGAATATTGCACAATGGGCGGAAGCCTGATGCAGCAACGCCGCGTGCGG

GATGACGGCCTTCGGGTTGTAAACCGCTTTCGCCTGTGACGAAGCGTGAG

TGACGGTAATGGGTAAAGAAGCACCGGCTAACTACGTGCCAGCAGCCGCG

GTAATACGTAGGGTGCGAGCGTTGTCCGGATTTATTGGGCGTAAAGGGCT

CGTAGGTGGTTGATCGCGTCGGAAGTGTAATCTTGGGGCTTAACCCTGAG

CGTGCTTTCGATACGGGTTGACTTGAGGAAGGTAGGGGAGAATGGAATTC

CTGGTGGAGCGGTGGAATGCGCAGATATCAGGAGGAACACCAGTGGCGAA

GGCGGTTCTCTGGGCCTTTCCTGACGCTGAGGAGCGAAAGCGTGGGGAGC

GAACAGGCTTAGATACCCTGGTAGTCCACGCTGTAAACGGTGGGTACTAG

GTGTGGGGTCCATTCCACGGGTTCCGTGCCGTAGCTAACGCTTTAAGTAC

CCCGCCTGGGGAGTACGGCCGCAAGGCTAAAACTCAAAGGAATTGACGGG

GCCCCGCACAAGCGGCGGAGCATGCGGATTAATTCGATGCAACGCGTAGA

ACCTTACCTGGGTTTGACATGGATCGGGAGTGCTCAGAGATGGGTGTGCC

TCTTTTGGGGTCGGTTCACAGGTGGTGCATGGCTGTCGTCAGCTCGTGTC

GTGAGATGTTGGGTTAAGTCCCGCAACGAGCGCAACCCTTGTTCACTGTT

GCCAGCACGTTATGGTGGGGACTCAGTGGAGACCGCCGGGGTCAACTCGG

AGGAAGGTGGGGATGACGTCAAGTCATCATGCCCCTTATGTCCAGGGCTT

CACGCATGCTACAATGGCTGGTACAGAGAGTGGCGAGCCTGTGAGGGTGA

GCGAATCTCGGAAAGCCGGTCTCAGTTCGGATTGGGGTCTGCAACTCGAC

CTCATGAAGTCGGAGTCGCTAGTAATCGCAGATCAGCAACGCTGCGGTGA

ATACGTTCCCGGGGCTTGTACACACCGCCCGTCAAGTCATGAAAGTTGGT

AACACCCGAAGCCGGTGGCCTAACCGTTGTGGGGGAGCCGTCGAAGGTGG

-continued

GACTGGTGATTAGGACTAAGTCGTAACAAGGTAGCCGTACCGGAAGGTGC

GGCTGGATCACCTCCTTTCTAAGGA

SEQ ID NO: 8 is as follows (mutations compared to the 16S sequence of the type strain KPA171202 are underlined):

AGAGTTTGATCCTGGCTCAGGACGAACGCTGGCGGCGTGCTTAACACATG

CAAGTCGAACGGAAAGGCCCTGCTTTTGTGGGGTGCTCGAGTGGCGAACG

GGTGAGTAACACGTGAGTAACCTGCCCTTGACTTTGGGATAACTTCAGGA

AACTGGGGCTAATACCGGATAGGAGCTCCTGCTGCATGGTGGGGGTTGGA

AAGTTTCGGCGGTTGGGGATGGACTCGCGGCTTATCAGCTTGTTGGTGGG

GTAGTGGCTTACCAAGGCTTTGACGGGTAGCCGGCCTGAGAGGGTGACCG

GCCACATTGGGACTGAGATACGGCCCAGACTCCTACGGGAGGCAGCAGTG

GGGAATATTGCACAATGGGCGGAAGCCTGATGCAGCAACGCCGCGTGCGG

GATGACGGCCTTCGGGTTGTAAACCGCTTTCGCCTGTGACGAAGCGTGAG

TGACGGTAATGGGTAAAGAAGCACCGGCTAACTACGTGCCAGCAGCCGCG

GTGATACGTAGGGTGCGAGCGTTGTCCGGATTTATTGGGCGTAAAGGGCT

CGTAGGTGGTTGATCGCGTCGGAAGTGTAATCTTGGGGCTTAACCCTGAG

CGTGCTTTCGATACGGGTTGACTTGAGGAAGGTAGGGGAGAATGGAATTC

CTGGTGGAGCGGTGGAATGCGCAGATATCAGGAGGAACACCAGTGGCGAA

GGCGGTTCTCTGGGCCTTTCCTGACGCTGAGGAGCGAAAGCGTGGGGAGC

GAACAGGCTTAGATACCCTGGTAGTCCACGCTGTAAACGGTGGGTACTAG

GTGTGGGGTCCATTCCACGGGTTCCGTGCCGTAGCTAACGCTTTAAGTAC

CCCGCCTGGGGAGTACGGCCGCAAGGCTAAAACTCAAAGGAATTGACGGG

GCCCCGCACAAGCGGCGGAGCATGCGGATTAATTCGATGCAACGCGTAGA

ACCTTACCTGGGTTTGACATGGATCGGAAGCGCTCAGAGATGGGTGTGCC

TCTTTTGGGGTCGGTTCACAGGTGGTGCATGGCTGTCGTCAGCTCGTGTC

GTGAGATGTTGGGTTAAGTCCCGCAACGAGCGCAACCCTTGTTCACTGTT

GCCAGCACGTTATGGTGGGGACTCAGTGGAGACCGCCGGGGTCAACTCGG

AGGAAGGTGGGGATGACGTCAAGTCATCATGCCCCTTATGTCCAGGGCTT

CACGCATGCTACAATGGCTGGTACAGAGAGTGGCGAGCCTGTGAGGGTGA

GCGAATCTCGGAAAGCCGGTCTCAGTTCGGATTGGGGTCTGCAACTCGAC

CTCATGAAGTCGGAGTCGCTAGTAATCGCAGATCAGCAACGCTGCGGTGA

ATACGTTCCCGGGGCTTGTACACACCGCCCGTCAAGTCATGAAAGTTGGT

AACACCCGAAGCCGGTGGCCTAACCGTTGTGGGGGAGCCGTCGAAGGTGG

GACTGGTGATTAGGACTAAGTCGTAACAAGGTAGCCGTACCGGAAGGTGC

GGCTGGATCACCTCCTTTCTAAGGA

SEQ ID NO: 9 is as follows (a mutation compared to the 16S sequence of the type strain KPA171202 is underlined):

AGAGTTTGATCCTGGCTCAGGACGAACGCTGGCGGCGTGCTTAACACATG

CAAGTCGAACGGAAAGGCCCTGCTTTTGTGGGGTGCTCGAGTGGCGAACG

-continued

GGTGAGTAACACGTGAGTAACCTGCCCTTGACTTTGGGATAACTTCAGGA

AACTGGGGCTAATACCGGATAGGAGCTCCTGCTGCATGGTGGGGGTTGGA

AAGTTTCGGCGGTTGGGGATGGACTCGCGGCTTATCAGCTTGTTGGTGGG

GTAGTGGCTTACCAAGGCTTTGACGGGTAGCCGGCCTGAGAGGGTGACCG

GCCACATTGGGACTGAGATACGGCCCAGACTCCTACGGGAGGCAGCAGTG

GGGAATATTGCACAATGGGCGGAAGCCTGATGCAGCAACGCCGCGTGCGG

GATGACGGCCTTCGGGTTGTAAACCGCTTTCGCCTGTGACGAAGCGTGAG

TGACGGTAATGGGTAAAGAAGCACCGGCTAACTACGTGCCAGCAGCCGCG

GTGATACGTAGGGTGCGAGCGTTGTCCGGATTTATTGGGCGTAAAGGGCT

CGTAGGTGGTTGATCGCGTCGGAAGTGTAATCTTGGGGCTTAACCCTGAG

CGTGCTTTCGATACGGGTTGACTTGAGGAAGGTAGGGGAGAATGGAATTC

CTGGTGGAGCGGTGGAATGCGCAGATATCAGGAGGAACACCAGTGGCGAA

GGCGGTTCTCTGGGCCTTTCCTGACGCTGAGGAGCGAAAGCGTGGGGAGC

GAACAGGCTTAGATACCCTGGTAGTCCACGCTGTAAACGGTGGGTACTAG

GTGTGGGGTCCATTCCACGGGTTCCGTGCCGTAGCTAACGCTTTAAGTAC

CCCGCCTGGGGAGTACGGCCGCAAGGCTAAAACTCAAAGGAATTGACGGG

GCCCCGCACAAGCGGCGGAGCATGCGGATTAATTCGATGCAACGCGTAGA

ACCTTACCTGGGTTTGACATGGATCGGGAGTGCTCAGAGATGGGTGTGCC

TCTTTTGGGGTCGGTTCACAGGTGGTGCATGGCTGTCGTCAGCTCGTGTC

GTGAGATGTTGGGTTAAGTCCCGCAACGAGCGCAACCCTTGTTCACTGTT

GCCAGCACGTTATGGTGGGGACTCAGTGGAGACCGCCGGGGTCAACTCGG

AGGAAGGTGGGGATGACGTCAAGTCATCATGCCCCTTATGTCCAGGGCTT

CACGCATGCTACAATGGCTGGTACAGAGAGTGGCGAGCCTATGAGGGTGA

GCGAATCTCGGAAAGCCGGTCTCAGTTCGGATTGGGGTCTGCAACTCGAC

CTCATGAAGTCGGAGTCGCTAGTAATCGCAGATCAGCAACGCTGCGGTGA

ATACGTTCCCGGGGCTTGTACACACCGCCCGTCAAGTCATGAAAGTTGGT

AACACCCGAAGCCGGTGGCCTAACCGTTGTGGGGGAGCCGTCGAAGGTGG

GACTGGTGATTAGGACTAAGTCGTAACAAGGTAGCCGTACCGGAAGGTGC

GGCTGGATCACCTCCTTTCTAAGGA

SEQ ID NO: 10 is as follows (mutations compared to the 16S sequence of the type strain KPA171202 are underlined):

AGAGTTTGATCCTGGCTCAGGACGAACGCTGGCGGCGTGCTTAACACATG

CAAGTCGAACGGAAAGGCCCTGCTTTTGTGGGGTGCTCGAGTGGCGAACG

GGTGAGTAACACGTGAGTAACCTGCCCTTGACTTTGGGATAACTTCAGGA

AACTGGGGCTAATACCGGATAGGAGCTCCTGCTGCATGGTGGGGGTTGGA

AAGTTTCGGCGGTTGGGGATGGACTCGCGGCTTATCAGCTTGTTGGTGGG

GTAGTGGCTTACCAAGGCTTTGACGGGTAGCCGGCCTGAGAGGGTGACCG

GCCACATTGGGACTGAGATACGGCCCAGACTCCTACGGGAGGCAGCAGTG

GGGAATATTGCACAATGGGCGGAAGCCTGATGCAGCAACGCCGCGTGCGG

GATGACGGCCTTCGGGTTGTAAACCGCTTTCGCCTGTGACGAAGCGTGAG

```
-continued
TGACGGTAATGGGTAAAGAAGCACCGGCTAACTACGTGCCAGCAGCCGCG

GTGATACGTAGGGTGCGAGCGTTGCCCGGATTTATTGGGCGTAAAGGGCT

CGTAGGTGGTTGATCGCGTCGGAAGTGTAATCTTGGGGCTTAACCCTGAG

CGTGCTTTCGATACGGGTTGACTTGAGGAAGGTAGGGGAGAATGGAATTC

CTGGTGGAGCGGTGGAATGCGCAGATATCAGGAGGAACACCAGTGGCGAA

GGCGGTTCTCTGGGCCTTTCCTGACGCTGAGGAGCGAAAGCGTGGGGAGC

GAACAGGCTTAGATACCCTGGTAGTCCACGCTGTAAACGGTGGGTACTAG

GTGTGGGGTCCATTCCACGGGTTCCGTGCCGTAGCTAACGCTTTAAGTAC

CCCGCCTGGGGAGTACGGCCGCAAGGCTAAAACTCAAAGGAATTGACGGG

GCCCCGCACAAGCGGCGGAGCATGCGGATTAATTCGATGCAACGCGTAGA

ACCTTACCTGGGTTTGACATGGATCGGGAGTGCTCAGAGATGGGTGTGCC

TCTTTTGGGGTCGGTTCACAGGTGGTGCATGCCTGTCGTCAGCTCGTGTC

GTGAGATGTTGGGTTAAGTCCCGCAACGAGCGCAACCCTTGTTCACTGTT

GCCAGCACGTTATGGTGGGGACTCAGTGGAGACCGCCGGGGTCAACTCGG

AGGAAGGTGGGGATGACGTCAAGTCATCATGCCCCTTATGTCCAGGGCTT

CACGCATGCTACAATGGCTGGTACAGAGAGTGGCGAGCCTGTGAGGGTGA

GCGAATCTCGGAAAGCCGGTCTCAGTTCGGATTGGGGTCTGCAACTCGAC

CTCATGAAGTCGGAGTCGCTAGTAATCGCAGATCAGCAACGCTGCGGTGA

ATACGTTCCCGGGGCTTGTACACACCGCCCGTCAAGTCATGAAAGTTGGT

AACACCCGAAGCCGGTGGCCTAACCGTTGTGGGGGAGCCGTCGAAGGTGG

GACTGGTGATTAGGACTAAGTCGTAACAAGGTAGCCGTACCGGAAGGTGC

GGCTGGATCACCTCCTTTCTAAGGA
```

In embodiments, the at least one additional bacterium comprises, consists essentially of, or consists of a probiotic bacterium. In embodiments, the at least one bacterium includes 1, 2, 3, 4, 5, 6, 7, 8, 9, or 10 bacterial strains and/or species, less than about 10, 9, 8, 7, 6, 5, 4, 3, or 2 bacterial strains and/or species, or 1-10, 2-10, 3-10, 4-10, 5-10, 1-5, 2-5, 3-5, or 4-5 bacterial strains and/or species. In embodiments, the at least one bacterium includes a plurality of bacterial strains and/or species, e.g., at least about 2, 3, 4, 5, 6, 7, 8, 9, 10 bacterial strains and/or species. In embodiments, the least one bacterium includes an isolated *Propionibacterium granulosum* bacterium, an isolated *Propionibacterium avidum* bacterium, an isolated *Staphylococcus epidermidis* bacterium, an isolated *Staphylococcus aureus* bacterium, and/or an isolated *Corynebacterium jeikeium* bacterium. In embodiments, the least one bacterium includes 1, 2 (of any combination of), 3 (of any combination of), 4 (of any combination of), or 5 of an isolated *Propionibacterium granulosum* bacterium, an isolated *Propionibacterium avidum* bacterium, an isolated *Staphylococcus epidermidis* bacterium, an isolated *Staphylococcus aureus* bacterium, and/or an isolated *Corynebacterium jeikeium* bacterium.

In embodiments, a composition or combination provided herein includes an enhancing peptide or enzyme. In embodiments, the enhancing peptide or enzyme has one or more or any combination of the following properties: biofilm degradation, improving skin penetration, antibacterial, reducing inflammation (e.g., of the skin), reducing irritation (e.g., of the skin), reducing redness (e.g., of the skin), firming skin, removing lines, removing wrinkles, or otherwise improving appearance (e.g., of the skin).

In an aspect, a composition that includes a *P. acnes* bacteriophage and an anti-acne compound is provided. In embodiments, the composition includes a pharmaceutically acceptable carrier. In embodiments, the dose of the *P. acnes* bacteriophage is adjusted (e.g., increased or decreased) for stability. In embodiments, the dose of the *P. acnes* bacteriophage is adjusted up or down depending on the anti-acne compound to adjust for its stability in combination with the anti-acne compound.

In an aspect, a combination or system that includes a *P. acnes* bacteriophage and one or more anti-acne compounds is provided. In an example, the bacteriophage is within one composition (e.g., within one vessel such as a bottle, tube, or other container), and the one or more anti-acne compounds are in a separate composition (within another vessel such as a bottle, tube, or other container). In embodiments, the composition that includes the bacteriophage includes a pharmaceutically acceptable carrier. In embodiments, the composition that includes the anti-acne compound includes a pharmaceutically acceptable carrier. In embodiments, an additional one or more compounds (e.g. an enzyme, a hydrating compound, an ultraviolet radiation absorbing or blocking compound, etc.) are present in the composition that includes the bacteriophage, the composition that includes the one or more anti-acne compounds, or a third separate composition (within a third vessel such as a bottle, tube, or other container). In embodiments, one or more probiotic bacteria are present in the composition that includes the bacteriophage, the composition that includes the one or more anti-acne compounds, or a third separate composition (within a third vessel such as a bottle, tube, or other container). In embodiments, the combination or system further includes instructions for administration. In embodiments, the combination or system includes at least about 2, 3, 4, 5, 6, 7, 8, 9, or 10 *P. acnes* bacteriophages.

In an aspect, a combination or system that includes a *P. acnes* bacteriophage and one or more probiotic bacteria and/or one or more compounds (such as one or more enzymes or anti-acne compounds) is provided. In an example, the bacteriophage is within one composition (e.g., within one vessel such as a bottle, tube, or other container), and the one or more probiotic bacteria are in a separate composition (within another vessel such as a bottle, tube, or other container), and optionally, an additional one or more compounds are present in the composition that includes the bacteriophage, the composition that includes the one or more probiotic bacteria, or a third separate composition (within a third vessel such as a bottle, tube, or other container). In embodiments, the combination or system further includes instructions for administration. In embodiments, the combination or system includes at least about 2, 3, 4, 5, 6, 7, 8, 9, or 10 *P. acnes* bacteriophages.

In embodiments, a system, combination, or composition includes an enzyme such as a biofilm degradation enzyme or an anti-aging enzyme. Non-limiting examples of biofilm degradation enzymes include DNAses (e.g., DNAse I), proteases (e.g., papain, bromelain, Trypsin, Proteinase K, Subtilisin, or serratiopeptidase), glycosidases (e.g., dispersin, alginate lyase, amylase, or cellulase). Non-limiting examples of anti-aging enzymes include superoxide dismutase, and peroxidase.

In embodiments, a system, combination, or composition includes a topical retinoid, an antibiotic, and/or an alpha-hydroxy acid. In embodiments, a system or composition further includes a topical retinoid. In embodiments, a system or composition further includes an antibiotic. In embodiments, a system or composition further includes an alpha-hydroxy acid. In embodiments, the system or composition further includes benzoyl peroxide, salicylic acid, sulfur, resorcinol, resorcinol monoacetate, or any combination thereof. In embodiments, the benzoyl peroxide is present at a concentration of 2.5% to 10%, e.g., about 2.5%, 3%, 3.5%, 4%, 4.5%, 5%, 5.5%, 6%, 6.5%, 7%, 7.5%, 8%, 8.5%, 9%, 9.5%, or 10% (weight/volume). In embodiments, the benzoyl peroxide is present at a concentration of less than 2.5% but greater than about 0.1%, 0.5%, 1%, 1.5%, or 2% (weight/volume). In embodiments, the salicylic acid is present at a concentration of 0.5% to 2%, e.g., about 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (weight/volume). In embodiments, the salicylic acid is present at a concentration of less than 0.5% but greater than about 0.1% (weight/volume). In embodiments, the sulfur is present at a concentration of 3% to 10%, e.g., about 3%, 3.5%, 4%, 4.5%, 5%, 5.5%, 6%, 6.5%, 7%, 7.5%, 8%, 8.5%, 9%, 9.5%, or 10% (weight/volume). In embodiments, the sulfur is present at a concentration of less than 3% but greater than about 0.1%, 0.5%, 1, 1.5%, 2%, or 2.5% (weight/volume). In embodiments, resorcinol is present at a concentration of 2% and sulfur is present at a concentration of 3% to 8% (e.g., about 2.5%, 3%, 3.5%, 4%, 4.5%, 5%, 5.5%, 6%, 6.5%, 7%, 7.5%, or 8%) (weight/volume). In embodiments, resorcinol monoacetate is present at a concentration of 3% and sulfur is present at a concentration of 3% to 8% (e.g., about 2.5%, 3%, 3.5%, 4%, 4.5%, 5%, 5.5%, 6%, 6.5%, 7%, 7.5%, or 8%) (weight/volume). In embodiments, the resorcinol is present at a concentration of less than 2% but greater than about 0.1%, 0.5%, 1%, 1.5% (weight/volume). In embodiments, the resorcinol monoacetate is present at a concentration of less than 3% but greater than about 0.1%, 0.5%, 1%, 1.5%, 2%, or 2.5% (weight/volume).

In embodiments, a composition provide herein includes a moisturizer.

Methods of Treating Acne

In an aspect, provided herein is a method of preventing or treating acne in a subject in need thereof, the method including administering an effective amount of a composition or combination provided herein. In embodiments, an effective amount of a composition comprising, consisting essentially of, or consisting of at least one *P. acnes* bacteriophage, at least one anti-acne compound, and a pharmaceutically acceptable carrier is administered to the subject. In embodiments, an effective amount of a composition that includes at least one *P. acnes* bacteriophage, at least one anti-acne compound and a pharmaceutically acceptable carrier, wherein the composition does not comprise a probiotic bacterium, is administered to the subject.

In embodiments, an effective amount of a composition that includes a *P. acnes* bacteriophage and an enzyme is administered to the subject.

In embodiments, an effective amount of a composition that includes a bacteriophage as described herein, including embodiments thereof, is administered to the subject. In embodiments, the bacteriophage is a wild-type bacteriophage.

In embodiments, the bacteriophage is administered topically. In embodiments, the bacteriophage is in a composition (e.g., a pharmaceutical or cosmetic composition) that further includes a pharmaceutically or cosmetically acceptable carrier.

In embodiments, the method further includes administering a probiotic bacterium to the subject.

In an aspect, a method of treating acne in a subject in need thereof is provided. The method includes administering an effective amount of a probiotic *P. acnes* bacterium to the subject. In embodiments, the method further includes administering a bacteriophage to the subject.

In embodiments, the *P. acnes* bacterium has a 16S rDNA sequence that includes a T992C, T838C, C1322T, and/or a C986T mutation compared to the KPA171202 type strain 16S rDNA sequence set forth as SEQ ID NO: 2. In embodiments, the *P. acnes* bacterium includes a 16S rDNA sequence with a T838C and a C1322T mutation compared to the KPA171202 type strain 16S rDNA sequence set forth as SEQ ID NO: 2. In embodiments, the *P. acnes* bacterium is the ProI strain. In embodiments, the *P. acnes* bacterium includes a 16S rDNA sequence with a C986T and a T992C mutation compared to the KPA171202 type strain 16S rDNA sequence set forth as SEQ ID NO: 2. In embodiments, the *P. acnes* bacterium is the ProII strain.

In embodiments, the *P. acnes* bacterium: (a) includes a 16S rDNA sequence with a T992C mutation compared to the KPA171202 type strain 16S rDNA sequence set forth as SEQ ID NO: 2; (b) includes a 16S rDNA sequence with a T838C mutation compared to the KPA171202 type strain 16S rDNA sequence set forth as SEQ ID NO: 2; (c) includes a 16S rDNA sequence with a C1322T mutation compared to the KPA171202 type strain 16S rDNA sequence set forth as SEQ ID NO: 2; (d) includes a 16S rDNA sequence with a C986T mutation compared to the KPA171202 type strain 16S rDNA sequence set forth as SEQ ID NO: 2; (e) includes a 16S rDNA sequence that is identical to the sequence of SEQ ID NO: 3; (g) includes a 16S rDNA sequence that is identical to the sequence of SEQ ID NO: 4; (h) does not comprise a linear plasmid; (i) does not include a plasmid that includes a virulence factor; and/or (j) does not include a plasmid that encodes an extrachromosomal lipase and/or a tight adhesion virulence factor.

In embodiments, the method further includes administering at least one additional probiotic bacterium to the subject.

In embodiments, the at least one additional bacterium comprises, consists essentially of, or consists of a probiotic bacterium. In embodiments, the at least one bacterium includes 1, 2, 3, 4, 5, 6, 7, 8, 9, or 10 bacterial strains and/or species, less than about 10, 9, 8, 7, 6, 5, 4, 3, or 2 bacterial strains and/or species, or 1-10, 2-10, 3-10, 4-10, 5-10, 1-5, 2-5, 3-5, or 4-5 bacterial strains and/or species. In embodiments, the at least one bacterium includes a plurality of bacterial strains and/or species, e.g., at least about 2, 3, 4, 5, 6, 7, 8, 9, 10 bacterial strains and/or species. In embodiments, the least one bacterium includes a *Propionibacterium* sp., *Staphylococcus* sp., and/or *Corynebacterium* sp. bacterium. In embodiments, the least one bacterium includes bacterium within the class Betaproteobacteria. In embodiments, the least one bacterium includes an isolated *Propionibacterium granulosum* bacterium, an isolated *Propionibacterium avidum* bacterium, an isolated *Staphylococcus epidermidis* bacterium, an isolated *Staphylococcus aureus* bacterium, and/or an isolated *Corynebacterium jeikeium* bacterium. In embodiments, the least one bacterium includes 1, 2, 3, 4, or 5 of an isolated *Propionibacterium granulosum* bacterium, an isolated *Propionibacterium avidum* bacterium, an isolated *Staphylococcus epidermidis* bacterium, an isolated *Staphylococcus aureus* bacterium, and/or an isolated *Corynebacterium jeikeium* bacterium.

In embodiments, the subject has been administered a bacteriophage as described herein, including embodiments thereof.

In embodiments, the subject has been administered an antibiotic that kills *P. acnes*. In embodiments, the antibiotic is clindamycin, doxycycline, erythromycin, or tetracycline, or a derivative of clindamycin, doxycycline, erythromycin, or tetracycline.

In embodiments, the antibiotic is clindamycin, doxycycline, erythromycin, or tetracycline, or a derivative of clindamycin, doxycycline, erythromycin, or tetracycline.

In embodiments, the method further includes administering an enzyme to the subject such as a biofilm degradation enzyme or an anti-aging enzyme. Non-limiting examples of biofilm degradation enzymes include DNAses (e.g., DNAse I), restriction endonucleases, proteases (e.g., papain, bromelain, Trypsin, Proteinase K, Subtilisin, or serratiopeptidase), glycosidases (e.g., dispersin, alginate lyase, amylase, or cellulase). Non-limiting examples of anti-aging enzymes include superoxide dismutase, and peroxidase.

In embodiments, the method further includes administering a topical retinoid, an antibiotic, and/or an alpha-hydroxy acid. In embodiments, the method further includes administering a topical retinoid. In embodiments, the method further includes administering an antibiotic. In embodiments, the method further includes administering an alpha-hydroxy acid. In embodiments, the method further includes administering benzoyl peroxide, salicylic acid, sulfur, resorcinol, and/or resorcinol monoacetate to the subject. In embodiments, the method further includes administering benzoyl peroxide. In embodiments, the method further includes administering salicylic acid. In embodiments, the method further includes administering sulfur. In embodiments, the method further includes administering resorcinol and/or sulfur. In embodiments, the method further includes administering resorcinol and/or resorcinol monoacetate.

In embodiments, the method further includes administering an enhancing peptide or enzyme. In embodiments, the enhancing peptide or enzyme has one or more or any combination of the following properties: biofilm degradation, improving skin penetration, antibacterial, reducing inflammation (e.g., of the skin), reducing irritation (e.g., of the skin), reducing redness (e.g., of the skin), firming skin, removing lines, removing wrinkles, or otherwise improving appearance (e.g., of the skin).

In embodiments, at least about 2, 3, 4, 5, 6, 7, 8, 9, or 10 *P. acnes* bacteriophages are administered to the subject. In embodiments, the *P. acnes* bacteriophages include more than one types of *P. acnes* bacteriophage.

Exemplary Methods and Compositions for Treating Acne

In an aspect, provided herein is a composition that includes a bacteriophage. In embodiments, the bacteriophage is present in a composition, such as a therapeutic or cosmetic composition. In embodiments, the composition further includes a strain of probiotic bacteria. In embodiments, the composition further includes an enzyme that degrades a bacterial biofilms (e.g., a component thereof) in or on human skin pores. In embodiments, the enzyme enhances penetration of the bacteriophage and/or the probiotic bacteria. In embodiments, a bacteriophage ("phage") destroys an acne-causing (i.e., pathogenic) strain of *P. acnes* with a high degree of specificity and efficacy, without killing beneficial skin bacteria. In embodiments, the biofilm-degrading enzyme dissolves the biofilm to increase the susceptibility of the pathogen (e.g., by reducing pathogen adherence to host cells and/or by increasing access of the bacteriophage to pathogenic cells). In embodiments, the probiotic bacteria are immune to the bacteriophage (e.g., the bacteria lack a cellular receptor to which the bacteriophage specifically binds). In embodiments, the probiotic bacteria occupy the niche left by a killed *P. acnes* pathogenic strain. In embodiments the probiotic bacteria reduce or prevent the recolonization or growth of a subject's skin (such as a pore) by surviving pathogenic bacteria.

In an aspect a composition for the therapeutic treatment of the skin disease acne is provided. In embodiments, the composition includes a lytic *P. acnes* bacteriophage, and optionally a probiotic bacterium sourced from healthy skin, and/or optionally a biofilm-degrading enzyme in the composition as an adjuvant to increase penetration of the active components.

In embodiments, a lytic *P. acnes* bacteriophage infects virulent *P. acnes* in a skin comedone. In embodiments, the bacteriophage replicates and lyses within the *P. acnes*. In embodiments, when the *P. acnes* lyses, it releases new virions. In embodiments, enzymes unclog the blocked comedones, dissolve the *P. acnes* biofilms and increase access of virions to *P. acnes*. In embodiments, the exponential proliferation of lytic *P. acnes* phages rapidly kills the *P. acnes* with high specificity, without disturbing the growth beneficial skin commensal bacteria. In embodiments, the niche vacated by the *P. acnes* is then be filled by the probiotic bacteria. In embodiments, the bacteria are sourced from healthy skin and expand to occupy the niche, thereby preventing any surviving *P. acnes* bacteria from growing back. In embodiments, this strategy helps to balance the skin microbiome in subjects and recalibrates their microbiome toward a healthy skin bacterial community. In embodiments, the biofilm-degrading enzyme is in a formulation as an adjuvant that helps unclog blocked comedones and increase access of the phage and probiotic bacteria to the pores.

In an aspect, a combination that includes a bacteriophage, a probiotic bacterium, and (optionally) an enzyme that enhances the penetration of the bacteriophage is provided. In embodiments, the pathogens are killed and the probiotic bacterium replaces the pathogen. In embodiments, a "kill and replace" approach to is used to treat acne. In embodiments, a biologic that selectively kills pathogenic bacteria that cause acne is administered to a subject. In embodiments, probiotic bacteria sourced from healthy skin are applied to occupy the niche of the killed pathogen. In embodiments, this approach avoids the problems of rampant drug resistance associated with antibiotics. In embodiments, the presence of actively dividing probiotic bacteria prevents relapses by not allowing any pathogens to grow back. In embodiments, dysbiosis on the skin of the subject is treated. In embodiments, a microbiome associated with acne is recalibrated into a healthy one.

In embodiments, the bacteriophage is a naturally occurring *P. acnes* bacteriophage.

Non-limiting examples of enzymes that may be co-administered with a bacteriophage include BL00275 from *Bacillus licheniformis*; DNase I; restriction endonucleases; deoxyribonucleases (e.g. from *Staphylococcus aureus* thermonuclease, *B. licheniformis* NucB, DNase 1L2); glycoside hydrolases (e.g. Dispersin B, alginate lyase, amylase, cellulase, glycanase); and proteases (e.g. subtlisin, proteinase K, trypsin, serratiopeptidase).

Non-limiting examples of probiotic bacteria that may be administered or present in a system or composition include one or more or any combination of the following bacterial species: *Propionibacterium* acnes, *Propionibacterium* granulosum, *Propionibacterium avidum, Staphylococcus epidermidis, Staphylococcus aureus*, and *Corynebacterium jeikeium*. In embodiments, a probiotic bacterial strain is be selected based on its ability to (a) colonize the skin without eliciting an adverse immune response, characterized by low lipase activity and reduced adhesion to human keratinocytes; and (b) occupy a niche similar to *Propionibacterium* acnes.

In embodiments, a biofilm degrading enzyme is present in the formulation and acts as an adjuvant, to increase the efficacy of the active ingredients (such as a bacteriophage). In embodiments, the enzyme has the capacity to degrade *P. acnes* biofilms in vitro.

EMBODIMENTS

Embodiments and examples are provided below to facilitate a more complete understanding of the invention. The following embodiments and examples illustrate the exemplary modes of making and practicing the invention. However, the scope of the invention is not limited to specific embodiments disclosed in these embodiments and examples, which are for purposes of illustration only, since alternative methods can be utilized to obtain similar results.

Embodiments include Embodiments P1 to P56 following:

Embodiment P1. A composition consisting essentially of at least one *Propionibacterium acnes* bacteriophage, at least one anti-acne compound, and a pharmaceutically acceptable carrier.

Embodiment P2. A composition comprising at least one *Propionibacterium acnes* bacteriophage, at least one anti-acne compound, and a pharmaceutically acceptable carrier, wherein the composition does not comprise a probiotic bacterium.

Embodiment P3. The composition of Embodiment P2, wherein the composition further comprises a *P. acnes* biofilm degrading enzyme.

Embodiment P4. The composition of any one of Embodiments P1-P3, wherein the at least one anti-acne compound is benzoyl peroxide.

Embodiment P5. The composition of Embodiment P4, wherein the benzoyl peroxide is present at a concentration of 2.5% to 10% (weight/volume).

Embodiment P6. The composition of Embodiment P4, wherein the benzoyl peroxide is present at a concentration of less than 2.5% but greater than about 0.1%, 0.5%, 1%, 1.5%, or 2% (weight/volume).

Embodiment P7. The composition of any one of Embodiments P1-P3, wherein the at least one anti-acne compound is salicylic acid.

Embodiment P8. The composition of Embodiment P7, wherein the salicylic acid is present at a concentration of 0.5% to 2% (weight/volume).

Embodiment P9. The composition of Embodiment P7, wherein the salicylic acid is present at a concentration of less than 0.5% but greater than about 0.1% (weight/volume).

Embodiment P10. The composition of any one of Embodiments P1-P3, wherein the at least one anti-acne compound is sulfur.

Embodiment P11. The composition of Embodiment P10, wherein the sulfur is present at a concentration of 3% to 10% (weight/volume).

Embodiment P12. The composition of Embodiment P10, wherein the sulfur is present at a concentration of less than 3% but greater than about 0.1%, 0.5%, 1%, 1.5%, 2%, or 2.5% (weight/volume).

Embodiment P13. The composition of any one of Embodiments P1-P3, wherein the at least one anti-acne compound is resorcinol and sulfur.

Embodiment P14. The composition of Embodiment P13, wherein the resorcinol is present at a concentration of 2% and sulfur is present at a concentration of 3% to 8% (weight/volume).

Embodiment P15. The composition of any one of Embodiments P1-P3, wherein the at least one anti-acne compound comprises resorcinol monoacetate and sulfur.

Embodiment P16. The composition of Embodiment P15, wherein the resorcinol monoacetate is present at a concentration of 3% and sulfur is present at a concentration of 3% to 8% (weight/volume).

Embodiment P17. The composition of any one of Embodiments P1-P3, wherein the anti-acne compound is an antibiotic, a retinoid, or an alpha-hydroxy acid.

Embodiment P18. A composition comprising a *Propionibacterium acnes* bacteriophage and an enzyme.

Embodiment P19. The composition of any one of Embodiments P1-P18, wherein the *P. acnes* bacteriophage is a lytic *P. acnes* bacteriophage.

Embodiment P20. The composition of any one of Embodiments P1-P19, wherein the *P. acnes* bacteriophage comprises a linear double stranded DNA genome.

Embodiment P21. The composition of any one of Embodiments P1-P20, wherein the *P. acnes* bacteriophage is within the bacteriophage family Siphoviridae.

Embodiment P22. The composition of any one of Embodiments P1-P21, wherein the genome of the *P. acnes* bacteriophage comprises a nucleotide sequence that is at least about 80%, 85%, 90%, 95%, 96%, 97%, 98%, or 99% identical to the nucleotide sequence of SEQ ID NO: 1.

Embodiment P23. The composition of any one of Embodiments P18-P21, wherein the enzyme is a *P. acnes* biofilm degrading enzyme.

Embodiment P24. The composition of any one of Embodiments P3 or P18-P23, wherein the enzyme is a glycosidase, a protease, a DNAse, or a restriction endonuclease.

Embodiment P25. The composition of any one of Embodiments P3 or P18-P24, wherein the enzyme is a glycosidase.

Embodiment P26. The composition of Embodiment P25, wherein the glycosidase is a glycoside hydrolase.

Embodiment P27. The composition of Embodiment P26, wherein the enzyme catalyzes the hydrolysis of linear polymers of N-acetyl-D-glucosamines.

Embodiment P28. The composition of Embodiment P27, wherein the enzyme is a (3-hexosaminidase.

Embodiment P29. The composition of Embodiment P28, wherein the enzyme is hydrolyzes β-1,6-glycosidic linkages of acetylglucosamine polymers.

Embodiment P30. The composition of any one of Embodiments P3 or P18-P24, wherein the enzyme is a DNAse I, a restriction endonuclease, papain, bromelain, Trypsin, Proteinase K, Subtilisin, serratiopeptidase, dispersin, alginate lyase, amylase, or cellulase.

Embodiment P31. The composition of any one of Embodiments P3 or P18-P24, wherein the enzyme is Dispersin B.

Embodiment P32. The composition of any one of Embodiments P3 or P18-P24, wherein the enzyme is a protease, and the protease is proteinase K or subtilisin.

Embodiment P33. composition of any one of Embodiments P18-P22, wherein the enzyme is an anti-aging enzyme.

Embodiment P34. The composition of Embodiment P33, wherein the anti-aging enzyme is a superoxide dismutase or a peroxidase.

Embodiment P35. The composition of any one of Embodiments P18-P34, further comprising a probiotic bacterium.

Embodiment P36. The composition of Embodiment P35, wherein the probiotic bacterium is a probiotic a P. sp., *Staphylococcus* sp., and/or *Corynebacterium* sp. bacterium.

Embodiment P37. The composition of Embodiment P35, wherein the probiotic bacterium is a bacterium within the class Betaproteobacteria.

Embodiment P38. The composition of Embodiment P36, wherein the probiotic bacterium is a probiotic *P. acnes* bacterium.

Embodiment P39. The composition of Embodiment P38, wherein the *P. acnes* bacterium (a) comprises a 16S DNA sequence with a T992C mutation compared to the KPA171202 type strain 16S DNA sequence set forth as SEQ ID NO: 2;

(b) comprises a 16S DNA sequence with a T838C mutation compared to the KPA171202 type strain 16S DNA sequence set forth as SEQ ID NO: 2;

(c) comprises a 16S DNA sequence with a C1322T mutation compared to the KPA171202 type strain 16S DNA sequence set forth as SEQ ID NO: 2;

(d) comprises a 16S DNA sequence with a C986T mutation compared to the KPA171202 type strain 16S DNA sequence set forth as SEQ ID NO: 2;

(e) comprises a 16S DNA sequence that is identical to the sequence of SEQ ID NO: 3;

(f) comprises a 16S DNA sequence that is identical to the sequence of SEQ ID NO: 4;

(g) does not comprise a linear plasmid;

(h) does not comprise a plasmid that comprises a virulence factor; and/or (i) does not comprises a plasmid that encodes an extra-chromosomal lipase and/or a tight adhesion virulence factor.

Embodiment P40. The composition of Embodiment P38, wherein the *P. acnes* bacterium:

(a) produces less than about 20% of the level of lipase that is produced by a pathogenic *P. acnes* strain when grown in a planktonic culture;

(b) produces less than about 10% of the level of lipase that is produced by a pathogenic *P. acnes* strain when grown in an adherent culture;

(c) adheres to epithelial cells at least 50% less than a pathogenic *P. acnes* strain; and/or (d) is less inflammatory than a pathogenic *P. acnes* strain.

Embodiment P41. The composition of any one of Embodiments P35-P40, further comprising at least one additional probiotic bacterium.

Embodiment P42. The composition of Embodiment P41, wherein said at least one additional probiotic bacterium comprises *Propionibacterium granulosum* and/or *Propionibacterium avidum*.

Embodiment P43. The composition of Embodiment P40, wherein said pathogenic *P. acnes* strain (a) comprises a 16S DNA sequence with a G1058C mutation compared to the KPA171202 type strain 16S DNA sequence set forth as SEQ ID NO: 2;

(b) comprises a 16S DNA sequence with a G1058C and an A1201C mutation compared to the KPA171202 type strain 16S DNA sequence set forth as SEQ ID NO: 2;

(c) comprises a 16S DNA sequence with a G529A mutation compared to the KPA171202 type strain 16S DNA sequence set forth as SEQ ID NO: 2;

(d) comprises a 16S DNA sequence with a G1004A and a T1007C mutation compared to the KPA171202 type strain 16S DNA sequence set forth as SEQ ID NO: 2;

(e) comprises a 16S DNA sequence with a G1268A mutation compared to the KPA171202 type strain 16S DNA sequence set forth as SEQ ID NO: 2;

(f) comprises a 16S DNA sequence with a T554C and a G1058C mutation compared to the KPA171202 type strain 16S DNA sequence set forth as SEQ ID NO: 2;

(g) comprises a 16S DNA sequence that is identical to the sequence of SEQ ID NO: 5;

(h) comprises a 16S DNA sequence that is identical to the sequence of SEQ ID NO: 6;

(i) comprises a 16S DNA sequence that is identical to the sequence of SEQ ID NO: 7;

(j) comprises a 16S DNA sequence that is identical to the sequence of SEQ ID NO: 8;

(k) comprises a 16S DNA sequence that is identical to the sequence of SEQ ID NO: 9; and/or (l) comprises a 16S DNA sequence that is identical to the sequence of SEQ ID NO: 10.

Embodiment P44. The composition of any one of Embodiments P18-P43, further comprising at least one additional *P. acnes* bacteriophage.

Embodiment P45. The composition of any one of Embodiments P1-P44, comprising a pharmaceutically acceptable carrier.

Embodiment P46. The composition of Embodiment P45, wherein the pharmaceutically acceptable carrier comprises an emulsion.

Embodiment P47. The composition of Embodiment P46, wherein the emulsion is an oil-in-water emulsion or a water-in-oil emulsion.

Embodiment P48. The composition of any one of Embodiments P1-P47, which is in the form of a cream, lotion, suspension, or aqueous solution.

Embodiment P49. A combination consisting essentially of at least one *Propionibacterium acnes* bacteriophage, and at least one anti-acne compound, wherein each of the at least one *Propionibacterium acnes* bacteriophage and the at least one anti-acne compound is in a composition that further comprises a pharmaceutically acceptable carrier.

Embodiment P50. The combination of Embodiment P49, wherein the at least one *P. acnes* bacteriophage and the at least one anti-acne compound are within separate compositions.

Embodiment P51. The combination of Embodiment P50, wherein the at least one *P. acnes* bacteriophage and the at least one anti-acne compound are within separate containers.

Embodiment P52. A combination comprising a *Propionibacterium acnes* bacteriophage and an enzyme.

Embodiment P53. The combination of Embodiment P52, wherein the *P. acnes* bacteriophage and the enzyme are within separate compositions.

Embodiment P54. The combination of Embodiment P53, wherein the *P. acnes* bacteriophage and the enzyme are within separate containers.

Embodiment P55. A method of treating acne in a subject in need thereof, the method comprising administering an effective amount of the composition of any one of Embodiments P1-P46 or the combination of any one of Embodiments P49-P54 to the subject.

Embodiment P56. The method of Embodiment P55, wherein the composition is administered topically.

Additional embodiments include Embodiments 1 to 55 following:

Embodiment 1. A composition comprising at least one *Propionibacterium acnes* bacteriophage, at least one anti-acne compound, and a pharmaceutically acceptable carrier.

Embodiment 2. The composition of Embodiment 1, which does not comprise a probiotic bacterium.

Embodiment 3. The composition of Embodiment 1 or 2, wherein the composition further comprises a *P. acnes* biofilm degrading enzyme.

Embodiment 4. The composition of any one of Embodiments 1-3, wherein the at least one anti-acne compound is salicylic acid.

Embodiment 5. The composition of Embodiment 4, wherein the salicylic acid is present at a concentration of 0.5% to 2% (weight/volume).

Embodiment 6. The composition of Embodiment 5, wherein the salicylic acid is present at a concentration of less than 0.5% but greater than about 0.1% (weight/volume).

Embodiment 7. The composition of any one of Embodiments 1-3, wherein the at least one anti-acne compound is sulfur.

Embodiment 8. The composition of Embodiment 7, wherein the sulfur is present at a concentration of 3% to 10% (weight/volume).

Embodiment 9. The composition of Embodiment 7, wherein the sulfur is present at a concentration of less than 3% but greater than about 0.1%, 0.5%, 1%, 1.5%, 2%, or 2.5% (weight/volume).

Embodiment 10. The composition of any one of Embodiments 1-3, wherein the at least one anti-acne compound is resorcinol and sulfur.

Embodiment 11. The composition of Embodiment 10, wherein the resorcinol is present at a concentration of 2% and sulfur is present at a concentration of 3% to 8% (weight/volume).

Embodiment 12. The composition of any one of Embodiments 1-3, wherein the at least one anti-acne compound comprises resorcinol monoacetate and sulfur.

Embodiment 13. The composition of Embodiment 12, wherein the resorcinol monoacetate is present at a concentration of 3% and sulfur is present at a concentration of 3% to 8% (weight/volume).

Embodiment 14. The composition of any one of Embodiments 1-3, wherein the anti-acne compound is an antibiotic, a retinoid, or an alpha-hydroxy acid.

Embodiment 15. The composition of any one of Embodiments 1-14, wherein the *Propionibacterium acnes* bacteriophage is a naturally occurring *Propionibacterium acnes* bacteriophage.

Embodiment 16. The composition of any one of Embodiments 1-15, wherein the *P. acnes* bacteriophage is a lytic *P. acnes* bacteriophage.

Embodiment 17. The composition of any one of Embodiments 1-16, wherein the *P. acnes* bacteriophage comprises a linear double stranded DNA genome.

Embodiment 18. The composition of any one of Embodiments 1-17, wherein the *P. acnes* bacteriophage is within the bacteriophage family Siphoviridae.

Embodiment 19. The composition of any one of Embodiments 1-19, wherein the genome of the *P. acnes* bacteriophage comprises a nucleotide sequence that is at least about 80%, 85%, 90%, 95%, 96%, 97%, 98%, or 99% identical to the nucleotide sequence of SEQ ID NO: 1.

Embodiment 20. The composition of any one of Embodiments 3-19, wherein the enzyme is a *P. acnes* biofilm degrading enzyme.

Embodiment 21. The composition of any one of Embodiments 3-20, wherein the enzyme is a glycosidase, a protease, a DNAse, or a restriction endonuclease.

Embodiment 22. The composition of any one of Embodiments 3-21, wherein the enzyme is a glycosidase.

Embodiment 23. The composition of Embodiment 22, wherein the glycosidase is a glycoside hydrolase.

Embodiment 24. The composition of Embodiment 23, wherein the enzyme catalyzes the hydrolysis of linear polymers of N-acetyl-D-glucosamines.

Embodiment 25. The composition of Embodiment 24, wherein the enzyme is a (3-hexosaminidase.

Embodiment 26. The composition of Embodiment 25, wherein the enzyme is hydrolyzes β-1,6-glycosidic linkages of acetylglucosamine polymers.

Embodiment 27. The composition of any one of Embodiments 3-20, wherein the enzyme is a DNAse I, a restriction endonuclease, papain, bromelain, Trypsin, Proteinase K, Subtilisin, serratiopeptidase, dispersin, alginate lyase, amylase, or cellulase.

Embodiment 28. The composition of any one of Embodiments 3-20, wherein the enzyme is Dispersin B.

Embodiment 29. The composition of any one of Embodiments 3-20, wherein the enzyme is a protease, and the protease is proteinase K or subtilisin.

Embodiment 30. The composition of any one of Embodiments 1-29, further comprising an anti-aging enzyme.

Embodiment 31. The composition of Embodiment 30, wherein the anti-aging enzyme is a superoxide dismutase or a peroxidase.

Embodiment 32. The composition of any one of Embodiments 1-31, further comprising a probiotic bacterium.

Embodiment 33. The composition of Embodiment 32, wherein the probiotic bacterium is a probiotic a P. sp., *Staphylococcus* sp., and/or *Corynebacterium* sp. bacterium.

Embodiment 34. The composition of Embodiment 32, wherein the probiotic bacterium is a bacterium within the class Betaproteobacteria.

Embodiment 35. The composition of Embodiment 33, wherein the probiotic bacterium is a probiotic *P. acnes* bacterium.

Embodiment 36. The composition of Embodiment 35, wherein the *P. acnes* bacterium (a) comprises a 16S rDNA sequence with a T992C mutation compared to the KPA171202 type strain 16S rDNA sequence set forth as SEQ ID NO: 2;

(b) comprises a 16S rDNA sequence with a T838C mutation compared to the KPA171202 type strain 16S rDNA sequence set forth as SEQ ID NO: 2;

(c) comprises a 16S rDNA sequence with a C1322T mutation compared to the KPA171202 type strain 16S rDNA sequence set forth as SEQ ID NO: 2;

(d) comprises a 16S rDNA sequence with a C986T mutation compared to the KPA171202 type strain 16S rDNA sequence set forth as SEQ ID NO: 2;

(e) comprises a 16S rDNA sequence that is identical to the sequence of SEQ ID NO: 3;

(f) comprises a 16S rDNA sequence that is identical to the sequence of SEQ ID NO: 4;

(g) does not comprise a linear plasmid;

(h) does not comprise a plasmid that comprises a virulence factor; and/or (i) does not comprises a plasmid that encodes an extrachromosomal lipase and/or a tight adhesion virulence factor.

Embodiment 37. The composition of Embodiment 35 or 36, wherein the *P. acnes* bacterium:

(a) produces less than about 20% of the level of lipase that is produced by a pathogenic *P. acnes* strain when grown in a planktonic culture;

(b) produces less than about 10% of the level of lipase that is produced by a pathogenic *P. acnes* strain when grown in an adherent culture;

(c) adheres to epithelial cells at least 50% less than a pathogenic *P. acnes* strain; and/or (d) is less inflammatory than a pathogenic *P. acnes* strain.

38. The composition of any one of Embodiments 32-37, further comprising at least one additional probiotic bacterium.

Embodiment 39. The composition of Embodiment 38, wherein said at least one additional probiotic bacterium comprises *Propionibacterium granulosum* and/or *Propionibacterium avidum*.

Embodiment 40. The composition of Embodiment 37, wherein said pathogenic *P. acnes* strain (a) comprises a 16S rDNA sequence with a G1058C mutation compared to the KPA171202 type strain 16S rDNA sequence set forth as SEQ ID NO: 2;

(b) comprises a 16S rDNA sequence with a G1058C and an A1201C mutation compared to the KPA171202 type strain 16S rDNA sequence set forth as SEQ ID NO: 2;

(c) comprises a 16S rDNA sequence with a G529A mutation compared to the KPA171202 type strain 16S rDNA sequence set forth as SEQ ID NO: 2;

(d) comprises a 16S rDNA sequence with a G1004A and a T1007C mutation compared to the KPA171202 type strain 16S rDNA sequence set forth as SEQ ID NO: 2;

(e) comprises a 16S rDNA sequence with a G1268A mutation compared to the KPA171202 type strain 16S rDNA sequence set forth as SEQ ID NO: 2;

(f) comprises a 16S rDNA sequence with a T554C and a G1058C mutation compared to the KPA171202 type strain 16S rDNA sequence set forth as SEQ ID NO: 2;

(g) comprises a 16S rDNA sequence that is identical to the sequence of SEQ ID NO: 5;

(h) comprises a 16S rDNA sequence that is identical to the sequence of SEQ ID NO: 6;

(i) comprises a 16S rDNA sequence that is identical to the sequence of SEQ ID NO: 7;

(j) comprises a 16S rDNA sequence that is identical to the sequence of SEQ ID NO: 8;

(k) comprises a 16S rDNA sequence that is identical to the sequence of SEQ ID NO: 9; and/or (l) comprises a 16S rDNA sequence that is identical to the sequence of SEQ ID NO: 10.

Embodiment 41. The composition of any one of Embodiments 1-40, further comprising at least one additional *P. acnes* bacteriophage.

Embodiment 42. The composition of any one of Embodiments 1-41, wherein the pharmaceutically acceptable carrier comprises an emulsion.

Embodiment 43. The composition of Embodiment 42, wherein the emulsion is an oil-in-water emulsion or a water-in-oil emulsion.

Embodiment 44. The composition of any one of Embodiments 1-44, which is in the form of a cream, lotion, suspension, or aqueous solution.

Embodiment 45. A combination comprising at least one *Propionibacterium acnes* bacteriophage and at least one anti-acne compound, wherein each of the at least one *Propionibacterium acnes* bacteriophage and the at least one anti-acne compound is in a composition that further comprises a pharmaceutically acceptable carrier.

Embodiment 46. The combination of Embodiment 45, wherein the at least one *P. acnes* bacteriophage and the at least one anti-acne compound are within separate compositions.

Embodiment 47. The combination of Embodiment 46, wherein the at least one anti-acne compound is benzoyl peroxide.

Embodiment 48. The combination of Embodiment 47, wherein the benzoyl peroxide is present at a concentration of 2.5% to 10% (weight/volume).

Embodiment 49. The combination of Embodiment 47, wherein the benzoyl peroxide is present at a concentration of less than 2.5% but greater than about 0.1%, 0.5%, 1%, 1.5%, or 2% (weight/volume).

Embodiment 50. A method of treating acne in a subject in need thereof, the method comprising administering an effective amount of the composition of any one of Embodiments 1-44 to the subject.

Embodiment 51. The method of Embodiment 50, wherein the composition is administered topically.

Embodiment 52. A method of treating acne in a subject in need thereof, the method comprising administering an effective amount of the combination of any one of Embodiments 45-49 to the subject.

Embodiment 53. A composition comprising a *Propionibacterium acnes* bacteriophage and an enzyme.

Embodiment 54. A combination comprising a *Propionibacterium acnes* bacteriophage and an enzyme.

Embodiment 55. A composition consisting essentially of at least one *Propionibacterium acnes* bacteriophage, at least one anti-acne compound, and a pharmaceutically acceptable carrier.

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1. *P. acnes* Bacteriophage PHIT-101 Kills *P. acnes* Selectively and Efficiently

Figure 1:
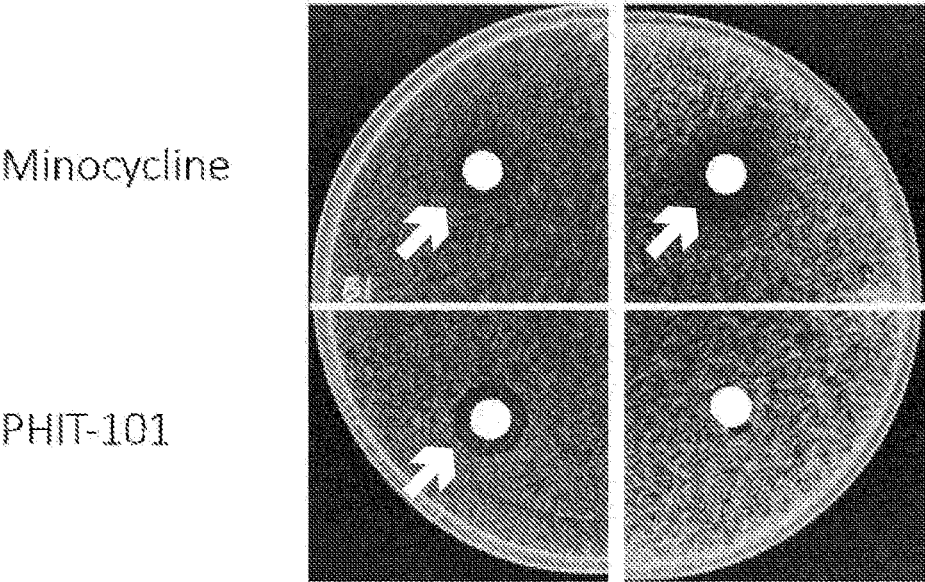
FIG. 1. *P. acnes* (acne-causing, left half plate) or *P. granulosum* (commensal, right half plate) bacteria was plated on RCM-agar petri dishes. Sterile half-pads soaked in either minocycline or PHIT-101 ($10^7$ pfu/mL) were placed on each plate. After anaerobic incubation at 37° C. for 3 days, zones of killing (arrows) appear, indicating that minocycline kills both pathogenic and commensal bacteria while PHIT-101 kills the acne-causing bacteria without disturbing commensal *P. granulosum*.
Figure 2:
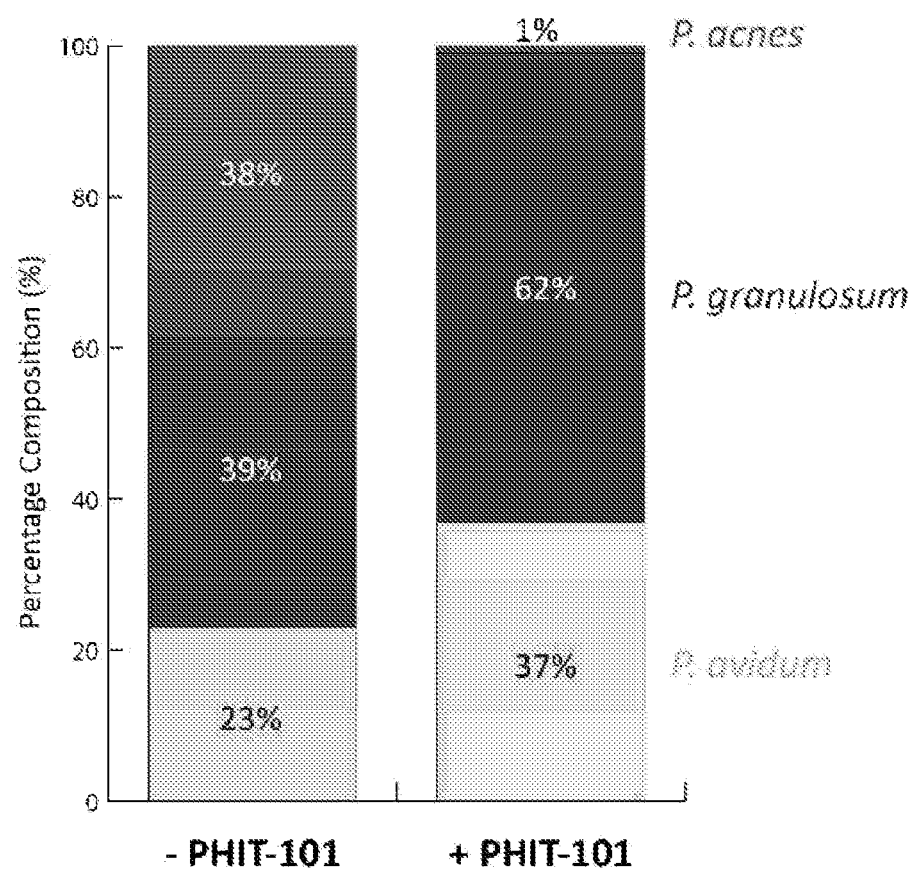
FIG. 2. A synthetic skin microbiome that includes *P. acnes, P. granulosum*, and *P. avidum* was grown to confluence in a test tube. It was then incubated in the presence or absence of PHIT-101 for 48 hours. The relative proportions of the three species were quantified by NGS sequencing of the 16S amplicon of the washed bacterial pellets using the Illumina MiSeq platform. PHIT-101 was able to almost completely wipe out acne-causing *P. acnes*, without affecting the growth of the other two commensal species.

*P. acnes* bacteriophages have been shown to be genetically highly similar and exhibit a broad range against multiple strains of *P. acnes*. A lead bacteriophage (PHIT-101) was used for experimentation. PHIT-101 is a single lytic phage that killed all the strain types of *P. acnes* tested (data not shown). PHIT-101 has the sequence of SEQ ID NO: 1. In order to showcase the efficacy and specificity of this phage, a plate assay was performed as follows. *P. acnes* KPA171202 and *P. granulosum* (a closely related but benign skin bacterium) were plated on separate BHI-agar plates. Sterile cotton pads were placed on each plate. The sterile cotton pads were soaked in either minocycline, an antibiotic commonly used to treat acne, or a phage solution with a titer of $2 \times 10^7$ pfu/mL. After incubating the plates anaerobically for 72 hours at 37° C., the minocycline pads killed bacteria indiscriminately, showing a zone of killing on both the acne-causing *P. acnes* and the commensal *P. granulosum* (FIG. 1). In contrast, the PHIT-101 pads killed only the *P. acnes*, without disturbing the growth of beneficial *P. granulosum*. Further evidence of the ability of PHIT-101 to kill selectively was obtained in a synthetic skin microbiome assay. A synthetic skin microbiome was formulated comprising *P. acnes, P. granulosum*, and *P. avidum*, three skin bacteria that comprise 60-80% of microbiota in the skin pore [Science (2009) 324:1190-1192]. This synthetic skin microbiome was grown anaerobically in the presence or absence of PHIT-101 (final concentration 5×10$^5$ pfu/mL). After 48 hours of incubation at 37° C., the cells were pelleted and washed, and the relative proportions of the three species was determined using 16S amplicon next-generation sequencing (NGS) on Illumina MiSeq. The results in FIG. 2 show that PHIT-101 is able to kill *P. acnes* almost completely, without negatively affecting the growth of the commensal *P. granulosum* and *P. avidum*.

Screening Biofilm Degrading Enzymes (BDEs) to Disrupt *P. acnes* Biofilms.

Figure 3:
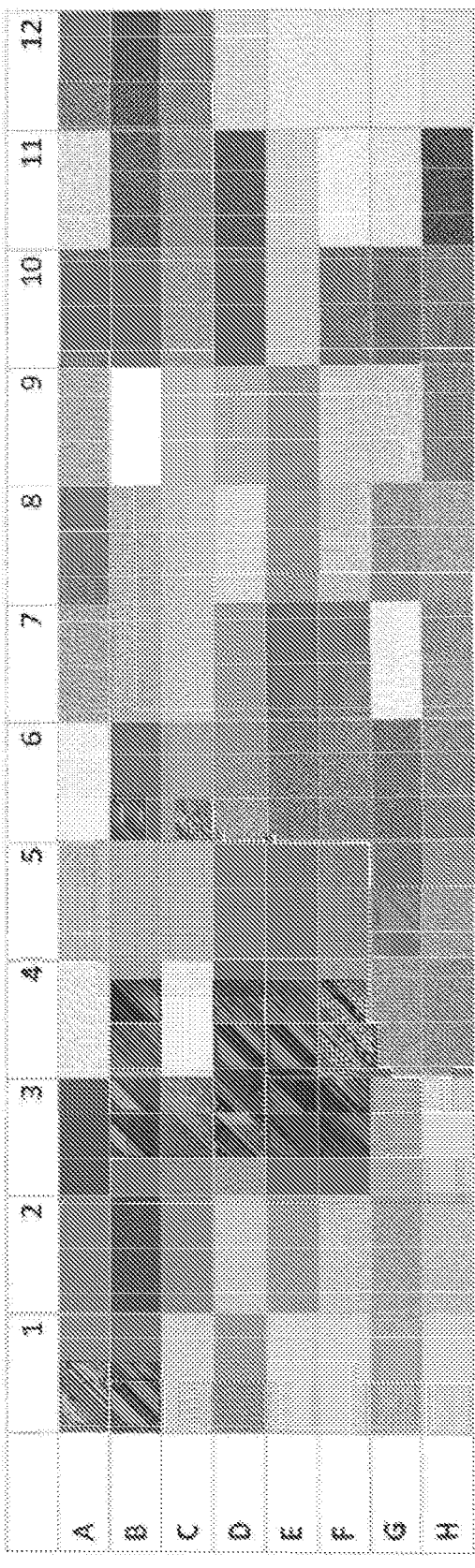
FIG. 3. Biofilm production amongst *P. acnes* strains is highly variable. 96 strains of *P. acnes* were grown in a 96-well polystyrene microtiter plate to stimulate biofilm production, and the biofilm produced by each strain was quantified. The variability demonstrated within this set of strains demonstrates the need to quantify biofilm formation under growth conditions more similar to those found in the human pore.
Figure 3:
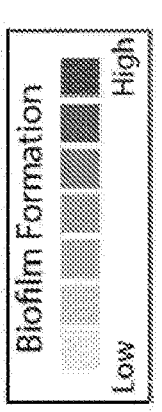

Several recent reports (Exp Dermatol (2014) 23:687, Br J Dermatol (2015) 172:13) have established that *P. acnes* produces significant amounts of biofilm in skin pores, which prevents antibiotic penetration and results in poor treatment outcomes. In order to validate this, biofilm production of several strains of *P. acnes* was quantified. FIG. 3 shows that adherent cultures of multiple strains isolated from the microbiota of a single subject produce markedly different levels of biofilm under similar conditions. Thus the previous proof-of-concept using planktonic cells did not reflect the true conditions under which *P. acnes* grows on the skin.

Figure 4:
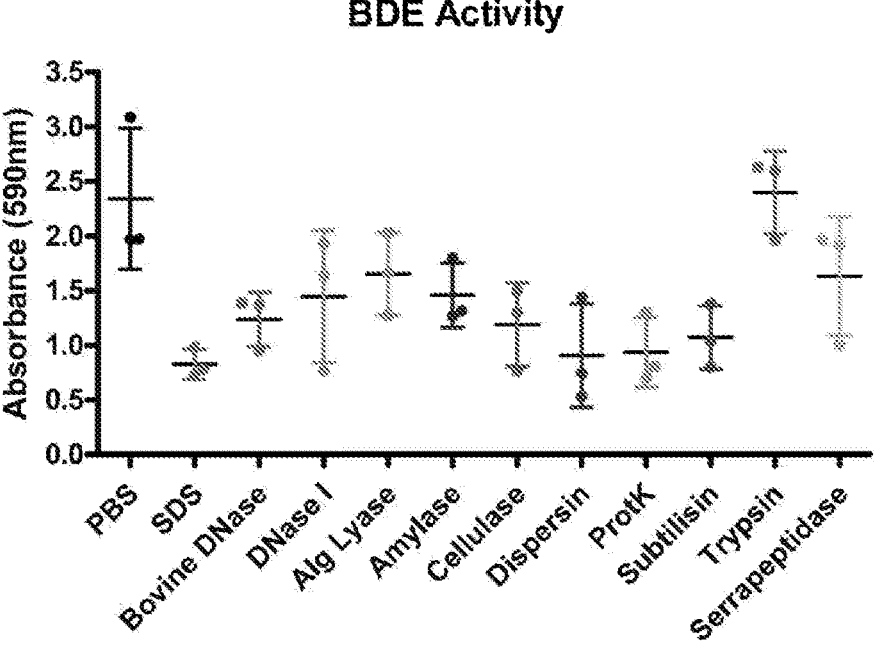
FIG. 4. A screen to select enzymes that can degrade *P. acnes* biofilms. *P. acnes* was grown in polystyrene microtiter plates to stimulate biofilm production. Enzymes were added at 0.01 mg/mL to the wells and incubated at 30° C. for 30 mins. The degraded biofilm was washed away with phosphate buffered saline (PBS), and the residual biofilm in each well was quantified by staining with crystal violet and recording absorbance at 590 nm. Proteases like proteinase K and subtilisin showed good activity, and dispersin was the best glycoside depolymerase amongst those tested.

Without being bound by any scientific theory, we hypothesized that biofilms might present a significant barrier to phage killing of sessile *P. acnes* cells. This hypothesis was validated in a cell survival assay (FIG. 5) which showed that unlike planktonic *P. acnes* (99% killing, FIG. 2), PHIT-101 was only able to kill about 50% of the *P. acnes* cells encased in biofilms. In order to determine whether biofilm degradation would improve phage killing, a number of enzymes was screened to find a BDE specific for *P. acnes*. The screen comprised three classes of enzymes that might degrade types of materials that may be found in biofilms: DNA, polysaccharides, and proteins. FIG. 4 shows that in the screen, DNAses had moderate activity while the best rates of biofilm degradation were found in proteases and dispersin, a glycoside hydrolase from Aggregatibacter *actinomycetemcomitans*.

Figure 5:
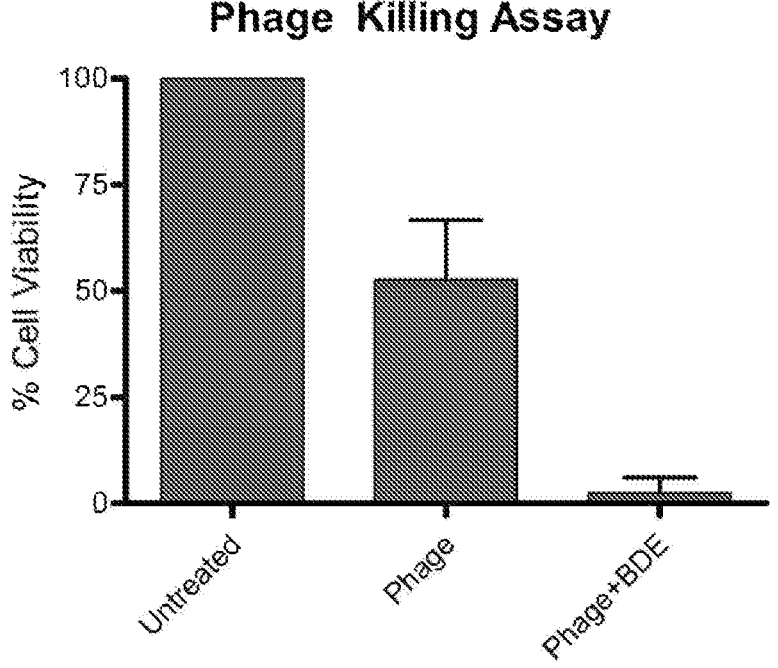
FIG. 5. Enhancement of phage with biofilm degrading enzyme (BDE) greatly increases bacterial killing. Sessile *P. acnes* cells were incubated with PBS (untreated), PHIT-101, or PHIT-101 and Dispersin. Cell survival was measured using the CellTiter-Blue reagent, and fluorescence was recorded at $560_{Ex}/590_{Em}$. PHIT-101 was unable to kill *P.*

In selecting the BDE to pair with the phage, dispersin was selected for two reasons: firstly, as a glycoside hydrolase it was unlikely to attack the protein coat of the phage itself, thereby avoiding possible degradation of the phage. Secondly, *P. acnes* co-forms robust biofilms with *Staphylococcus aureus* [Anaerobe (2016) 40:63-67] and dispersin is active against biofilms from both organisms. Whether the addition of dispersin would increase the efficiency of phage killing in sessile *P. acnes* was determined. FIG. 5 shows that bacterial killing of PHIT-101 was enhanced in the presence of dispersin, restoring a ~99% killing efficiency to the phage.

Example 2. Probiotic Bacteria

Genotypic Characterization of Probiotic Strains.

Strains of *P. acnes* were characterized based on point mutations in the 16S rDNA sequence which leads to phylogenetic sorting into pathogenic and probiotic strain types, and the absence of a linear plasmid found in pathogenic strains, which carries virulence factors. Using 16S-specific primers the full 16S rDNA sequence of each *P. acnes* strain was amplified and Sanger-sequenced. A probiotic strain was identified as having ribosequence (RS) of ProI or ProII. ProI strains have T838C and C1322T mutations relative to the KPA171202 type strain's 16S rDNA sequence (NIH Accession No. NC_006085.1). ProII strains have C986T and T992C mutations relative to the KPA171202 sequence. Further, using specific primer pairs, the presence or absence of a linear plasmid within each strain was determined. Probiotic strains were identified as lacking this plasmid, which carries an extrachromosomal lipase as well as the Tad (tight adhesion) virulence factor.

In embodiments, the probiotic strains are characterized primarily by their 16S sequences, e.g., SEQ ID NO: 3 and SEQ ID NO: 4. In embodiments, they can be genotypically identified by the lack of the plasmid bearing virulence factors, such as an extrachromosomal lipase and a Tad locus.

The cohort of probiotic strains was further characterized for their immunogenic potential. A lead probiotic candidate based on two factors: low lipase production, and less tight adherence to epithelial cells. The phenotypic validation of these features was important in selecting the probiotic lead candidate.

Testing the Immunogenic Potential of Probiotic *P. acnes* Strains: Lipase Activity.

Lipases play an important role in pathogenesis of acne by hydrolyzing sebum triglycerides and releasing irritating free fatty acids in the pilosebaceous follicles. Lipase is a strong chemotactic and proinflammatory antigen. Therefore, lipase is of high interest as a pharmacological target for anti-acne drugs. In embodiments, the overall strategy is to replace the pathogenic *P. acnes* that secretes high levels of lipase with a low-secreting probiotic *P. acnes*. In order to quantify the lipase expression phenotype for each strain in our panel, lipase production of the probiotic *P. acnes* strains was compared against pathogenic *P. acnes* strains with a fluorescent lipase activity assay.

One of the most interesting findings was that each strain secreted different amounts of lipases when grown in planktonic vs adherent culture. This has been previously reported in *P. acnes* strains [Res Microbiol, (2007) 158:386-392]. Further, the data showed that when these strains were grown in liquid culture, there was no significant difference between the lipase output of the pathogenic and probiotic strains. However, when these strains were grown under biofilm conditions, an interesting change was seen. While variability in production between strains could still be observed, several probiotic strains had significantly less lipase activity than pathogenic strains (FIG. 11). Interestingly, not all strains within the probiotic cohort had low lipase activity. For example, the lipase production of strains Pr-1 and Pr-5 was over the threshold for a probiotic strain, and was not developed further. Thus by quantifying lipase production in sessile *P. acnes* cells, it was possible to screen amongst probiotic strains and select those lead candidates with the most consistent low levels of lipase activity.

Thus, while pathogenic and probiotic strains secreted similar amounts of lipase in planktonic culture, the probiotic strains secreted far less lipase in adherent culture than pathogenic strains. FIG. 8 shows that the top probiotic candidates had a low lipase profile compared to the pathogenic strain.

Testing the Immunogenic Potential of Probiotic *P. acnes* Strains: Cell Adherence.

Available pathogenic strains were confirmed to possess a tight adhesion (tad) locus that plays a role in the virulence of other mammalian pathogens [J Bacteriol (2000) 182: 6169-6176; Nat Rev Microbiol (2007) 5:363-375; PNAS (2003) 100:7295-7300]. Greater adherence to host cells may increase virulence or induce an inflammatory host response. The probiotic strains were previously genotypically verified to not contain the tad locus, and thus predicted to adhere less tightly to epithelial cells. The adhesion of pathogenic and probiotic strains to A-431 dermal epithelial cells was compared, in order to assess whether there was an appreciable difference in adherence. FIG. 9 shows that the top three probiotic candidates adhered less tightly to epithelial cells than the pathogenic strain. Interestingly, once again a subtle but persistent difference in cell adhesion was found between different strain families of *P. acnes*. Thus the strains of *P. acnes* with ProI ribosequence exhibited a slightly higher cell adherence (Pr-2 in FIG. 9) while the ProII strains adhered to cells less tightly (Pr-B, Pr-C in FIG. 9).

Comparison of Pathogenic and Probiotic *P. acnes* in Mouse Ear Inflammation Model.

Upon validating the low immunogenic potential of the probiotic strains showing that they produced less lipase and adhered less tightly to epithelial cells, the inflammatory response of these strains was tested in a mouse ear inflammation model, which is well established and has been used previously to evaluate the inflammatory potential of *P. acnes* in the context of acne. The inflammatory potential of pathogenic and probiotic strains was compared in the following study: $10^{10}$ cfu of a strain was injected into the ears of CBA/J mice. A cohort of 5 mice was assigned to each strain. After 5 days the ears were excised and examined for inflammation. The levels of several inflammatory cytokines (IL-1β, IL-6, IL-17, TNFα) were measured and the sections of the tissue were examined by histology. FIG. 10 shows that the pathogenic strain had significantly higher levels of IL-1β, IL-6, IL-17, and TNFα compared to the probiotic strain.

Acute Dermal Safety and Toxicity of Probiotic Strains in Miniswine Skin Model.

A miniswine model was used to test the probiotic strain for skin irritation. Swine are one of the major animals used in translational research, and pig skin is physiologically, anatomically, biochemically and immunologically similar to human skin. Miniswine are particularly commonly used to model human dermal diseases and conditions like acne [Vet Pathol (2012) 49:344-356]. The probiotic strain was applied to the skin of three separate miniswine in two doses—$10^{8}$ cfu and $10^{9}$ cfu—in delimited skin areas. The animals were observed daily for clinical signs and the dosing site skin was scored using the Draize Scoring System at pre-dose, 0.5, 1, 4, 8, and 24 hours post dose administration. There was no erythema or edema associated with the lead probiotic strain during the entire period (Table 1), and a Draize score of 0 was observed throughout. This demonstrates the safety to acute exposure of our probiotic strain in an animal skin model.

TABLE 1

Acute dermal safety/tox in miniswine skin model shows good safety profile of probiotic strain. Probiotic bacteria was applied at normal ($10^8$ cfu) and acute ($10^9$ cfu) doses on delimited skin areas in 3 male miniswine and monitored for 24 hours post-application. Erythema and edema were quantified using the Draize Scoring System. The Draize score provides the relative severity of erythema and edema. A Draize score of 0, indicating complete absence of erythema and edema, was observed on all the skin areas throughout the monitoring period.

| Group (Animal) | Dose Site | Treatment | Dose Level | Total Sites with non-zero Draize score* |
|---|---|---|---|---|
| 3 Male | Left #1 | *P. acnes* Normal | ~$10^8$ CFU | 0 |

TABLE 1-continued

Acute dermal safety/tox in miniswine skin model shows good safety profile of probiotic strain. Probiotic bacteria was applied at normal ($10^8$ cfu) and acute ($10^9$ cfu) doses on delimited skin areas in 3 male miniswine and monitored for 24 hours post-application. Erythema and edema were quantified using the Draize Scoring System. The Draize score provides the relative severity of erythema and edema. A Draize score of 0, indicating complete absence of erythema and edema, was observed on all the skin areas throughout the monitoring period.

| Group (Animal) | Dose Site | Treatment | Dose Level | Total Sites with non-zero Draize score* |
|---|---|---|---|---|
| | Right #1 | *P. acnes* Acute | ~$10^9$ CFU | 0 |
| | Left #2 | PHIT-101 Normal | ~$10^8$ CFU | 0 |
| | Right #2 | PHIT-101 Acute | ~$10^9$ CFU | 0 |

Example 3. Bacteriophage Stability in Compositions with Anti-Acne Compounds

In order to determine whether the phage was stable in co-formulation with either salicylic acid or benzoyl peroxide (BPO), the phage was co-incubated with these agents at a low and high concentration. The range of concentrations was determined by the permitted concentrations of these agents specified in the United States Food and Drug Administration (FDA) acne monograph for over-the-counter use. For salicylic acid, this is 0.5% to 2% (w/v), while for BPO the range is 2.5% to 10% (w/v). Buffered solutions of phage were added to these agents, and its stability at 4° C. was tested over 60-90 days. FIG. 15 shows that the phages are stable in the presence of both low and high doses of salicylic acid. In contrast, FIG. 16 shows that benzoyl peroxide destabilizes the phages, and the observed rate of decrease in phage viability is steeper at a higher concentration of BPO.

Example 4 (Prophetic). Treatment with a Combination of Bacteriophage with Salicylic Acid A double-blind, placebo-controlled study of a composition comprising *Propionibacterium acnes* bacteriophage and salicylic acid is conducted determine the comparative efficacy of this treatment with placebo, *Propionibacterium acnes* bacteriophage alone, and salicylic acid alone. Concentrations of 0.5% and 2% (w/v) salicylic acid are administered with and without *Propionibacterium acnes* bacteriophage. In all conditions that include the *Propionibacterium acnes* bacteriophage, the phage is present in a dose of $10^9$ pfu (plaque forming units) per dose. Ten subjects who have comparably severe acne are treated for each of the following groups:

(i) Placebo (no active agent)

(ii) 0.5% salicylic acid as the sole active agent (iii) 2% salicylic acid as the sole active agent (iv) *Propionibacterium acnes* bacteriophage as the sole active agent (v) the combination of 0.5% salicylic acid and *Propionibacterium acnes* bacteriophage (in a single composition)

(vi) the combination of 2% salicylic acid and *Propionibacterium acnes* bacteriophage (in a single composition)

The combination of the *Propionibacterium* acne bacteriophage with salicylic acid achieves more than an additive effect, i.e., a synergistic effect (the combined effect of the bacteriophage and the salicylic acid is greater than the sum of the effects of the bacteriophage and the salicylic acid when each agent is used separately) in treating acne. The effectiveness of treatment is measured using lesion counts and an IGA (investigator global assessment) score.

Example 5 (Prophetic). Treatment with a Combination of Bacteriophage with Sulfur A double-blind, placebo-controlled study of a composition comprising *Propionibacterium acnes* bacteriophage and sulfur is conducted determine the comparative efficacy of this treatment with placebo, *Propionibacterium acnes* bacteriophage alone, and sulfur alone. Concentrations of 3% and 10% (w/v) sulfur are administered with and without *Propionibacterium acnes* bacteriophage. In all conditions that include the *Propionibacterium acnes* bacteriophage, the phage is present in a dose of $10^9$ pfu per dose. Ten subjects who have comparably severe acne are treated for each of the following groups:

(i) Placebo (no active agent)
   (ii) 3% sulfur as the sole active agent
   (iii) 10% sulfur as the sole active agent
   (iv) *Propionibacterium acnes* bacteriophage as the sole active agent
   (v) the combination of 3% sulfur and *Propionibacterium acnes* bacteriophage (in a single composition)
   (vi) the combination of 10% sulfur and *Propionibacterium acnes* bacteriophage (in a single composition)

The combination of the *Propionibacterium* acne bacteriophage with sulfur achieves more than an additive effect, i.e., a synergistic effect (the combined effect of the bacteriophage and the sulfur is greater than the sum of the effects of the bacteriophage and the sulfur when each agent is used separately) in treating acne. The effectiveness of treatment is measured using lesion counts and an IGA (investigator global assessment) score.

Example 6 (Prophetic). Treatment with a Combination of Bacteriophage with Benzoyl Peroxide A double-blind, placebo-controlled study of a composition comprising *Propionibacterium acnes* bacteriophage and BPO is conducted determine the comparative efficacy of this treatment with placebo, *Propionibacterium acnes* bacteriophage alone, and BPO alone. Concentrations of 2.5% and 10% (w/v) BPO are administered with and without *Propionibacterium acnes* bacteriophage. In all conditions that include the *Propionibacterium acnes* bacteriophage, the phage is present in a dose of $10^9$ pfu per dose. Ten subjects who have comparably severe acne are treated for each of the following groups:

(i) Placebo (no active agent)
   (ii) 2.5% BPO as the sole active agent
   (iii) 10% BPO as the sole active agent
   (iv) *Propionibacterium acnes* bacteriophage as the sole active agent
   (v) the combination of 2.5% BPO and *Propionibacterium acnes* bacteriophage (in separate compositions)
   (vi) the combination of 10% BPO and *Propionibacterium acnes* bacteriophage (in a single compositions)

The combination of the *Propionibacterium* acne bacteriophage with BPO achieves more than an additive effect, i.e., a synergistic effect (the combined effect of the bacteriophage and the BPO is greater than the sum of the effects of the bacteriophage and the BPO when each agent is used separately) in treating acne. The effectiveness of treatment is measured using lesion counts and an IGA (investigator global assessment) score.

Example 7 (Prophetic). Assay with a Combination of Bacteriophage with Benzoyl Peroxide An in vitro study is performed to determine the efficacy of (i) BPO; (ii) *Propionibacterium* acne bacteriophage; or (iii) *Propionibacterium* acne bacteriophage+BPO in killing planktonic and sessile pathogenic *P. acnes* bacteria.

The combination of the *Propionibacterium* acne bacteriophage with BPO achieves more than an additive effect, i.e., a synergistic effect (the combined effect of the bacteriophage and the BPO is greater than the sum of the effects of the bacteriophage and the BPO when each agent is used separately) in killing sessile pathogenic *P. acnes* bacteria. The keratolytic action of BPO (similar to salicylic acid and retinoids) assists the phage in penetrating skin pores to access the *P. acnes* deep within the pores.

---

What is claimed is:

1. A composition formulated for topical administration comprising:

(a) a *Propionibacterium* bacteriophage, wherein the genome of the *Propionibacterium* bacteriophage comprises a nucleotide sequence that is at least 90%, 95%, 96%, 97%, 98%, or 99% identical to the nucleotide sequence of SEQ ID NO: 1;

(b) a dispersin enzyme; and (c) a probiotic bacteria comprising a strain of *Propionibacterium acnes* (*P. acnes*), wherein the *P. acnes* strain comprises 16S rDNA sequences comprising SEQ ID NO: 3 and SEQ ID NO: 4.

2. The composition of claim 1, wherein the dispersin enzyme comprises dispersin B.

3. The composition of claim 2, wherein the dispersin B comprises SEQ ID NO: 12.

4. The composition of claim 1, further comprising salicylic acid.

5. The composition of claim 1, wherein the dispersin comprises SEQ ID NO: 12, and wherein the composition further comprises salicylic acid.

6. A method for treating acne in a subject in need thereof, the method comprising: topically administering a therapeutically effective amount of the composition of claim 1 to a region of the subject's skin having the acne.

7. The method of claim 6, comprising:

prior to topical administration, pretreating the region of the subject's skin with a composition comprising benzoyl peroxide.

8. The method of claim 6, wherein the benzoyl peroxide composition is washed off of the region of the subject's skin prior to the topical administration of the composition.

9. A method for treating acne in a subject in need thereof, the method comprising:

(a) topically administering a therapeutically effective amount of a composition comprising a dispersin enzyme to a region of the subject's skin having the acne;

(b) topically administering a therapeutically effective amount of a composition comprising a *Propionibacterium* bacteriophage to the region of the subject's skin having the acne, wherein the genome of the *Propionibacterium* bacteriophage comprises a nucleotide sequence that is at least 90%, 95%, 96%, 97%, 98%, or 99% identical to the nucleotide sequence of SEQ ID NO: 1; and (c) topically administering a therapeutically effective amount of a composition comprising a strain of *Propionibacterium acnes* (*P. acnes*), wherein the *P. acnes* strain comprises 16S rDNA sequences comprising SEQ ID NO: 3 and SEQ ID NO: 4 to the region of the subject's skin having the acne.

10. The method of claim 9, wherein the dispersin enzyme comprises dispersin B.

11. The method of claim 10, wherein the dispersin B enzyme comprises SEQ ID NO: 12.

12. The method of claim 9, wherein before step (a), the region of the subject's skin comprising the acne is pretreated with benzoyl peroxide.

13. The method of claim 12, wherein the benzoyl peroxide is removed prior to step (a).

14. The method of claim 9, further comprising:

(d) topically administering a therapeutically effective amount of a composition comprising one or more of salicylic acid, resorcinol, and sulfur to the region of the subject's skin having the acne.

15. The method of claim 9, wherein the composition comprising the bacteriophage further comprises salicylic acid.

16. The method of claim 9, wherein the composition comprising the dispersin enzyme and the composition comprising the bacteriophage are the same.

17. The method of claim 9, wherein the composition comprising the bacteriophage and the composition comprising the probiotic bacteria are the same.

18. The method of claim 17, wherein the composition comprising the bacteriophage and the probiotic bacteria also comprises salicylic acid.

* * * * *

SEQUENCE LISTING

```
Sequence total quantity: 28
SEQ ID NO: 1           moltype = DNA  length = 29752
FEATURE                Location/Qualifiers
misc_feature           1..29752
                       note = Propionibacterium acnes bacteriophage
source                 1..29752
                       mol_type = genomic DNA
                       organism = Cutibacterium acnes
SEQUENCE: 1
agtgaaatac ctcccttttg tggttttgtc tgtttgtcga cttttttgtgt tggtggtgag   60
tgttgtgcag cctgagcttc ctgagtctcg tgagtggtgt ggggagacgc gtcgttggtg  120
gcgtgtgtgg ggtgaggata gtcgcgcgcc gtatgtgtct gatgaggagt ggttgtttct  180
tatggatgct gcggtgattc atgattgtgt gtggcgtgag ggtcgcgcgg atttggtggc  240
ttcgcttcgt gcgcatgtga aggcttttat gggcatgttg gataggtatt cggttgatgt  300
ggcgtctggt ggccgtggtg ggggttctgc tgtggcgatg attgaccggt ataggaagcg  360
taggggggct tgagtaggtg tctggtgttg ttgggtctca ggttcctcgt caccgtgtgg  420
ctgcggcgta ttcggtgtct gctggggggtg atgctgggga gcttggtcgt gcgtatgggt  480
tgacgcctga tccgtggcag cagcaggtgt tggatgattg gctggctgtc ggtagcaatg  540
gcaggcttgc ttctggtgtg tgtgggggtgt ttgttccgcg gcagaatggc aagaatgcta  600
ttttggagat tgtggagttg tttaaggcga ctattcaggg tcgccgtatt ttgcatacgg  660
ctcacgagtt gaagtcggct cgtaaggcgt ttatgcggtt gaggtcgttt tttgagaatg  720
```

-continued

```
agcggcagtt tcctgacttg tatcgtatgg tgaagtcgat tcgtgcgacg aatggtcagg   780
aggctattgt gttgcatcat ccggattgtg ccacttttga gaagaagtgt ggctgcagcg   840
gttgggggttc ggttgagttt gtggctcgta gccggggttc ggctcgcggg tttacggttg   900
atgatttggt gtgtgatgag gctcaggagt tgtcggatga gcagttggag gctttgcttc   960
ctacggtaag tgctgccccg tctggtgatc cgcagcagat tttccttggt acgccgcctg  1020
ggccgttggc tgatggttct gtggtgttgc gtttgcgtgg gcaggcgctt ggtggcggta  1080
aaaggtttgc gtggacggag ttttcgattc ctgacgagtc tgatccggat gatgtgtcgc  1140
ggcagtggcg gaagttggcg ggggatacga atccggcgtt ggggcgtcgc ctgaattttg  1200
ggaccgtaag cgatgagcat gagtcgatgt ctgctgccgg ttttgctcgg gagcggcttg  1260
gctggtggga tcgtggccag tctgctgcgt ctgtggttcc tgctgataag tgggctcagt  1320
ctgcggtgga tgaggcgagt ctggttggcg ggaaagtgtt tggtgtctcg ttttctcgtt  1380
ctggggggatcg ggttgctttg gcgggtgccg gcaagactga tgctgggggtt catgttgagg  1440
ttattgatgg gctgtcggga acgattgttg atggtgtggg ccggttggct gactggttgg  1500
cggttcgttg gggtgatact gaccggatca tggttgccgg gtctggtgcg gtgttgttgc  1560
agaaggcgtt gacggatcgt ggtattccgg gccgtggcgt ggtggttgct gatactggcg  1620
tttatgtgga ggcttgtcag gcgtttcttg agggtgtcag gtcgggtgtg atcagtcatc  1680
ctcgtgctga ttctcgccgt gacatgttgg atattgctgt gaggtcggct gtgcagaagc  1740
gtaagggggtc tgcgtgggggt tgggggttcct cgtttaagga tggttctgag gttcctttgg  1800
aggctgtgtc tttggcgttt ttgggggggcta aacgtgttcg tcgtggccgt cgggagcgta  1860
gtggtaggaa gcgggtgtct gtggtatgaa ctcggatgag ttggctctga ttgagggcat  1920
gtacgatcgt atccaaaggt tgtcttcgtg gcattgttgt attgagggct actatgaggg  1980
ctctaatcgg gtgcgtgacc ttggtgtggc tattccgccg gagttgcagc gtgtgcagac  2040
tgtggtgtcg tggcctggta tagctgtgga tgctttggag gagcgtctgg attggcttgg  2100
ctggactaat ggtgacggct acggccttga tggtgtgtat gctgcgaatc ggcttgctac  2160
ggcgtcgtgt gatgtgcatt tggatgcgct gattttttggg ttgtcgtttg ttgcgatcat  2220
tcctcatggt gatggtacgg tgtcggttcg tccgcagtca ccaaagaatt gtacgggcaa  2280
gttttcggct gacgggtctc gtttggatgc gggtttggtg gtgcagcaga cgtgtgatcc  2340
tgaggttgtt gaggctgagc ttttgcttcc tgatgtgatt gttcaggtgg agcggcgggg  2400
ttcgcgtgaa tgggttgagg tggatcgtat accgaatgtg ttgggtgcgg ttccgttggt  2460
gcctattgtg aatcgtcgcc gtacttctag gattgatggc cgttcggaga ttacgaggtc  2520
tattagggct tacacggatg aggctgtgcg cacactgttg gggcagtctg tgaatcgtga  2580
tttttatgcg tatcctcagc gttgggtgac tggcgtgagc gcggatgagt tttcgcagcc  2640
tggctgggtc ctgtcgatgg cttctgtgtg ggctgtggat aaggatgatg acggtgacac  2700
tccgaatgtg gggtcgtttc ctgtcaatag tcctacaccg tattcggatc agatagagct  2760
gttggcgcag ttgactgcgg gtgaggcggc tgttccggaa cgctatttcg ggtttatcac  2820
gtctaaccca cctagtgggg aggctttggc tgccgaggaa tctcggcttg tgaagcgtgc  2880
tgagcggcgt caaacgtcgt ttggtcaggg ttggctgtcg gttggttttt tggctgccaa  2940
ggcgttggat tctcgtgttg atgaggccga tttttttggt gatgttggtt tgcgttggcg  3000
tgatgcttcg acgcctaccc gggcggctac ggctgatgct gtgacgaagc ttgttggtgc  3060
cggtatttg cctgctgatt ctcgtacggt gttggagatg ttggggcttg atgatgtgca  3120
ggttgaggct gtgatgcgtc atcgtgctga gtcgtctgac ccgttggcgg tgcttgctgg  3180
ggctatatcg cgtcaaacta acgaggtatg ataggcgatg gcttcggggg ttgaggcgag  3240
gcttgcggcg actgagtatc agcgtgaggc ggtcaggttt gctgggaagt atgcgggcta  3300
ttattctgag cttggtcgtt tgtggcgtgc cggcaggatg agtgacacgc agtatgtgcg  3360
tttgtgtgtg gagttggagc gtgccggcca tgatggttcg gcatcgttgg ctgccaggtt  3420
tgtgtcggat tttcgccggt tgaatggtgt ggatccgggt ttgattgtgt atgacgagtt  3480
tgatgctgcg gcggctttgg ctaggtctat ttcgaccacg aagattcttg agagtgaccc  3540
ggataggggcg aatgacacga ttgatgcgat ggcggcgggt tttgatcggg ctgttatgaa  3600
tgctggccgt gacacggttg agtggtctgc gggtgcgcag ggtaggtcgt ggcgtcgggt  3660
gacggatggt gatccgtgtg cttttttgtgc catgttggct acgaggtcgg attatacgac  3720
aaaagagagg gcacttacta ctggacatac tcggcgtcat aagcgtggtg gtaagcgtcc  3780
gtttggttcg aagtatcatg atcattgtgg ttgtacggtg gttgaggttg ttggcccttg  3840
ggaaccaaat agggctgatg ccgagtatca gaggacgtat gagaaggcct gtgagtgggt  3900
tgatgatcat gggttgcagc aatcgcctgg caatattttg aaggctatgc gtactgttgg  3960
cgacatgaga taatttgatg tggtttccgg ttgtgcgccg ccggttattg gtgcacaggg  4020
ttgtctcccg cacggggggtc aacaatattg tgttgttttc cgcaaggagt gtagggttag  4080
gctatggccg atcagagtgt tgaggaacag aatgttgaca atgatgttgt ggagtccgga  4140
aaggataacg gcattgttga tacagtaaaa gacgatggcg ggcaggaggt agccgacaat  4200
cagttgaaga atgaaggcga gggtaaatcg ccggggactg attggaaggc tgaggcccgt  4260
aagtgggagt ctcgtgctaa aagtaatttt gcccagatgg agaagcttcg cgcctcggat  4320
ggtgatgcgg ggtctacgat tgatgagctt cgccgcaaga atgaggaact cgaagaccgg  4380
atcaatgggt ttgttcttga gggtgtgaag cgcgaggtgg ctgccgagtg tggcctgtcg  4440
ggtgatgctg tcgctttctt gtcgggtggc gataaggagt cgcttgccga gtctgcgaaa  4500
gctttgaagg gtttgatcga ccatagtagt ggtggcgcgg gtgtgcgcgc tcttgcgggg  4560
agtgcccccg ttgatgatgt taaacgacgt gagggtgtcg cgtttgtgga tgctcttgtc  4620
aataattcta ggagatgatt tgtgatggct gacgatttttc tttctgcagg gaagcttgag  4680
cttcctggtt ctatgattgg tgcggttcgt gaccgtgcta tcgattctgg tgttttggcg  4740
aagctttcgc cggagcagcc gactattttc ggggcctgtga agggtgccgt gtttagtggt  4800
gttcctcgcg ccaagattgt tggtgaggggc gaggttaagc cttccgcgtc tgttgatgtt  4860
tcggcgttta ctgcgcagcc tatcaaggtt gtgactcagc agcgtgtctc cgatgagttt  4920
atgtgggctg atgctgatta ccgtctgggt gtgcttcagg atctgatttc cccggctctt  4980
ggtgcttcga ttggtcgcgc cgtggatctg attgctttcc atggtattga tcctgccact  5040
ggtaaagcgg cttccgctgt gcatacttcg ctgaataaga cgaagaatat tgttgatgcc  5100
acggattctg ctacggctga tcttgttaag gctgtcgggt tgattgctgg tgctggtttg  5160
caggttccta acggggggttgc tttggatccg gcgttctcgt ttgcgctgtc tactgaggtg  5220
tatccgaagg ggtctccgct tgccggtcag cctatgtatc ctgccgccgg gtttgccggt  5280
ttggataatt ggcgcgggct gaatgttggt gcttcttcga ctgtttctgg cgccccggag  5340
atgtcgcctg cctctggcgt taaggctatt gttggtgatt tctctcgtgt tcattggggt  5400
ttccagcgta acttcccgat cgagcttatc gagtatggtg acccggatca gactgggcgt  5460
```

-continued

```
gacttgaagg gccataatga ggttatggtt cgtgccgagg ctgtcctgta tgttgcgatt   5520
gagtcgcttg attcgtttgc tgttgtgaag gagaaggctg ccccgaagcc taatccgccg   5580
gccgagaact gattcatttg ttgcggtgat gtttttctatg tgcagggggt ggtgttgatg   5640
ggtatcattt tgaagcctga ggatattgag cctttcgccg atattcctag agagaagctt   5700
gaggcgatga ttgccgatgt ggaggctgtg gctgtcagtg tcgcccctg tatcgctaaa   5760
ccggatttca aatacaagga tgccgctaag gctattctgc gcagggccct gttgcgctgg   5820
aatgataccg gggtttcggg tcaggtgcag tacgagtctg cgggcccgtt tgctcagact   5880
acacggtcga atactcccac gaatttgttg tggccttctg agattgccgc gttgaagaag   5940
ttgtgtgagg gtgatggtgg ggctggtaaa gcgttcacta ttacaccgac catgaggagt   6000
agtgtgaatc attctgaggt gtgttccacg gtgtggggtg agggttgctc gtgcggatct   6060
gatattaacg gctatgctgg ccctttgtgg gagatatgat atgaccggtt ttccttacgg   6120
tgaaacggtt gtgatgcttc aaccgactgt tcgtgtcgat gatcttggcg acaaggtgga   6180
agactggtct aagcctgtcg agactgtgta ccataacgtg gccatctatg cttccgtttc   6240
gcaggaggat gaggctgccg gccgtgactc tgactatgag cattggtcga tgcttttcaa   6300
gcagcctgtt gtgggtgccg gttatcgttg ccggtggcgt attcggggtg tggtttggga   6360
ggcggacggg tctcctatcg tgtggcatca tccgatgtct ggttgggatg ctggtacgca   6420
ggttaatgtg aagcgtaaga agggctgatg ggttgtggct caggatgtga atgtgaagct   6480
gaacttgccg ggtattcgtg aggtgttgaa gtcttctggg gtgcagtcga tgttggctga   6540
gcgtggcgag cgggtgaggc gtgcggcttc ggcgaatgtt ggcggtaatg cttttgatag   6600
ggcccaatac cgtagtggtt tgtcgtcgga ggtgcaggtt caccgtgtgg aggctgtggc   6660
gaggattggc accacctata agggtgggaa gcgtattgag gcgaagcatg gcacgttggc   6720
gaggtcgatt ggggctgacgt cgtgatcgtt tacggtgatc tgcgtgtgtg ggctaaacgt   6780
gtgctcaagg atgatggctg gctgtccgat atacccigtg tggggacggt gcctgacgat   6840
ttcagcggtg acctgatttg gttggcgttg gatggcggcc cacagttgca tgttcgcgag   6900
caggtgtttt tgcgggtgaa cgtgtttct gatatgcctg atcgtgccat gtcgctagcc   6960
aggcgaggtg aggctgtcct tgtagacggt gtggacggtg acccggtggt gttttgctgg   7020
cggtctactg gccctgattt gctggttgat ggtgcacgtt ttgatgtgta ttcgctgttt   7080
gagctgatat gcaggcctgt cgaatccgag taaacgtttt gttttgatat tgttgtttgt   7140
tttttgtttt atattgtttt tggggggttat gatggctgga acacgtaaag cgtctaatgt   7200
tcgttccgcg gttacgggtg acgtctatat tggtaaagct catgccggtg acactattga   7260
tggtgtgaag acggttcctg acgggcttac agctttaggg tatctgtctg atgacgggt   7320
taagattaaa ccggagcgta aaacggatga tttgaaggct tggcagaatg cggatgttgt   7380
tcgcactgtg gctacggaat cgtctatcga gatttcttc cagctgatcg agtctaagaa   7440
ggaggttatc gagctgtttt ggcagtcgaa ggttactgcc ggagccgatt cgggttcgtt   7500
cgatatttct cctggtgcca cgacgggtgt tcatgccctg ttgatggata ttgttgatgg   7560
cgatcaggtt attcgctact atttccctga ggttgagttg atcgatcgtg acgagattaa   7620
gggtaagaat ggcgaggtgt atgggtatgg tgtgacgttg aaggcgtatc ctgcccagat   7680
taataagaag ggtgatgcgg tgtctggtcg ggggtggatg acggctttaa aagctgatac   7740
tcctccgact cctcctccgg ccccgaatcc tccgaagcct gagccgatc cgaatccgcc   7800
gtctaataac tgatacacat agtttgaggg attgttgata gatgagtgac acgggttaca   7860
cgttgaagat tggtgaccgt agctgggtgt tggcggatgc ggaggagacg gctcaggctg   7920
ttcctgcccg cgttttccgt cgtgctgcta agattgccca gtcgggtgag tctgcggatt   7980
tcgcccaggt tgaggtgatg ttttctatgt tggaggctgc cgccccggct gacgcggtgg   8040
aggccctgga ggggcttcct atggttcgtg tggccgagat tttccgccag tggatggaat   8100
acaagcctga cggtaagggt gcctcgctgg gggaatagtt tggctccacg gcctgattga   8160
tgattatcgt ggggccatcg aatacgattt ccgcaccaag tttggtgttt ctgtttatag   8220
tgttggtggc ccgcagatgt gttggggtga ggctgtccgg ctggctggcg tgttgtgtac   8280
cgatacgtct agccagttgg cggcccacct gaatggttgg aagcgcccgt ttgagtggtg   8340
cgagtgggct gtgttggaca tgctggatca ttacaggtct gctaatagtg aggggcagcc   8400
ggagcctgtg gcgaggccta cggatgagcg tagggccccgg tttacgtctg ggcaggtgga   8460
cgatattttg gcgcgtgttc gtgctggtgg cggggtgtct cgcgagatta atattatggg   8520
gtgaatagtg tatgtctggt gagattgctt ccgcatatgt gtcgttgtat acgaagatgc   8580
ctggtttgaa ggcggatgtt ggtaaacagc tttctggggt gatgcctgct gagggtcagc   8640
gttcgggtag tttgtttgct aagggaatga agttggctct tggtggtgcg gcgatgatgg   8700
gtgccatcaa tgttgctaag aagggcctca agtcgattta tgatgtgact attggtggcg   8760
gtattgctag ggcgatggct attgatgagg ctcaggctaa gttgactggt ttgggtcata   8820
cgtcttctga cacgtcttcg attatgaatt cggctattga ggctgttact ggtacgtcgt   8880
atgcgttggg ggatgcggcg tctacggctg cggcgttgtc tgcttcgggt gtgaagtctg   8940
gcgggcagat gacggatgtg ttgaagactg tcgccgatgt gtcttatatt tcgggtaagt   9000
cgtttcagga tacgggcgct attttttacgt ctgtgatggc tcgcggtaag ttgcagggcg   9060
atgacatgtt gcagcttact atggcggggtg ttcctgtcct gtctttgctt gccaggcaga   9120
ctggtaaaac gtctgctgag gtgtcgcaga tggtgtcaaa ggggcagatt gattttaaca   9180
cgtttgcggc tgcgatgaag cttggcatgg gtggtgctgc gcaggcgtct ggtaagacgt   9240
ttgagggcgc tatgaagaat gttaagggcg ccctgggtta tcttggtgct acggctatgg   9300
ccccgtttct taacgggttg cggcagattt ttgttgcgtt gaatccggtt atcaagtctg   9360
tcacggattc cgtgaagccg atgtttgctg ccgtcgatgc tggtattcag cgtatgatgc   9420
cgtctatttt ggcgtggatt aaccgtatgc cggctatgat cactcgaatg aatgcacaga   9480
tgcgcgccaa ggtggagcag ttgaagggcg tttttgcaag gttgcatttg cctgttccta   9540
aggtgaattt gggtgccatg tttgctggcg gcaccgacat gttcggtatt gttgctgcga   9600
gtgttgggaa gcttgtcgcg gggtttgccc cgttggcggg gtcgttgaag aatctgttgc   9660
cgtcgtttgg tgctttgagg ggtgccgccg ggggcttgg tggcgtgttt cgcgccttgg   9720
gtggccctgt tggtattgtg atcggcttgt ttgctgccat gtttgctacg aacgcccagt   9780
tccgtgccgc tgttatgcag cttgtggggg tggttggccg ggctttgggg cagattatgg   9840
tcgccttgca gccattgttc gggattgttg ctggcctggt tgcaggttg gctcccgttt   9900
ttggccagat tattggtatg gttgctggtt tggctgcccg gctggtgcct gttattggta   9960
tgcttattgc ccggctggtt cctgttatca cccagattat tggtatggta acccaggttg  10020
ctgccatgtt gttgccatg ctgatgccgg ttattcaggc tgttgttgct gtgatacggc  10080
aggttattgg tgtggtcatg cagttgatac ctgtttgat gccggttgtg cagcagattt  10140
tgggtgctgt catgtctgtt ttgccgccga ttgttggttt gatacggtcg ctgataccgg  10200
```

-continued

```
tgatcatgtc gattatgcgt gtggtggtgc aggttgttgg tgccgtgcta caggtggtgg   10260
cccgtattat tccggttgtt atgccgattt atgtttcggt gattggattc attgccaaga   10320
tttatgctgc ggttatcgtt tttgaggcta aggttattgg cgctattctt cgtactatta   10380
cgtggattgt gaatcattca gtgtctggcg tgaggtctat gggcacggcc atccagaatg   10440
gctggaatca tatcaaatcg tttacgtcgg cgtttattaa cggtttcaag tcgatcattt   10500
ctgccggtgt tgccgcggtt gtggggtttt ttacgcggct tggtttgtcg gttgcctccc   10560
atgtgaggtc tggttttaac gcggcccgtg gtgctgtttc ttctgcgatg aatgctattc   10620
ggagtgttgt gtcttcggtg gcgtctgctg ttggcgggtt tttcgggtcg atggcgtcta   10680
gggttcgtag tggtgctgtg cgcgggttta atggtgcccg gagtgcggct tcttctgcta   10740
tgcatgctat ggggtctgcg gtgtctaacg gtgtgcatgg tgtgctgggg tttttccgga   10800
atttgcctgg caatattagg ggcgccttgg gtagtatggg gtccctgttg gtgtcggctg   10860
gccgtgatgt ggtgtctggt ttgggtaacg gtatccggaa tgctttgagt ggcctgttgg   10920
atacggtgcg taacatgggt tcccagattg cgaacgcggc gaagtctgcg ctgggtattc   10980
attccccgtc tcgggtgttt cgtgacgagg ttggccgtca ggttgttgcc ggtttggctg   11040
aggggatcac cgggaatgct ggttttggcgt tggatgcgat gtctggtgtg gctggccgtc   11100
ttccggatgc tgtggatgcc cggtttggtg tgcgatcgtc tgtgggctcg tttaccccgt   11160
acgaccggta tcggcgtgcg aacgagaaga gtgttgtggg gaatgtgaac ggacccacgt   11220
atggggatcc tgccgagttt gcgaagcgga ttgagcgtca gcagcgtgac gctttgaatg   11280
cgttggctta cgtgtgatcg agggggtgtt gtgcatgttt attcctgacc cgtctgatcg   11340
tgccggtttg actgtggatt ggactatgtt tccgttggtg ggtaatgctc cggagcgtgt   11400
gcttcatttg acggattata cggggtcgtc tccggtcatg ttgttgaatg attcgttgcg   11460
cggcctgggt atgcctgagg tggagcagtt ttctcaaacg catgttggtg tgcatggttc   11520
ggagtggcgc gggtttaatg tgaagcctcg cgaggtgact ttgccggtgt tggtgtcggg   11580
tgttgacccg gatccggtgg gcgggtttcg tgacggtttt ttgaaggcgt atgacgcgtt   11640
gtggtctgcg tttcctccgg gcgaggtggg ggagttgtct gtgaagactc ctgccggtcg   11700
tgagcgtgtg ttgaagtgcc ggtttgattc ggctgatgac acgtttacgg ttgatccggt   11760
gaaccgtggc tatgcgcgct atctgttgca tttgacagct tatgatccgt tttggtatgg   11820
ggatgagcaa aagtttcgtt ttagtaacgc gaagttgcag gattggttgg gtggcggccc   11880
tgtcggcaag aagggtaccg cgtttcctgt ggtgttaaca ccgggtgtgg gctcgggctg   11940
ggataacctg tctaataagg gtgatgtgcc tgcgtggcct gtgattcgtg ttgagggtcc   12000
tttggagtcg tggtctgtgc agattgatgg tttgcgtgtg tcttcggact atccggtcga   12060
ggagtttgat tggatcacta ttgatacgga tcctcgccag cagtctgcgt tgttgaacgg   12120
gtttgaggat gtgatggatc gtttgacaga gtgggagttt gcgcctatcc cgcctggcgg   12180
ttctaagagt gtgaatattg agatggttgg tttgggtgct attgttgtgt cggtgcagta   12240
caggtttttg agggcttggt gaatagttga tggctggtct tgttccgcat gtaacattgt   12300
ttacacctga ttatcgccgt gtggcgccta tcaatttttt tgagtcgttg aagttgtcgt   12360
tgaagtggaa tggtttgtcg actttggagt tggtggtgtc gggggatcat tcgaggcttg   12420
acggggttgac gaagccgggt gcgcggctgg ttgttgatta tggtggtggc cagatttttt   12480
ctgggcctgt gcgtaaagtg catggtgtgg gtccgtggcg ttcttcccgt gtgactataa   12540
cgtgtgagga tgatattcgg ctgttgtggc gtatgttgat gtggcctgtg aattatcgtc   12600
ctggtttggt tggtatggag tggcgtgcgg acagggatta tgcccactat tcgggtgcgg   12660
ctgagtcggt tgctaagcag gtgttggggg ataatgcttg gcgttttccg cctgtttgt   12720
ttatgaacga tgatgagagt cgtggccgct atattaagga ttttcaggtg cggtttcacg   12780
tgtttgccga taagttgttg ccggtgttgt cgtgggctcg gatgactgtc acggtgaacc   12840
agtttgagaa tgcgaagttt gatcagcgtg gtttgttgtt tgattgtgtg cctgctgtga   12900
cccggacgca tgtgttgact gccgagtctg gttcgattgt gtcgtgggag tatgtgcgtg   12960
acgccccgaa ggctacttcg gtggtggttg gtggccgacg cgagggcaaa gatcggctgt   13020
tttgcgagga tgttgattcg atggccgagg atgactggtt tgatcgtgtc gaggtgttta   13080
aggatgcccg taacacggat tccgagaatg tgcatcttat tgatgaggct gagcgggtgt   13140
tgtccgagtc gggggctacg tcggggttta agatcgagtt ggctgagtcg gatgtgttgc   13200
ggttcggcc tggccgcctg atgccgggtg atcttatcta tgtggatgtg ggctcggggc   13260
ctattgcgga gattgtgcgc cagattgatg tggagtgtga ttcgcctggt gatgggtgga   13320
cgaaggtgac tccggttgct ggggattatg aggataatcc gtcggcgctg ttggctcgcc   13380
gtgtggctgg tttggctgcg ggtgtgcggg atttgcaaaa attctaattg ttaggggttt   13440
gttgtgggta ttgtgtgtaa agggtttgat ggtgtgttga ccgagtatga ttgggctcaa   13500
atgtctggtc tgatgggtaa tatgccgtcc gtgaaagggc cggatgattt tcgtgtcggc   13560
actacgattc agggttccac ggtgttgtgt gaggtcctgc cggggcaggc ttgggctcac   13620
ggggtgatgt gcacgtcgaa tgctgttgag acggtgacag gtcagcttcc gggcccgggt   13680
gagacccgct acgactatgt tgtcctgtcg cgggattggc aggagaaatac ggccaagttg   13740
gagattgttc ctgggggggcg tgcggagcgt gcccgtgacg tgttgcgtgc ggagcctggc   13800
gtgtaccatc agcagttgtt ggctactttg gtggtgtcgt ctaacgggtt gcagcagcag   13860
cttgacagga gggctatagc ggcccgtgtg gcgtttgggg agtctactgc atgtgatcct   13920
accccctgtgg agggtgaccg ggtgatggtg ccttctgggg ctgtgttggc taatcatgct   13980
aacgagtgga tgctgttgtc tccgcgggatt gagacgggca ctaagtcgat catgtttggc   14040
gggtctgctg tgtatgctta cacgattccg tttgatcgcc agtttgctag tccgcctgtt   14100
gtggtggcgt ctatggctac ggcggctggg ggcacgaccc agattgatgt gaaagcctac   14160
aatgtgactc cccaaaattt tagtttggcg tttattacga atgatggttc gaagccgaat   14220
ggtgtgcctg cggtggctaa ttggattgct gtcggcgtgt gactgtacag gtgttgtggc   14280
ggatggttgg atgttggggg gctgtggtgt cgtggtttac tcctgcactg gtggcctcta   14340
tttgtaccgc gttggccacg gtttttgggtt ctgttcaggc tgtcacgtct aaatctagga   14400
ggcgtttgcg ccgcctgtcg gcgcaggtgg atgcgatgga agagtatacg tggggtgtgc   14460
ggcgcgaggt gcgaaggttt aacgccgggc ttcctgacga ggtggagcct atgcatctcc   14520
ctgatttgcc cgagtttttg aaagatactg ttgatggtgt aggtgagtag ggttgaggga   14580
gttggaggag gagaacggc agcgccgcaa ttttgagaag gcttcactgg tgttgctgtt   14640
tttgtcgctt gtgttattgg ctgtggttgc tgcgggtgct ttgcgtttcg gggctgtatc   14700
ctctgagcgg gattcggagc aggcgagggc ccagtcgaat ggtacagccg ccaagggttt   14760
agccagcagt gtgcggcagg tgtgtgctca gggtggacgg gagtctgtgc ggcttcacca   14820
gtctggtttg tgtgtggatg ctcagcgtgt tgagcgtagt gtgcagggtg tgccgggtcc   14880
tgccggtgag cgcggcccgc aaggcccggc aggtgtggac ggccgggatg gtgttaatgg   14940
```

-continued

```
ttcggctggg ctggttggcc ctgtgggtcc gcaggggtcc ccgggtttga atggtgtgaa    15000
aggtcctgac gggttgcctg gcgctaacgg ttcggatggc cgtgatggtg tggacggtgt    15060
gaacggcaat gatggcgctg atggtcggga tggttcggcc ggtgagcgcg gtgatgtggg    15120
cccctcaggt cctgccggcc cgcaaggtgc acagggtgaa cggggtgagc gcggccccgc    15180
cggtcgcgaat ggcacgaatg gcaaggacgg taaggatggt gccgacggcc gtgatgggcg    15240
ttcggttgtg tctgtgtact gtttcggtgg cctgccaggg tgtgaaacca tcacctgtgg    15300
ttaccgtgtc atcccgtaaa tagaagaaga gggaagggtg ttactagtgt tgattgtggt    15360
ttttggtggt ggtgtgtggt gagatacatt cctgcagcgc atcactctgc cggctctaat    15420
aatccggtga acagggttgt gattcatgca acatgcccgg atgtggggtt tccgtccgcc    15480
tcacgtaagg ggcgggcggt gtctacagca aactatttcg cttccccatc gtctggtggt    15540
tcggcgcatt atgtgtgtga tattgggggag acggtgcaat gcttgtcgga gtctacgatt    15600
ggttggcatg ccccgccgaa tccgcattct ttgggtatcg agatttgcgc ggatgggggt    15660
tcgcatgcct cgttccgtgt gccggggcat gcttacactc gggagcagtg gcttgatccg    15720
caggtgtggc ctgccgttga gagggcggcg gtgctgtgta gacgtttgtg tgacaaatat    15780
aatgttccga aaaggaaact gtcggctgcc gatttgaagg ctggcaggcg gggtgtgtgt    15840
ggccatgtgg atgttacgga tgcgtggcat cagtcggatc atgacgatcc tgggccgtgg    15900
tttccgtggg acaaatttat ggccgtcgtc aacggcggca gtggagatag tggggagtta    15960
actgtggctg atgtgaaagc cttgcatgat cagattaaac aattgtctgc tcagcttact    16020
ggttcggtga ataagctgca ccatgatgtt ggtgtggttc aggttcagaa tggtgatttg    16080
ggtaaacgtg ttgatgcctt gtcgtgggtg aagaatcctg tgacgggggaa gctgtggcgc    16140
actaaggatg ccctgtggag tgtctggtat tacgtgttgg agtgtcgtag ccgtcttgac    16200
aggctcgagt ctgctgtcaa cgatttgaaa aagtgatggt ggtttgttgt gggtaaacag    16260
ttttggttag gtttgctaga gcgggcggct aagacttttg tgcaaacgtt tgttgctgtg    16320
ttggggggtga cggcgggtgt cacgtatacg gcggagtcgt ttcgtggttt gccgtgggag    16380
tctgcgttga ttacggctac ggttgctgcg gtcctgtcgg tggctacctc gtttggtagc    16440
ccgtcgtttg tggctggtaa gccgaaaacc acgcctggtg atgcgggttt ggttccggca    16500
gatgatcccg gaatagtgga gcctcacatg gtggatgtgt cggatcctgg catgatcgag    16560
cctgcagatg atgtggatct tggtgtaggc tatgtgccga aacatgctgc cgagtcggag    16620
gttggcacgg tagagtcgac tgttgcataa gtgaatatag atgtgtgccc cagcggtgct    16680
gccacgattg tgtggtggtt gccgctgggg cactatttt gtatattgcg gtgtggctat    16740
gattcgttgc tgtcgatggt gtcttcgagc atctggtaca ggtggaggca ggtagagata    16800
gtttcgctgg cctggtcgag aacgttccgg ccgataacat ttttgttgtt gtcgcggtgg    16860
cggatgatga accacatgat ctcgtcggct gccgcctgca atagtttgc ctggtatgcg    16920
attccagcga gccagtctag tgcttcctgg cttgcatagg gtgtctggtc ctcgctgttg    16980
cttgtggggt gtcctgcact gtcgcatagc cacaggattt cgctgcactc gtctagcgtg    17040
tcctggtcta tagcgagatc gtcgaggctg acattgttga cggtaaggtt cacgttgtcg    17100
agggagatgg gtacaccgta ctggttttcg acaccgtcaa caatgttttc caattgctgc    17160
atgttggtgg gctgttgttg gacgatacgg tgtatcgctg tgttgagggt ggtgtaggtg    17220
atattgtcgt tgttgttcat cgtgttatgc cattccttcg ttatcgtctg gcctgtagta    17280
tgtgctgttt gcgtactcgg ttaacgtcat cagtgtttgg tctgcccact gtttcacagt    17340
ctgccttgtc actccgagtc gttgggcggc tgtggcgtag gtttggtcat acccgtatac    17400
ttccctgaat gctgccaacc gtgccaaatg ttttcgctgt ttggatggct ggcaggcgag    17460
ggtgtagtcg tcgatggcta gctgtagatc gatcatggtg gcaatgttgt tgccgtgggg    17520
ttgtggcgcg gttggtgggg gtggcattcc tggctccaca ctgggtttcc atgggcctcc    17580
gttccagatc cattgggcgg cttggatgat gtctgcggtg gtgtaggttc ggttcactgg    17640
tcatcccctg aacaggttgt ctgggttgct ggtgcggatt gtgtcgaatc gtccgacgca    17700
gtggcagtag tcgtacatga gtttgataat gtgttggtgg tctcccaaat ggtgtttcc    17760
gctgatgctg taggtggctg tgccgtcttt actaatagtg tatttggcgg tgatggtttc    17820
ggggtttcg gtgtcggtga tgatggctgt ggtggtggtg cctacggttt ggagcacggt    17880
ggtttggggtt ccgtcgtcga tggtggtttt aaccatgagg tgtgttctcc ctttgtgtta    17940
gttgctggtt tggttgtcgg ctagatgaat gatgtcgggt aagggtttcg gctggtcaa    18000
atgttgtgtg gttttgttgg ctagccgttt ggctaccctg tagcacattt tggtgtagtg    18060
tttgttgtct aggttgtggt attgttcccg caccgcaata tatagcaggg agtcttggta    18120
caggtcgtct gcattgattg cggggtagtg tgcggctgtt ttagtgcatg cccggttgag    18180
tgtgcgtaga tgatggtctg tggcccacac ccacgatgcg ggtcggcttt ggtcggcttt    18240
tgttggtcgt cggctcatgg catctctttc atctggctat ctggtagttg tttggtgttt    18300
tgttgttgat agtgtagcac acgagtccgg ggtttccggt ggtgcccgtc ttgtgccggt    18360
accatgtgga ttcgccttcc atggatgggc attggatgaa ggtgcgttgt ccttgttcgg    18420
agatttctag gtggtgcctg tgtccggcca tgaggatgtg ggatgtggtg ccgttgtgga    18480
attcttgtcc gcgccaccaa tcatagtgtt tgccggtgcg ccattggtgg ccgtgggcgt    18540
gtagtatccg tgtgccggct acttgacggg tggtggtcat ttcgtctcgg ctggggaaat    18600
aaaagtgtag gttggggtat tggttggtga gctggtaggc ttctgcgatg gcgcggcagc    18660
agtctacgtc gaaggagtcg tcgtaggtgg tgactccttt gccgaagcgt acggcttctc    18720
cgtggttgcc ggggatggat gtgatggtca cgtttttgca gtggtcgaac atgtggatga    18780
gttgcatcat ggccatgcgg gtgagcctga tttgttccgt caaggggggtt tgtgtgcgcc    18840
aggcgttgtt gcctccttgt gacacgtatc cttcgatcat gtcgccgagg aatgcgatgt    18900
ggactcgttc gggtttgcct gcctgctgcc agtagtgttt agctgatgtg agggagcgca    18960
ggtagtcgtc ggcgaagtgt gatgtttccc cgccggggat gcctttgccg atttggaagt    19020
cgcctgcccc gatgacgaag gccgcagtgc tgtagtcggt gcgggtgtcc tgttcgggtt    19080
ttggggggtgt ccattcggct agtttatcga cgagttcgtc tacagggtag gggtttgttg    19140
cgggttggtg gtcgatgatt ttttgtacgg atctgcctgt ttctccgttg gggagtgtcc    19200
attcggagat gcgtgtgcgg cgtacggtgc cgtttgcgag atcatcgcag atggtgtctg    19260
cttcgctatc gtggttggct agctgggtga gtagccggtc tatgttgtct atcactgggt    19320
atcctcttct tgcgggggtgg tgttggcttg tttgcggcag tagtctttta taacgggtag    19380
ggagatgggg tatcctgcct gggtgagctg ttttgctagc catgaggcgg ggatggtttt    19440
gtcggcgagc acgtcggcag ccttgttgcc gtagcgttgg atgagtgttt cagttttggt    19500
tgccatggtg tcctatcggt tgtgtggtgg gctgccatcc tgtgcggcag tcgccgtcgt    19560
ggcctggttt gcgtgtgcac cacgatacgg ttctgtctgt gtggttgagt gttttgccgc    19620
acatgacgtt ttgtagatgc tctggcagtg cgccgtcacc ctggttgctg gtttgtgtgt    19680
```

-continued

```
cgaagagtgt tttctggttg gtgaaatgct cggacacggt gccattatgt acgggtagta  19740
tccatgtttt ccattgttgt tgtagccggg tgttccagtg gaattgtttt gctgcgttcg  19800
tggcttgttt gatggtttg tagtagccga cgaggatgcg ctggtgttca ctgtcgggag  19860
ggttttggcc tcgccagtat tgtgccgcca cggcgtagcg gttgctggct gtgaaggcgt  19920
cccagcagta ttcaataatg tgttgtagta cactatcggt catgtctcgt acttggtttt  19980
cgtcgagcca cgcgtcgaca atgatgttgc gtatggcgcg tttgtctttg gtggtgggt   20040
tgaatgcgat gctcacagta cgggcctgtc gtcttgcatg aaatcattaa aggatgattc  20100
gcttgcgcgg cgtgcttgtg tgatttgctg gtcagaccag tcggggtgtt gctgtttcag  20160
atagtaccag tggcacgcat tgtaggtttc gtcttgtagc cgggtgagat ggttttcggt  20220
gatgatttgt ttccacatag tccatgacac gtcgagccgg tccaatattt ccattgctgg  20280
aatgttgaac tggttcagga agagtatttc gtgggtgtag tattccttct cgtactggtc  20340
ccatccactt cggtgcctgt tgggctggtt tttggggtag gcttcccggc atactttgtg  20400
caaatgtttg gccatgtcgt cgggtagttt aatgtcaggg ttggcgcgga tcatggatcg  20460
catcccatca taggtggtgc cccaggtgtg catgatgtag gtggggtctt caccatcagc  20520
ccatttttct gcacagatgg cgaggcggat gcgtctcctg gctgattggc tggtgttgcg  20580
ccggttgggg atgggcacg tgtcgagggg atccatgatg ttttggtgta cctttcttgg   20640
tttaggttgc ttgtgtggtt ttattgtagc actgtgtcta gtgcttgtgt caaccctgtt  20700
ttgccggcct gaaggtaggt gtctgtgaca tcccccaggg tgaggggcac atgggtggct  20760
tgggggagtg cggcctggag tgtttgggcc atctcggtggc ccgccttgtc tgggtctgac  20820
cagatgtaga tgtggtcgta gccttcaaaa aatttggtcc aaaaagtttg ccacgaggtt  20880
gcgccgggta gggctacggc tggccatccg cattgttcga ggatcatgga gtcgaattcg  20940
ccttcgcaaa tgtgcatttc ggctgccggg ttggccatgt cggccacatt gtagatggag  21000
cctgtgtctc ctgccggggt tagatatttg gggtggttgt gggtttttgca atcatgttgg  21060
agtgagcagc ggaaacgcat ttttcgtatt tcggctggcc cttccagac ggggtacatg   21120
tatgggatgg tgatgcactg gttgtagttt tcgtggcctt ggatgggggtc attgtcgatg  21180
tatccaaggt ggtggtagcg ggctgtttct tcgctgacgg ctcttgccga gagcaggtcg  21240
agtatgtttt cgaggtgggt ttcgtagcgg gctgaggctt tctggattcg gcggcgttcc  21300
gcaatgttgt aggggcgtat gctgtcgtac attcgggttt tcttcctcta atcgttgttt  21360
cagtttgtgt agtccgcctc cgataccgca tgtgtggcag taccagacgc ccttgtcgag  21420
gttgatgctc atggagggct ggtggtcgtc gtggaacggg cagaggatgt gttgctcgtt  21480
ccgtgacggg ttgtagcgta tctggtgggc gtctaggagg cggcaggtgt cagaggtgtg  21540
ggaggagctc gttgagggtt gataccacat aggcttcgct ccagggtttg ttgcgctgtt  21600
tcatgatgac gagtccgatg gtggattggt tttcgcggtt tcggtgtgtt tcgtagttgc  21660
gtgcctcccg gctggcttgt ttcacgaatt cggctaggtg tgcctgtcct gctttggctt  21720
cgatcacata ggttttgttg ccggttgtga ggatgaggtc gccttcgtct tctttaccgt  21780
tgaggtggag gcgttctata tcatagccgg tgtcgcgtag ctggtggagg agtcttgttt  21840
cccattcggc gccggctcgg cggttgcgtg cctgttgtgt tgacatgata gtcctttatg  21900
ttcttgtgtc atgttccagg gctgtttttc tactaggggc ccgaagaatg tgtattcggg  21960
gtaggctcgt agtcgttcgt attttgttcc gtctgggctg gatttgccgg ttctctgttt  22020
caggacggcg atgcgtgcct cggcggggat ggtgaggccg ttgccgttgt cttcgccacc  22080
atacagggag actcccaata tgagttgtgg ttttttcggag aggccgtttt tgatttcccg  22140
cctagctggg gggtgttcga tgtcggtgcc ggttttgtcg gttgcgtggt gggtgacgat  22200
gatggtgaag ccagtatctc tacctaaggc tgtgatccat tgcatggctt cttgctgtgc  22260
ctgatagtcg gattcgcagt cttggatgtc catcaggttg tctataacaa taatgggtgg  22320
gaaggtgttc cacatttcca tgtaggcttg cagttccatg gtgatgtctg tccatgtgat  22380
gggtgactgg aatgagaagg tgatgtgtcc gccgtggtgg atgctgtctc gatagtattc  22440
tggcccgtag ttgtcgatgt tgtgttgtat ctgttgggtg gtgtgttggg tgttgagtga  22500
gatgattcgt gtggaggcct cccaggtgt catgtcccct gatatgtaga gggctggctg   22560
gttgagcatc gcggtgatga acatggctag ccctgatttt tggctgccgg accgccccgc  22620
gatcatgacc aaatcccctt tgtggatgtg catgtccagg ttgtcataca agggtgctag  22680
ttggggtatg cggggcagtt cggcggctgt ttgggaggcc ctctcgaagg atctttggag  22740
agagagcatc gggaccttaa tctatctgtt ggttgggtgt gttttggtgg tcagatggag  22800
tcgatgtcga tgtcagcatc ggcgggggct gtggtgtcgt ctagctggcc gttgtcgcgt  22860
ttgtctacat attcggcaac cttatcgtag atggcgtcgt cgaggggttt gaggacgacc  22920
gcgttgaacc cgtttttggt gcgcacggtg gcaagtttga aggcttgttc ttcgccgaga  22980
tatgcttcta ggtcgcggat catggagtgt gggcggtcgt tgttgccgcg tgctttttcg  23040
atgatggcgt tggggatggt ttctggggtg ccgttgttga gatcctggag ggtgtggaag  23100
attgtgacat cagcgtagat gcggtctgcg acctgtccac cgtagccttc ggtgttgtgt  23160
tctacgtcgc ggattttgaa ggcgatggcg gtggcgtcct ggtttcggga ggggttgaag  23220
aaggtgctgt tgctgttgtt gtggtagttg gcgagtgcca tgattgtgtt atcctttact  23280
gttgtgtctg tttttgttgt cttatattgg tttatcgggt gaggctgttt cgtttgctgc  23340
ggaaagcctc ggaaacgtca ctgttactgg tgatggtctt cttgtactgt ttgagtaggt  23400
ctgctagctg tgtcttgctg gtggctttgt ttatccggtc gatgatgatg tcgttttcct  23460
gtgatgcgat tttgttgacg tagtctttgg cggctttatc gtatcggtct tgaagcagga  23520
ttgctgcgct agcgatgagg gttgcgagat cccagtcttt ggatacggtt tcgtctttca  23580
atcctcctag cagatcaata atggattgtt tgatgtcttc tgcggtgtct ccgcggatga  23640
ctgtccatgg ggcggcatag tcgccaccgt atttgagtgt gatagttagt tttccgctgt  23700
ctgtggtgtg ctcgtcggtc acgtgtttc cttttcgttg ttttcggctt ctggtggctg   23760
tacggtgtt tctatcggtg atctgtaggc gtctttcccg ttgacggccc agcaggcgtc  23820
cttgacgggg catcctttgc agagtgtggt gacgtggggt acgaagatgc cttggctgat  23880
tcctttcatt gcttgactgt acatggatga tacatgccgg taggtgttgt tgtcaagatc  23940
aatgagttcg gttgctgtgc cctgctcgac tgattgctcg tctcccttgg tggtggcggg  24000
tgtccaaaac atgcctttcg tcacatggat gccgtgttgg gcgagcatgt accggtatgt  24060
gtgcagctgc atactgtctg cgggtaggcg tccggtttta ggtccaaaa tgaaggtttc   24120
gccggtgtcg gtgtcggtga ataccggtc aatatatccg actattttg tgtcatcgtc   24180
gagggtggtt ctaccgggt attcgatgcc tggctggccg tcaataacag cggtggcgta  24240
ttctgggtgg ttgcgcctcc atgtttttcca gcggtccaca aaggtggggc cgtacatcat  24300
ccaccaattg tagtctttct tgtgtggccc gcctgactcg cacatgtttt tgcatattct  24360
gccggagggc tttatgtttg tgccttcgga ttcggcgagg cgatttggg tgtcgaaaat   24420
```

-continued

```
gtttgtgaag gatgagagtt tgtctggcag tgcagggtat tcggcggggt tgtacaggtg   24480
taggtcgtat tgttcggtga tgtggtgtat ggcgcttccg gcgatggtgg cgtaccaggt   24540
gtggtgttgg gcgtggtagc cgtgtgctag gcgccatttt tcgccgcatt cggcccactg   24600
tgtgagtgaa ctgtaggaga tgtggcctgg atggttgatg gttttcgggt attgtgctag   24660
gggcattact tgtcgccttt gtgggtgttc catgggttgc gggtgtcttt gccggcgtgg   24720
tgttgctggt aggcgaggag tgcgaggcag tgccaggcag cgtgtgccag atgcggcaaa   24780
tgtgattcgt tgtcgaggtt gttgccttgc tgccatgata acaggtgccg gtagagggcg   24840
tcgacactgt ggctccacgg gtatcctccg gtccagttgt tgtcgccgta cttggtggca   24900
ccgtagcctg ccacggagcc tagggcgtgc aaggctgcgg ggtcgatgag ggagagcctg   24960
cagagtttca attcttttcg ggcaccgctg ttggggtcgg tgtacatgct ggtgggctca   25020
tccatggtgt gtgtgctcct taagcgtggg ttactggtta ttgtcgtggg cgagtgctac   25080
ggcgagaata atgatggcga gggtttcagc gatcagtatg ggtgttgtga tcatttagtg   25140
tctcggggat tattggtgag tgttgatgca cctaggaggg tggcgagggc gcatgcggcg   25200
atggtggcga gggctgcctt gtgtggggtg ccggttgcgt acatccatgt gatgatgccg   25260
ccttggatcc aggctagact ggtgaagaac gtttcgtaac tgtgtagctc aatgttgttg   25320
ttgggtgtgt tcatgcttgc tcctgaagaa tggtgttgat ggtttttataa atgttgtaca   25380
ggtcggtttc gatagataac agttggttga tttggtggtc gagatcaatg tctgggttga   25440
gggtgtcgat gcgggcggcg atatcggtgg cggtgcgtag gcttactgct gcaccgtgga   25500
tgatgtggca catgtcggtg aggccgactt tggcgatata gtgtgacatg agaggccataa   25560
taggtgtgct gtctttctgg tcagcgtgaa gggttgatgg acatatcctc tacctgtggt   25620
ttgtcttcgg tgccggagac ttggcagaag actttcacat gcgtcttgga tgctccggcc   25680
tgtttggcgg tggcaccgta ggcgatagta aaggtgtctt tgtgggcgcc gatgactttg   25740
tgtaggaaga ggtcgatgtc ggggttgccg ttccatttga caccgtttttc tgcggctgtc   25800
tgggtggctt tctgattgca ggcgtgtgcg gcggtgatca tggtgagacc cttgctggtt   25860
tcttcacccc ttgcttgggc ttgccggtgg gctttggcct gctcggcttg tagggagcgg   25920
actgctgcgg cctggcgggc cttcttctca gccttgcgct gctggacggt tttgggtgtc   25980
cattcggtgt tggctgtggt tacctgtggt gcgggttgtg aggcgagtgg cggattgtcg   26040
tctggggctg gcatgaagga tgctgcggca ataatggcga ctgtggcgcc tgcgatggtg   26100
tagcctgttt tcttgttcat gattttatgt tcccctttcc ggggtgttgt tcgttgctga   26160
catggttaat actttcagcg gctgggccca ctgtcaaggc tgcgctcagt ttgtgtgagc   26220
gtttcttgtg tggctagggg tgatggcttc tttcgcccaa taggatgtgc caccgctggt   26280
ccagtatccg agtttgttgc gctgcatgcc cttggcgtcc atctcgtcga tagtgaggca   26340
cctgcggcga ttggggcctg tcttgacccc gtggtcgcct gtccggtgca tgtcgcctga   26400
ggtggtactc gtgaatgttt catggcagat ggtacagtgc tctggtcgat atccggtgat   26460
tgtgctcatcg cacttgtggc atgtccattc catgattgct cctattttcc attataagac   26520
ttcctgtagt gccattttag cgccttgcgg gtcttggggg tacaactata taggtcaggt   26580
gtttctaggc gattctaggc tcattgtgtg tggctggggt tttatcgggc acacagggtg   26640
agcaggtggc caacattgat gcgggtcaca ttccagtaga gttgcgtggc ttccccactg   26700
gtgagcggct tccactcgtc atggctgaac acggtgccat cggatgcgat gaacgtgttg   26760
gggcgtagct tgtggagttc ggcttccacg ctctgccggt aggcttcggc gaggccctca   26820
aaatccatgt ggtcgcaggg gaggttttcg aggcgtgtca ggtcgaaggg tgtggggcag   26880
tcgtagctgg cggggggtgta gagctgggtg aagtggttgg cgatcttctg catcatgatt   26940
ccttttctga tgatggtgtg ttgagggttt atcgggtgga tgcgacaagg atggcgtcta   27000
catcgatcat gtcgatgaga tcgtggagtt cctcggcctc gttctcagtg agtggctgcc   27060
aggcgtagtc gccgtatacg gcgccgtcga gggtgacagt ccacgggggc cggatgagtc   27120
gtatggcttc ttgtactttta gcgtggtaca tgcggcgcac catatccaga tcgatgtcgt   27180
ctgaatggtt tccggtgagg ctgtggaggc tgagcgggtc gatgtctgtc tgcctgtaga   27240
gggatgtgaa ggatggggtg atgagtgtgc catccatgag tgtgctcctt tcggtggttg   27300
tagggggttgt tgtggtttct agagtgtgcg ggctgcgacc ccacagtcaa ggtgtcgctc   27360
aaaactcagtg agcgtttcat atgggtgtgt tgggtgtgac agatgtcact taagccttga   27420
tggcctctct cagcgcctca aatcttctag gggtaggatt atgaagggtt ggccctgctg   27480
atcgattcta ggccccatac agggcgtctg aggggtgtgt ctgagtgata gtgggtgtgg   27540
cagatgatct agcgagtcaa ggtgccgagc tgagacataa gatctatcat ctaggtgtgt   27600
gagatgtatc acatcctccc ggcttggtgt gcaccctcaa ggccacccag tcgatctgac   27660
gtggagggtg tagcccagaa atactgttta aagccttcac acggcgccta ggagcgcctt   27720
acagggtggg ggctaggtat ttatacccc agcacattct gatcgattct agacgcctac   27780
aggagcccga tacacgatca gccatccaga cgcagatcat cagcacctat catggttagc   27840
taagcctcaa ctatgtggac agtgttggtt actgtggggg aagaaggaca cggtaaaaga   27900
aagaggggga gtatcagctt taaagccttta aggtcttagc gcttagcacc gatggtctta   27960
gcagttagca ccgagccccc tcaagggctc ggcatcagcc cgaacaggca cagccatgaa   28020
aggagtacac gccatcaggg aaggctttcg agtacgagga gcctcagcga cgagtactcg   28080
aaagcctgag ggaacaccca tcagcactga tgagcctagc gtattcggaa aggacacaag   28140
agtgaagtgt gacagctgtc cgggagtgaa ccccgttctg actaggggtt tcagccttaa   28200
ccaccctcaa aggttacaag actctaagaa aatttaagga aaagtttagg tttaattttt   28260
ggacctttac taccaaaaac acccgtttac agccctcaaa cccgcctata gagccaaaac   28320
caccagtttg actcatccca ggtggggtat gataggctgg acaggtagcc agctggacgc   28380
aaggccggaa agtgctaacg cacttttcaa cctcgcttac catcagtcta ccaaacactt   28440
aaagacctaa gggcttagcg ctaaggtgct gatagcttag caccgagccc cctcaagggc   28500
tcggcatcag tcttaaagcc ttaaatactt aaagtaacta taaaacttta aaagcttaac   28560
acttaaggat ataaacttta catcagtgtt taagacttaa aaacttaaaa taactattaa   28620
gacttaaagt aactataaaa cattaaagac cttaagtact taaagttaac catcagtctt   28680
aaactttact atgataacct ataagtctta aagcttatag gtataataat ataatataag   28740
tattaaagct tataagttat aaaagtttta gaagagttaa agggtaact tctttacttc   28800
tcttctctct ttggttcttt ctctcttctc ttctttttct catcggggga gaagaggaac   28860
ctttaacgtc aacgctgatg gacttttcgc cgtgtgtctc gtgtgcttct ggtcgcaagc   28920
tcccatcgca cactccccac actctttcac ctgtgtccct ttcaggctta gcgtgttcag   28980
ctgaaggcgt acagcgtgtc acgcttaaac ccttaacacc aggtaagact taaagtgcat   29040
attataagta gaagactttta aaaccttaag ggtgttcctg cttagcctgt gtcctttaac   29100
gctaggcgct aagccgtgaa acgtgaacac ccatccaccc ctcttctttt taccgtgtcc   29160
```

-continued

```
ttcttctttt gacaccgctg gggggcgatg tgatctttttt aacatgccag ggggtgcggg   29220
tagaaaacaa ccaccccacc acaaacagaa caccccctca aacgcacaaa acagcccca    29280
ggatcgatga acagggcaag ggcaaggtat tcataccccc agacgattcc aggccgttag   29340
agaggcaaat aagacccgta cagggctagg tgaggaatag acacatcatg gcacgcacca   29400
atcgcacagc tagccaagcc caccgacgct ggcggcaacg actcatcacc caagcccaac   29460
aacaaggcca aaccgaatgc ccactctgcg gagtcaccat cacctgggac acacacgacc   29520
taccaaccag ccccgaagcc gaccacatca cacccgtcag caggggagga ctcaacaccc   29580
tcgacaacgg gcaaatcatc tgcagaacat gcaacagaag caaaggcaat cgcagcgaac   29640
caaacatcaa attccaacaa caaaccacaa aaacattgat tccatggtga caaacccgcc   29700
aaccccacc ggggacaccc cctgcacagg cgtgcaagac ctcgtacggc tt            29752
```

```
SEQ ID NO: 2                moltype = DNA   length = 1537
FEATURE                     Location/Qualifiers
misc_feature                1..1537
                            note = 16S DNA sequence for the KPA171202 type strain
source                      1..1537
                            mol_type = other DNA
                            organism = synthetic construct
SEQUENCE: 2
tttttcattg gagagtttga tcctggctca ggacgaacgc tggcggcgtg cttaacacat   60
gcaagtcgaa cggaaaggcc ctgcttttgt ggggtgctcg agtggcgaac gggtgagtaa   120
cacgtgagta acctgcccttt gactttggga taacttcagg aaactggggc taataccgga   180
taggagctcc tgctgcatgg tgggggttgg aaagtttcgg cggttgggga tggactcgcg   240
gcttatcagc ttgttggtgg ggtagtggct taccaaggct ttgacgggta gccggcctga   300
gagggtgacc ggccacattg ggactgagat acggcccaga ctcctacggg aggcagcagt   360
ggggaatatt gcacaatggg cggaagcctg atgcagcaac gccgcgtgcg ggatgacggc   420
cttcgggttg taaaccgctt tcgcctgtga cgaagcgtga gtgacggtaa tgggtaaaga   480
agcaccggct aactacgtgc cagcagccgc ggtgatacgt agggtgcgag cgttgtccgg   540
atttattggg cgtaaagggc tcgtaggtgg ttgatcgcgt cggaagtgta atcttggggc   600
ttaaccctga gcgtgctttc gatacgggtt gacttgagga aggtaggggga gaatggaatt   660
cctggtggag cggtggaatg cgcagatatc aggaggaaca ccagtggcga aggcggttct   720
ctgggccttt cctgacgctg aggagcgaaa gcgtgggggag cgaacaggct tagataccct   780
ggtagtccac gctgtaaacg gtgggtacta ggtgtggggt ccattccacg ggttccgtgc   840
cgtagctaac gctttaagta ccccgcctgg ggagtacggc cgcaaggcta aaactcaaag   900
gaattgacgg ggccccgcac aagcggcgga gcatgtggat taattcgatg caacgcgtag   960
aaccttacct gggtttgaca tggatcggga gtgctcagat atgggtgtgc ctcttttggg   1020
gtcggttcac aggtggtgca tggctgtcgt cagctcgtgt cgtgagatgt tgggttaagt   1080
cccgcaacga gcgcaaccct tgttcactgt tgccagcacg ttatggtggg gactcagtgg   1140
agaccgccgg ggtcaactcg gaggaaggtg gggatgacgt caagtcatca tgcccccttat   1200
gtccagggct tcacgcatgc tacaatggct ggtacagaga gtggcgagcc tgtgagggtg   1260
agcgaatctc ggaaagccgg tctcagttcg gattgggggtc tgcaactcga cctcatgaag   1320
tcggagtcgc tagtaatcgc agatcagcaa cgctgcggtg aatacgttcc cggggcttgt   1380
acacaccgcc cgtcaagtca tgaaagttgg taacacccga gccggtggc ctaaccgttg   1440
tggggggagcc gtcgaaggtg ggactggtga ttaggactaa gtcgtaacaa ggtagccgta   1500
ccggaaggtg cggctggatc acctccttttc taaggag                            1537
```

```
SEQ ID NO: 3                moltype = DNA   length = 1537
FEATURE                     Location/Qualifiers
misc_feature                1..1537
                            note = 16S DNA sequence for the ProI probiotic strain
source                      1..1537
                            mol_type = other DNA
                            organism = synthetic construct
SEQUENCE: 3
tttttcattg gagagtttga tcctggctca ggacgaacgc tggcggcgtg cttaacacat   60
gcaagtcgaa cggaaaggcc ctgcttttgt ggggtgctcg agtggcgaac gggtgagtaa   120
cacgtgagta acctgcccttt gactttggga taacttcagg aaactggggc taataccgga   180
taggagctcc tgctgcatgg tgggggttgg aaagtttcgg cggttgggga tggactcgcg   240
gcttatcagc ttgttggtgg ggtagtggct taccaaggct ttgacgggta gccggcctga   300
gagggtgacc ggccacattg ggactgagat acggcccaga ctcctacggg aggcagcagt   360
ggggaatatt gcacaatggg cggaagcctg atgcagcaac gccgcgtgcg ggatgacggc   420
cttcgggttg taaaccgctt tcgcctgtga cgaagcgtga gtgacggtaa tgggtaaaga   480
agcaccggct aactacgtgc cagcagccgc ggtgatacgt agggtgcgag cgttgtccgg   540
atttattggg cgtaaagggc tcgtaggtgg ttgatcgcgt cggaagtgta atcttggggc   600
ttaaccctga gcgtgctttc gatacgggtt gacttgagga aggtaggggga gaatggaatt   660
cctggtggag cggtggaatg cgcagatatc aggaggaaca ccagtggcga aggcggttct   720
ctgggccttt cctgacgctg aggagcgaaa gcgtgggggag cgaacaggct tagataccct   780
ggtagtccac gctgtaaacg gtgggtacta ggtgtgggggt ccattccacg ggttccgcgc   840
cgtagctaac gctttaagta ccccgcctgg ggagtacggc cgcaaggcta aaactcaaag   900
gaattgacgg ggccccgcac aagcggcgga gcatgcggat taattcgatg caacgcgtag   960
aaccttacct gggtttgaca tggatcggga gtgctcagat atgggtgtgc ctcttttggg   1020
gtcggttcac aggtggtgca tggctgtcgt cagctcgtgt cgtgagatgt tgggttaagt   1080
cccgcaacga gcgcaaccct tgttcactgt tgccagcacg ttatggtggg gactcagtgg   1140
agaccgccgg ggtcaactcg gaggaaggtg gggatgacgt caagtcatca tgcccccttat   1200
gtccagggct tcacgcatgc tacaatggct ggtacagaga gtggcgagcc tgtgagggtg   1260
agcgaatctc ggaaagccgg tctcagttcg gattgggggtc tgcaactcga cctcatgaag   1320
ttggagtcgc tagtaatcgc agatcagcaa cgctgcggtg aatacgttcc cggggcttgt   1380
acacaccgcc cgtcaagtca tgaaagttgg taacacccga gccggtggc ctaaccgttg   1440
tggggggagcc gtcgaaggtg ggactggtga ttaggactaa gtcgtaacaa ggtagccgta   1500
```

```
ccggaaggtg cggctggatc acctcctttc taaggag                         1537

SEQ ID NO: 4            moltype = DNA   length = 1537
FEATURE                 Location/Qualifiers
misc_feature            1..1537
                        note = 16S DNA sequence for the ProII probiotic strain
source                  1..1537
                        mol_type = other DNA
                        organism = synthetic construct
SEQUENCE: 4
ttttcattg gagagtttga tcctggctca ggacgaacgc tggcggcgtg cttaacacat  60
gcaagtcgaa cggaaaggcc ctgcttttgt ggggtgctcg agtggcgaac gggtgagtaa  120
cacgtgagta acctgcccct gactttggga taacttcagg aaactggggc taataccgga  180
taggagctcc tgctgcatgg tgggggttgg aaagtttcgg cggttgggga tggactcgcg  240
gcttatcagc ttgttggtgg ggtagtggct taccaaggct ttgacgggta gccggcctga  300
gagggtgacc ggccacattg ggactgagat acggcccaga ctcctacggg aggcagcagt  360
ggggaatatt gcacaatggg cggaagcctg atgcagcaac gccgcgtgcg ggatgacggc  420
cttcgggttg taaaccgctt cgcctgtga cgaagcgtga gtgacggtaa tgggtaaaga  480
agcaccggct aactacgtgc cagcagccgc ggtgatacgt agggtgcgag cgttgtccgg  540
atttattggg cgtaaagggc tcgtaggtgg ttgatcgcgt cggaagtgta atcttggggc  600
ttaaccctga gcgtgctttc gatacgggtt gacttgagga aggtagggga gaatggaatt  660
cctggtggag cggtggaatg cgcagatatc aggaggaaca ccagtggcga aggcggttct  720
ctgggccttt cctgacgctg aggagcgaaa gcgtggggag cgaacaggct agatacccct  780
ggtagtccac gctgtaaacg gtgggtacta ggtgtggggt ccattccacg gttccgtgc  840
cgtagctaac gctttaagta ccccgcctgg ggagtacggc cgcaaggcta aaactcaaag  900
gaattgacgg ggccccgcac aagcggcgga gcatgcggat taattcgatg caacgcgtag  960
aaccttacct gggtttgaca tggattggga gcgctcagag atgggtgtgc ctcttttggg  1020
gtcggttcac aggtggtgca tggctgtcgt cagctcgtgt cgtgagatgt tgggttaagt  1080
cccgcaacga gcgcaaccct tgttcactgt tgccagcacg ttatggtggg gactcagtgg  1140
agaccgccgg ggtcaactcg gaggaaggtg gggatgacgt caagtcatca tgccccttat  1200
gtccagggct tcacgcatgc tacaatggct ggtacagaga gtggcgagcc tgtgagggtg  1260
agcgaatctc ggaaagccgg tctcagttcg gattgggggtc tgcaactcga cctcatgaag  1320
tcggagtcgc tagtaatcgc agatcagcaa cgctgcggtg aatacgttcc cggggcttgt  1380
acacaccgcc cgtcaagtca tgaaagttgg taacacccga agccggtggc ctaaccgttg  1440
tggggagcc gtcgaaggtg ggactcggtga ttaggactaa gtcgtaacaa ggtagccgta  1500
ccggaaggtg cggctggatc acctcctttc taaggag                          1537

SEQ ID NO: 5            moltype = DNA   length = 1525
FEATURE                 Location/Qualifiers
misc_feature            1..1525
                        note = 16S DNA sequence
source                  1..1525
                        mol_type = other DNA
                        organism = synthetic construct
SEQUENCE: 5
agagtttgat cctggctcag gacgaacgct ggcggcgtgc ttaacacatg caagtcgaac  60
ggaaaggccc tgcttttgtg gggtgctcga gtggcgaacg gtgagtaac acgtgagtaa  120
cctgcccttg actttgggat aacttcagga aactggggct aataccggat aggagctcct  180
gctgcatggt gggggttgga aagtttcggc ggttggggat ggactcgcgg cttatcagct  240
tgttggtggg gtagtggctt accaaggctt tgacgggtag ccggcctgag agggtgaccg  300
gccacattga gactgagata cggcccagac tcctacgggg ggcagcagtg gggaatattg  360
cacaatgggc ggaagcctga tgcagcaacg ccgcgtgcgg gatgacggcc ttcgggttgt  420
aaaccgcttt cgcctgtgac gaagcgtgag tgacggtaat gggtaaagaa gcaccggcta  480
actacgtgcc agcagccgcg gtgatacgta gggtgcgagc gttgtccgga tttattgggc  540
gtaaagggct cgtaggtggt tgatcgcgtc ggaagtgtaa tcttggggct taaccctggg  600
cgtgctttcg atacgggttg acttgaggaa ggtaggggga aatggaattc ctggtggagc  660
ggtggaatgc gcagatatca ggaggaacac cagtggcgaa ggcggttctc tgggcctttc  720
ctgacgctga ggagcgaaag cgtggggagc gaacaggctt agatacccctg gtagtccacg  780
ctgtaaacgg tgggtactag gtgtgggggtc cattccacgg ttccgtgcc gtagctaacg  840
ctttaagtac cccgcctggg gagtacggcc gcaaggctaa aattgacggg gccccgcaca  900
agcggcggag catgcggatt aattcgatgc aacgcgtaga accttacctg ggtttgacat  960
ggatcgggag tgctcagaga tgggtgtgcc tcttttgggg tcggttcaca ggtggtgcat  1020
gcctgtcgtc agctcgtgtc gtgagatgtt gggttaagtc ccgcaacgag cgcaaccctt  1080
gttcactgtt gccagcacgt tatggtgggg actcagtgga gaccgccggg gtcaactcgg  1140
aggaaggtgg ggatgacgtc aagtcctcat gcccttatg tccagggctt cacgcatgct  1200
acaatggctg gtacagagag tggcgagcct gtgagggtga gcgaatctcg gaaagccggt  1260
ctcagttcgg attgggtct gcaactcgac ctcatgaagt cggagtcgct agtaatcgca  1320
gatcagcaac gctgcggtga atacgttccc ggggcttgta cacaccgccc gtcaagtcat  1380
gaaagttggt aacacccgaa gccggtggcc taaccgttgt gggggagccg gctggatca  1440
ccggaaggtg cggctggatca cctcctttct aagga                           1500
ggctggatca cctcctttct aagga                                       1525

SEQ ID NO: 6            moltype = DNA   length = 1525
FEATURE                 Location/Qualifiers
misc_feature            1..1525
                        note = 16S Sequence
source                  1..1525
                        mol_type = other DNA
                        organism = synthetic construct
```

```
SEQUENCE: 6
agagtttgat cctggctcag gacgaacgct ggcggcgtgc ttaacacatg caagtcgaac   60
ggaaaggccc tgctttgtg  gggtgctcga gtggcgaacg ggtgagtaac acgtgagtaa  120
cctgcccttg actttgggat aacttcagga aactgggggct aataccggat aggagctcct  180
gctgcatggt gggggttgga aagtttcggc ggttgggggat ggactcgcgg cttatcagct  240
tgttggtggg gtagtggctt accaaggctt tgacgggtag ccggcctgag agggtgaccg  300
gccacattgg gactgagata cggcccagac tcctacggga ggcagcagtg gggaatattg  360
cacaatgggc ggaagcctga tgcagcaacg ccgcgtgcgg gatgacggcc ttcgggttgt  420
aaaccgcttt cgcctgtgac gaagcgtgag tgacggtaat gggtaaagaa gcaccggcta  480
actacgtgcc agcagccgcg gtgatacgta gggtgcgagc gttgtccgga tttattgggc  540
gtaaagggct cgtaggtggt tgatcgcgtc ggaagtgtaa tcttgggggct taaccctgag  600
cgtgctttcg atacgggttg acttgaggaa ggtaggggag aatggaattc ctggtggagc  660
ggtggaatgc gcagatatca ggaggaacac cagtggcgaa ggcggttctc tgggcctttc  720
ctgacgctga ggagcgaaag cgtggggagc gaacaggctt agatacccctg gtagtccacg  780
ctgtaaacgg tgggtactag gtgtgggggtc cattccacgg gttccgtgcc gtagctaacg  840
ctttaagtac cccgcctggg gagtacggcc gcaaggctaa aactcaaagg aattgacggg  900
gccccgcaca agcggcggag catgcggatt aattcgatgc aacgcgtaga accttacctg  960
ggtttgacat ggatcgggag tgctcagaga tgggtgtgcc tctttggggg tcggttcaca 1020
ggtggtgcat gcctgtcgtc agctcgtgtc gtgagatgtt gggttaagtc ccgcaacgag 1080
cgcaaccctt gttcactgtt gccagcacgt tatggtgggg actcagtgga gaccgccggg 1140
gtcaactcgg aggaaggtgg ggatgacgtc aagtcatcat gccccttatg tccagggctt 1200
cacgcatgct acaatggctg gtacagagag tggcgagcct gtgagggtga gcgaatctcg 1260
gaaagccggt ctcagttcgg attggggggtct gcaactcgac ctcatgaagt cggagtcgct 1320
agtaatcgca gatcagcaac gctgcggtga atacgttccc gggggcttgta cacaccgccc 1380
gtcaagtcat gaaagttggt aacacccgaa gccggtggcc taaccgttgt gggggagccg 1440
tcgaaggtgg gactggtgat taggactaag tcgtaacaag gtagccgtac cggaaggtgc 1500
ggctggatca cctcctttct aagga                                       1525

SEQ ID NO: 7          moltype = DNA  length = 1525
FEATURE               Location/Qualifiers
misc_feature         1..1525
                     note = 16S Sequence
source               1..1525
                     mol_type = other DNA
                     organism = synthetic construct
SEQUENCE: 7
agagtttgat cctggctcag gacgaacgct ggcggcgtgc ttaacacatg caagtcgaac   60
ggaaaggccc tgctttgtg  gggtgctcga gtggcgaacg ggtgagtaac acgtgagtaa  120
cctgcccttg actttgggat aacttcagga aactggggggct aataccggat aggagctcct  180
gctgcatggt gggggttgga aagtttcggc ggttggggat ggactcgcgg cttatcagct  240
tgttggtggg gtagtggctt accaaggctt tgacgggtag ccggcctgag agggtgaccg  300
gccacattgg gactgagata cggcccagac tcctacggga ggcagcagtg gggaatattg  360
cacaatgggc ggaagcctga tgcagcaacg ccgcgtgcgg gatgacggcc ttcgggttgt  420
aaaccgcttt cgcctgtgac gaagcgtgag tgacggtaat gggtaaagaa gcaccggcta  480
actacgtgcc agcagccgcg gtaatacgta gggtgcgagc gttgtccgga tttattgggc  540
gtaaagggct cgtaggtggt tgatcgcgtc ggaagtgtaa tcttgggggct taaccctgag  600
cgtgctttcg atacgggttg acttgaggaa ggtaggggag aatggaattc ctggtggagc  660
ggtggaatgc gcagatatca ggaggaacac cagtggcgaa ggcggttctc tgggcctttc  720
ctgacgctga ggagcgaaag cgtggggagc gaacaggctt agatacccctg gtagtccacg  780
ctgtaaacgg tgggtactag gtgtgggggtc cattccacgg gttccgtgcc gtagctaacg  840
ctttaagtac cccgcctggg gagtacggcc gcaaggctaa aactcaaagg aattgacggg  900
gccccgcaca agcggcggag catgcggatt aattcgatgc aacgcgtaga accttacctg  960
ggtttgacat ggatcgggag tgctcagaga tgggtgtgcc tctttggggg tcggttcaca 1020
ggtggtgcat ggctgtcgtc agctcgtgtc gtgagatgtt gggttaagtc ccgcaacgag 1080
cgcaaccctt gttcactgtt gccagcacgt tatggtgggg actcagtgga gaccgccggg 1140
gtcaactcgg aggaaggtgg ggatgacgtc aagtcatcat gccccttatg tccagggctt 1200
cacgcatgct acaatggctg gtacagagag tggcgagcct gtgagggtga gcgaatctcg 1260
gaaagccggt ctcagttcgg attggggggtct gcaactcgac ctcatgaagt cggagtcgct 1320
agtaatcgca gatcagcaac gctgcggtga atacgttccc gggggcttgta cacaccgccc 1380
gtcaagtcat gaaagttggt aacacccgaa gccggtggcc taaccgttgt gggggagccg 1440
tcgaaggtgg gactggtgat taggactaag tcgtaacaag gtagccgtac cggaaggtgc 1500
ggctggatca cctcctttct aagga                                       1525

SEQ ID NO: 8          moltype = DNA  length = 1525
FEATURE               Location/Qualifiers
misc_feature         1..1525
                     note = 16S Sequence
source               1..1525
                     mol_type = other DNA
                     organism = synthetic construct
SEQUENCE: 8
agagtttgat cctggctcag gacgaacgct ggcggcgtgc ttaacacatg caagtcgaac   60
ggaaaggccc tgctttgtg  gggtgctcga gtggcgaacg ggtgagtaac acgtgagtaa  120
cctgcccttg actttgggat aacttcagga aactggggggct aataccggat aggagctcct  180
gctgcatggt gggggttgga aagtttcggc ggttggggat ggactcgcgg cttatcagct  240
tgttggtggg gtagtggctt accaaggctt tgacgggtag ccggcctgag agggtgaccg  300
gccacattgg gactgagata cggcccagac tcctacggga ggcagcagtg gggaatattg  360
cacaatgggc ggaagcctga tgcagcaacg ccgcgtgcgg gatgacggcc ttcgggttgt  420
aaaccgcttt cgcctgtgac gaagcgtgag tgacggtaat gggtaaagaa gcaccggcta  480
```

```
actacgtgcc agcagccgcg gtgatacgta gggtgcgagc gttgtccgga tttattgggc   540
gtaaagggct cgtaggtggt tgatcgcgtc ggaagtgtaa tcttgggggct taaccctgag   600
cgtgctttcg atacgggttg acttgaggaa ggtaggggag aatggaattc ctggtggagc   660
ggtggaatgc gcagatatca ggaggaacac cagtggcgaa ggcggttctc tgggcctttc   720
ctgacgctga ggagcgaaag cgtggggagc gaacaggctt agataccctg gtagtccacg   780
ctgtaaacgg tgggtactag gtgtggggtc cattccacgg gttccgtgcc gtagctaacg   840
ctttaagtac cccgcctggg gagtacggcc gcaaggctaa aactcaaagg aattgacggg   900
gccccgcaca agcggcggag catgcggatt aattcgatgc aacgcgtaga accttacctg   960
ggtttgacat ggatcggaag cgctcagaga tgggtgtgcc tcttttgggg tcggttcaca  1020
ggtggtgcat ggctgtcgtc agctcgtgtc gtgagatgtt gggttaagtc ccgcaacgag  1080
cgcaacccctt gttcactgtt gccagcacgt tatggtgggg actcagtgga gaccgccggg  1140
gtcaactcgg aggaaggtgg ggatgacgtc aagtcatcat gccccttatg tccagggctt  1200
cacgcatgct acaatggctg gtacagagag tggcgagcct gtgagggtga gcgaatctcg  1260
gaaagccggt ctcagttcgg attggggtct gcaactcgac ctcatgaagt cggagtcgct  1320
agtaatcgca gatcagcaac gctgcggtga atacgttccc ggggcttgta cacaccgccc  1380
gtcaagtcat gaaagttggt aacacccgaa gccggtggcc taaccgttgt gggggagccg  1440
tcgaaggtgg gactggtgat taggactaag tcgtaacaag gtagccgtac cggaaggtgc  1500
ggctggatca cctcctttct aagga                                        1525
```

```
SEQ ID NO: 9              moltype = DNA  length = 1525
FEATURE                  Location/Qualifiers
misc_feature             1..1525
                         note = 16S Sequence
source                   1..1525
                         mol_type = other DNA
                         organism = synthetic construct
SEQUENCE: 9
agagtttgat cctggctcag gacgaacgct ggcggcgtgc ttaacacatg caagtcgaac   60
ggaaaggccc tgcttttgtg gggtgctcga gtggcgaacg ggtgagtaac acgtgagtaa  120
cctgcccttg actttgggat aacttcagga aactggggct aataccggat aggagctcct  180
gctgcatggt gggggttgga aagtttcggc ggttggggat ggactcgcgg cttatcagct  240
tgttggtggg gtagtggctt accaaggctt gacgggtag ccggcctgag agggtgaccg   300
gccacattgg gactgagata cggcccagac tcctacggga ggcagcagtg gggaatattg  360
cacaatgggc ggaagcctga tgcagcaacg ccgcgtgcgg gatgacggcc ttcgggttgt  420
aaaccgcttt cgcctgtgac gaagcgtgag tgacggtaat gggtaaagaa gcaccggcta  480
actacgtgcc agcagccgcg gtgatacgta gggtgcgagc gttgtccgga tttattgggc   540
gtaaagggct cgtaggtggt tgatcgcgtc ggaagtgtaa tcttgggggct taaccctgag   600
cgtgctttcg atacgggttg acttgaggaa ggtaggggag aatggaattc ctggtggagc   660
ggtggaatgc gcagatatca ggaggaacac cagtggcgaa ggcggttctc tgggcctttc   720
ctgacgctga ggagcgaaag cgtggggagc gaacaggctt agataccctg gtagtccacg   780
ctgtaaacgg tgggtactag gtgtggggtc cattccacgg gttccgtgcc gtagctaacg   840
ctttaagtac cccgcctggg gagtacggcc gcaaggctaa aactcaaagg aattgacggg   900
gccccgcaca agcggcggag catgcggatt aattcgatgc aacgcgtaga accttacctg   960
ggtttgacat ggatcgggag tgctcagaga tgggtgtgcc tcttttgggg tcggttcaca  1020
ggtggtgcat ggctgtcgtc agctcgtgtc gtgagatgtt gggttaagtc ccgcaacgag  1080
cgcaacccctt gttcactgtt gccagcacgt tatggtgggg actcagtgga gaccgccggg  1140
gtcaactcgg aggaaggtgg ggatgacgtc aagtcatcat gccccttatg tccagggctt  1200
cacgcatgct acaatggctg gtacagagag tggcgagcct atgagggtga gcgaatctcg  1260
gaaagccggt ctcagttcgg attggggtct gcaactcgac ctcatgaagt cggagtcgct  1320
agtaatcgca gatcagcaac gctgcggtga atacgttccc ggggcttgta cacaccgccc  1380
gtcaagtcat gaaagttggt aacacccgaa gccggtggcc taaccgttgt gggggagccg  1440
tcgaaggtgg gactggtgat taggactaag tcgtaacaag gtagccgtac cggaaggtgc  1500
ggctggatca cctcctttct aagga                                        1525
```

```
SEQ ID NO: 10             moltype = DNA  length = 1525
FEATURE                  Location/Qualifiers
misc_feature             1..1525
                         note = 16S Sequence
source                   1..1525
                         mol_type = other DNA
                         organism = synthetic construct
SEQUENCE: 10
agagtttgat cctggctcag gacgaacgct ggcggcgtgc ttaacacatg caagtcgaac   60
ggaaaggccc tgcttttgtg gggtgctcga gtggcgaacg ggtgagtaac acgtgagtaa  120
cctgcccttg actttgggat aacttcagga aactggggct aataccggat aggagctcct  180
gctgcatggt gggggttgga aagtttcggc ggttggggat ggactcgcgg cttatcagct  240
tgttggtggg gtagtggctt accaaggctt gacgggtag ccggcctgag agggtgaccg   300
gccacattgg gactgagata cggcccagac tcctacggga ggcagcagtg gggaatattg  360
cacaatgggc ggaagcctga tgcagcaacg ccgcgtgcgg gatgacggcc ttcgggttgt  420
aaaccgcttt cgcctgtgac gaagcgtgag tgacggtaat gggtaaagaa gcaccggcta  480
actacgtgcc agcagccgcg gtgatacgta gggtgcgagc gttgcccgga tttattgggc   540
gtaaagggct cgtaggtggt tgatcgcgtc ggaagtgtaa tcttgggggct taaccctgag   600
cgtgctttcg atacgggttg acttgaggaa ggtaggggag aatggaattc ctggtggagc   660
ggtggaatgc gcagatatca ggaggaacac cagtggcgaa ggcggttctc tgggcctttc   720
ctgacgctga ggagcgaaag cgtggggagc gaacaggctt agatacctg gtagtccacg   780
ctgtaaacgg tgggtactag gtgtggggtc cattccacgg gttccgtgcc gtagctaacg   840
ctttaagtac cccgcctggg gagtacggcc gcaaggctaa aactcaaagg aattgacggg   900
gccccgcaca agcggcggag catgcggatt aattcgatgc aacgcgtaga accttacctg   960
ggtttgacat ggatcgggag tgctcagaga tgggtgtgcc tcttttgggg tcggttcaca  1020
```

-continued

```
ggtggtgcat gcctgtcgtc agctcgtgtc gtgagatgtt gggttaagtc ccgcaacgag   1080
cgcaaccctt gttcactgtt gccagcacgt tatggtgggg actcagtgga gaccgccggg   1140
gtcaactcgg aggaaggtgg ggatgacgtc aagtcatcat gcccttatg tccaggcgtt    1200
cacgcatgct acaatggctg gtacagagag tggcgagcct gtgagggtga gcgaatctcg    1260
gaaagccggt ctcagttcgg attggggtct gcaactcgac ctcatgaagt cggagtcgct    1320
agtaatcgca gatcagcaac gctgcggtga atacgttccc ggggcttgta cacaccgccc    1380
gtcaagtcat gaaagttggt aacacccgaa gccggtggcc taaccgttgt gggggagccg    1440
tcgaaggtgg gactggtgat taggactaag tcgtaacaag gtagccgtac cggaaggtgc    1500
ggctggatca cctcctttct aagga                                          1525
```

```
SEQ ID NO: 11         moltype = DNA   length = 1089
FEATURE               Location/Qualifiers
misc_feature          1..1089
                      note = DNA sequence that encodes Dispersin B
source                1..1089
                      mol_type = other DNA
                      organism = synthetic construct
SEQUENCE: 11
atgaattgtt gcgtaaaagg caattccata tatccgcaaa aaacaagtac caagcagacc   60
ggattaatgc tggacatcgc ccgacatttt tattcacccg aggtgattaa atcctttatt    120
gataccatca gcctttccgg cggtaatttt ctgcacctgc attttttccga ccatgaaaac   180
tatgccgatag aaagccattt acttaatcaa cgtgcggaaa atgccgtgca gggcaaagac   240
ggtatttata ttaatcctta taccggaaag ccattcttga gttatcggca acttgacgat   300
atcaaagcct atgctaaggc aaaaggcatt gagttgattc ccgaacttga cagcccgaat   360
cacatgacgg cgatctttaa actggtgcaa aaagacagag gggtcaagta ccttcaagga    420
ttaaaatcac gccaggtaga tgatgaaatt gatattacca atgctgacag tattactttt    480
atgcaatctt taatgagtga ggttattgat atttttggcg cacgagtca gcattttcat    540
attggtggcg atgaatttgg ttattctgtg gaaagtaatc atgagtttat tacgtatgcc   600
aataaactat cctacttttt agagaaaaaa gggttgaaaa cccgaatgtg gaatgacgga    660
ttaattaaaa atacttttga gcaaatcaac ccgaatattg aaattactta ttggagctat    720
gatggcgata cgcaggacaa aaatgaagct gccgagcgcc gtgatatgcg ggtcagtttg    780
ccggagttgc tggcgaaagg ctttactgtc ctgaactata attcctatta tctttacatt    840
gttccgaaag cttcaccaac cttctcgcaa gatgccgcct ttgccgccaa agatgttata    900
aaaaattggg atcttggtgt ttgggatgga cgaaacacca aaaaccgcgt acaaaatact    960
catgaaatag ccggcgcagc attatcgatc tggggagaag atgcaaaagc gctgaaagac   1020
gaaacaattc agaaaaacac gaaaagttta ttggaagcgg tgattcataa gacgaatggg   1080
gatgagtga                                                            1089
```

```
SEQ ID NO: 12         moltype = AA   length = 362
FEATURE               Location/Qualifiers
source                1..362
                      mol_type = protein
                      organism = Aggregatibacter actinomycetemcomitans
SEQUENCE: 12
MNCCVKGNSI YPQKTSTKQT GLMLDIARHF YSPEVIKSFI DTISLSGGNF LHLHFSDHEN    60
YAIESHLLNQ RAENAVQGKD GIYINPYTGK PFLSYRQLDD IKAYAKAKGI ELIPELDSPN   120
HMTAIFKLVQ KDRGVKYLQG LKSRQVDDEI DITNADSITF MQSLMSEVID IFGDTSQHFH   180
IGGDEFGYSV ESNHEFITYA NKLSYFLEKK GLKTRMWNDG LIKNTFEQIN PNIEITYWSY   240
DGDTQDKNEA AERRDMRVSL PELLAKGFTV LNYNSYLYI VPKASPTFSQ DAAFAAKDVI    300
KNWDLGVWDG RNTKNRVQNT HEIAGAALSI WGEDAKALKD ETIQKNTKSL LEAVIHKTNG   360
DE                                                                   362
```

```
SEQ ID NO: 13         moltype = DNA   length = 1103
FEATURE               Location/Qualifiers
misc_feature          1..1103
                      note = DNA sequence that encodes an alginate lyase
source                1..1103
                      mol_type = other DNA
                      organism = synthetic construct
SEQUENCE: 13
atgaaaacgt cccacctgat ccgtatcgcc ctgcccggtg ccctcgccgc ggcattgctc   60
gccagccagg tcagccaggc cgccgacctg gtacccccgc ccggctacta cgcggcggtc   120
ggcgagcgca agggcagcgc cggcagctgc cccgcggtgc cgccgccgta taccggcagc   180
ctggtcttca ccagcaagta cgaaggctcc gattcgggcg accct caacgtcaag  240
gcggagaaga ccttccgctc gcagatcaag gacatcaccg acatggagcg cggcgccacc   300
aagctggtca cccagtacat gcgcagcggc gcgacggcg acctggcctg cgcactgaac    360
tggatgagcg cctgggcccg cgccggcgcc ctgcagagcg acgacttcaa ccacaccggc   420
aagtccatgc gcaaatgggc gctgggcagc ctctccggcg cctacatgcg cctgaagttc   480
tccagctcgc ggccgctcgc ggcccacgcc gagcagagcc gggaaatcga ggactggttc   540
gcccggctcg gcacccaggt agtccgcgac tggagcggcc tgccgctgaa gaagatcaac    600
aaccattcct actgggcggc ctggtcggtg atgtccaccg cggtggtgac caaccgccgc   660
gacctcttcg actgggcggt gagcgagttc aaggtcgccg ccaaccaggt cgacgagcag   720
ggcttcctgc ccaacgaact caagcgccgc cagcgcgccc tcgcctacca caactatgcg    780
ctgccaccgc tggcgatgat cgccgcgttc gcccagctca cctgcgccag cctgcgccac   840
gagaaccacg gcgccctgca gcgcctggcc gagcgggtga tgaagggagt cgacgacgag    900
gaaaccttcg aggagaagac cggcgaggac caggacatga ccgacctcaa ggtcgacaac    960
aagtacgcct ggctggagcc ctactgcgcc ctctaccgct gcgagccgaa gatgctcgag   1020
gcgaagaagg accgcgagcc gttcaacagt ttccgcctcg gcggcgaagt gacgcgggtg   1080
ttcagccgcg aagggggaag ttg                                            1103
```

-continued

```
SEQ ID NO: 14            moltype = AA   length = 367
FEATURE                  Location/Qualifiers
source                   1..367
                         mol_type = protein
                         organism = Flavobacterium multivorum
SEQUENCE: 14
MKTSHLIRIA LPGALAAALL ASQVSQAADL VPPPGYYAAV GERKGSAGSC PAVPPPYTGS   60
LVFTSKYEGS DSARATLNVK AEKTFRSQIK DITDMERGAT KLVTQYMRSG RDGDLACALN  120
WMSAWARAGA LQSDDFNHTG KSMRKWALGS LSGAYMRLKF SSSRPLAAHA EQSREIEDWF  180
ARLGTQVVRD WSGLPLKKIN NHSYWAAWSV MSTAVVTNRR DLFDWAVSEF KVAANQVDEQ  240
GFLPNELKRR QRALAYHNYA LPPLAMIAAF AQVNGVDLRQ ENHGALQRLA ERVMKGVDDE  300
ETFEEKTGED QDMTDLKVDN KYAWLEPYCA LYRCEPKMLE AKKDREPFNS FRLGGEVTRV  360
FSREGGS                                                           367

SEQ ID NO: 15            moltype = DNA   length = 1539
FEATURE                  Location/Qualifiers
misc_feature             1..1539
                         note = DNA sequence that encodes an amylase
source                   1..1539
                         mol_type = other DNA
                         organism = synthetic construct
SEQUENCE: 15
atgaaacaac aaaaacggct ttacgcccga ttgctgacgc tgttatttgc gctcatcttc    60
ttgctgcctc attctgcagc agcggcggca aatcttaatg ggacgctgat gcagtatttt   120
gaatggtaca tgcccaatga cggccaacat tggaagcgtt tgcaaaacgt ctcggcatat   180
ttggctgaac acggtattac tgccgtctgg attcccccgg catataaggg aacgagccaa   240
gcggatgtgg gctacggtgc ttacgacctt tatgatttag gggagtttca tcaaaaaggg   300
acggttcgga caaagtacgg cacaaaagga gagctgcaat ctgcgatcaa aagtcttcat   360
tcccgcgaca ttaacgttta cgggatgtgt gtcatcaacc acaaaggcgg cgctgatgcg   420
accgaagatg taaccgcggt tgaagtcgat cccgctgacc gcaaccgcgt aatttcagga   480
gaacacctaa ttaaagcctg gacacatttt cattttccgg ggcgcggcag cacatacagc   540
gattttaaat ggcattggta ccattttgac ggaaccgatt gggacgagtc ccgaaagctg   600
aaccgcatct ataagtttca aggaaaggct tgggattggg aagtttccaa tgaaaacggc   660
aactatgatt atttgatgta tgccgacatc gattatgacc atcctgatgt cgcagcagac   720
attaagagat ggggcacttg gtatgccaat gaactgcaat tggacggttt ccgtcttgat   780
gctgtcaaac acattaaatt ttcttttttg cgggattggg ttaatcatgt cagggaaaaa   840
acggggaagg aaatgtttac ggtagctgaa tattggcaga atgacttggg cgcgctggaa   900
aactatttga acaaaacaaa ttttaatcat tcagtgtttg acgtgccgct tcattatcag   960
ttccatgctg catcgacaca gggaggcggc tatgatatga ggaaattgct gaacggtacg  1020
gtcgtttcca agcatccgtt gaaatcggtt acatttgtcg ataaccatga tacacagccg  1080
gggcaatcgc ttgagtcgac tgtccaaaca tggtttaagc cgcttgctta cgcttttatt  1140
ctcacaaggg aatctggata ccctcaggtt ttctacgggg atatgtacgg gacgaaaggg  1200
gactcccagc gcgaaattcc tgccttgaaa cacaaaattg aaccgatctt aaaagcgaga  1260
aaacagtatg cgtacggagc acagcatgat tatttcgacc accatgacat tgtcggctgg  1320
acaagggaag gcgacagctc ggttgcaaat tcaggtttgg cggcattaat aacagacgga  1380
cccggtgggg caaagcgaat gtatgtcggc cggcaaaacg gcaatgcgac catggcatgac  1440
attaccggaa accgttcgga gccggttgtc atcaattcgg aaggctgggg agagtttcac  1500
gtaaacggcg ggtcggtttc aatttatgtt caaagatag                          1539

SEQ ID NO: 16            moltype = AA   length = 512
FEATURE                  Location/Qualifiers
source                   1..512
                         mol_type = protein
                         organism = Bacillus licheniformis
SEQUENCE: 16
MKQQKRLYAR LLTLLFALIF LLPHSAAAAA NLNGTLMQYF EWYMPNDGQH WKRLQNDSAY   60
LAEHGITAVW IPPAYKGTSQ ADVGYGAYDL YDLGEFHQKG TVRTKYGTKG ELQSAIKSLH  120
SRDINVYGDV VINHKGGADA TEDVTAVEVD PADRNRVISG EHLIKAWTHF HFPGRGSTYS  180
DFKWHWYHFD GTDWDESRKL NRIYKFQGKA WDWEVSNENG NYDYLMYADI DYDHPDVAAE  240
IKRWGTWYAN ELQLDGFRLD AVKHIKFSFL RDWVNHVREK TGKEMFTVAE YWQNDLGALE  300
NYLNKTNFNH SVFDVPLHYQ FHAASTQGGG YDMRKLLNGT VVSKHPLKSV TFVDNHDTQP  360
GQSLESTVQT WFKPLAYAFI LTRESGYPQV FYGDMYGTKG DSQREIPALK HKIEPILKAR  420
KQYAYGAQHD YFDHHDIVGW TREGDSSVAN SGLAALITDG PGGAKRMYVG RQNAGETWHD  480
ITGNRSEPVV INSEGWGEFH VNGGSVSIYV QR                                512

SEQ ID NO: 17            moltype = DNA   length = 996
FEATURE                  Location/Qualifiers
misc_feature             1..996
                         note = DNA sequence that encodes a cellulase
source                   1..996
                         mol_type = other DNA
                         organism = synthetic construct
SEQUENCE: 17
atgaagtttc agagcacttt gcttcttgcc gccgcggctg ttccgcgtt ggctgtgcct    60
catggctccg acataagaa gagggcgtct gtgtttgaat ggttcggatc gaacgagtct   120
ggtgctgaat ttgggaccaa tatcccaggc gtctggggaa ccgactacat cttccccgac   180
ccctcgacca tctctacgtt gattggcaag ggaatgaact cttccgcgt ccagttcatg   240
atggagaggt tgcttcctga ctcgatgact ggttcatacg acgaggagta tctggccaac   300
```

-continued

```
ttgacgactg tggtgaaagc ggtcacggat ggaggcgcgc atgcgctcat cgaccctcat  360
aactatggca gatacaacgg ggagatcatc tccagtacat cggatttcca gactttctgg  420
cagaatctgg cgggccagta caaagataac gacttggtca tgtttgatac caacaacgaa  480
tactacgaca tggaccagga tctcgtgctg aatctcaacc aagcagccat taacggcatc  540
cgcgctgcag gtgcaagcca gtacattttc gtcgaaggca actcctggac cggagcttgg  600
acatgggtcg atgtcaacga taatatgaag aatttgaccg acccagaaga caagatcgtc  660
tatgaaatgc accagtacct agactccgac ggttccggca cttcggagac ctgtgtctcc  720
gggacaatcg gaaaggagcg gatcactgat gctacacagt ggctcaagga caataagaag  780
gtcggcttca tcggcgaata tgccggggggg tccaatgatg tgtgtcggag tgccgtgtcc  840
gggatgctag agtacatggc gaacaacacc gacgtatgga agggtgcgtc gtggtgggca  900
gccgggccat ggtgggggaga ctacattttc agcctggagc ccccagatgg aactgcttac  960
acgggtatgc tggatatcct ggagacgtat ctctga                             996
```

```
SEQ ID NO: 18              moltype = AA   length = 331
FEATURE                    Location/Qualifiers
source                     1..331
                           mol_type = protein
                           organism = Aspergillus niger
SEQUENCE: 18
MKFQSTLLLA AAAGSALAVP HGSGHKKRAS VFEWFGSNES GAEFGTNIPG VWGTDYIFPD  60
PSTISTLIGK GMNFFRVQFM MERLLPDSMT GSYDEEYLAN LTTVVKAVTD GGAHALIDPH  120
NYGRYNGEII SSTSDFQTFW QNLAGQYKDN DLVMFDTNNE YYDMDQDLVL NLNQAAINGI  180
RAAGASQYIF VEGNSWTGAW TWVDVNDNMK NLTDPEDKIV YEMHQYLDSD GSGTSETCVS  240
GTIGKERITD ATQWLKDNKK VGFIGEYAGG SNDVCRSAVS GMLEYMANNT DVWKGASWWA  300
AGPWWGDYIF SLEPPDGTAY TGMLDILETY L                                 331
```

```
SEQ ID NO: 19              moltype = DNA   length = 1155
FEATURE                    Location/Qualifiers
misc_feature               1..1155
                           note = DNA sequence that encodes proteinase K
source                     1..1155
                           mol_type = other DNA
                           organism = synthetic construct
SEQUENCE: 19
atgcgtttgt ctgttcttct gagtcttctt cccctcgctc tcggcgctcc tgccgttgag  60
cagcgctccg aggctgctcc tctgatcgag gcccgcggcg agatggttgc caacaagtac  120
attgtcaagt tcaaggaggg tagcgctctt tctgctctcg atgctgccat ggagaagatt  180
tctggcaagc ccgaccacgt ctacaagaac gtcttcagtg gtttcgctgc gaccgttgac  240
gagaacatgg ttcgggttct ccgcgcccat cccgatgtgg agtacattga gcaggatgct  300
gttgtcacca tcaacgctgc gcagaccaac gctccctggg gccttgctcg catctccagc  360
accagccccg gtacctctac ttactactat gacgaatctg ccggccaagg ctcctgcgtc  420
tacgtgattg acaccggtat cgaggcatcg cacccccagt ttgagggtcg tgcccagatg  480
gtcaagacct actactactc cagtcgcgac ggtaacggtc acggcactca ctgcgctggt  540
accgttggct cccgaaccta cggtgtcgcc aagaagaccc agctctttgg tgtcaaggtc  600
ctcgatgaca acggcagtgg ccagtactcc accatcatcg ccggtatgga ctttgttgcc  660
agcgacaaga acaaccgcaa ctgccccaaa ggtgtcgttg cctccttgtc ccttggcggt  720
ggttactcct cctccgtgaa cagcgccgct gccaggctac agatcctcag tctgtcatgg  780
gccgtcgctg ccggtaacaa caacgctgac gcccgcaact actcccctgc ttctgagccc  840
tcggtctgca ctgtcggtgc ttctgaccgc tacgacagac gctccagctt ctccaactac  900
ggcagcgttt tggacatctt tggccctggt accagcattc tctccacctg gatcggcggc  960
agcacccgct ccatctctgg aacttccatg gctactcccc acgttgccgg tctcgctgcc  1020
tacctcatga ctcttggaaa gactaccgcc gccagcgctt gccgatacat tgccgacacc  1080
gccaacaagg gcgacttgag caacattccc ttcggcactg tcaacctgct tgcctacaac  1140
aactaccagg cttaa                                                    1155
```

```
SEQ ID NO: 20              moltype = AA   length = 384
FEATURE                    Location/Qualifiers
source                     1..384
                           mol_type = protein
                           organism = Parengyodontium album
SEQUENCE: 20
MRLSVLLSLL PLALGAPAVE QRSEAAPLIE ARGEMVANKY IVKFKEGSAL SALDAAMEKI  60
SGKPDHVYKN VFSGFAATLD ENMVRVLRAH PDVEYIEQDA VVTINAAQTN APWGLARISS  120
TSPGTSTYYY DESAGQGSCV YVIDTGIEAS HPEFEGRAQM VKTYYYSSRD GNGHGTHCAG  180
TVGSRTYGVA KKTQLFGVKV LDDNGSGQYS TIIAGMDFVA SDKNNRNCPK GVVASLSLGG  240
GYSSSVNSAA ARLQSSGVMV AVAAGNNNAD ARNYSPASEP SVCTVGASDR YDRRSSFSNY  300
GSVLDIFGPG TSILSTWIGG STRSISGTSM ATPHVAGLAA YLMTLGKTTA ASACRYIADT  360
ANKGDLSNIP FGTVNLLAYN NYQA                                         384
```

```
SEQ ID NO: 21              moltype = DNA   length = 1140
FEATURE                    Location/Qualifiers
misc_feature               1..1140
                           note = DNA sequence that encodes subtilisin
source                     1..1140
                           mol_type = other DNA
                           organism = synthetic construct
SEQUENCE: 21
atgatgagga aaaagagttt ttggcttggg atgctgacgg ccttcatgct cgtgttcacg  60
atggcattca gcgattccgc ttctgctgct caaccggcga aaaatgttga aaaggattat  120
```

-continued

```
attgtcggat ttaagtcagg agtgaaaacc gcatctgtca aaaaggacat catcaaagag    180
agcggcggaa aagtggacaa gcagtttaga atcatcaacg cggcaaaagc gaagctagac    240
aaagaagcgc ttaaggaagt caaaaatgat ccggatgtcg cttatgtgga agaggatcat    300
gtggcccatg ccttggcgca aaccgttcct tacggcattc ctctcattaa agcggacaaa    360
gtgcaggctc aaggctttaa gggagcgaat gtaaaagtag ccgtcctgga tacaggaatc    420
caagcttctc atccggactt gaacgtagtc ggcggagcaa gctttgtggc tggcgaagct    480
tataacaccg acggcaacgg acacggcaca catgttgccg gtacagtagc tgcgcttgac    540
aatacaacgg gtgtattagg cgttgcgcca agcgtatcct tgtacgcggt taaagtactg    600
aattcaagcg gaagcggaac ttacagcggc attgtaagcg gaatcgagtg ggcgacgaca    660
aacggcatgg atgttatcaa catgagtctt ggaggaccat caggctcaac agcgatgaaa    720
caggcggttg acaatgcata tgcaagaggg gttgtcgttg tggcggctgc tgggaacagc    780
ggatcttcag gaaacacgaa tacaatcggc tatcctgcga aatacgactc tgtcatcgca    840
gttggcgcgg tagactctaa cagcaacaga gcttcatttt ccagcgtcgg agcagagctt    900
gaagtcatgg ctcctggcgc aggcgtgtac agcacttacc caaccagcac ttatgcaaca    960
ttgaacggaa cgtcaatggc ttctcctcat gtagcgggag cagcagcttt gatcttgtca   1020
aaacatccga acctttcagc ttcacaagtc cgcaaccgtc tctccagtac ggcgacttat   1080
ttgggaagct ccttctacta tggaaaaggt ctgatcaatg tcgaagctgc cgctcaataa   1140
```

```
SEQ ID NO: 22            moltype = AA   length = 379
FEATURE                  Location/Qualifiers
source                   1..379
                         mol_type = protein
                         organism = Bacillus licheniformis
SEQUENCE: 22
MMRKKSFWLG MLTAFMLVFT MAFSDSASAA QPAKNVEKDY IVGFKSGVKT ASVKKDIIKE    60
SGGKVDKQFR IINAAKAKLD KEALKEVKND PDVAYVEEDH VAHALAQTVP YGIPLIKADK   120
VQAQGFKGAN VKVAVLDTGI QASHPDLNVV GGASFVAGEA YNTDGNGHGT HVAGTVAALD   180
NTTGVLGVAP SVSLYAVKVL NSSGSGSYSG IVSGIEWATT NGMDVINMSL GGASGSTAMK   240
QAVDNAYAKG VVVVAAAGNS GSSGNTNTIG YPAKYDSVIA VGAVDSNSNR ASFSSVGAEL   300
EVMAPGAGVY STYPTNTYAT LNGTSMASPH VAGAAALILS KHPNLSASQV RNRLSSTATY   360
LGSSFYYGKG LINVEAAAQ                                                379
```

```
SEQ ID NO: 23            moltype = DNA   length = 669
FEATURE                  Location/Qualifiers
misc_feature             1..669
                         note = DNA sequence that encodes trypsin
source                   1..669
                         mol_type = other DNA
                         organism = synthetic construct
SEQUENCE: 23
atcgtcgggg gctacacctg cgcagagaat tccgtccctt accaggtgtc cctgaatgct    60
ggctaccact tctgcggggg ctccctcatc aatgaccagt gggtggtgtc cgcggctcac   120
tgctaccagt accacatcca ggtgaggctg ggagaataca acattgatgt cttggagggt   180
ggtgagcagt tcatcgatgc gtccaagatc atccgccacc ccaagtacag cagctggact   240
ctggacaatg acatcctgct gatcaaactc tccacgcctg cggtcatcaa tgcccggggtg   300
tccaccttgc tgctgcccag tgcctgtgct tccgcaggca cagagtgcct catctccggc   360
tggggcaaca ccctgagcag tggcgtcaac tacccggacc tgctgcaatg cctggtggcc   420
ccgctgctga gccacgccga ctgtgaagcc tcataccctg gacagatcac taacaacatg   480
atctgcgctg gcttcctgga aggaggcaag gattcctgcc agggtgactc tggcggccct   540
gtggcttgca acgacagct ccagggcatt gtgtcctggg gctacggctg tgcccagaag   600
ggcaagcctg gggtctacac caaggtctgc aactacgtgg actggattca ggagaccatc   660
gccgccaac                                                          669
```

```
SEQ ID NO: 24            moltype = AA   length = 223
FEATURE                  Location/Qualifiers
source                   1..223
                         mol_type = protein
                         organism = Bos taurus
SEQUENCE: 24
IVGGYTCGAN TVPYQVSLNS GYHFCGGSLI NSQWVVSAAH CYKSGIQVRL GEDNINVVEG    60
NEQFISASKS IVHPSYNSNT LNNDIMLIKL KSAASLNSRV ASISLPTSCA SAGTQCLISG   120
WGNTKSSGTS YPDVLKCLKA PILSDSSCKS AYPGQITSNM FCAGYLEGGK DSCQGDSGGP   180
VVCSGKLQGI VSWGSGCAQK NKPGVYTKVC NYVSWIKQTI ASN                    223
```

```
SEQ ID NO: 25            moltype = DNA   length = 1464
FEATURE                  Location/Qualifiers
misc_feature             1..1464
                         note = DNA sequence that encodes serratiopeptidase
source                   1..1464
                         mol_type = other DNA
                         organism = synthetic construct
SEQUENCE: 25
atgcaatcta ctaaaaaggc aattgaaatt actgaatcca gcctcgctgc cgcgacaacc    60
ggttacgatg ctgtagacga cctgctgcat tatcatgagc ggggtaacgg gattcagatt   120
aatggcaagg attcattttc taacgagcaa gctgggctgt ttattacccg tgagaaccaa   180
acctggaacg gttacaaggt atttggccag ccggtcaaat taaccttctc gttcccggac   240
tataagttct cttccaccaa cgtcgccggc gacaccgggc tgagcaagtt cagcgcggaa   300
cagcagcagc aggctaagct gtcgctgcag tcctgggccg acgtcgccaa tatcaccttc   360
accgaagtgg cggccggtca aaaggccaat atcaccttcg gcaactacag ccaggatcgt   420
```

-continued

```
cccggccact atgattacgg cacccaggcc tacgccttcc tgccgaacac catttggcag   480
ggccaggatt tgggcggcca gacttggtac aacgtaaacc aatccaacgt gaagcatccg   540
gcgaccgaag actacggccg ccagacgttc acccatgaga ttggccatgc gctgggcctg   600
agccacccgg gcgactacaa cgccggtgag ggcaacccga cctatagaga tgtcacctat   660
gcggaagata cccgccagtt cagcctgatg agctactgga gtgaaaccaa taccggtggc   720
gacaacggcg gtcactatgc cgcggctccg ctgctggatg acattgccgc cattcagcat   780
ctgtatggcg ccaacctgtc gacccgcacc ggcgacaccg tgtacggctt taactccaat   840
accggtcgtg acttcctcag caccaccagc aactcgcaga aagtgatctt tgcggcctgg   900
gatgcgggcg gcaacgatac cttcgacttc tccggttaca ccgctaacca gcgcatcaac   960
ctgaacgaga aatggttctc cgacgtgggc ggcctgaagg gcaacgtgtc gatcgccgcc  1020
ggtgtgacca ttgagaacgc cattggcggt tccggcaacg acgtgatcgt cggcaacgcg  1080
gccaataacg tgctgaaagg cggcgcgggt aacgacgtgc tgttcggcgg cggcggggcg  1140
gatgaattgt ggggcggtgc cggcaaagac atcttcgtgt tctctgccgc cagcgattcc  1200
gcaccgggcg cttcagactg gatccgcgac ttccagaaag ggatcgacaa gatcgacctg  1260
tcgttcttca ataaagaagc gcagagcagc gatttcattc acttcgtcga tcacttcagc  1320
ggcacggccg gtgaggcgct gctgagctac aacgcgtcca gcaacgtgac cgatttgtcg  1380
gtgaacatcg gtgggcatca ggcgccggac ttcctggtga aaatcgtcgg ccaggtagac  1440
gtcgccacgg actttatcgt gtaa                                         1464
```

```
SEQ ID NO: 26          moltype = AA   length = 487
FEATURE                Location/Qualifiers
source                 1..487
                       mol_type = protein
                       organism = Serratia sp.
SEQUENCE: 26
MQSTKKAIEI TESSLAAATT GYDAVDDLLH YHERGNGIQI NGKDSFSNEQ AGLFITRENQ   60
TWNGYKVFGQ PVKLTFSFPD YKFSSTNVAG DTGLSKFSAE QQQQAKLSLQ SWADVANITF  120
TEVAAGQKAN ITFGNYSQDR PGHYDYGTQA YAFLPNTIWQ GQDLGGQTWY NVNQSNVKHP  180
ATEDYGRQTF THEIGHALGL SHPGDYNAGE GNPTYRDVTY AEDTRQFSLM SYWSETNTGG  240
DNGGHYAAAP LLDDIAAIQH LYGANLSTRT GDTVYGFNSN TGRDFLSTTS NSQKVIFAAW  300
DAGGNDTFDF SGYTANQRIN LNEKWFSDVG GLKGNVSIAA GVTIENAIGG SGNDVIVGNA  360
ANNVLKGGAG NDVLFGGGGA DELWGGAGKD IFVFSAASDS APGASDWIRD FQKGIDKIDL  420
SFFNKEAQSS DFIHFVDHFS GTAGEALLSY NASSNVTDLS VNIGGHQAPD FLVKIVGQVD  480
VATDFIV                                                            487
```

```
SEQ ID NO: 27          moltype = DNA   length = 783
FEATURE                Location/Qualifiers
misc_feature           1..783
                       note = DNA sequence that encodes a bovine pancreatic DNAse I
source                 1..783
                       mol_type = other DNA
                       organism = synthetic construct
SEQUENCE: 27
ttgaagattg ctgctttcaa cattagaact ttcggtgaaa ctaaaatgtc taacgctact   60
ttggcatctt acatcgttag aattgtcaga agatatgata tcgttttaat tcaagaagtt  120
agagactctc acttggttgc agttggtaaa ttgttagact acttgaacca agatgaccca  180
aacacttacc actacgttgt ttctgaacca ttgggtaaga actcttacaa agaaagatac  240
ttattcttgt tcagaccaaa caaagtttca gttttggata cttaccaata cgacgacggt  300
tgcgaatctt gtggtaacga ttctttctcc agagaacctg ctgttgttaa attctcatca  360
cactctacca aggttaaaga gttcgctatc gttgctttgc attctgctcc ttctgacgct  420
gttgctgaaa ttaactcttt gtacgacgtt tacttagatg ttcaacagaa atggcacttg  480
aacgacgtca tgttgatggg tgactttaac gctgattgct cttatgttac ttcttctcaa  540
tggtcttcaa ttagattgag aacatcttca actttccaat ggttaattcc tgattccgct  600
gataccactg ctactagtac caactgtgct tacgatagaa tcgttgttgc tggatcatta  660
ttgcaatctt ctgttgtccc aggttcagcg gcccctttcg atttccaagc tgcatatggt  720
ttgtctaatg aaatggcttt agccatttct gatcactacc cagttgaagt cacattgaca  780
taa                                                                783
```

```
SEQ ID NO: 28          moltype = AA   length = 260
FEATURE                Location/Qualifiers
source                 1..260
                       mol_type = protein
                       organism = Bos taurus
SEQUENCE: 28
LKIAAFNIRT FGETKMSNAT LASYIVRIVR RYDIVLIQEV RDSHLVAVGK LLDYLNQDDP   60
NTYHYVVSEP LGRNSYKERY LFLFRPNKVS VLDTYQYDDG CESCGNDSFS REPAVVKFSS  120
HSTKVKEFAI VALHSAPSDA VAEINSLYDV YLDVQQKWHL NDVMLMGDFN ADCSYVTSSQ  180
WSSIRLRTSS TFQWLIPDSA DTTATSTNCA YDRIVVAGSL LQSSVVPGSA APFDFQAAYG  240
LSNEMALAIS DHYPVEVTLT                                              260
```